United States Patent
Tsai et al.

(10) Patent No.: US 11,793,823 B2
(45) Date of Patent: Oct. 24, 2023

(54) COMPOUNDS AND PHARMACEUTICAL USES THEREOF

(71) Applicant: SyneuRx International (Taiwan) Corp., New Taipei (TW)

(72) Inventors: Guochuan Emil Tsai, Pasadena, CA (US); Yi-Wen Mao, New Taipei (TW); Lu-Ping Lu, New Taipei (TW); Wei-Hua Chang, New Taipei (TW); Han-Yi Hsieh, New Taipei (TW); Jhe Wei Hu, New Taipei (TW); Tsai-Miao Shih, New Taipei (TW); ChanHui Huang, New Taipei (TW)

(73) Assignee: SyneuRx International (Taiwan) Corp., New Taipei (TW)

( * ) Notice: Subject to any disclaimer, the term of this patent is extended or adjusted under 35 U.S.C. 154(b) by 0 days.

(21) Appl. No.: 17/699,784

(22) Filed: Mar. 21, 2022

(65) Prior Publication Data
US 2022/0218730 A1 Jul. 14, 2022

Related U.S. Application Data

(63) Continuation of application No. PCT/CN2021/089301, filed on Apr. 23, 2021.

(60) Provisional application No. 63/014,448, filed on Apr. 23, 2020.

(51) Int. Cl.
| | |
|---|---|
| *C07D 207/34* | (2006.01) |
| *A61K 31/7048* | (2006.01) |
| *A23L 33/10* | (2016.01) |
| *A23L 33/00* | (2016.01) |
| *A61P 25/18* | (2006.01) |
| *A61K 31/235* | (2006.01) |
| *A61K 31/36* | (2006.01) |
| *A61K 31/40* | (2006.01) |
| *A61K 31/415* | (2006.01) |
| *A61K 31/7034* | (2006.01) |
| *C07C 69/90* | (2006.01) |
| *C07D 231/14* | (2006.01) |
| *C07D 317/68* | (2006.01) |
| *C07H 15/22* | (2006.01) |
| *C07H 15/26* | (2006.01) |

(52) U.S. Cl.
CPC .......... *A61K 31/7048* (2013.01); *A23L 33/10* (2016.08); *A23L 33/40* (2016.08); *A61K 31/235* (2013.01); *A61K 31/36* (2013.01); *A61K 31/40* (2013.01); *A61K 31/415* (2013.01); *A61K 31/7034* (2013.01); *A61P 25/18* (2018.01); *C07C 69/90* (2013.01); *C07D 207/34* (2013.01); *C07D 231/14* (2013.01); *C07D 317/68* (2013.01); *C07H 15/22* (2013.01); *C07H 15/26* (2013.01); *A23V 2002/00* (2013.01)

(58) Field of Classification Search
CPC .. C07D 207/34; C07D 231/14; C07D 317/68; A61K 31/36; A61K 31/235; A61K 31/40; A61K 31/415; A61K 31/7034; A61P 25/18; C07H 15/22; C07H 15/26
USPC .............................................. 536/4.1; 514/25
See application file for complete search history.

(56) References Cited

U.S. PATENT DOCUMENTS

| | | | |
|---|---|---|---|
| 5,571,551 A | 11/1996 | Fusi et al. | |
| 5,639,500 A | 6/1997 | Fusi et al. | |
| 6,489,287 B1 | 12/2002 | Gauthier et al. | |
| 8,652,533 B2 | 2/2014 | Hara et al. | |
| 10,105,378 B2 | 10/2018 | Tsai et al. | |
| 10,265,336 B2 | 4/2019 | Tsai et al. | |
| 10,927,138 B2 * | 2/2021 | Tsai .......................... | A61P 3/04 |
| 2007/0197610 A1 | 8/2007 | Kennis et al. | |
| 2008/0096959 A1 | 4/2008 | Hara et al. | |

(Continued)

FOREIGN PATENT DOCUMENTS

| | | |
|---|---|---|
| CN | 1398871 A | 2/2003 |
| CN | 1450077 A | 10/2003 |

(Continued)

OTHER PUBLICATIONS

Smith, et. al., Open Med Chem J. 2010; 4: 3-9. (Year: 2010).*

(Continued)

*Primary Examiner* — Jeffrey H Murray

(74) *Attorney, Agent, or Firm* — McDermott Will & Emery LLP

(57) ABSTRACT

A compound of Formula (I):

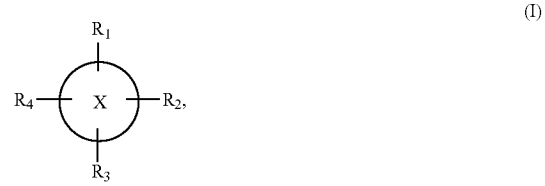

or a pharmaceutically acceptable salt thereof, in which Ring X is a 3 to 7 membered monocyclic ring, at least one of $R_1$, $R_2$, $R_3$, and $R_4$ is $OR_5$ or $CH_2OR_5$ and the other $R_1$, $R_2$, $R_3$, and $R_4$ each independently are halogen, OH, $OR_5$, $CH_2OR_5$, $CO_2H$, OC=$OR_6$, (C=O)$R_6$, $R_6$, C1-10 alkyl, C2-10 alkenyl, C2-10 alkynyl, H, or absent. Also provided herein are therapeutic uses of the compound of Formula (I).

14 Claims, 4 Drawing Sheets

(56) References Cited

U.S. PATENT DOCUMENTS

| | | |
|---|---|---|
| 2009/0118202 A1 | 5/2009 | Thekkumkara |
| 2009/0170928 A1 | 7/2009 | Bruno et al. |
| 2011/0287109 A1 | 11/2011 | Bagley et al. |
| 2017/0362394 A1 | 12/2017 | Chigumpati et al. |
| 2018/0092935 A1 | 4/2018 | Tsai et al. |
| 2018/0133237 A1 | 5/2018 | Tsai et al. |
| 2019/0201427 A1 | 7/2019 | Tsai et al. |
| 2019/0367549 A1 | 12/2019 | Tsai et al. |
| 2020/0390791 A1 | 12/2020 | Tsai et al. |

FOREIGN PATENT DOCUMENTS

| | | |
|---|---|---|
| CN | 1454599 A | 11/2003 |
| CN | 1560077 A | 1/2005 |
| CN | 1568968 A | 1/2005 |
| CN | 1602853 A | 4/2005 |
| CN | 101618066 A | 1/2010 |
| CN | 102127125 A | 7/2011 |
| CN | 102180917 A | 9/2011 |
| CN | 102250159 A | 11/2011 |
| CN | 102743419 A | 10/2012 |
| CN | 105687226 A | 6/2016 |
| EP | 0413056 A1 | 2/1991 |
| JP | 2005-538987 A | 12/2005 |
| JP | 2012-116791 A | 6/2012 |
| JP | 2013-249263 A | 12/2013 |
| JP | 2013-075849 A | 3/2016 |
| KR | 2009-0072527 A | 7/2009 |
| KR | 2009-0084159 A | 8/2009 |
| WO | WO 2000/015044 A1 | 3/2000 |
| WO | WO 2008/131047 A2 | 10/2008 |
| WO | WO 2009/000864 A1 | 12/2008 |
| WO | WO 2010/056413 A2 | 5/2010 |
| WO | WO 2011/085454 A1 | 7/2011 |
| WO | WO 2012/144754 A2 | 10/2012 |
| WO | WO 2013/096182 A2 | 6/2013 |
| WO | WO 2017/167168 A1 | 10/2017 |
| WO | WO 2019/109300 A1 | 6/2019 |
| WO | WO 2019/228408 A1 | 12/2019 |

OTHER PUBLICATIONS

Lavoie, et. al., Magnetic Resonance in Chemistry (2016), 54(2), 168-174. (Year: 2016).*

Niemetz, et. al., Chemical Communications (Cambridge) (2001), (1), 35-36. (Year: 2001).*

Ren, et. al., Journal of Medicinal Chemistry (2006), 49(9), 2829-2837. (Year: 2006).*

[No Author Listed], Daurgandhyahara Udvartana. Rasaratnakara-Rasendra. Datto Vallal Borakara, 2nd Ed. Shri Gajanan Book Depot (Pune). 1986, 2 pages.

[No Author Listed], Nuts and Seeds in Health and Disease Prevention, 1st Edition. Preedy, Ed. Academic Press. Apr. 14, 2011:506.

[No Author Listed], The use of tannic acid in the local treatment of burn wounds: intriguing old and new perspectives. Wounds. 2001;13(4):1-19,.

Abdelwahed et al., Study of antimutagenic and antioxidant activities of gallic acid and 1,2,3,4,6-pentagalloylglucose from Pistacia lentiscus. Confirmation by microarray expression profiling. Chem Biol Interact. Jan. 5, 2007;165(1):1-13. Epub Oct. 21, 2006.

Chen et al., Inhibition of SARS-CoV 3C-like Protease Activity by Theaflavin-3,3'-digallate (TF3). Evid Based Complement Alternat Med. Jun. 2005;2(2):209-215, Epub Apr. 7, 2005.

Chiou et al., The inhibitory effects of PGG and EGCG against the SARS-CoV-2 3C-like protease. Biochem Biophys Res Commun, Jan. 6, 2021:S0006-291X(20)32299-3.

Crabtree et al., 1274. Gallotannins. Part XI. Synthesis of m-digallic and m-trigallic acids and their derivatives. J Chem Soc. Dec. 31, 1965;0:6888-93.

Fan et al., Inhibitory effects of tannic acid on fatty acid synthase and 3T3-L1 preadipocyte. Biochim Biophys Acta. Jul. 2013; 1831(7):1260-6.

Fiuza et al., Phenolic acid derivatives with potential anticancer properties—a structure-activity relationship study. Part 1: methyl, propyl and octyl esters of caffeic and gallic acids. Bioorg Med Chem. Jul. 1, 2004;12(13):3581-9.

Hatano et al., Gallotannins having a 1,5-anhydro-D-glucitol core and some ellagitannins from Acer species. Chem Pharm Bull. Dec. 31, 1990;38(7):1902-5.

Hu et al., Mitogenic activity of (-)epigallocatechin gallate on B-cells and investigation of its structure-function relationship, Int J Immunopharmacol. Nov. 1992;14(8):1399-407.

Jeyaseelan et al., Antibacterial activity of sequentially extracted organic solvent extracts of fruits, flowers and leaves of Lawsonia inermis L. from Jaffna. Asian Pac J Trap Biomed. Oct. 2012;2(10):798-802.

Karas et al., Galloylation of polyphenols alters their biological activity. Food Chem Toxicol. Jul. 2017;105:223-240. doi: 10.1016/j.fct.2017.04.021. Epub Apr. 18, 2017.

Lavoie et al., Complete (1)H and (13)C NMR assignments of a series of pergalloylated tannins. Magn Reson Chem. Feb. 2016;54(2):168-74, Epub Sep. 9, 2015.

Liou et al., Optimal operating conditions on batch extraction. J Nat Chiao Tung Univ. Dec. 1976;2:83-94.

Liu et al., In Vivo and In Vitro Anti-Arthritic Effects of Cardenolide-Rich and Caffeoylquinic Acid-Rich Fractions of Periploca forrestii. Molecules. Aug. 9, 2018;23(8):1988(1-16).

Liu et al., Tannic acid stimulates glucose transport and inhibits adipocyte differentiation in 3T3-L1 cells. JNutr. Feb. 2005;135(2):165-71.

Nakazono et al., Chemiluminescence enhancement of 1,2-di[3,4,5-tri(3,4,5-trihydroxybenzoyloxy)benzoyloxy] benzene in the presence of quaternary ammonium ions. Luminescence. Sep.-Oct. 2010;25(5):360-3.

Niemetz et al., Ellagitannin biosynthesis: oxidation of pentagalloylglucose to tellimagrandin II by an enzyme from Tellima grandiflora leaves. Chem Commun, Dec. 11, 2000:35-36.

Nishizawa et al., Structure of Gallotannins in Paeoniae Radix. Chem Pharm Bull. Dec. 31, 1980;28(9):2850-2.

Nishizawa et al., Tannins and related compounds. Part 5. Isolation and characterization of polygalloylglucoses from Chinese gallotannin, J Chem Soc, Perkin Trans 1. 1982;(0):2963-8.

Ono et al., Anti-amyloidogenic activity of tannic acid and its activity to destabilize Alzheimer's beta-amyloid fibrils in vitro, Biochim Biophys Acta. Nov. 5, 2004; 1690(3):193-202.

Park et al., Dieckol, a SARS-CoV 3CL(pro) inhibitor, isolated from the edible brown algae Ecklonia cava. Bioorg Med Chem, Jul. 1, 2013;21(13):3730-7. Epub Apr. 22, 2013.

Qiao et al., Research progress in Galla chinensis and gallic tannins. Sci Tech Food Industry. Jul. 31, 2011:458-462.

Ren et al., Synthesis and structure-activity relationship study of antidiabetic penta-O-galloyl-D-glucopyranose and its analogues. J Med Chem, May 4, 2006;49(9):2829-37.

Sancheti et al., 1,2,3,4,6-penta-O-galloyl-β-d-glucose: A cholinesterase inhibitor from Termmalia chebula. S Afr J Bot. Apr. 2010;76(2):285-8.

Sekowski et al., Interaction of αa-synuclein with Rhus typhina tannin—Implication for Parkinson's disease. Colloids Surf B Biointerfaces. Jul. 1, 2017;155:159-165, Epub Apr. 10, 2017.

Sieniawska et al., Activities of Tannins—From In Vitro Studies to Clinical Trials. Nat Prod Commun. Nov. 2015;10(11):1877-84.

Sylla et al., Gallotannins and Tannic Acid: First Chemical Syntheses and In Vitro Inhibitory Activity on Alzheimer's Amyloid β-Peptide Aggregation. Angew Chem Int Ed Engl. Jul. 6, 2015;54(28):8217-21. Epub May 26, 2015.

Theisen et al., Tannins from Hamamelis virginiana bark extract: characterization and improvement of the antiviral efficacy against influenza A virus and human papillomavirus. PLoS One. Jan. 31, 2014;9(1):e88062(1-14).

Tian et al., Antioxidant and antimicrobial activities of consecutive extracts from Galla chinensis:The polarity affects the bioactivities. Food Chem, Mar. 1, 2009;113(1):173-9.

Toda et al., Inhibitory effects of ellagi- and gallotannins on rat intestinal alpha-glucosidase complexes. Biosci Biotechnol Biochem, Mar. 2001;65(3):542-7.

(56) References Cited

OTHER PUBLICATIONS

Venter et al., Comprehensive analysis of tara tannins by reversed-phase and hydrophilic interaction chromatography coupled to ion mobility and high-resolution mass spectrometry. Anal Bioanal Chem. Sep. 2019;411(24):6329-6341. Epub Jun. 19, 2019.
Viswanatha et al., Anticonvulsant activity of 1,2,3,4,6-penta-O-galloyl-β-D-glucopyranose isolated from leaves of Mangifera indica. Naunyn Schmiedebergs Arch Pharmacol. Jul. 2013;386(7):599-604. Epub Apr. 9, 2013.
Wu et al., Preparation of gallnut tannins liposome and its quality evaluation. Sci Tech Food Industry. Mar. 31, 2015;36(3):74-77, 81.
U.S. Appl. No. 17/058,920, filed Nov. 25, 2020, Tsai et al.
U.S. Appl. No. 17/590,771, filed Feb. 1, 2022, Tsai et al.
Goff, Future perspectives on the treatment of cognitive deficits and negative symptoms in schizophrenia. World Psychiatry. Jun. 2013;12(2):99-107.
Ma et al., The hydrolyzable gallotannin, penta-O-galloyl-β-D-glucopyranoside, inhibits the formation of advanced glycation endproducts by protecting protein structure. Mol Biosyst. May 2015;11(5). Accepted Manuscript. 40 pages.

* cited by examiner

COMPOUNDS AND PHARMACEUTICAL USES THEREOF

CROSS REFERENCE TO RELATED APPLICATIONS

This application is a continuation of International Application No. PCT/CN2021/089301, filed Apr. 23, 2021, which claims the benefit of the filing dates of U.S. Provisional Application No. 63/014,448, filed on Apr. 23, 2020, the entire contents of which are incorporated by reference herein.

BACKGROUND OF THE INVENTION

Coronaviruses, members of the family Coronaviridae and subfamily Coronavirinae, are enveloped viruses containing single-strand, positive-sense RNA genome ranging from 26 to 32 kilobases in length. Coronaviruses have been identified in several vertebrate hosts including bird, bat, pig, rodent, camel and human. Human can acquire coronavirus infection from other host of mammals. Human coronavirus infection is one of the major causes of detrimental upper respiratory tract illness in human. Besides encoding structural proteins, majority part of the coronavirus genome is transcribed and translated into a polyprotein, which encodes proteins essential for viral replication and gene expression. The functional polypeptides are released from the polyproteins by extensive proteolytic processing which is one of the crucial steps in the life cycle of coronaviruses. The virus will not be packaged without the proteolysis. This is primarily achieved by the 33.1-kDa main protease (MPro), which is also known as 3C-like protease (3CLPro).

The central nervous system (CNS) includes the brain and spinal cord. The CNS is vulnerable to various disorders, which may be caused by various factors, including genetic, trauma, infections, degeneration, structural defects and/or damage, tumors, blood flow disruption, and autoimmune disorders. Symptoms of a CNS disorder depend on the area of the nervous system that is involved and the cause of the disorder.

The development of effective therapies for CNS disorders has lagged behind other therapeutic areas due to the complexity of such disorders and the lack of efficient technology for delivering therapeutic agents through the blood-brain barrier. As such, it is of great interest to develop new treatment approaches for CNS disorders.

SUMMARY OF THE INVENTION

The present disclosure is based, at least in part, on the development of various compounds having the structures shown herein that exhibit inhibitory activities against D-amino acid oxidase and/or 3C-like protease (3CLPro). Certain compounds disclosed herein also exhibited therapeutic effects in an animal model for central nervous system (CNS) diseases (the MK801 mouse model). Accordingly, the compounds disclosed here are expected to be effective in treating CNS disorders (e.g., those associated with DAAO) and/or for alleviating viral infection caused by coronavirus such as SARS-CoV-2.

Accordingly, one aspect of the present disclosure provides a compound of formula (I):

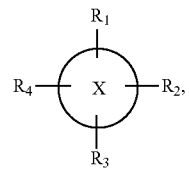

or a pharmaceutically acceptable salt thereof, wherein:
Ring X is a 3 to 7 membered monocyclic ring, which can be aryl, heteroaryl, cycloalkyl, or cycloheteroalkyl;
at least one of $R_1$, $R_2$, $R_3$, and $R_4$ is $OR_5$ or $CH_2OR_5$ and the other $R_1$, $R_2$, $R_3$, and $R_4$ each independently are halogen, OH, $OR_5$, $CH_2OR_5$, $CO_2H$, $OC=OR_6$, $(C=O)R_6$, $R_6$, C1-10 alkyl, C2-10 alkenyl, C2-10 alkynyl, H, or absent
$R_5$ is of the formula

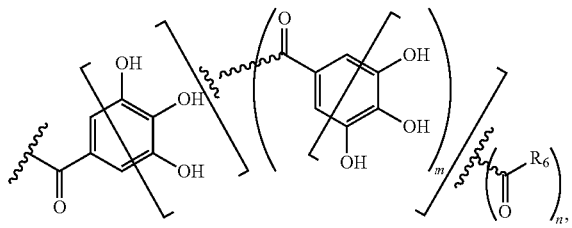

in which
m independently is 1, 2, 3, 4, 5, 6, or 7;
n independently is 0, 1, 2, or 3; and
$R_6$ is of the formula:

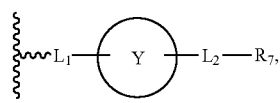

in which Ring Y is a 3 to 7 membered monocyclic ring, which can be aryl, heteroaryl, cycloalkyl, or cycloheteroalkyl;
Each of $L_1$ and $L_2$, independently, is a moiety selected from the group consisting of N, O, S, $CH_2$, $C=O$, $C_{2-10}$ alkyl, $C_{2-10}$ alkenyl, $C_{2-10}$ alkynyl, $—(W—(CH_2)_s)—$, and absent, wherein s is 0, 1, 2, 3, 4, or 5, and W is O, S, or N; and
$R_7$ is selected from the group consisting of aryl, heteroaryl, aralkyl, $C_{2-10}$ alkyl, $C_{2-10}$ alkenyl, $C_{2-10}$ alkynyl, and H.

In some embodiments, the X ring is

$R_1$, $R_2$, $R_3$, and $R_4$ are each $OR_5$, each of m is 0, 1, 2, 3, 4, 5, 6, or 7, and n is 0.

In some embodiments, the X ring is

$R_1$, $R_2$, $R_3$, and $R_4$ are each $OR_5$ or $CH_2OR_5$, m is 0, 1, 2, 3, 4, 5, 6, or 7, and n is 0.

In some embodiments, the X ring is

$R_1$, $R_2$, and $R_3$ are each $OR_5$ or $OC=OR_6$, m is 0, 1, 2, 3, 4, 5, 6, or 7, and n is 0 or 1.

In some embodiments, at least one of $R_1$, $R_2$, or $R_3$ is $OC=OR_6$.

In some embodiments, the X ring is an aryl, heteroaryl or cycloalkyl ring; $R_1$, $R_2$, $R_3$, and $R_4$ are each OH, $CO_2H$, $OR_5$ or $(C=O)R_6$, m is 0, 1, 2, 3, 4, 5, 6, or 7, and n is 0 or 1.

In some embodiments, the X ring is

$R_1$, $R_2$, $R_3$, and $R_4$, are each OH, $CO_2H$, $OR_5$ or $(C=O)R_6$, m is 0, 1, 2, 3, 4, 5, 6, or 7 and n is 0 or 1.

In some embodiments, the X ring is

$R_1$, $R_2$, $R_3$, and $R_4$ are each OH, $CO_2H$, or $OR_5$, m is 0, 1, 2, 3, 4, 5, 6, or 7, and n is 1.

In some embodiments, the X ring is

$R_1$, $R_2$, $R_3$, and $R_4$ are each OH, $OR_5$, or $(C=O)R_6$, at least one of $R_1$, $R_2$, or $R_3$ and $R_4$ being $(C=O)R_6$, m is 0, 1, 2, 3, 4, 5, 6, or 7, and n is 0.

In some embodiments, the X ring is

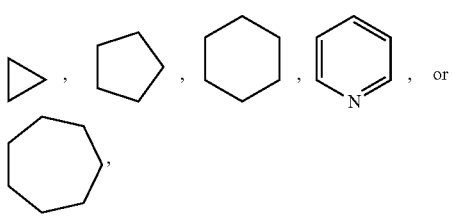

$R_1$ is $OR_5$, m is 0, 1, 2, 3, 4, 5, 6, or 7, and n is 0 or 1.

In some embodiments, the X ring is

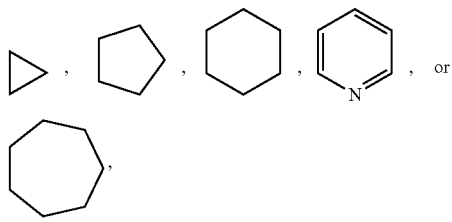

$R_1$ is $OR_5$, m is 0, 1, 2, 3, 4, 5, 6, or 7, and n is 0.

In some embodiments, the X ring is

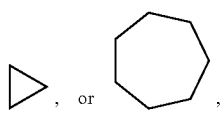

$R_1$ is $OR_5$, m is 0, 1, 2, 3, 4, 5, 6, or 7, and n is 0.

In some embodiments, the ring Y is

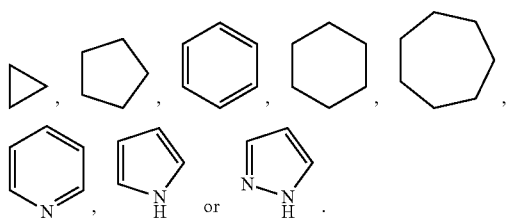

In some embodiments, the $R_7$ is

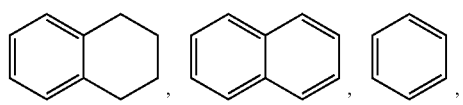

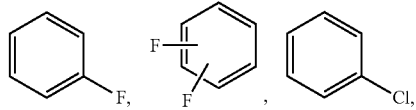

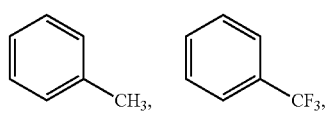

or absent.

In some embodiments, the compound is of the Formula (II):

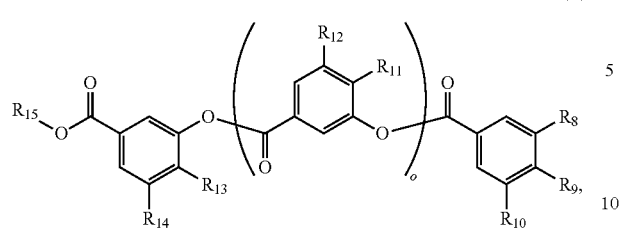
in which
- $R_9$-$R_{14}$ are each independently H, OH, $NH_2$, halogen, $C_{1-3}$ alkyl, or $C_{1-3}$ alkoxy;
- $R_8$ is H, OH, $NH_2$, halo, $C_{1-3}$ alkyl, $C_{1-3}$ alkoxy, aryl, heteroaryl, or $O(CO)R_6$; and
- $R_{15}$ is H, alkyl, cycloalkyl, aryl, alkylaryl, heteroaryl, or alkylheteroaryl; o is 1, 2, 3, 4, or 5.
In some embodiments, each of $R_9$-$R_{14}$ is OH.
In some embodiments, $R_6$ is
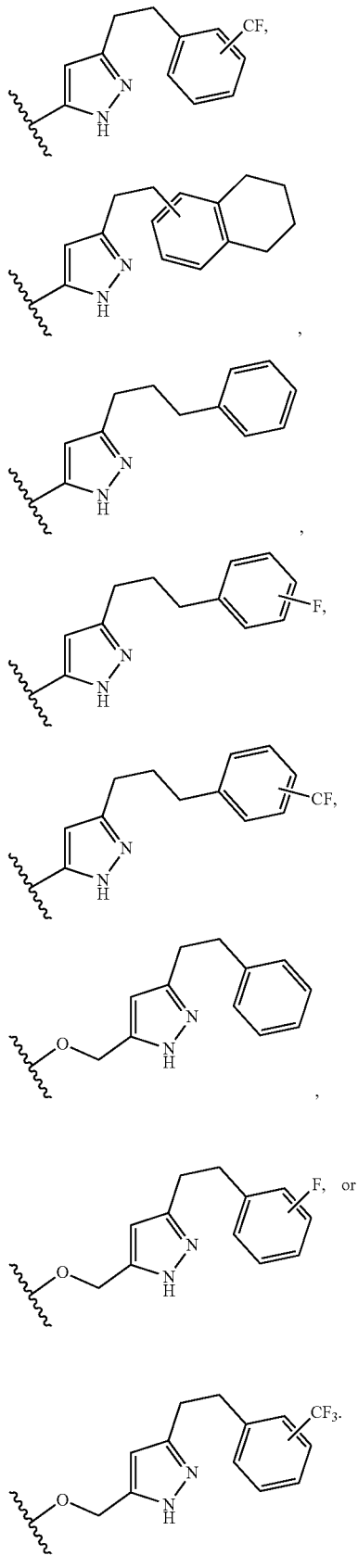

In some embodiments, $R_{15}$ is:

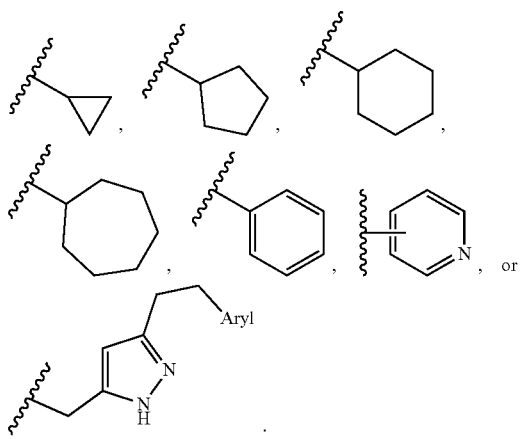

In some embodiments, the compound is selected from the compounds listed in Table 1.

In other aspects, the present disclosure provides a composition comprising any of the compounds disclosed herein and a carrier.

In some embodiments, the composition is a pharmaceutical composition, a nutraceutical composition, a health food, or a medical food.

The present disclosure also features a method of treating coronavirus infection, comprising administering to a subject in need thereof an effective amount of the compounds or the compositions disclosed herein.

In some embodiments, the coronavirus virus is selected from the group consisting of SARS-CoV-2, severe acute respiratory syndrome coronavirus (SARS-CoV), middle east respiratory syndrome coronavirus (MERS-CoV), 229E alpha coronavirus, NL63 alpha coronavirus, OC43 beta coronavirus, and HKU1 beta coronavirus.

In some embodiments, the compound or composition is administered by oral, by injection, by external use, or by inhalation.

In some embodiments, the composition is placed in a medical device selected from the group consisting of an inhaler, a nebulizer, a nasal spray, and a vaporization aerosol device for administration to the subject.

In some embodiments, the subject is a human subject.

In some embodiments, the subject is administered the composition continuously or at a frequency of every five minutes to one time every three months.

In some embodiments, any of the methods disclosed herein further comprises administering the human subject one or more additional anti-viral agents. In some embodiments, the one or more additional anti-viral agents comprise a viral entry inhibitor, a viral uncoating inhibitor, a viral reverse transcriptase inhibitor, a viral protein synthesis inhibitor, a viral protease inhibitor, a viral polymerase inhibitor, a viral integrase inhibitor, an interferon, or the combination thereof.

In some examples, the viral entry inhibitor is selected from the group consisting of maraviroc, enfuvirtide, ibalizumab, fostemsavir, plerixafor, epigallocatechin gallate, vicriviroc, aplaviroc, maraviroc, tromantadine, nitazoxanide, umifenovir, and podofilox.

In some examples, the viral uncoating inhibitor is selected from the group consisting of amantadine, rimantadine, and pleconaril.

In some examples, the viral reverse transcriptase inhibitor is selected from the group consisting of zidovudine, didanosine, zalcitabine, stavudine, lamivudine, abacavir, emtricitabine, entecavir, truvada, nevirapine, raltegravir, and tenofovir disoproxil.

In some examples, the viral protease inhibitor is selected from the group consisting of fosamprenavir, ritonavir, atazanavir, nelfinavir, indinavir, saquinavir, saquinavir, famciclovir, fomivirsen, lopinavir, ribavirin, darunavir, oseltamivir, and tipranavir.

In some examples, the viral polymerase inhibitor is selected from the group consisting of amatoxins, rifamycin, cytarabine, fidaxomicin, tagetitoxin, foscarnet sodium, idoxuridine, penciclovir, sofosbuvir, trifluridine, valacyclovir, valganciclovir, vidarabine, and remdesivir.

In some examples, the viral integrase inhibitor is selected from the group consisting of raltegarvir, elvitegravir, dolutegravir, bictegravir, and cabotegravir.

In some examples, the interferon is selected from the group consisting of type I interferon, type II interferon, type III interferon, and peginterferon alfa-2a.

In yet other aspects, the present disclosure provides a method of inhibiting D-amino acid oxidase (DAAO) in a subject, comprising administering to a subject in need thereof an effective amount of any of the compounds or the compositions disclosed herein. In some embodiments, the subject is a human having, suspected of having, or at risk for a central nervous system (CNS) disorder, a metabolic disorder, or pain.

Exemplary CNS disorders include, but are not limited to, schizophrenia, psychotic disorders, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorders, attention deficit disorder, obsessive compulsive disorder, tic disorders, childhood learning disorders, premenstrual syndrome, depression, major depressive disorder, anhedonia, suicidal ideation and/or behaviors, bipolar disorder, anxiety disorders, panic disorder, post-traumatic stress disorder, chronic mild and unpredictable stress, eating disorders, addiction disorders, personality disorders, Parkinson's disorder, Huntington's disorder, multiple sclerosis, amyotrophic lateral sclerosis, ataxia, Friedreich's ataxia, Tourette's syndrome, nocturnal enuresis, non-epileptic seizures, blepharospasm, Duchenne muscular dystrophy, and stroke.

Exemplary metabolic disorders include, but are not limited to, obesity, hyperlipidemia, hypercholesterolemia, hyperglycemia, hyperinsulinemia, insulin resistance, and diabetes.

Exemplary pain disease include, but are not limited to, psychogenic pain, acute pain, chronic pain, chronic pain syndromes, neuropathic pain, nociceptive pain, and hyperalgesia. For example, psychogenic pain may be headache, muscle pain, back pain and stomach pain, the neuropathic pain is selected from the group consisting of sciatica, carpal tunnel syndrome, diabetic neuropathy, postherpetic neuralgia, and central pain syndrome, and the nociceptive pain is selected from the group consisting of radicular pain, somatic pain, or visceral pain.

In some embodiments, the method disclosed herein may further comprise administering to the subject one or more additional pharmaceutical agents (e.g., those disclosed herein) for treating and/or reducing the risk for a CNS disorder.

Further, the present disclosure provides methods for preparing the compounds disclosed herein.

In some embodiments, the preparation method disclosed herein may comprise:

(a) providing compounds of formula (Ia) and (Ib)

$$\text{(Ia)}$$

HO—C(=O)—$R_6$, $$\text{(Ib)}$$

[structure of formula (Ib) with $R_{16}$, Ph groups, and repeating unit m]

wherein $R_{16}$ is the group selected from alkyl group, alkylsilyl group, or arylsilyl group;

(b) reacting the compound of formula (Ia) with formula (Ib) to produce intermediate I;
(c) de-protecting the $R_{16}$ group to produce intermediate II; and
(d) de-protecting the cyclic acetal groups and purifying the reaction mixture to obtain a compound as disclosed herein.

In other embodiments, the preparation method disclosed herein may comprise:

(a) providing compounds of formula (Ic) and (Id)

$$\text{(Ic)}$$

X—(L$_3$—H)$_p$, $$\text{(Id)}$$

[structure of formula (Id) with HO, $R_{17}$, Ph groups, and repeating unit m]

wherein p=1, 2, 3, or 4; each of $L_3$, independently, is a moiety selected from the group consisting of NH, O, S, —((CH$_2$)$_s$—W)—, or absent; $R_{17}$ is the group selected from benzyl group, allyl group, ethoxylmethyl group, methoxylmethyl group, ethoxylethyl group, alkyl silyl group, or aryl silyl group;

(b) reacting the compound of formula (Ic) with formula (Id), to allow conjugation of formula (Id) to one or more of $L_3$ of the formula (Ic), thereby producing intermediate III;
(c) de-protecting the $R_{17}$ group to produce intermediate IV; and
(d) de-protecting the cyclic acetal groups and purifying the reaction mixture to obtain a compound disclosed herein.

Any of the preparation methods disclosed herein may further comprise the following step after step (c)

(e) reacting the intermediate II with formula (Ic) and allowing conjugation of the intermediate II to one or more $L_3$ of the formula (Ic) to produce intermediate V.

In some embodiments, the method further comprises the following step after step (c):

(e) reacting the intermediate IV with formula (Ia) to produce intermediate VI.

Further, the present disclosure provides a method of preparing the compound (Ia), comprising:

(a) providing compound of formula (Ie);

$$\text{(Ie)}$$

[structure of formula (Ie) with L$_2$, R$_7$]

(b) reacting the compound of formula (Ie) with strong organic base under −78° C. to 0° C. to produce intermediate VII;
(c) reacting the first intermediate VII with alkyl group protected oxalic acid to produce intermediate VIII;
(d) reacting the second intermediate VIII with a cycloling reagent to produce intermediate IX; and,
(e) de-protecting the alkyl group of the protected oxalic acid to obtain the formula (Ia).

In some embodiments, the strong organic base in step (b) is alkali alkoxide, alkyl lithium, lithium alkylamide, lithium alkylsilylamide.

In some embodiments, the cycloling reagent in step (d) is hydrazine, hydrazine hydrate, hydroxyl amine, or any acceptable salts of which thereof.

In some embodiments, $L_1$, $L_2$, and $L_3$, independently, is a moiety selected from the group consisting of N, O, S, CH$_2$, C$_2$H$_4$, C$_3$H$_6$, OCH$_2$, OC$_2$H$_4$, OC$_3$H$_6$, NCH$_3$, NC$_2$H$_5$, and C=O.

DETAILED DESCRIPTION

Definitions

Figure 1:
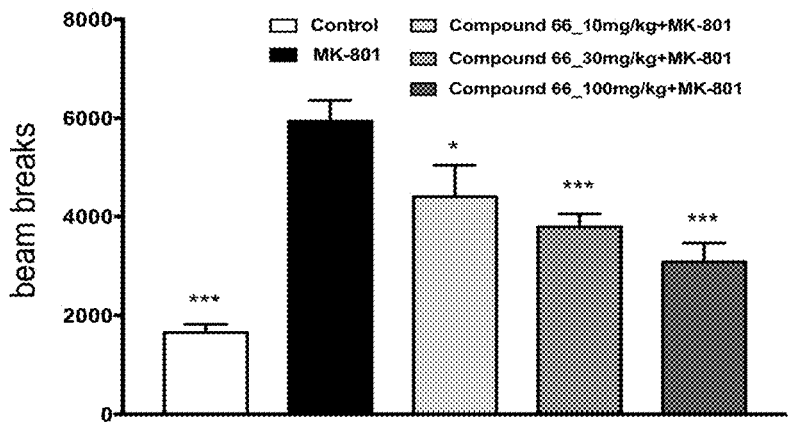
FIG. 1 is a diagram showing the effect of compound 66 on locomotion in MK-801 treated mice.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry, University Science Books*, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, Ind. 1972). The disclosure additionally encompasses compounds described herein as individual isomers substantially free of other isomers, and alternatively, as mixtures of various isomers.

When a range of values is listed, it is intended to encompass each value and sub-range within the range. For example, "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —CH$_2$-cyclopropyl, vinyl, allyl, n-butyl, secbutyl, isobutyl, tert-butyl, cyclobutyl, —CH$_2$-cyclobutyl, n-pentyl, sec-pentyl, isopentyl, tertpentyl, cyclopentyl, —CH$_2$-cyclopentyl, n-hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group or a saturated carbocyclyl ring having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("C1 alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, iso-butyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F, or —OH). In certain embodiments, the alkyl group is an unsubstituted $C_{1-10}$ alkyl (such as unsubstituted $C_{1-6}$ alkyl, e.g., —CH$_3$). In certain embodiments, the alkyl group is a substituted $C_{1-10}$ alkyl (such as substituted $C_{1-6}$ alkyl or substituted $C_{1-3}$ alkyl, e.g., —CF$_3$ or —CH$_2$OH).

"Alkenyl" refers to a radical of a straight-chain or branched hydrocarbon group or a saturated carbocyclyl ring having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl. In an alkenyl group, a C=C double bond for which the stereochemistry is not specified (e.g., —CH=CHCH$_3$ or) may be an (E)- or (Z)-double bond.

"Alkynyl" refers to a radical of a straight-chain or branched hydrocarbon group or a saturated carbocyclyl ring having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl (C), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of C5-6 cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-10 membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl. In some embodiments, the aralkyl is a subset of heteroaryl and aryl, optionally linked by alkyl groups.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of 10 attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., 5 unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO2R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$, —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$_{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$_{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N($R^{cc}$)$_2$, —C(=O)S$R^{cc}$, —C(=S)S$R^{cc}$, —P(=O)($R^{aa}$)$_2$, —P(=O)(O$R^{cc}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —O$R^{ee}$, —ON($R^{ff}$)$_2$, —N($R^{ff}$)$_2$, —N($R^{ff}$)$_3^+$$X^-$, —N(O$R^{ee}$)$R^{ff}$, —SH, —S$R^{ee}$, —SS$R^{ee}$, —C(=O)$R^{ee}$, —CO$_2$H, —CO$_2$$R^{ee}$, —OC(=O)$R^{ee}$, —OCO$_2$$R^{ee}$, —C(=O)N($R^{ff}$)$_2$, —OC(=O)N($R^{ff}$)$_2$, —N$R^{ff}$C(=O)$R^{ee}$, —N$R^{ff}$CO$_2$$R^{ee}$, —N$R^{ff}$C(=O)N($R^{ff}$)$_2$, —C(=N$R^{ff}$)O$R^{ee}$, —OC(=N$R^{ff}$)$R^{ee}$, —OC(=N$R^{ff}$)O$R^{ee}$, —C(=N$R^{ff}$)N($R^{ff}$)$_2$, —OC(=N$R^{ff}$)N($R^{ff}$)$_2$, —N$R^{ff}$C(=N$R^{ff}$)N($R^{ff}$)$_2$, —N$R^{ff}$SO$_2$$R^{ee}$, —SO$_2$N($R^{ff}$)$_2$, —SO$_2$$R^{ee}$, —SO$_2$O$R^{ee}$, —OSO$_2$$R^{ee}$, —S(=O)$R^{ee}$, —Si($R^{ee}$)$_3$, —OSi($R^{ee}$)$_3$, —C(=S)N($R^{ff}$)$_2$, —C(=O)S$R^{ee}$, —C(=S)S$R^{ee}$, —SC(=S)S$R^{ee}$, —P(=O)(O$R^{ee}$)$_2$, —P(=O)($R^{ee}$)$_2$, —OP(=O)($R^{ee}$)$_2$, —OP(=O)(O$R^{ee}$)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S; wherein $X^-$ is a counterion;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups; each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3^+$$X^-$, —NH($C_{1-6}$ alkyl)$_2^+$$X^-$, —NH$_2$($C_{1-6}$ alkyl)$^+$$X^-$, —NH$_3^+$$X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —CO$_2$H, —CO$_2$($C_{1-6}$ alkyl), —OC(=O)($C_{1-6}$ alkyl), —OCO$_2$($C_{1-6}$ alkyl), —C(=O)NH$_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)NH$_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl)$_2$, —C(=NH)NH($C_{1-6}$ alkyl), —C(=NH)NH$_2$, —OC(=NH)N($C_{1-6}$ alkyl)$_2$, —OC(NH)NH($C_{1-6}$ alkyl), —OC(NH)NH$_2$, —NHC(NH)N($C_{1-6}$ alkyl)$_2$, —NHC(=NH)NH$_2$, —NHSO$_2$($C_{1-6}$ alkyl), —SO$_2$N($C_{1-6}$ alkyl)$_2$, —SO$_2$NH($C_{1-6}$ alkyl), —SO$_2$NH$_2$, —SO$_2$$C_{1-6}$ alkyl, —SO$_2$O$C_{1-6}$ alkyl, —OSO$_2$$C_{1-6}$ alkyl, —SO$C_{1-6}$ alkyl, —Si($C_{1-6}$ alkyl)$_3$, —OSi($C_{1-6}$ alkyl)$_3$-C(=S)N($C_{1-6}$ alkyl)$_2$, C(=S)NH($C_{1-6}$ alkyl), C(=S)NH$_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl)$_2$, —P(=O)($C_{1-6}$ alkyl)$_2$, —OP(=O)($C_{1-6}$ alkyl)$_2$, —OP(=O)(O$C_{1-6}$ alkyl)$_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4^-$, PF$_4^-$, PF$_6^-$, AsF$_6^-$, SbF$_6^-$, B[3,5-(CF$_3$)$_2$C$_6$H$_3$]$_4$]$^-$, BPh$_4^-$, Al(OC(CF$_3$)$_3$)$_4^-$, and a carborane anion (e.g., CB$_{11}$H$_{12}^-$ or (HCB$_{11}$Me$_5$Br$_6$)$^-$). Exemplary counterions which may be multivalent include CO$_3^{2-}$, HPO$_4^{2-}$, PO$_4^{3-}$, —B$_4$O$_7^{2-}$, SO$_4^{2-}$, S$_2$O$_3^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)$R^{aa}$, —CHO, —CO$_2$$R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —C(=O)N$R^{bb}$SO$_2$$R^{aa}$, —C(=S)N($R^{bb}$)$_2$, —C(=O)S$R^{aa}$, or —C(=S)S$R^{aa}$, wherein $R^{aa}$ and $R^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2$$R^{aa}$, —SO$_2$$R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2$$R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)(O$R^{cc}$)$_2$, —P(=O)($R^{aa}$)$_2$, —P(=O)(N($R_{cc}$)$_2$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$, and $R^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$_{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$_{cc}$)$_2$, —C(=O)SR$^{cc}$, —C(=S)SR$^{cc}$, C$_{1-10}$ alkyl (e.g., aralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethylcarbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), #3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p- nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys). Exemplary oxygen atom substituents include, but are not limited to, —$R^{aa}$, —C(=O)$SR^{aa}$, —C(=O)$R^{aa}$, —$CO_2R^{aa}$, —C(=O)N($R^{bb}$)$_2$, —C(=N$R^{bb}$)$R^{aa}$, —C(=N$R^{bb}$)O$R^{aa}$, —C(=N$R^{bb}$)N($R^{bb}$)$_2$, —S(=O)$R^{aa}$, —$SO_2R^{aa}$, —Si($R^{aa}$)$_3$, —P($R^{cc}$)$_2$, —P($R^{cc}$)$_3^+X^-$, —P(O$R^{cc}$)$_2$, —P(O$R^{cc}$)$_3^+X^-$, —P(=O)($R^{aa}$)$_2$, —P(=O)(O$R^{cc}$)$_2$, and —P(=O)(N($R^{bb}$)$_2$)$_2$, wherein $X^-$, $R^{aa}$, $R^{bb}$, and $R^{cc}$ are as defined herein.

In certain embodiments, the oxygen atom substituent present on an oxygen atom is an oxygen protecting group (also referred to as a hydroxyl protecting group). Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference. Exemplary oxygen protecting groups include, but are not limited to, methyl, t-butyloxycarbonyl (BOC or Boc), methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio.

Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4^-$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, dimethyl sulfoxide (DMSO), tetrahydrofuran (THF), diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers."

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see, Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkyl esters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

The terms "inhibition", "inhibiting", "inhibit," or "inhibitor" refer to the ability of a compound to reduce, slow, halt or prevent activity of a particular biological process in a cell relative to vehicle.

When a compound, pharmaceutical composition, method, use, or kit is referred to as "selectively," "specifically," or "competitively" binding a first protein, the compound binds the first protein with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein or that is different from the first protein. When a compound is referred to as "selectively," "specifically," or "competitively" modulating (e.g., increasing or inhibiting) the activity of a protein, the compound modulates the activity of the protein to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the first protein.

The term "aberrant activity" refers to activity deviating from normal activity. The term "increased activity" refers to activity higher than normal activity.

The terms "composition" and "formulation" are used interchangeably.

A "subject", "individual," or "patient" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. A "subject" may be human, but also include other mammals, particularly those mammals useful as laboratory models for human disease, e.g. mouse, rat, rabbit, dog, etc. A "patient" refers to a human subject in need of treatment of a disease. In certain embodiments, a subject is a human of having, or at risk for a central nervous system (CNS) disorder, obesity, diabetes, or hyperlipidemia.

The terms "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The term "continuously" refers to an administration uninterrupted for a period according to medically or therapeutically need, for example, but not limited to, infusion with or without pump, respiratory therapy, inhalation therapy.

Alleviating a target disease/disorder includes delaying the development or progression of the disease or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

To achieve any of the intended therapeutic effects described herein, an effective amount of a composition herein may be administered to a subject in need of the treatment via a suitable route.

The terms "condition", "disease", and "disorder" are used interchangeably.

An "effective amount" of a compound described herein refers to an amount sufficient to elicit the desired biological response, i.e., treating the condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "neuropsychiatric disorder," including either neurological diseases or psychiatric disorders or CNS (central nervous system) disorders or refers to a disorder that involves either behavioral or psychiatric symptoms or syndromes caused by neurodegenerative or organic brain disorders. The main characteristics of neuropsychiatric symptoms include occurrence of the various psychiatric symptoms, cognitive impairment, neurological symptoms or the possibility of early cerebral development symptoms. For example, the neuropsychiatric disorder can include, but is not limited to, schizophrenia, psychotic disorders, major depressive disorder, suicidal ideation and/or behavior, Alzheimer's disease, dementia, frontotemporal dementia, mild cognitive impairment, benign forgetfulness, closed head injury, an autistic spectrum disorder, Asperger's disorder, Fragile X syndrome, attention deficit hyperactivity disorders, combined attention-deficit hyperactivity disorder and tic disorder, obsessive compulsive disorder, tic disorders, Tourette's syndrome, childhood learning disorders, premenstrual syndrome, depression, bipolar disorders, anxiety disorders, panic disorders, post-traumatic stress disorder, chronic pain, eating disorders, addiction disorders, personality disorders, Parkinson's disorder, Huntington's disorder, amyotrophic lateral sclerosis, nocturnal enuresis, stroke, Duchenne muscular dystrophy, blepharospasm and non-epileptic seizures.

The term "neurological disease" refers to any disease of the nervous system, including diseases that involve the central nervous system (brain, brainstem, spinal cord and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, frontotemporal dementia, Parkinson's disease, amyotrophic lateral sclerosis, tauopathies (including frontotemporal 30 dementia), multiple system atrophy, and Huntington's disease. Examples of neurological diseases include, but are not limited to, headache, stupor and coma, dementia, seizure, sleep disorders, trauma, infections, neoplasms, neuro-ophthalmopathy, movement disorders, demyelinating diseases, spinal cord disorders, and disorders of peripheral nerves, muscle and neuromuscular junctions. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; chronic pain; Batten disease; Behcet's disease; Bell's palsy; benign essential blepharospasm; benign focal amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal cord tumor; BrownSequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; DejerineKlumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; LambertEaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; ministrokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal 5 cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette 10 syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger 15 syndrome.

The term "pain" encompasses psychogenic pain, acute pain, chronic pain, chronic pain syndromes, neuropathic pain, nociceptive pain, hyperalgesia and allodynia.

Psychogenic pain is physical pain that is caused, increased, or prolonged by mental, emotional, or behavioral factors. Headache, back pain, or stomach pain are some of the most common types of psychogenic pain. The psychogenic pain is selected from the group consisting of headache, muscle pain, back pain and stomach pain.

Neuropathic pain is pain caused by damage or disease affecting the somatosensory nervous system. Neuropathic pain may result from disorders of the peripheral nervous system or the central nervous system (brain and spinal cord). Thus, neuropathic pain may be divided into peripheral neuropathic pain, central neuropathic pain, or mixed (peripheral and central) neuropathic pain. The neuropathic pain is selected from the group consisting of sciatica, carpal tunnel syndrome, diabetic neuropathy, postherpetic neuralgia, and central pain syndrome.

Nociceptive pain is the most common type of pain people experience. It develops when the nociceptive nerve fibers are triggered by inflammation, chemicals, or physical events. The nociceptive pain is selected from the group consisting of radicular pain, somatic pain, and visceral pain.

The term "psychiatric disorder" refers to mental disorders and includes diseases and disorders listed in the Diagnostic and Statistical Manual of Mental Disorders—Fourth Edition and Fifth Edition (DSM-IV, DSM-V), published by the American Psychiatric Association, Washington D. C. (1994, 2015). Psychiatric disorders include, but are not limited to, anxiety disorders (e.g., acute stress disorder, agoraphobia, generalized anxiety disorder, obsessivecompulsive disorder, panic disorder, posttraumatic stress disorder, separation anxiety disorder, social phobia, and specific phobia), childhood disorders, (e.g., attentiondeficit/hyperactivity disorder, conduct disorder, and oppositional defiant disorder), eating disorders (e.g., anorexia nervosa and bulimia nervosa), mood disorders (e.g., depression, bipolar disorder I and II, cyclothymic disorder, dysthymic disorder, and major depressive disorder), suicidal ideation and/or behavior, personality disorders (e.g., antisocial personality disorder, avoidant personality disorder, borderline personality disorder, dependent personality disorder, histrionic personality disorder, narcissistic personality disorder, obsessivecompulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence or abuse, amphetamine dependence or abuse, cannabis dependence or abuse, cocaine dependence or abuse, hallucinogen dependence or abuse, inhalant dependence or abuse, nicotine dependence or abuse, opioid dependence or abuse, phencyclidine dependence or abuse, and sedative dependence or abuse), adjustment disorders, autism, Asperger's disorder, autistic disorder, delirium, dementia, multi-infarct dementia, learning and memory disorders (e.g., amnesia and age-related memory loss), and Tourette's disorder.

The term "metabolic disorder" refers to any disorder that involves an alteration in the normal metabolism of carbohydrates, lipids, proteins, nucleic acids, or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 in the brain), or the like. Examples of metabolic disorders include, but are not limited to, diabetes (e.g., Type I diabetes, Type II diabetes, gestational diabetes), hyperglycemia, hyperlipidemia, hypercholesterolemia, hyperinsulinemia, insulin resistance, and obesity.

The terms "health food" or "health food product" refers to any kind of liquid and solid/semi-solid materials that are used for nourishing humans and animals, for improving basic behavioral functioning, hyperactivity, anxiety, depression, suicidal ideation and/or behavior, sensorimotor gating, pain threshold, memory and/or cognitive functioning, body weight, or for facilitating treatment of any of the target diseases noted herein. The term "nutraceutical composition" refers to compositions containing components from food sources and conferring extra health benefits in addition to the basic nutritional value found in foods. The term "medical food product" refers to a food product formulated to be consumed or administered enterally, including a food product that is usually used under the supervision of a physician for the specific dietary management of a target disease, such as those described herein. A "medical food product" composition may refer to a composition that is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management).

(I). The Active Ingredient

In some aspects, the present disclosure provides a compound of formula (I):

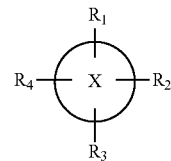

or a pharmaceutically acceptable salt thereof,
wherein:
Ring X is a 3 to 7 membered monocyclic ring, which is aryl, heteroaryl, cycloalkyl, or cycloheteroalkyl;
at least one of $R_1$, $R_2$, $R_3$, and $R_4$ is $OR_5$ or $CH_2OR_5$ and the other $R_1$, $R_2$, $R_3$, and $R_4$ each independently are halogen, OH, $OR_5$, $CH_2OR_5$, $CO_2H$, $OC=OR_6$, $(C=O)R_6$, $R_6$, C1-10 alkyl, C2-10 alkenyl, C2-10 alkynyl, H, or absent
$R_5$ is of the formula

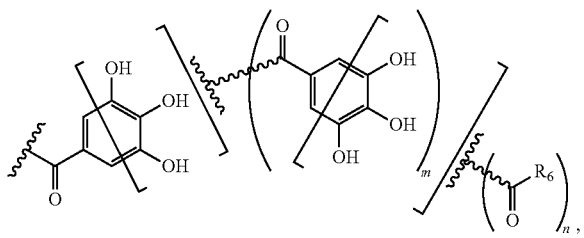

in which
m independently is 1, 2, 3, 4, 5, 6, or 7;
n independently is 0, 1, 2, or 3; and
$R_6$ is of the formula:

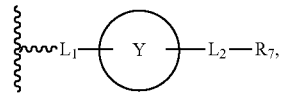

in which Ring Y is a 3 to 7 membered monocyclic ring, which is selected from the group consisting of aryl, heteroaryl, cycloalkyl, and cycloheteroalkyl;
each of $L_1$ and $L_2$, independently, is a moiety selected from the group consisting of N, O, S, $CH_2$, C=O, $C_{2-10}$ alkyl, $C_{2-10}$ alkenyl, $C_{2-10}$ alkynyl, —(W—$(CH_2)_s$)—, and absent, wherein s is 0, 1, 2, 3, 4, or 5, and W is O, S, or N; and
$R_7$ is selected from the group consisting of aryl, heteroaryl, aralkyl, C2-10 alkyl, C2-10 alkenyl, C2-10 alkynyl, and H.

In some aspects, the X ring is

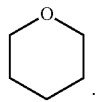

Each of $R_1$, $R_2$, $R_3$, and $R_4$ are each $OR_5$. Alternatively or in addition, each of m is 0, 1, 2, 3, 4, 5, 6, or 7. In some instances, n is 0.

In some aspects, the X ring is

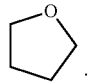

Each of $R_1$, $R_2$, $R_3$, and $R_4$ independently can be $OR_5$. Alternatively, each of $R_1$, $R_2$, $R_3$, and $R_4$ independently can be or $CH_2OR_5$. In some examples, at least one of $R_1$, $R_2$, $R_3$, and $R_4$ can be $OR_5$, and at least one of $R_1$, $R_2$, $R_3$, and $R_4$ can be $CH_2OR_5$. Alternatively or in addition, m is 0, 1, 2, 3, 4, 5, 6, or 7. In some instances, n is 0.

In some aspects, the X ring is

$R_1$, $R_2$, $R_3$, and $R_4$, can each be OH, $CO_2H$, $OR_5$ or $(C=O)R_6$. In some instances, at least two of $R_1$, $R_2$, $R_3$, and $R_4$ are identical moieties. In other instances $R_1$, $R_2$, $R_3$, and $R_4$ are different moieties. In some examples, at least one of $R_1$, $R_2$, $R_3$, and $R_4$ is $OR_5$. In some examples, at least one of $R_1$, $R_2$, $R_3$, and $R_4$ is $(C=O)R_6$. In some instances, m is 0, 1, 2, 3, 4, 5, 6, or 7. In some instances, n is 0 or 1.

In some embodiments, the present disclosure provides a compound of (II):

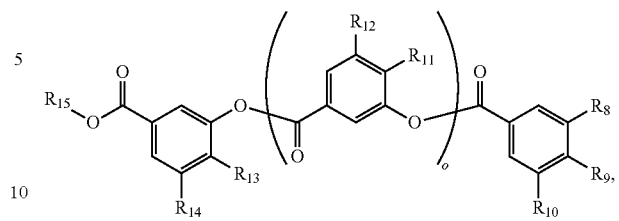

in which
- $R_9$-$R_{14}$ are each independently H, OH, $NH_2$, halogen, $C_{1-3}$ alkyl, or $C_{1-3}$ alkoxy;
- $R_8$ is H, OH, $NH_2$, halogen, $C_{1-3}$ alkyl, $C_{1-3}$ alkoxy, aryl, heteroaryl, or $O(CO)R_6$; and
- $R_{15}$ is H, alkyl, cycloalkyl, aryl, alkylaryl, heteroaryl, or alkylheteroaryl; and
- o is 1, 2, 3, 4, or 5.

In some instances, a compound of formula (II) may have at least one of the $R_8$, $R_9$, and $R_{10}$ being —OH. In some instances, at least two of the $R_8$, $R_9$, and $R_{10}$ are —OH. In some examples, all of the $R_8$, $R_9$, and $R_{10}$ are —OH. In other examples, two of the $R_8$, $R_9$, and $R_{10}$ are —OH and the other one is $O(CO)R_6$.

In some instances, at least one of $R_{13}$ and $R_{14}$ is —OH. In some examples, both $R_{13}$ and $R_{14}$ are —OH. Alternatively or in addition, $R_{15}$ may be H. In other examples, $R_{15}$ may be aryl or heteroaryl. In yet other examples, $R_{15}$ can be alkylarl or alkylheteroaryl. In still other examples, $R_{15}$ can be cycloalkyl.

Exemplary compounds of Formula (I) are provided in Table 1 below.

TABLE 1

Exemplary Compounds

| Compound name (#) | Structure |
|---|---|
| 3G (14) | 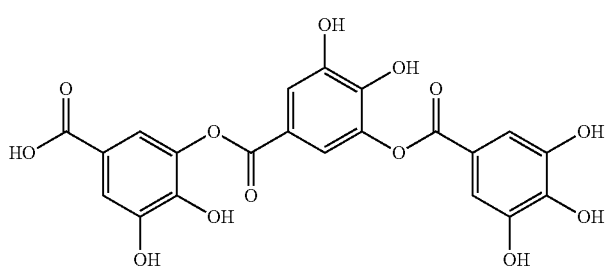 [SMILES: O=C(O)c1cc(O)c(O)c(OC(=O)c2cc(O)c(O)c(OC(=O)c3cc(O)c(O)c(O)c3)c2)c1] |
| 4G (149) | 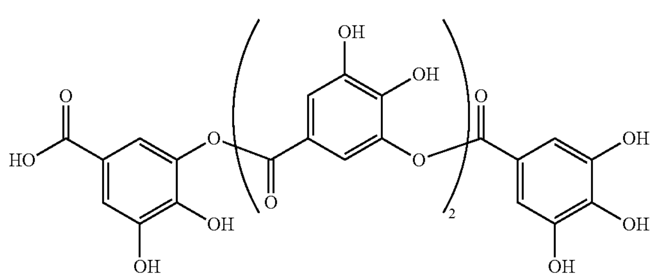 |

TABLE 1-continued

Exemplary Compounds

| Compound name (#) | Structure |
|---|---|
| 5G (18) | 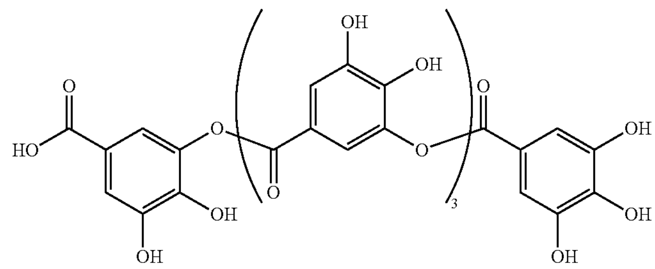 |
| 6G | 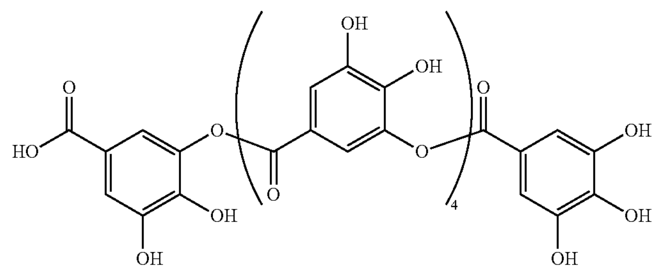 |
| 7G (22) | 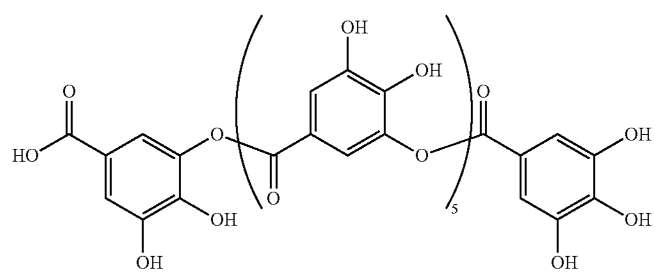 |
| 1NPCA-5G (25) | 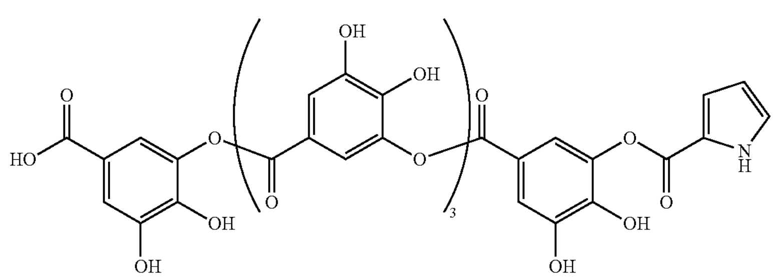 |
| 1NPCA-7G (28) | 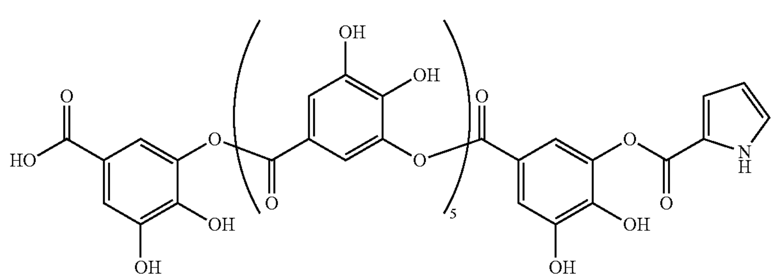 |

TABLE 1-continued
Exemplary Compounds
| Compound name (#) | Structure |
|---|---|
| 2NPCA-5G | 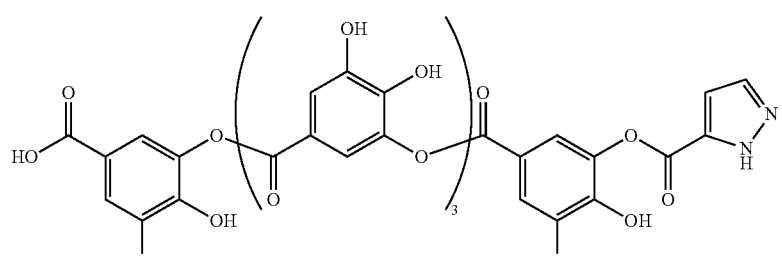 |
| 2NPCA-7G | 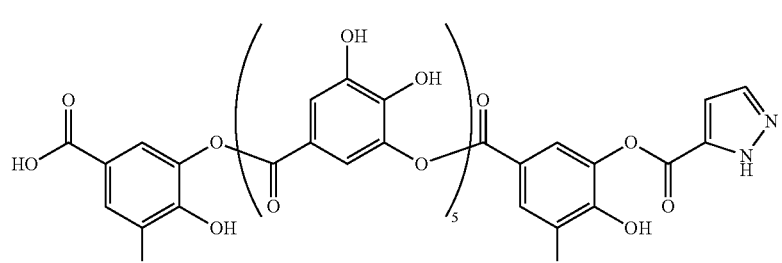 |
| Ph-2N1C-5G | 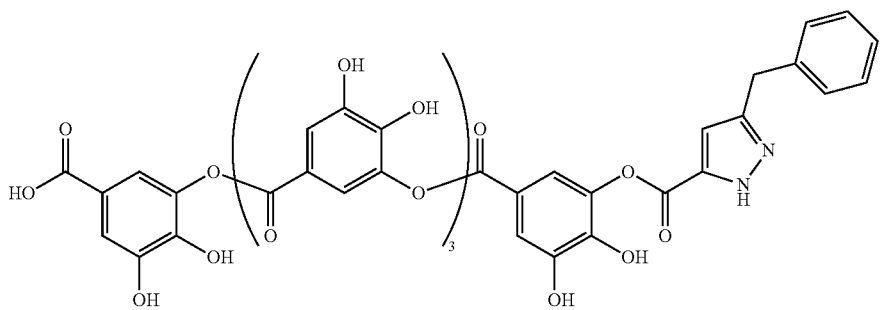 |
| Ph-1N-5G | 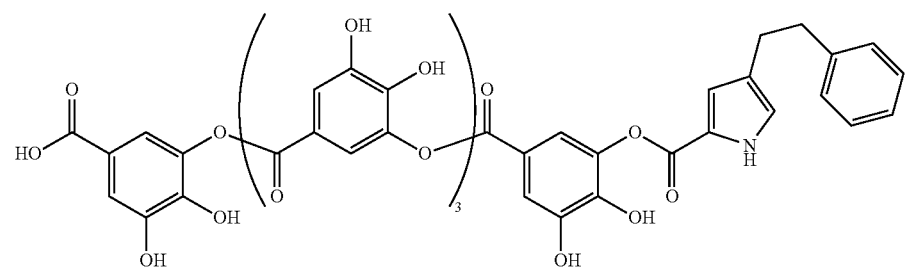 |
| Ph-2N-5G (34) | 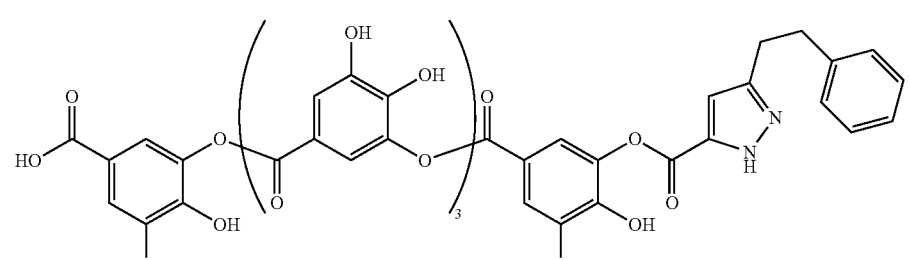 |

TABLE 1-continued

Exemplary Compounds

| Compound name (#) | Structure |
|---|---|
| Ph-2N-7G | 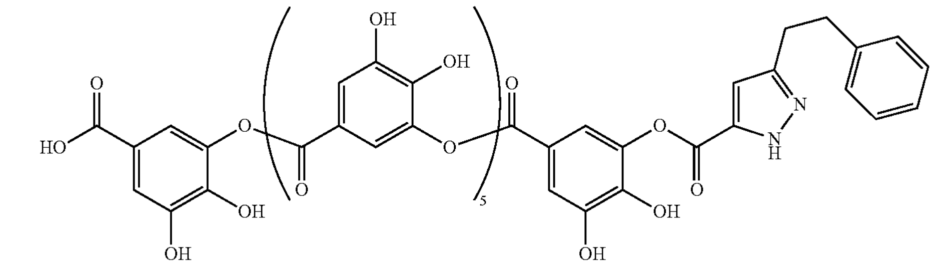 |
| Ph-2N3C-5G | 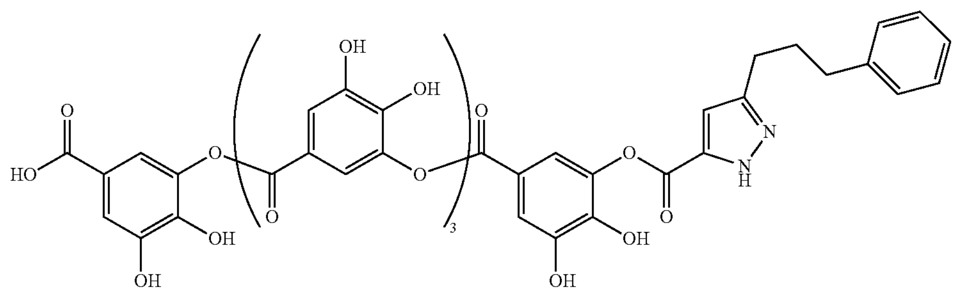 |
| 1Naph-2N-5G | 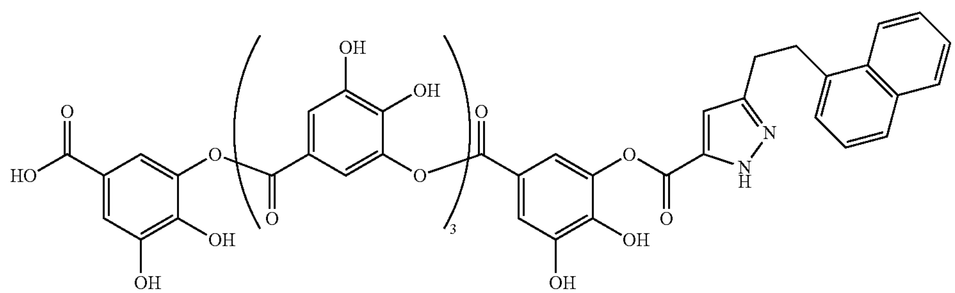 |
| 2Naph-2N-5G | 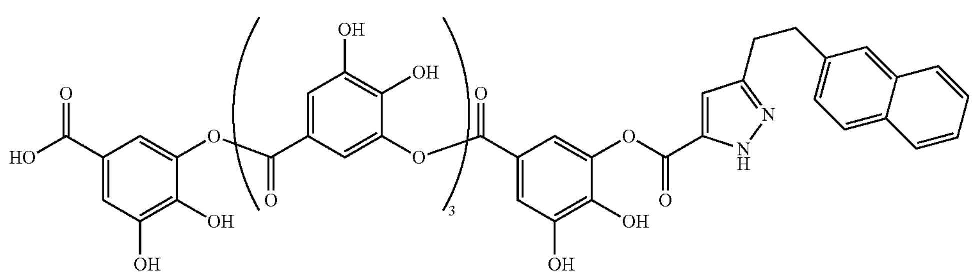 |
| 1Naph-ovH-2N-5G (42) | 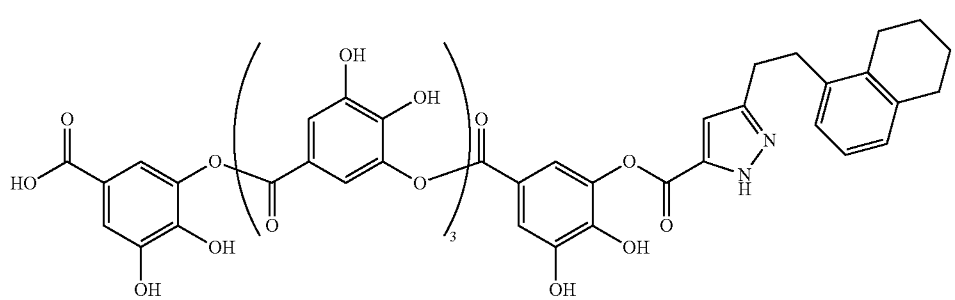 |

TABLE 1-continued

Exemplary Compounds

| Compound name (#) | Structure |
|---|---|
| pF-2N-5G (50) | |
| mmF₂-2N-5G (58) | |
| pCF₃-2N-5G (66) | |
| oCF₃-2N-5G (74) | |
| Bnz-5G (77) | |

TABLE 1-continued

Exemplary Compounds

| Compound name (#) | Structure |
|---|---|
| cHAcl-5G (80) | 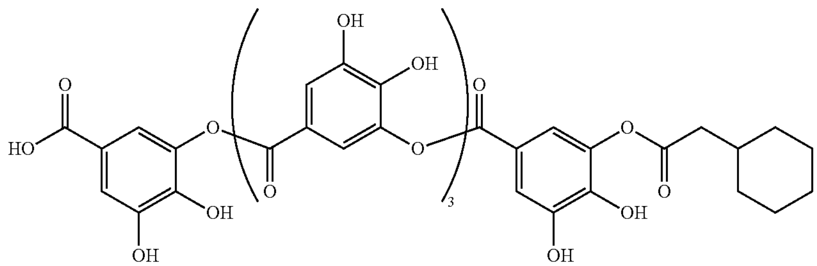 |
| Bnz-5G-OPh (85) | 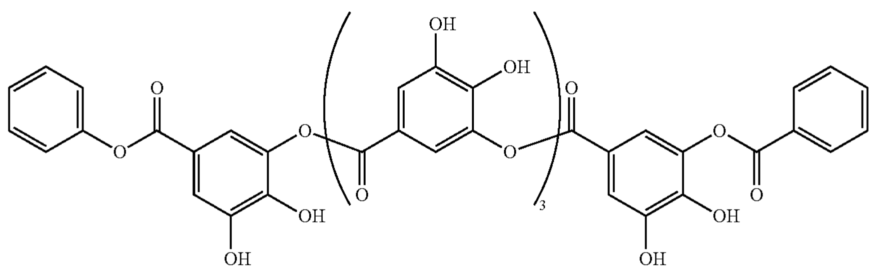 |
| pF-2NAlc-5G (92) | 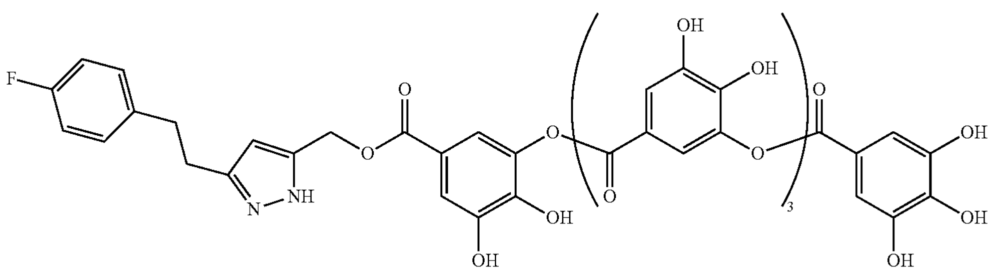 |
| Ph-2NAlc-5G | 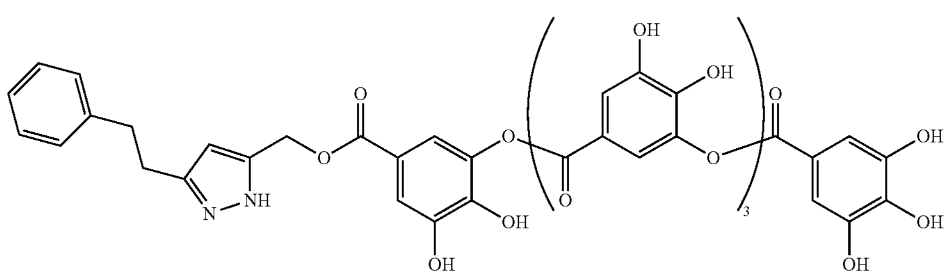 |
| mPyr-5G (94) | 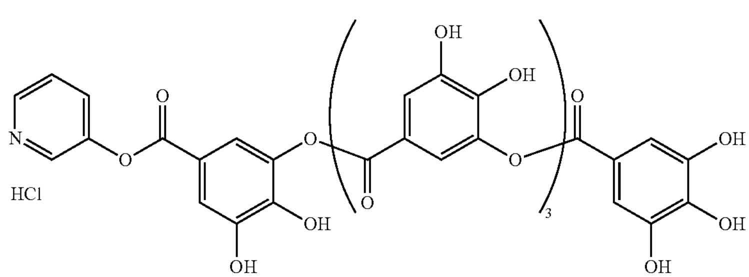 |

TABLE 1-continued

Exemplary Compounds

| Compound name (#) | Structure |
|---|---|
| cHexO-5G (96) | 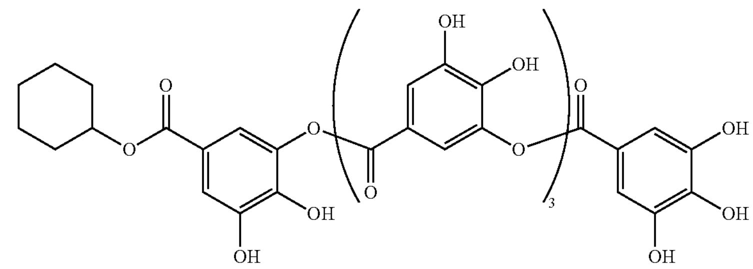 |
| cPropO-5G (98) | 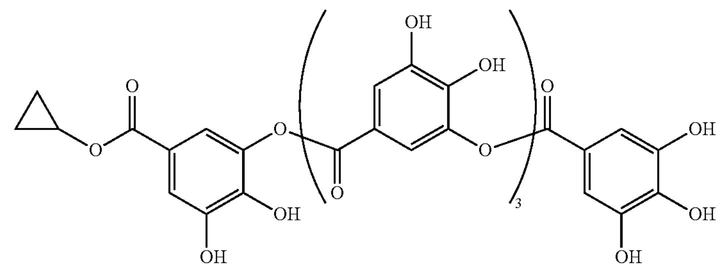 |
| cPentO-5G | 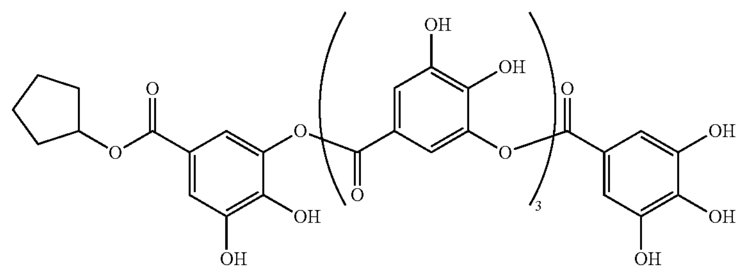 |
| cHeptO-5G (100) | 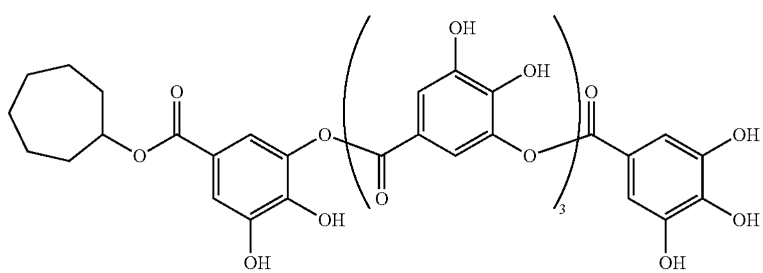 |
| cHeptO-7G | 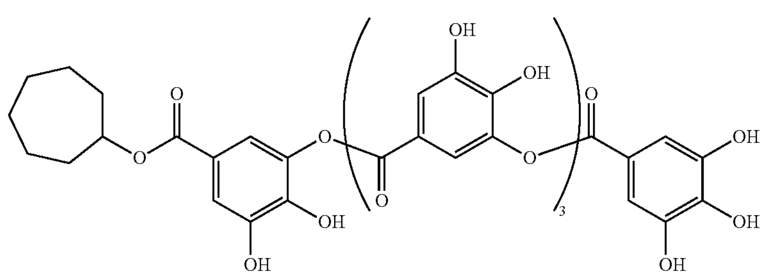 |

TABLE 1-continued
Exemplary Compounds
| Compound name (#) | Structure |
|---|---|
| Bnz-Phlo-10G (103) | 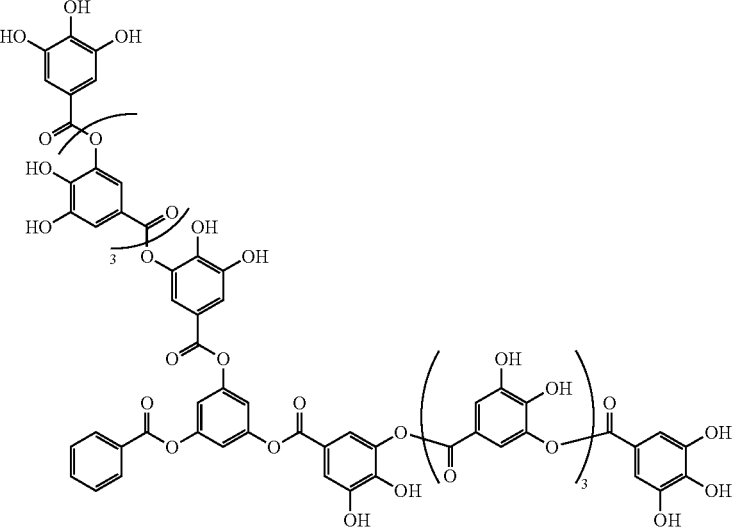 |
| pCF$_3$-2N-Phlo-10G (107) | 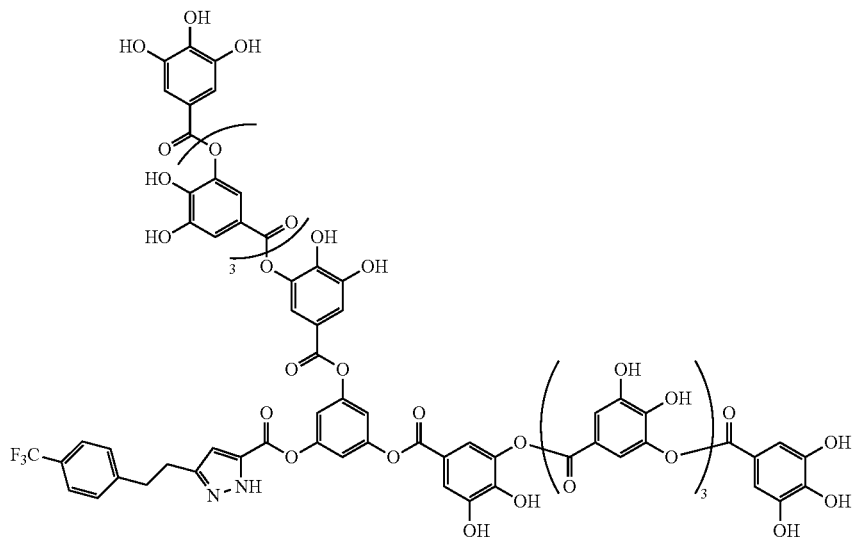 |

TABLE 1-continued

Exemplary Compounds

| Compound name (#) | Structure |
|---|---|
| pCF₃-2N-Phlo-14G | (structure) |
| Ph-2N-Phlo-10G | (structure) |

TABLE 1-continued
Exemplary Compounds
| Compound name (#) | Structure |
|---|---|
| α-Xyl-8G (117) | 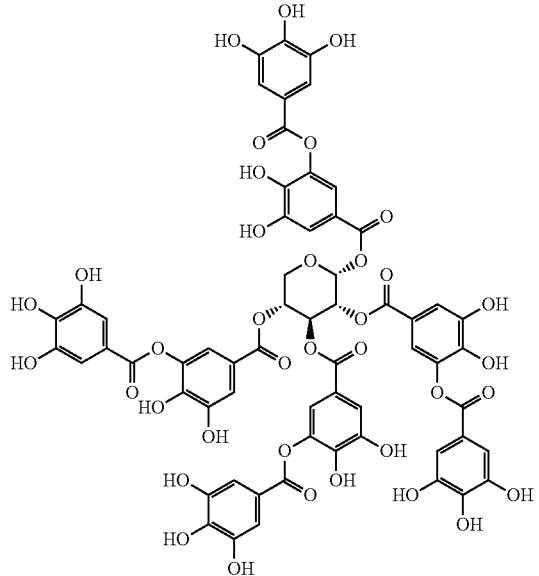 [SMILES: O=C(Oc1cc(C(=O)O[C@H]2OC[C@@H](OC(=O)c3cc(O)c(O)c(OC(=O)c4cc(O)c(O)c(O)c4)c3)[C@H](OC(=O)c3cc(O)c(O)c(OC(=O)c4cc(O)c(O)c(O)c4)c3)[C@H]2OC(=O)c2cc(O)c(O)c(OC(=O)c3cc(O)c(O)c(O)c3)c2)cc(O)c1O)c1cc(O)c(O)c(O)c1] |
| α-Xyl-12G (119) | 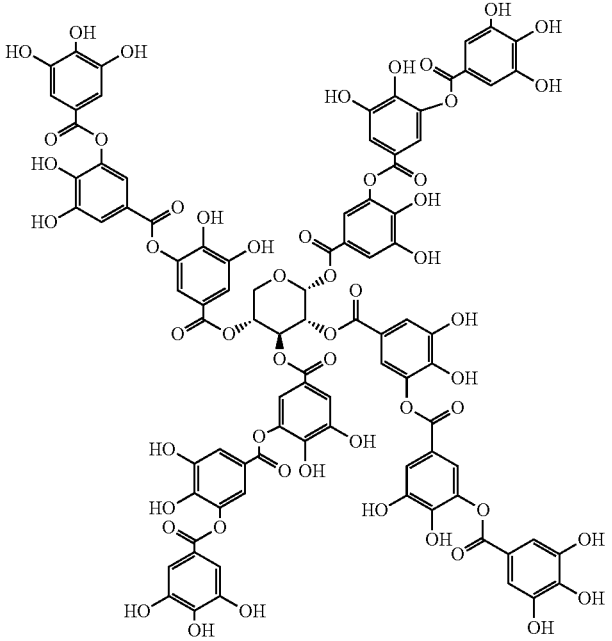 [SMILES: O=C(Oc1cc(C(=O)Oc2cc(C(=O)O[C@H]3OC[C@@H](OC(=O)c4cc(O)c(O)c(OC(=O)c5cc(O)c(O)c(OC(=O)c6cc(O)c(O)c(O)c6)c5)c4)[C@H](OC(=O)c4cc(O)c(O)c(OC(=O)c5cc(O)c(O)c(OC(=O)c6cc(O)c(O)c(O)c6)c5)c4)[C@H]3OC(=O)c3cc(O)c(O)c(OC(=O)c4cc(O)c(O)c(OC(=O)c5cc(O)c(O)c(O)c5)c4)c3)cc(O)c2O)cc(O)c1O)c1cc(O)c(O)c(O)c1] |

TABLE 1-continued
Exemplary Compounds
| Compound name (#) | Structure |
|---|---|
| α-Xyl-16G (121) | 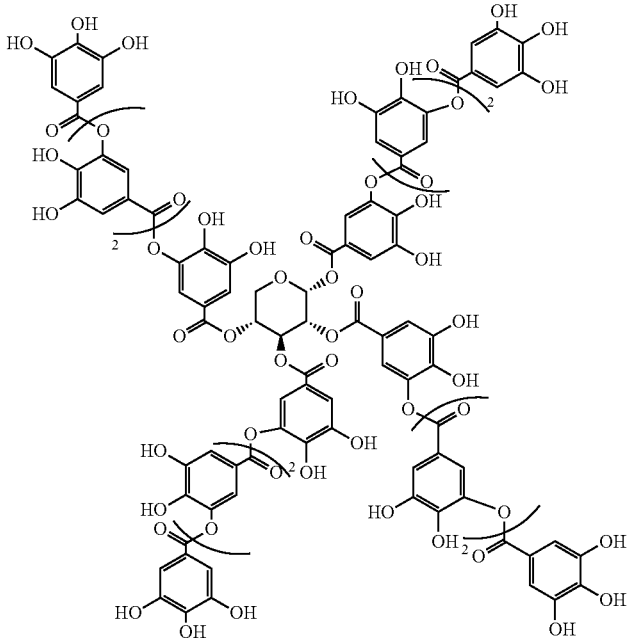 |
| α-Xyl-20G (123) | 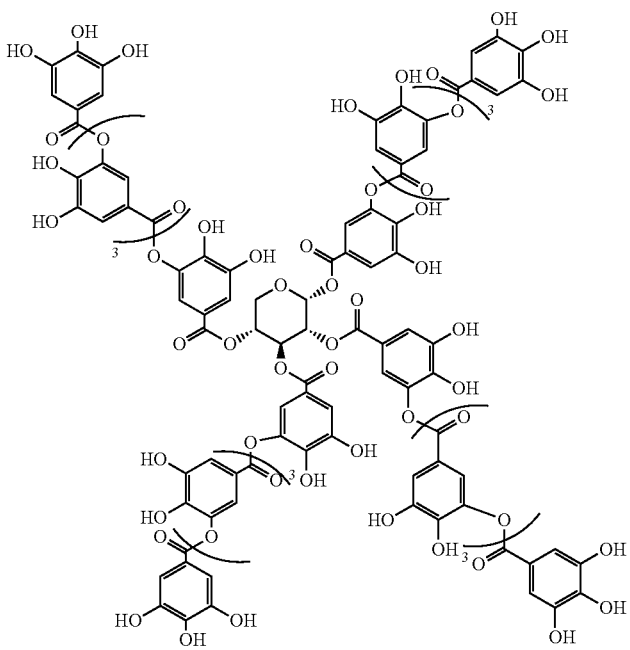 |

TABLE 1-continued
Exemplary Compounds
| Compound name (#) | Structure |
|---|---|
| α-Xyl-24G | 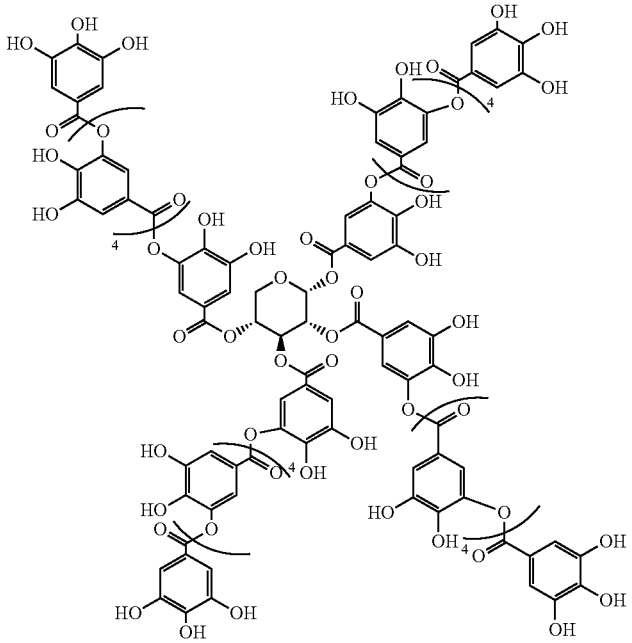 |
| β-Xyl-8G | 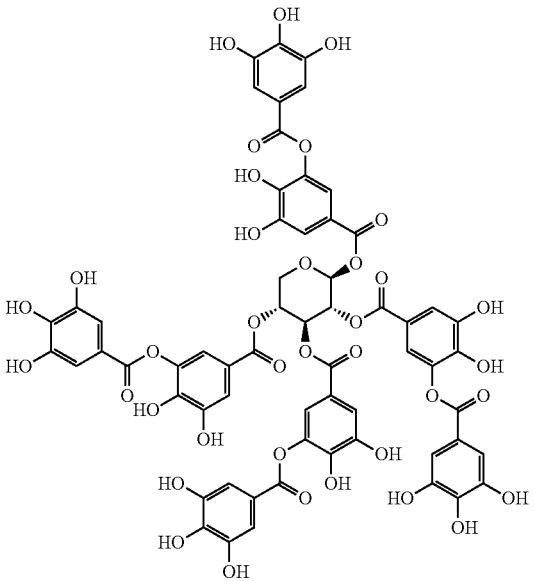 [SMILES: O=C(Oc1cc(C(=O)O[C@@H]2OC[C@@H](OC(=O)c3cc(O)c(O)c(OC(=O)c4cc(O)c(O)c(O)c4)c3)[C@H](OC(=O)c3cc(O)c(O)c(OC(=O)c4cc(O)c(O)c(O)c4)c3)[C@H]2OC(=O)c2cc(O)c(O)c(OC(=O)c3cc(O)c(O)c(O)c3)c2)cc(O)c1O)c1cc(O)c(O)c(O)c1] |

TABLE 1-continued
Exemplary Compounds
| Compound name (#) | Structure |
|---|---|
| β-Xyl-12G (126) | 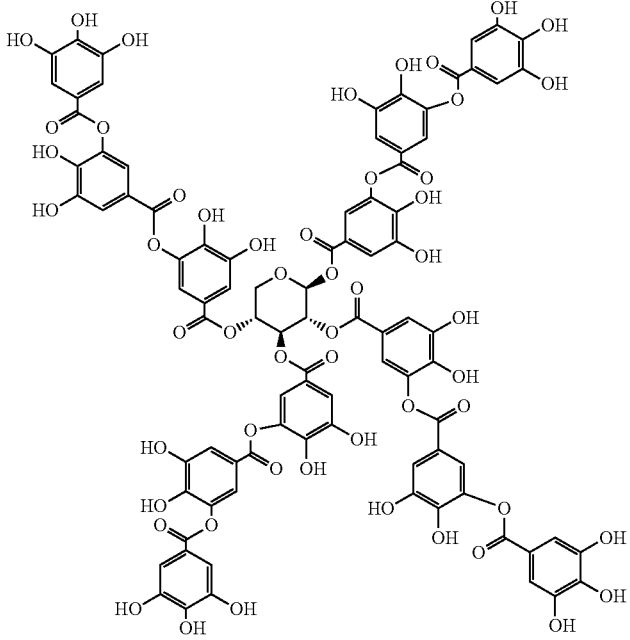 [SMILES: O=C(Oc1cc(C(=O)Oc2cc(C(=O)O[C@@H]3OC[C@@H](OC(=O)c4cc(O)c(O)c(OC(=O)c5cc(O)c(O)c(OC(=O)c6cc(O)c(O)c(O)c6)c5)c4)[C@H](OC(=O)c4cc(O)c(O)c(OC(=O)c5cc(O)c(O)c(OC(=O)c6cc(O)c(O)c(O)c6)c5)c4)[C@H]3OC(=O)c3cc(O)c(O)c(OC(=O)c4cc(O)c(O)c(OC(=O)c5cc(O)c(O)c(O)c5)c4)c3)cc(O)c2O)cc(O)c1O)c1cc(O)c(O)c(O)c1] |
| β-Xyl-16G (128) | 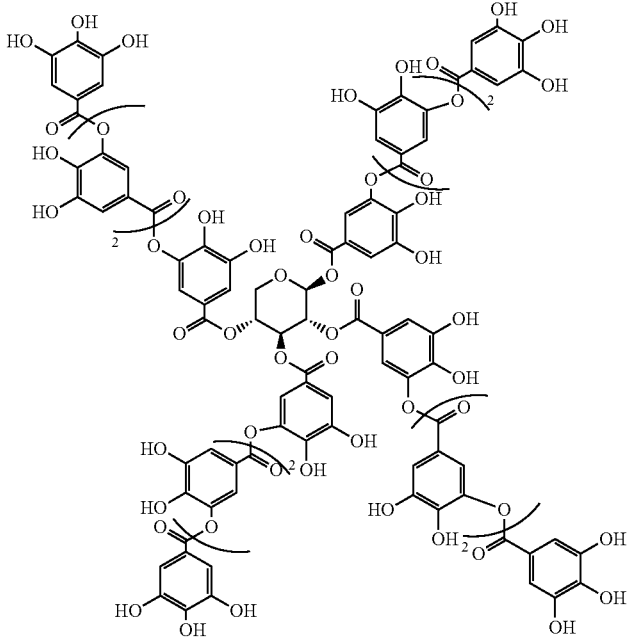 |

TABLE 1-continued

Exemplary Compounds

| Compound name (#) | Structure |
|---|---|
| β-Xyl-20G | 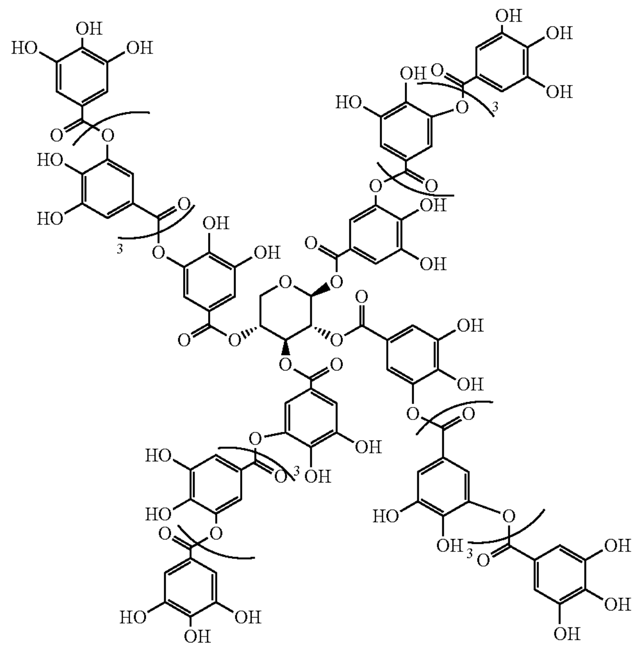 |
| β-Xyl-24G | 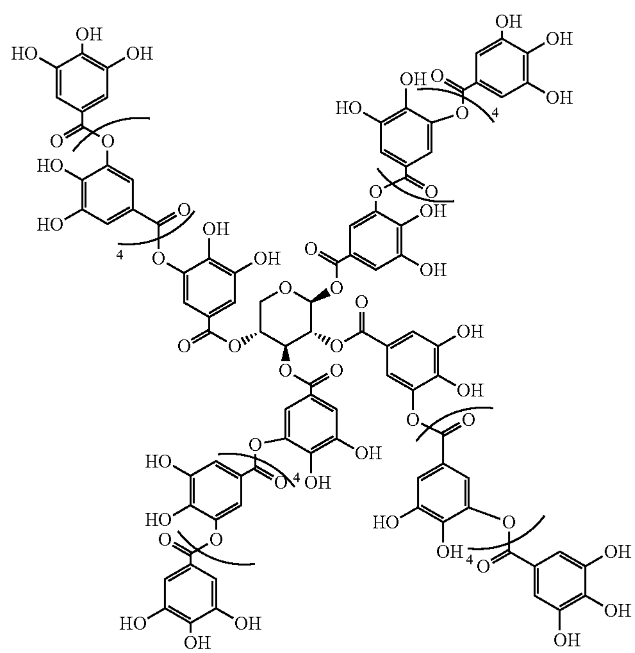 |

TABLE 1-continued
Exemplary Compounds
| Compound name (#) | Structure |
|---|---|
| α-Rib-8G (134) | 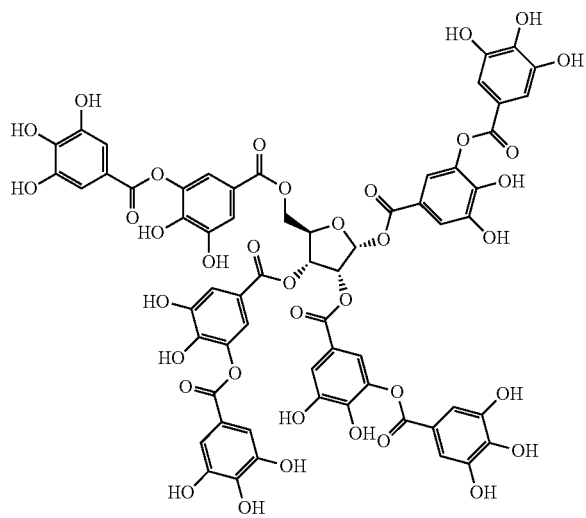 [SMILES: O=C(OC[C@H]1O[C@H](OC(=O)c2cc(O)c(O)c(OC(=O)c3cc(O)c(O)c(O)c3)c2)[C@H](OC(=O)c2cc(O)c(O)c(OC(=O)c3cc(O)c(O)c(O)c3)c2)[C@@H]1OC(=O)c1cc(O)c(O)c(OC(=O)c2cc(O)c(O)c(O)c2)c1)c1cc(O)c(O)c(OC(=O)c2cc(O)c(O)c(O)c2)c1] |
| α-Rib-12G (136) | 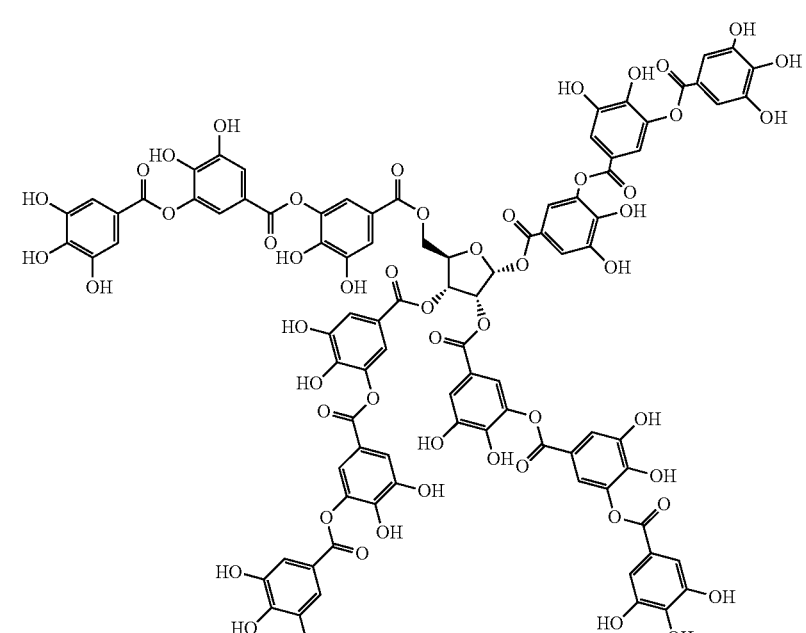 |

TABLE 1-continued

Exemplary Compounds

| Compound name (#) | Structure |
|---|---|
| α-Rib-16G (138) | 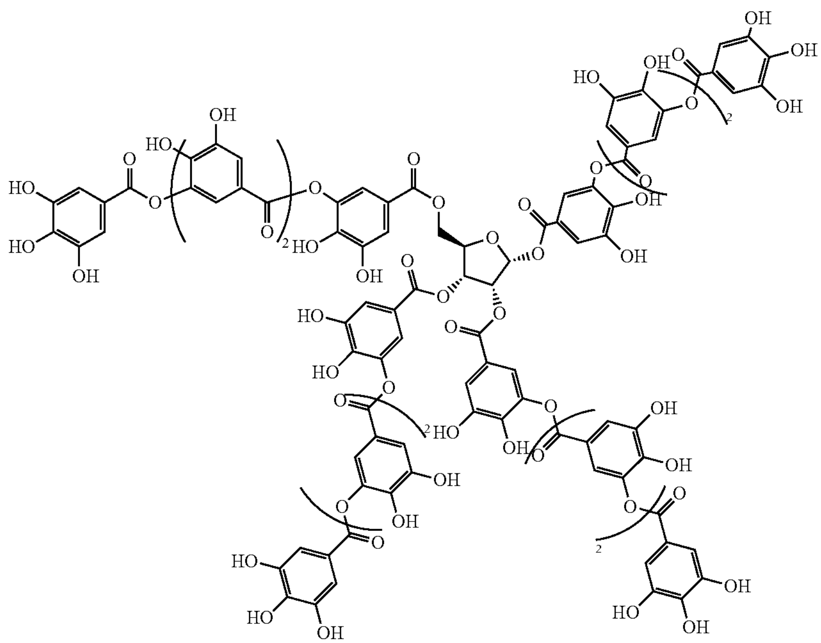 |
| α-Rib-20G (140) | 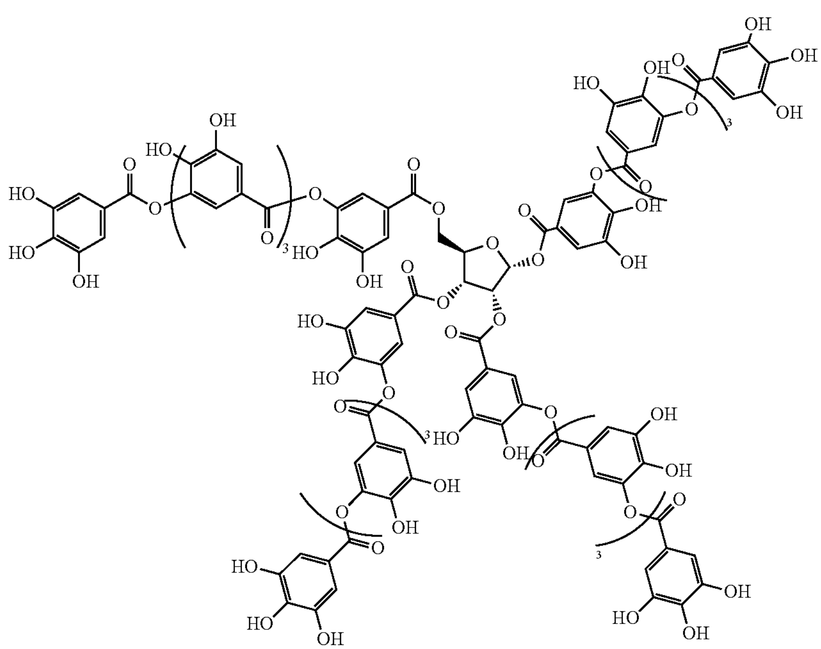 |

TABLE 1-continued
Exemplary Compounds
| Compound name (#) | Structure |
|---|---|
| α-Rib-24G | 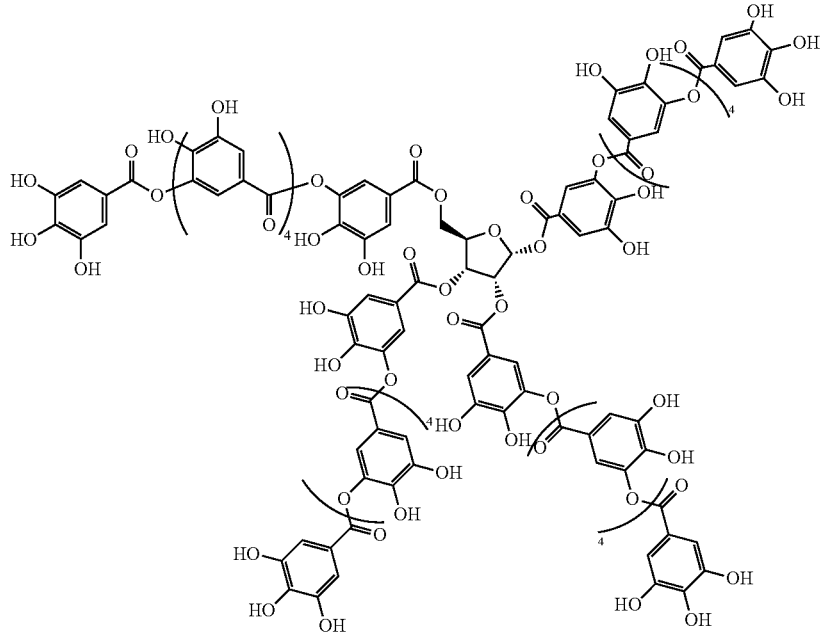 |
| β-Rib-8G (142) | 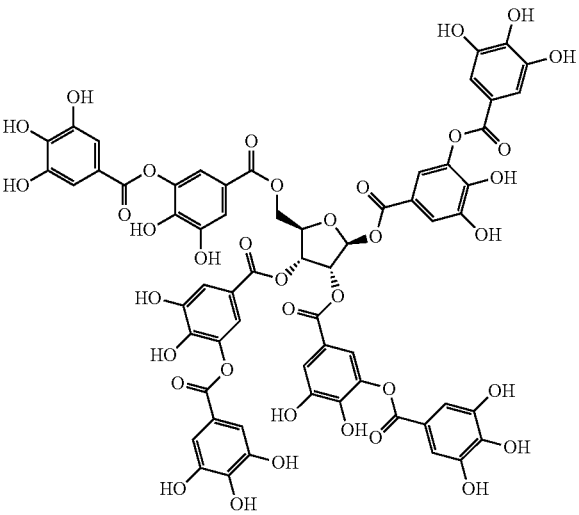 [SMILES: O=C(OC[C@H]1O[C@@H](OC(=O)c2cc(O)c(O)c(OC(=O)c3cc(O)c(O)c(O)c3)c2)[C@H](OC(=O)c2cc(O)c(O)c(OC(=O)c3cc(O)c(O)c(O)c3)c2)[C@@H]1OC(=O)c1cc(O)c(O)c(OC(=O)c2cc(O)c(O)c(O)c2)c1)c1cc(O)c(O)c(OC(=O)c2cc(O)c(O)c(O)c2)c1] |

TABLE 1-continued
Exemplary Compounds
| Compound name (#) | Structure |
|---|---|
| β-Rib-12G (144) | 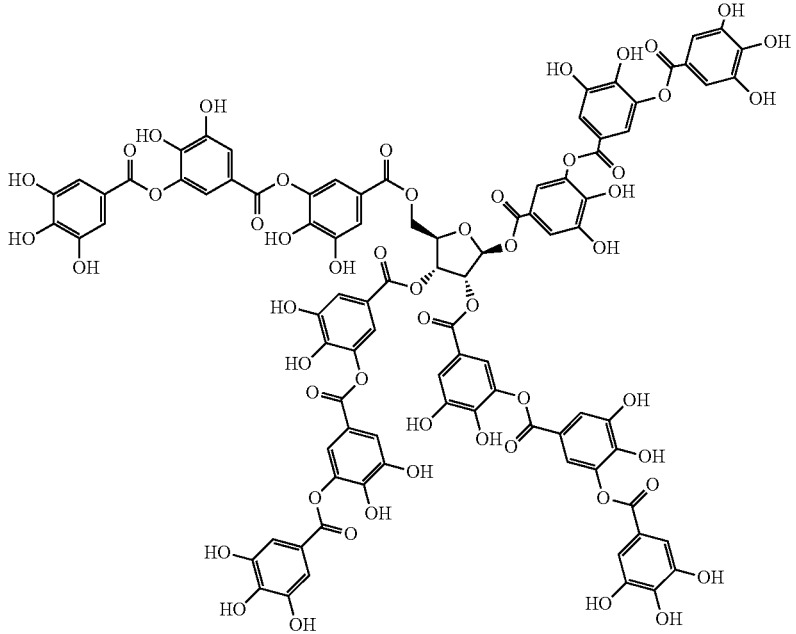 |
| β-Rib-16G (146) | 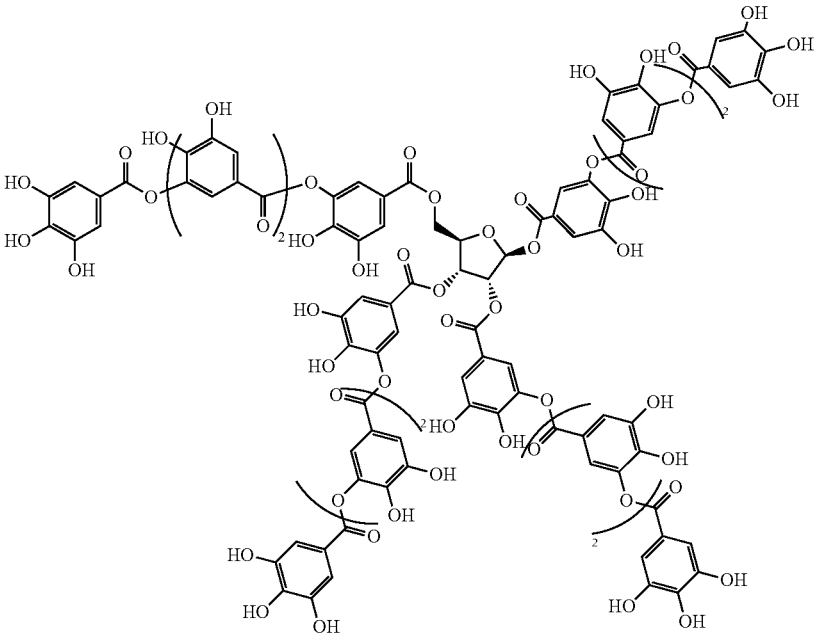 |

TABLE 1-continued

Exemplary Compounds

| Compound name (#) | Structure |
|---|---|
| β-Rib-20G (148) | 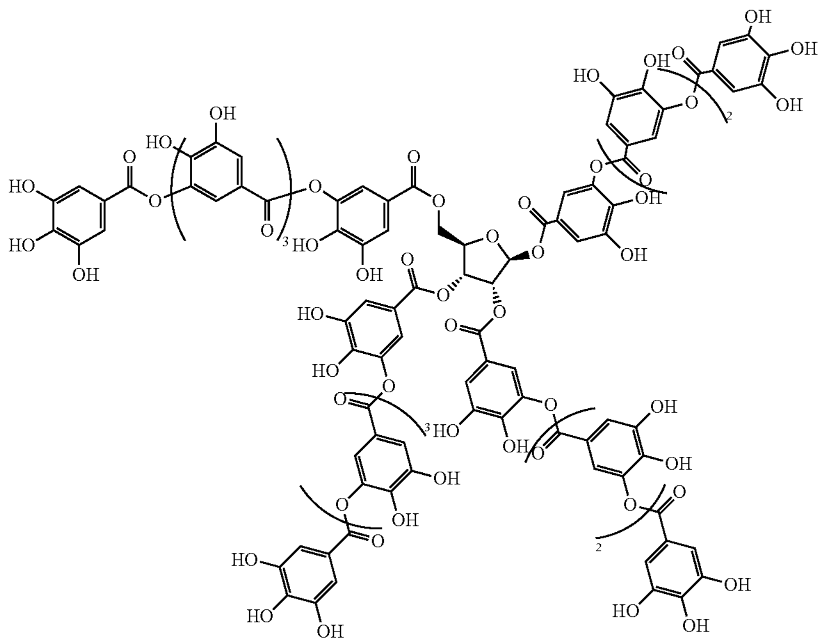 |
| β-Rib-24G | 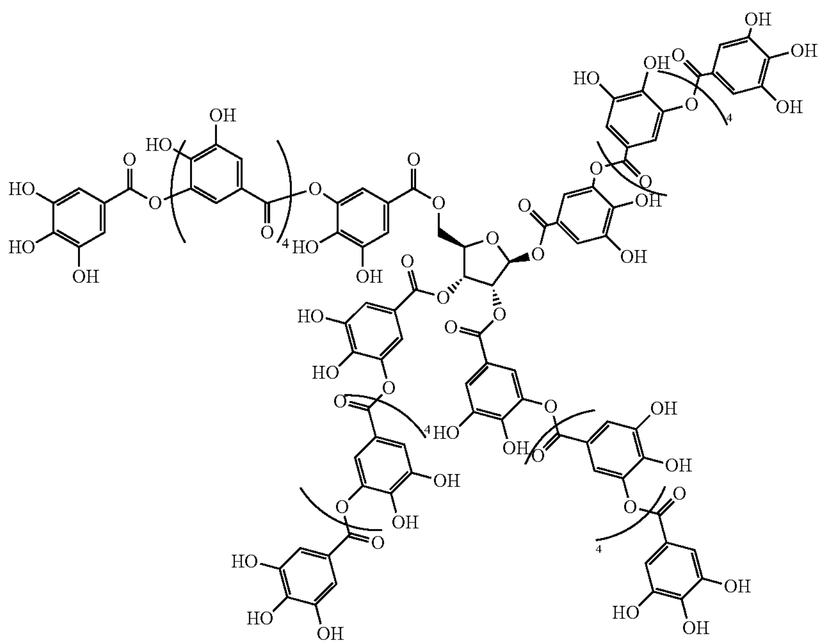 |

(II) Pharmaceutical Composition and Kit Containing Such

One aspect of the present disclosure relates to compositions, for example, pharmaceutical compositions, health food product such as nutraceutical compositions, and medical food that comprise one or more compound of Formula (I) and a carrier, e.g., a pharmaceutically acceptable carrier and/or an edible carrier. Such carriers, either naturally occurring or non-naturally occurring (synthetic), may confer various benefits to the compound of Formula (I) in the composition, for example, improving in vitro and/or in vivo stability of the Formula (I) compound, enhancing bioavailability of the compound of Formula (I), increasing the associated bioactivity and/or reducing side effects. Suitable carriers include, but are not limited to, diluents, fillers, salts, buffers, stabilizers, solubilizers, buffering agents, preservatives, or a combination thereof.

(A) Pharmaceutical Compositions

The compositions as described herein, e.g., a pharmaceutical composition comprising a pharmaceutically acceptable carrier, can be used for treating any of the target diseases as described herein. Pharmaceutically acceptable carriers include diluents, fillers, salts, buffers, stabilizers, solubilizers and other material which are well-known in the art. Exemplary pharmaceutically acceptable carriers in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from a suitable inorganic base, (e.g., sodium hydroxide, barium hydroxide, iron (ii) hydroxide, iron (III) hydroxide, magnesium hydroxide, calcium hydroxide, aluminium hydroxide, ammonium hydroxide, potassium hydroxide, caesium hydroxide, or lithium hydroxide) or a suitable organic base (e.g., pyridine, methyl amine, imidazole, benzimidazole, histidine, phosphazene bases, or a hydroxide of an organic cation such as quaternary ammonium hydroxide and phosphonium hydroxide). Also, pharmaceutically-acceptable salts can be prepared as alkaline metal or alkaline earth salts, such as lithium, sodium, potassium or calcium salts.

The pharmaceutical compositions as described herein can comprise pharmaceutically acceptable carriers, excipients, or stabilizers in the form of lyophilized formulations or aqueous solutions. Remington: *The Science and Practice of Pharmacy* $20^{th}$ Ed. (2000) Lippincott Williams and Wilkins, Ed. K. E. Hoover. Such carriers, excipients or stabilizers may enhance one or more properties of the active ingredients in the compositions described herein, e.g., bioactivity, stability, bioavailability, and other pharmacokinetics and/or bioactivities.

Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; benzoates, sorbate and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, serine, alanine or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ (polysorbate), PLURONICS™ (nonionic surfactants), or polyethylene glycol (PEG).

In some examples, the pharmaceutical composition described herein includes pulmonary compatible excipients. Suitable such excipients include, but not limited to, richloromono-fluoromethane, dichloro-difluoromethane, dichloro-tetrafluoroethane, chloropenta-fluoroethane, monochloro-difluoroethane, difluoroethane, tetrafluoroethane, heptafluoropropane, octafluoro-cyclobutane, purified water, ethanol, propylene glycol, glycerin, PEG (e.g. PEG400, PEG 600, PEG 800 and PEG 1000), sorbitan trioleate, soya lecithin, lecithin, oleic acid, Polysorbate 80, magnesium stearate and sodium laury sulfate, methylparaben, propylparaben, chlorobutanol, benzalkonium chloride, cetylpyridinium chloride, thymol, ascorbic acid, sodium bisulfite, sodium metabisulfite, EDTA, sodium hydroxide, tromethamine, ammonia, HCl, $H_2SO_4$, $HNO_3$, citric acid, $CaCl_2$, $CaCO_3$, sodium citrate, sodium chloride, disodium EDTA, saccharin, menthol, ascorbic acid, glycine, lysine, gelatin, povidone K25, silicon dioxide, titanium dioxide, zinc oxide, lactose, lactose monohydrate, lactose anhydrate, mannitol, and dextrose.

In other examples, the pharmaceutical composition described herein can be formulated in sustained-release format. Suitable examples of sustained-release preparations include semipermeable matrices of solid hydrophobic polymers which matrices are in the form of shaped articles, e.g., films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(–)-3-hydroxybutyric acid.

The pharmaceutical compositions to be used for in vivo administration must be sterile. This is readily accomplished by, for example, filtration through sterile filtration membranes. Therapeutic compositions are generally placed into a container having a sterile access port, for example, an intravenous solution bag or vial having a stopper pierceable by a hypodermic injection needle or a sealed container to be manually accessed.

The pharmaceutical compositions described herein can be in unit dosage forms such as solids, solutions or suspensions, or suppositories, for administration by inhalation or insufflation, intrathecal, intrapulmonary or intracerebral routes, oral, parenteral or rectal administration.

For preparing solid compositions, the principal active ingredient can be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound as disclosed herein, or a non-toxic pharmaceutically acceptable salt thereof.

When referring to these preformulation compositions as homogeneous, it is meant that the active ingredient is dispersed evenly throughout the composition so that the composition may be readily subdivided into equally effective unit dosage forms such as powder collections, tablets, pills and capsules. This solid preformulation composition is then subdivided into unit dosage forms of the type described above containing from 0.1 to about 5 grams of any of the compounds disclosed herein, for example, those listed in Table 1.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

In some examples, the pharmaceutical composition described herein include a liposome composition. Liposomes are artificially prepared spherical vesicle composition consisting of a lamellar phase lipid bilayer. Liposomes or lipid vesicles are usually composed of phosphatidylcholine-enriched phospholipids and may also contain mixed lipid chains with surfactant properties such as egg phosphatidyl ethanolamine. Preferably, the liposomal composition is composed of one or more vesicle forming lipid, selected from di-aliphatic chain lipid, such as phospholipids; diglycerides; di-aliphatic glycolipids; single lipids such as sphingomyelin or glycosphingolipid; steroidal lipids; hydrophilic polymer derivatised lipids, or mixtures thereof. Preferably, the vesicle forming lipid comprises one or more phospholipids, one or more steroidal lipids, and one or more hydrophilic polymer derivatized lipids. The one or more phospholipids that may be used in the liposome composition comprises phospholipids that form bilayer vesicular structure. The phospholipids that may be used include, but are not limited to, phospholipid such as phosphatidyl choline (PC); phosphatidyl ethanolamine (PE); phosphatidyl serine (PS), phosphatidylglycerol (PG), phosphatidylionositol (PI), sphingomyelin, phosphatidic acid (PA), lecithin; phosphatidylcholine lipid derivatives such as dipalmitoylphosphatidylcholine (DPPC), egg phosphatidylcholine (EPC), hydrogenated egg phosphatidylcholine (HEPC), partially hydrogenated egg phosphatidylcholine (PHEPC), distearylphosphatidyl choline (DSPC), dipalmitoyl phosphatidyl choline (DPPC), soy phosphatidyl choline (SPC), hydrogenated soy phosphatidyl choline (HSPC), diarachidoyl phosphatidyl choline, dimyristoyl phosphatidyl ethanolamine (DMPE), dipalmitoyl phosphatidyl ethanolamine (DPPE), distearoyl phosphatidyl ethanolamine (DSPE), diarachidoyl phosphatidyl ethanolamine (DAPE) and dipalmitoyl phosphatidyl glycerol (DPPG) and the like.

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. In some embodiments, the compositions are composed of particle sized between 10 nm to 100 mm. Compositions in preferably sterile pharmaceutically acceptable solvents may be nebulized by use of gases. Nebulized solutions may be breathed directly from the nebulizing device or the nebulizing device may be attached to a face mask, tent, endotracheal tube and/or intermittent positive pressure breathing machine (ventilator). Solution, suspension or powder compositions may be administered, preferably orally or nasally, from devices which deliver the formulation in an appropriate manner.

In some embodiments, any of the pharmaceutical compositions herein may further comprise a second therapeutic agent based on the intended therapeutic uses of the composition.

(B) Health Food Product

In some embodiments, the compositions described herein can be a health food product, which can be any kinds of liquid and solid/semi-solid materials that are used for nourishing humans and animals, for treatment of virus infection, or in particular, coronavirus infection. The health food product may be a food product (e.g., tea-based beverages, juice, soft drinks, coffee, milk, jelly, cookies, cereals, chocolates, snack bars, herbal extracts, dairy products (e.g., ice cream, and yogurt)), a food/dietary supplement, or a nutraceutical formulation.

The health food product described herein may comprise one or more edible carriers, which confer one or more of the benefits to the composition in the product as described herein. Examples of edible carriers include starch, cyclodextrin, maltodextrin, methylcellulose, carbon methoxy cellulose, xanthan gum, and aqueous solutions thereof. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art. In some examples, the healthy food products described herein may further include neuroprotective foods, such as fish oil, flax seed oil, and/or benzoate.

In some examples, the healthy food product is a nutraceutical composition, which refers to compositions containing components from food sources and conferring extra health benefits in addition to the basic nutritional value found in foods. A nutraceutical composition as described herein comprises the composition described herein and additional ingredients and supplements that promote good health and/or enhance stability and bioactivity.

The actions of nutraceutical compositions may be fast or/and short-term or may help achieve long-term health objectives as those described herein, e.g., improving health conditions, in, e.g., human subjects who have or are at risk for virus infection. The nutraceutical compositions may be contained in an edible material, for example, as a dietary supplement or a pharmaceutical formulation. As a dietary supplement, additional nutrients, such as vitamins, minerals or amino acids may be included. The composition can also be a drink or a food product, e.g., tea, soft drink, juice, milk, coffee, cookie, cereal, chocolate, and snack bar. If desired, the composition can be sweetened by adding a sweetener such as sorbitol, maltitol, hydrogenated glucose syrup and hydrogenated starch hydrolyzate, high fructose corn syrup, cane sugar, beet sugar, pectin, or sucralose.

The nutraceutical composition disclosed herein can be in the form of a solution. For example, the nutraceutical formulation can be provided in a medium, such as a buffer, a solvent, a diluent, an inert carrier, an oil, or a creme. In some examples, the formulation is present in an aqueous solution that optionally contains a non-aqueous co-solvent, such as an alcohol. The nutraceutical composition can also be in the form of powder, paste, jelly, capsule, or tablet. Lactose and corn starch are commonly used as diluents for capsules and as carriers for tablets. Lubricating agents, such as magnesium stearate, are typically added to form tablets.

The health food products may be formulated for a suitable administration route, for example, oral administration. For oral administration, the composition can take the form of, for example, tablets or capsules, prepared by conventional means with acceptable excipients such as binding agents (for example, pre-gelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets can be coated by methods well known in the art. Also included are bars and other chewable formulations.

In some examples, the health food product can be in a liquid form and the one or more edible carriers can be a solvent or dispersion medium comprising but not limited to, ethanol, polyol (e.g., glycerol, propylene glycol, liquid polyethylene glycol), lipids (e.g., triglycerides, vegetable oils, liposomes) or combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof. In many cases, it will be advisable to include an isotonic agent, such as, for example, sugars, sodium chloride or combinations thereof.

Liquid preparations for oral administration can take the form of, for example, solutions, syrups or suspensions, or they can be presented as a dry product for constitution with water or other suitable vehicle before use. In one embodiment, the liquid preparations can be formulated for administration with fruit juice. Such liquid preparations can be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates, benzoate or sorbate).

The health food products described herein may further comprise one or more second therapeutic agents, including those described herein.

(C) Medical Food Products

The present disclosure also provides compositions of medical food products, use in improving basic condition during or in the risk of virus infection. A medical food product is a food product formulated to be consumed or administered enterally. Such a food product is usually used under the supervision of a physician for the specific dietary management of a target disease, such as those described herein. In some instances, such a medical food composition is specially formulated and processed (as opposed to a naturally occurring foodstuff used in a natural state) for a patient in need of the treatment (e.g., human patients who suffer from illness or who requires use of the product as a major active agent for alleviating a disease or condition via specific dietary management.) In some examples, a medical food composition described herein is not one of those that would be simply recommended by a physician as part of an overall diet to manage the symptoms or reduce the risk of a disease or condition.

Any of the medical food compositions described herein, comprising one or more compounds of Formula (I) or salts thereof and at least one carrier (e.g., those described herein), can be in the form of a liquid solution; powder, bar, wafer, a suspension in an appropriate liquid or in a suitable emulsion, as detailed below. The at least one carrier, which can be either naturally-occurring or synthetic (non-naturally occurring), would confer one or more benefits to the composition, for example, stability, bioavailability, and/or bioactivity. Any of the carriers described herein may be used for making the medical food composition.

In some embodiments, the medical food composition may further comprise one or more additional ingredients selected from the group including, but not limited to natural flavors, artificial flavors, major trace and ultra-trace minerals, minerals, vitamins, oats, nuts, spices, milk, egg, salt, flour, lecithin, xanthan gum and/or sweetening agents. The medical food composition may be placed in a suitable container, which may further comprise at least an additional therapeutic agent such as those described herein.

(D) Kits

The present disclosure also provides kits for use in improving basic medical condition. Such kits can include one or more containers comprising the composition as described herein and optionally one or more of the second therapeutic agents as also described herein.

In some embodiments, the kit can comprise instructions for use in accordance with any of the methods described herein. The included instructions can comprise, for example, a description of administration of the composition of Formula (I) and optionally a description of administration of the second therapeutic agent(s) to improve medical conditions of virus infection or in the rick of virus infection. The kit may further comprise a description of selecting an individual suitable for treatment based on identifying whether that individual has the disease or is at risk for the disease. In still other embodiments, the instructions comprise a description of administering one or more agents of the disclosure to an individual at risk of virus infection.

The instructions relating to the use of the composition of Formula (I) to achieve the intended therapeutic effects generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk, or QR code) are also acceptable.

The label or package insert may indicate that the composition is used for the intended therapeutic utilities. Instructions may be provided for practicing any of the methods described herein.

The kits of this invention are in suitable packaging. Suitable packaging includes, but is not limited to, chambers, vials, bottles, jars, flexible packaging (e.g., sealed Mylar or plastic bags), and the like. Also contemplated are packages for use in combination with a specific device, such as an inhaler, nebulizer, ventilator, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as buffers and interpretive information. Normally, the kit comprises a container and a label or package insert(s) on or associated with the container. In some embodiments, the invention provides articles of manufacture comprising contents of the kits described above.

(III) Applications of Composition of Formula (I)

The present disclosure provides a pharmaceutical composition and method of treating certain disorders, diseases, and/or mitigating symptoms of which on subjects.

A virus is a small infectious agent that replicates only inside the living cells of a host organism. Viruses can infect all types of life forms, from animals and plants to microorganisms, including bacteria and archaea. While not inside an infected cell or in the process of infecting a cell, viruses exist in the form of independent particles, or virions, consisting of: (i) the genetic material, i.e. long molecules of DNA or RNA that encode the structure of the proteins by which the virus acts; (ii) a protein coat, the capsid, which surrounds and protects the genetic material; and in some cases (iii) an outside envelope of lipids.

Antiviral drugs are a class of medications designed to treat viral infections. As the human body is able to deal with the majority of viruses by immunity itself, these drugs target some specific virulent and life-threatening illnesses that the body either cannot fight by itself, or struggles to win against. Researchers working on "rational drug design" strategies for developing antivirals have tried to attack viruses at every stage of their life cycles (e.g., before cell entry, entry inhibition, uncoating inhibition), during viral synthesis, assembly and release phase.

Members of the corona viruses family include virus strains having different phylogenetic origin (www.thelancet.com Published online Jan. 29, 2020 https://doi.org/10.1016/S0140-6736(20)30251-8) and causing different severity in mortality and morbidity. As such, treatment for coronavirus infection varies depending on the specific strains that causes the infection. So far, there is no approved antiviral drug treatment for any coronavirus. Because of the conservation of the critical residues and its functional importance, 3CLPro is expected to be an important target for the design of ubiquitous anti-coronaviral drugs for the infection.

In some embodiments, the present disclosure provides a composition able to effectively inhibit 3C-like protease (3CLPro) and use thereof in inhibiting, treating, reducing the viral load, and/or reducing morbidity or mortality in the clinical outcomes, in patients suffering from the viral infection. The method comprises administering to a subject in need thereof an effective amount of a composition, which comprises (1) one or more compounds of Formula (I) or a pharmaceutically acceptable salt thereof and (2) a pharmaceutically acceptable carrier; In some embodiments, the effective amount is a prophylactically effective amount (e.g., amount effective for inhibiting viral 3CLPro in a subject in need thereof or amount effective in treating or reducing the viral load, and/or reducing morbidity or mortality in the clinical outcomes in subjects suffering from the viral infection).

In some embodiments, the target viral infection to be treated by the method disclosed herein is a pneumonia caused by the infection of genus Coronavirus, which may include the novel coronavirus (2019-nCoV), severe acute respiratory syndrome coronavirus (SARS-CoV), and middle east respiratory syndrome coronavirus (MERS-CoV). In some embodiments, the target viral infection to be treated by the method disclosed herein is caused by alpha coronavirus strain 229E and NL63, beta coronavirus strain OC43 and HKU1 and coronavirus strains caused by novel transmission from other mammals to human that share the protein homology and the proteolytic functioning of 3CLPro.

In yet another aspect, the present disclosure further provides methods of reducing the risk that an individual will develop a pathological coronavirus infection that has clinical sequelae. The methods generally involve administering a therapeutically effective amount of 3CLPro) inhibitor a composition comprising a therapeutically effective amount of the composition herein.

Any of the compounds described herein (e.g., a compound of Formula (I)) may be used to treating diseases or disorders. In certain embodiments, provided herein are methods to improve basic behavioral functioning, weight reduction, hyperactivity, anxiety, depression, suicidal ideation and/or behavior, sensorimotor gating, pain threshold, memory, and/or cognitive functioning in a subject in need of the treatment. Such compounds may also be used to treating diseases or disorders associated with DAAO such as a central nervous system disorder (e.g., those described herein). The compounds may also be used to treat an obesity disorder.

As used herein, the term "treating" refers to the application or administration of a composition including one or more active agents to a subject, who is in need of the treatment, for example, having a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

To achieve any of the intended therapeutic effects described herein, an effective amount of a compound described herein (e.g., a compound of Formula (I)) may be administered to a subject in need of the treatment via a suitable route.

The terms "subject," "individual," and "patient" are used interchangeably herein and refer to a mammal being assessed for treatment and/or being treated. Subjects may be human, but also include other mammals, particularly those mammals useful as laboratory models for human disease, e.g. mouse, rat, rabbit, dog, etc.

A human subject who needs the treatment may be a human patient having, at risk for, or suspected of having a target disease/disorder, such as a CNS disorder, or a disease associated with obesity, e.g., diabetes, hyperglycemia, hypercholesterolemia or hyperlipidemia. A subject having a target disease or disorder can be identified by routine medical examination, e.g., laboratory tests, organ functional tests, and/or behavior tests. A subject suspected of having any of such target disease/disorder might show one or more symptoms of the disease/disorder. A subject at risk for the disease/disorder can be a subject having one or more of the risk factors for that disease/disorder, for example, a genetic factor. In some instances, the human subject is a child who has, is suspected of having, or is at risk for obesity or a CNS disorder associated with children, for example, attention deficit/hyperactivity disorder (ADHD), autism, Asperger's disorder, obsessive compulsive disorder, depression, suicidal ideation and/or behavior, psychosis, chronic pain, and learning disorder.

The methods and compositions described herein may be used to treat a CNS disorder. Exemplary CNS disorders that can be treated by the methods and compositions described herein include schizophrenia, psychotic disorders, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorders, attention deficit disorder, obsessive compulsive disorder, tic disorders, childhood learning disorders, premenstrual syndrome, depression, major depressive disorder, anhedonia, suicidal ideation and/or behaviors, bipolar disorder, anxiety disorders, panic disorder, post-traumatic stress disorder, chronic mild and unpredictable stress, eating disorders, addiction disorders, personality disorders, Parkinson's disorder, Huntington's disorder, multiple sclerosis, amyotrophic lateral sclerosis, ataxia, Friedreich's ataxia, Tourette's syndrome, nocturnal enuresis, non-epileptic seizures, blepharospasm, Duchenne muscular dystrophy, stroke, chronic pain, neuropathic pain including hyperalgesia and allodynia, diabetic polyneuropathy, and chronic pain syndromes.

A disease associated with obesity includes diseases and disorders that lead to obesity, as well as diseases and disorders that have a high occurrence rate in obesity patients. Obesity is a medical condition characterized by accumulation of excess body fat to the extent that it may have a negative effect on health. Obesity may be determined by body mass index (BMI), a measurement obtained by dividing a person's weight by the square of the person's height. For example, BMI over 30 kg/m$^2$ may indicate obesity. Exemplary diseases associated with obesity include, but are not limited to, eating disorders, anorexia nervosa, bulimia nervosa, stroke, coronary heart disease, heart attack, congestive heart failure, congenital heart disease, hypertension, diabetes mellitus, hyperlipidemia, hypercholesterolemia, non-alcoholic steatohepatitis, insulin resistance, hyperuricemia, hypothyroidism, osteoarthritis, gallstones, infertility (e.g., hypogonadism and hyperandrogegism), obesity hypoventilation syndrome, obstructive sleep apnea, chronic obstructed pulmonary disease, and asthma.

In some embodiments, the human subject is administered with a compound described herein (e.g., a compound of formula (I)) at a frequency of four times a day to one time every three months, inclusive. In some embodiments, the human subject is administered with a compound described herein (e.g., a compound of formula (I)) at a frequency of four times a day, three doses a day, two doses a day, one dose a day, one dose every other day, one dose every third day, one dose every week, one dose every other week, one dose monthly, one dose every other month, or one time every three months. In some embodiments, the human subject is administered with a compound described herein (e.g., a compound of formula (I)) at a frequency of one time a day, two times a day, three times a day, four times a day, five times a day, six times a day, seven times a day, eight times a day, nine times a day, or ten times a day. In some embodiments, the human subject is administered with a compound described herein (e.g., a compound of formula (I)) at a frequency of four times a day. In some embodiments, the human subject is administered with a compound described herein (e.g., a compound of formula (I)) at a frequency of one time every three months. In some embodiments, the human subject is administered with a compound described herein (e.g., a compound of formula (I)) at a frequency of one time every one month, one time every two months, one time every three months, one time every four months, one time every five months, or one time every six months. In some embodiments, the human subject is treated concurrently with, prior to, or subsequent to, one or more additional pharmaceutical agents for treating and/or reducing the risk for a CNS disorder or a disease associated with obesity.

As used herein, "an effective amount" refers to the amount of each active agent (e.g., the compounds of Formula (I) as described herein) required to confer therapeutic effect on the subject, either alone or in combination with one or more other active agents, such as one or more of the second therapeutic agents described herein. In some embodiment, the therapeutic effect is to inhibit the activity of DAAO (e.g., by at least 20%, 30%, 40%, 50%, 60%, 70%, 80%, 90%, 95%, or higher) in the subject. In some embodiments, the therapeutic effect is improvement of basic behavioral functioning, weight reduction, hyperactivity, anxiety, depression, suicidal ideation and/or behavior, sensorimotor gating, pain threshold, memory, and/or improvement of cognitive functioning. In some embodiments, the therapeutic effect is alleviating one or more symptoms associated with any of the CNS disorders described herein. Alternatively, or in addition, the therapeutic effect is maintaining or reducing body weight of the subject.

N-methyl-D-aspartate (NMDA) receptor is a subtype glutamatergic receptor that plays a critical role in cognition, memory and neurotoxicity. Regulation of NMDA receptor is suggested to be beneficial for treating diseases of the central nervous system. D-amino acid oxidase (DAAO) is a peroxisomal enzyme that oxidizes D-amino acids to the corresponding imino acids. It has been reported that DAAO is involved in the metabolism of brain D-amino acids, including D-serine, and the regulation of the glutamatergic neurotransmission. As such, DAAO is a target for treating central nervous system (CNS) disorders that are associated with D-serine and/or glutamatergic neurotransmission. In addition, DAAO degrades D-serine to 3-hydroxypyruvate, a potential mediator of type II diabetes mellitus (Zhang, 2015). This suggests that DAAO inhibitors can be used to treat obesity, diabetes mellitus and hyperlipidemia.

Determination of whether an amount of the composition as described herein achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration, genetic factors and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration and/or route of administration may be determined and adjusted over the course of therapy, and is generally, but not necessarily, based on treatment and/or suppression and/or amelioration and/or delay of a target disease/disorder. Alternatively, sustained continuous release formulations of a composition as described herein may be appropriate. Various formulations and devices for achieving sustained release are known in the art.

Generally, for administration of any of the compositions, an exemplary daily dosage might range from about any of 0.1 µg/kg to 3 µg/kg to 30 µg/kg to 300 µg/kg to 3 mg/kg, to 30 mg/kg to 100 mg/kg, to 300 mg/kg, to 1 gram/kg or more, depending on the factors mentioned above. For repeated administrations over several days or longer, depending on the condition, the treatment is sustained until a desired suppression of symptoms occurs or until sufficient therapeutic levels are achieved to alleviate a target disease or disorder, or a symptom thereof. An exemplary dosing regimen comprises administering one or more initial doses at a suitable interval over a suitable period. If necessary, multiple maintenance doses can be given to the subject at a suitable interval over a suitable period of time. However, other dosage regimens may be useful, depending on the pattern of pharmacokinetic decay that the practitioner wishes to achieve. For example, dosing from one to twenty-four times a day or a week is contemplated. In some embodiments, dosing ranging from about 3 µg/mg to about 2 mg/kg (such as about 3 µg/mg, about 10 µg/mg, about 30 µg/mg, about 100 µg/mg, about 300 µg/mg, about 1 mg/kg, about 3 mg/kg, about 30 mg/kg, and about 300 mg/kg) may be used. In some embodiments, dosing frequency can be continuously for the period medically or therapeutically needed, every one hour, every two hour, four times a day, three times a day, twice a day, once a day, once every other day, once every week, once every 2 weeks, once every 4 weeks, once every 2 months, once every 3 months or only given once. The dosing regimen can vary over time.

In some embodiments, for an adult patient of normal weight, doses ranging from about 0.3 to 500.00 mg/kg/day (e.g., 0.5 to 400 mg/kg/day, 1-300 mg/kg/day, 5-300 mg/kg/day, or 10-200 mg/kg/day) may be administered. The particular dosage regimen, i.e., dose, timing and repetition, will depend on the particular individual and that individual's medical history, as well as the properties of the individual agents (such as the half-life of the agent, and other considerations well known in the art).

Conventional methods, known to those of ordinary skill in the art of medicine, can be used to administer the composition (e.g., a pharmaceutical composition, a health food composition, a nutraceutical composition or a medical food composition) to the subject, depending upon the type of viral infection disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques.

The composition can be administered by pulmonary delivery system, that is, the active pharmaceutical ingredient is administered into lung. The pulmonary delivery system can be an inhaler system. In some embodiments, the inhaler system is a pressurized metered dose inhaler, a dry powder inhaler, or a nebulizer. In some embodiments, the inhaler system is with a spacer.

In some embodiments, the pressurized metered dose inhaler includes a propellant, a co-solvent, and/or a surfactant. In some embodiments, the propellant is selected from the group comprising of fluorinated hydrocarbons such as trichloromono-fluoromethane, dichloro-difluoromethane, dichloro-tetrafluoroethane, chloropenta-fluoroethane, monochloro-difluoroethane, difluoroethane, tetrafluoroethane, heptafluoropropane, octafluoro-cyclobutane. In some embodiments, the co-solvent is selected from the group comprising of purified water, ethanol, propylene glycol, glycerin, PEG400, PEG600, PEG800 and PEG1000. In some embodiments, the surfactant or lubricants is selected from the group comprising of sorbitan trioleate, soya lecithin, lecithin, oleic acid, Polysorbate 80, magnesium stearate and sodium laury sulfate. In some embodiments, the preservatives or antioxidants is selected from the group comprising of methyparaben, propyparaben, chlorobutanol, benzalkonium chloride, cetylpyridinium chloride, thymol, ascorbic acid, sodium bisulfite, sodium metabisulfite, sodium bisulfate, EDTA. In some embodiments, the pH adjustments or tonicity adjustments is selected from the group comprising of sodium oxide, tromethamine, ammonia, HCl, $H_2SO_4$, $HNO_3$, citric acid, $CaCl_2$, $CaCO_3$.

In some embodiments, the dry powder inhaler includes a disperse agent. In some embodiments, the disperse agent or carrier particle is selected from the group comprising of lactose, lactose monohydrate, lactose anhydrate, mannitol, dextrose which their particle size is about 1-100 µm.

In some embodiments, the nebulizer may include a co-solvent, a surfactant, lubricant, preservative and/or antioxidant. In some embodiments, the co-solvent can be purified water, ethanol, propylene glycol, glycerin, PEG (e.g. PEG400, PEG600, PEG800, PEG1000), or a combination thereof.

In some embodiments, the surfactant or lubricant can be sorbitan trioleate, soya lecithin, lecithin, oleic acid, magnesium stearate, sodium laury sulfate, or a combination thereof.

In some embodiments, the preservative or antioxidant can be sodium benzoate, potassium benzoate, calcium benzoate, methyparaben, propyparaben, chlorobutanol, benzalkonium chloride, cetylpyridinium chloride, thymol, ascorbic acid, sodium bisulfite, sodium metabisulfite, sodium bisulfate, EDTA, or a combination thereof.

In some embodiments, the nebulizer further includes a pH adjustment or a tonicity adjustment, which can be sodium oxide, tromethamine, ammonia, HCl, $H_2SO_4$, $HNO_3$, citric acid, $CaCl_2$, $CaCO_3$, or a combination thereof.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water-soluble antibodies can be administered by the drip method, whereby a pharmaceutical formulation the composition described herein and a physiologically acceptable excipient is infused. Physiologically acceptable excipients may include, for example, 5% dextrose, 0.9% saline, Ringer's solution or other suitable excipients. Intramuscular preparations, e.g., a sterile formulation of a suitable soluble salt form of the composition herein, can be dissolved and administered in a pharmaceutical excipient such as Water-for-Injection, 0.9% saline, or 5% glucose solution.

In one embodiment, the composition is administered via a site-specific or targeted local delivery technique. Examples of site-specific or targeted local delivery techniques include various implantable depot sources of the compositions or local delivery catheters, such as infusion catheters, an indwelling catheter, or a needle catheter, endotracheal tube, endobronchial catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568. Treatment efficacy for a target disease/disorder can be assessed by methods well-known in the art.

In some embodiments, the invention is related to a method of treating coronavirus infection, comprising administering to a subject in need thereof an effective amount of the compound or the composition disclosed herein.

In some embodiments, the coronavirus virus is selected from the group consisting of SARS-CoV-2, severe acute respiratory syndrome coronavirus (SARS-CoV), middle east respiratory syndrome coronavirus (MERS-CoV), 229E alpha coronavirus, NL63 alpha coronavirus, OC43 beta coronavirus, and HKU1 beta coronavirus. In some embodiments, the subject to be treated by the method discloses has COVID-19, a disease caused by SARS-CoV-2 infection.

In some embodiments, the composition is placed in a medical device selected from the group consisting of an inhaler, a nebulizer, a nasal spray, and a vaporization aerosol device for administration to the subject.

In some embodiments, the subject is a human subject, for example, a human subject having infection or suspected of having infection by a coronavirus. In some examples, the human subject has COVID-19 or suspected of having COVID-19 (e.g., having one or more symptoms associated with COVID-19).

In some embodiments, the human subject is treated concurrently with, prior to, or subsequent to, one or more additional anti-viral agents. In some examples, the additional anti-viral agents comprise a viral entry inhibitor, a viral uncoating inhibitor, a viral reverse transcriptase inhibitor, a viral protein synthesis inhibitor, a viral protease inhibitor, a viral polymerase inhibitor, a viral integrase inhibitor, an interferon, and/or the combination thereof.

Exemplary viral entry inhibitors include maraviroc, enfuvirtide, ibalizumab, fostemsavir, plerixafor, epigallocatechin gallate, vicriviroc, aplaviroc, maraviroc, tromantadine, nitazoxanide, umifenovir, and podofilox. Exemplary viral uncoating inhibitors include amantadine, rimantadine, and pleconaril. Exemplary viral reverse transcriptase inhibitors include zidovudine, didanosine, zalcitabine, stavudine, lamivudine, abacavir, emtricitabine, entecavir, truvada, nevirapine, raltegravir, and tenofovir disoproxil. Exemplary viral protease inhibitors include fosamprenavir, ritonavir, atazanavir, nelfinavir, indinavir, saquinavir, saquinavir, famciclovir, fomivirsen, lopinavir, ribavirin, darunavir, oseltamivir, and tipranavir. Exemplary viral polymerase inhibitors include amatoxins, rifamycin, cytarabine, fidaxomicin, tagetitoxin, foscarnet sodium, idoxuridine, penciclovir, sofosbuvir, trifluridine, valacyclovir, valganciclovir, vidarabine, and remdesivir. Exemplary viral integrase inhibitors include raltegarvir, elvitegravir, dolutegravir, bictegravir, and cabotegravir. Exemplary interferons include type I interferon, type II interferon, type III interferon, and peginterferon alfa-2a.

In some embodiments, the subject is administered the composition continuously or at a frequency of every five minutes to one time every three months.

Combination therapy can also embrace the administration of the agents described herein (e.g., a compound of Formula (I) and an anti-CNS disorder, an anti-obesity agent, or an antiviral agent) in further combination with other biologically active ingredients (e.g., a drug which is therapeutically effective) and non-drug therapies (e.g., surgery).

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; *Animal Cell Culture* (R. I. Freshney, ed. 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds. 1993-8) J. Wiley and Sons; *Methods in Enzymology* (Academic Press, Inc.); *Handbook of Experimental Immunology* (D. M. Weir and C. C. Blackwell, eds.): *Gene Transfer Vectors for Mammalian Cells* (J. M. Miller and M. P. Calos, eds., 1987); *Current Protocols in Molecular Biology* (F. M. Ausubel, et al. eds. 1987); *PCR: The Polymerase Chain Reaction*, (Mullis, et al., eds. 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practice approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

(IV) Method of Preparation

Any of the Formula (I) compounds disclosed herein may be isolated and modified from a suitable natural source. Alternatively, such compounds may be chemically synthesized. The invention is related to a method of preparing the compound of Formula (I), comprising: (a) providing compounds of formula (Ia) and (Ib)

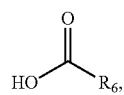
(Ia)

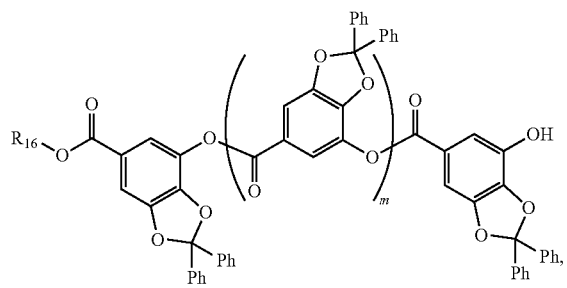
(Ib)

wherein $R_{16}$ is the group selected from alkyl group, alkylsilyl group, or arylsilyl group;
(b) reacting the compound of formula (Ia) with formula (Ib) to produce intermediate I;
(c) de-protecting the $R_{16}$ group to produce intermediate II; and
(d) de-protecting the cyclic acetal groups and purifying the reaction mixture to obtain a compound of current invention.

In some embodiments, provided herein is a method of preparing the compound, comprising:
(a) providing compounds of formula (Ic) and (Id)

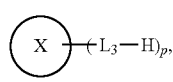
(Ic)

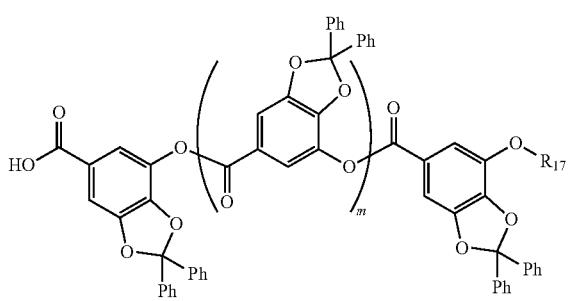
(Id)

wherein p=1, 2, 3, or 4; each of $L_3$, independently, is a moiety selected from the group consisting of NH, O, S, —$((CH_2)_s$—W)—, or absent; $R_{17}$ is the group selected from benzyl group, allyl group, ethoxylmethyl group, methoxylmethyl group, ethoxylethyl group, alkyl silyl group, or aryl silyl group;
(b) reacting the compound of formula (Ic) with formula (Id), to allow conjugation of formula (Id) to one or more of $L_3$ of the formula (Ic), thereby producing intermediate III;
(c) de-protecting the $R_{17}$ group to produce intermediate IV; and
(d) de-protecting the cyclic acetal groups and purifying the reaction mixture to obtain the a compound of current invention.

In some embodiments, the method further comprises the following step after step (c), (e) reacting the intermediate II with formula (Ic) and allowing conjugation of the intermediate II to one or more $L_3$ of the formula (Ic) to produce intermediate V.

In some embodiments, the method further comprises the following step after step (c),
(e) reacting the intermediate IV with formula (Ia) to produce intermediate VI.

In some embodiment, the invention is related to a method of preparing the compound (Ia), comprising:
(a) providing compound of formula (Ie);

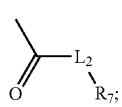
(Ie)

(b) reacting the compound of formula (Ie) with strong organic base under −78° C. to 0° C. to produce a first intermediate VII;
(c) reacting the first intermediate VII with alkyl group protected oxalic acid to produce a second intermediate VIII;
(d) reacting the second intermediate VIII with a cycloling reagent to produce a third intermediate IX; and,
(e) de-protecting the alkyl group of the protected oxalic acid to obtain the formula (Ia).

In some embodiment, the strong organic base in step (b) is alkali alkoxide, alkyl lithium, lithium alkylamide, lithium alkylsilylamide.

In some embodiment, the cycloling reagent in step (d) is hydrazine, hydrazine hydrate, hydroxyl amine, or any acceptable salts of which thereof.

EXAMPLES

In order that the invention described may be more fully understood, the following examples are set forth. The examples described in this application are offered to illustrate the methods and compositions provided herein and are not to be construed in any way as limiting their scope.

Example 1. Synthesis of 7-(allyloxy)-2,2-diphenyl-benzo[d][1,3]dioxole-5-carbonyl chloride (5)

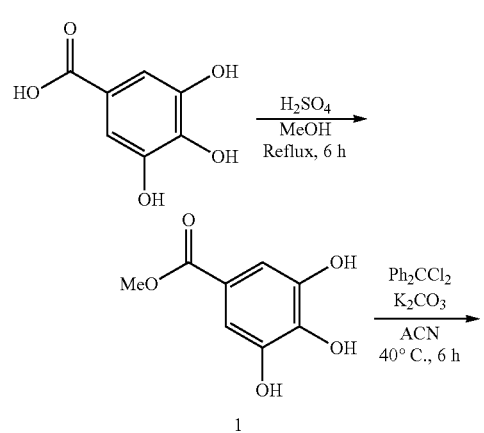

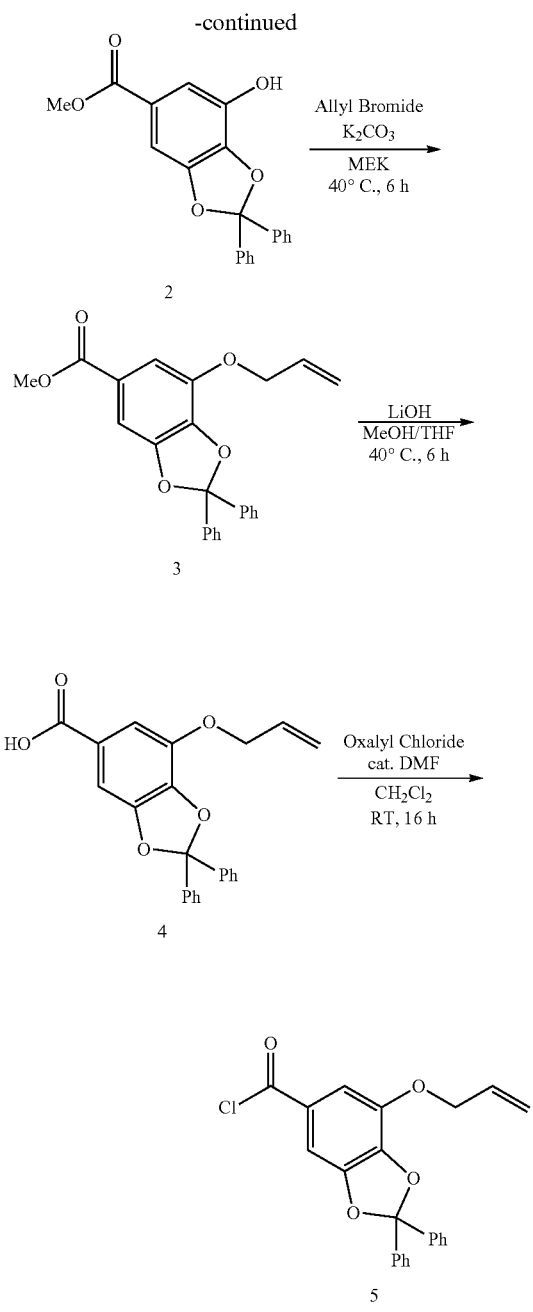

Preparation of methyl 3,4,5-trihydroxybenzoate (1)

To a solution of 3,4,5-trihydroxybenzoic acid (10.0 g, 58.8 mmol) in methanol (118.0 mL) at RT was added sulfuric acid (3.1 mL, 58.8 mmol). The resulting mixture was heated to reflux for 6 h. After the reaction was complete, the reaction mixture was concentrated under vacuum. The residue was diluted with EtOAc, extracted with water, washed with brine, dried over anhydrous magnesium sulfate and filtered. The filtrate was concentrated in vacuo to afford methyl 3,4,5-trihydroxybenzoate (1) as a white solid (9.6 g, 89%). $^1$H NMR (MeOD, 400 MHz) δ 7.03 (s, 2H), 3.81 (s, 3H).

Preparation of methyl 7-hydroxy-2,2-diphenylbenzo[d][1,3]dioxole-5-carboxylate (2)

To a solution of 3,4,5-trihydroxybenzoate (1, 10.0 g, 54.3 mmol) in acetonitrile (543.0 mL) was added potassium carbonate (15.0 g, 108.6 mmol) and α,α-dichlorodiphenylmethane (9.9 mL, 51.6 mmol). The mixture was stirred at 40° C. for 6 h. After the reaction was complete, the mixture was concentrated under vacuum. The residue was diluted with dichloromethane, extracted with water, washed with brine, dried over anhydrous magnesium sulfate and filtered. The filtrate was concentrated in vacuo. The resulting residue was purified by F.C. with EtOAc/hexanes (1:3) to afford methyl 7-hydroxy-2,2-diphenylbenzo[d][1,3]dioxole-5-carboxylate (2) as a white solid (10.5 g, 55%). $^1$H NMR (CDCl$_3$, 400 MHz) δ 7.57-7.55 (m, 4H), 7.39-7.34 (m, 7H), 7.20 (s, 1H), 3.84 (s, 3H).

Preparation of methyl 7-(allyloxy)-2,2-diphenylbenzo[d][1,3]dioxole-5-carboxylate (3)

To a solution of methyl 7-hydroxy-2,2-diphenylbenzo[d][1,3]dioxole-5-carboxylate (2, 10.0 g, 28.7 mmol) in methyl ethyl ketone (144.0 mL) was added potassium carbonate (7.9 g, 57.4 mmol) and allyl bromide (8.7 mL, 100.5 mmol). The mixture was stirred at 40° C. for 6 h. After the reaction was complete, the mixture was concentrated in vacuo. The residue was diluted with dichloromethane, extracted with water, washed with brine, dried over anhydrous magnesium sulfate and filtered. The filtrate was stripped down in vacuo. The residue was purified by F.C. with EtOAc/hexanes (1:4) to afford Methyl 7-(allyloxy)-2,2-diphenylbenzo[d][1,3]dioxole-5-carboxylate (3) as a white solid (10.4 g, 93%). $^1$H NMR (CDCl$_3$, 400 MHz) δ 7.59-7.57 (m, 4H), 7.37 (d, J=5.2 Hz, 6H), 7.32 (s, 1H), 7.26 (s, 1H), 6.09-6.02 (m, 1H), 5.40 (d, J=17.2 Hz, 1H), 5.28 (d, J=10.5 Hz, 1H), 4.70 (d, J=5.4 Hz, 2H), 3.85 (s, 3H).

Preparation of 7-(allyloxy)-2,2-diphenylbenzo[d][1,3]dioxole-5-carboxylic acid (4)

To a solution of methyl 7-(allyloxy)-2,2-diphenylbenzo[d][1,3]dioxole-5-carboxylate (3, 10.0 g, 28.7 mmol) in methanol/tetrahydrofuran (1:1, 102.0 mL) was added lithium hydroxide (1.2 g, 51.5 mmol). The resulting mixture was stirred at 40° C. for 6 h. The mixture was concentrated under vacuum. The resulting residue was made acidic (pH=5) with the dropwise addition of 10% hydrochloric acid. The solid was collected and purified by recrystallization with EtOAc/hexanes (1:4) to afford 7-(allyloxy)-2,2-diphenylbenzo[d][1,3]dioxole-5-carboxylic acid (4) as a white solid (9.0 g, 93%). $^1$H NMR (CDCl$_3$, 400 MHz) δ 7.60-7.58 (m, 4H), 7.38-7.37 (m, 7H), 7.32 (s, 1H), 6.11-6.01 (m, 1H), 5.41 (d, J=17.2 Hz, 1H), 5.29 (d, J=10.8 Hz, 1H), 4.71 (d, J=5.2 Hz, 2H).

Preparation of 7-(allyloxy)-2,2-diphenylbenzo[d][1,3]dioxole-5-carbonyl chloride (5)

To a stirring solution of 7-(allyloxy)-2,2-diphenylbenzo[d][1,3]dioxole-5-carboxylic acid (4, 9.0 g, 24.0 mmol) in dichloromethane (120.0 mL) was added oxalyl chloride (6.2 mL, 72.1 mmol) and DMF (0.1 mL) at 0° C. The mixture was stirred at RT for 16 h. The mixture was concentrated under vacuum to afford 7-(allyloxy)-2,2-diphenylbenzo[d][1,3]dioxole-5-carbonyl chloride (5, 9.1 g, crude) as a yellow solid. $^1$H NMR (CDCl$_3$, 400 MHz) δ 7.59-7.58 (m, 4H), 7.42-7.39 (m, 8H), 6.11-6.01 (m, 1H), 5.44 (dd, J=17.2, 1.2 Hz, 1H), 5.33 (dd, J=10.4, 0.9 Hz, 1H), 4.73 (d, J=5.4 Hz, 2H).

Example 2. Synthesis of 7-((7-(allyloxy)-2,2-diphenylbenzo[d][1,3]dioxole-5-carbonyl)oxy)-2,2-diphenylbenzo[d][1,3]dioxole-5-carboxylic acid (9)

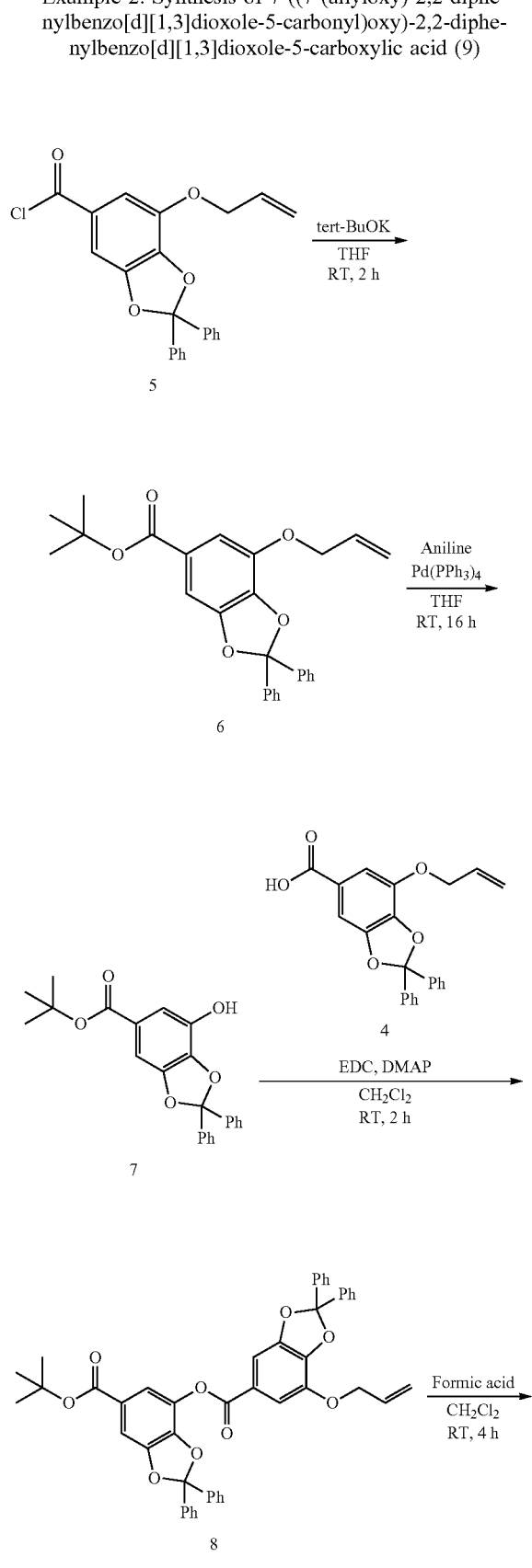

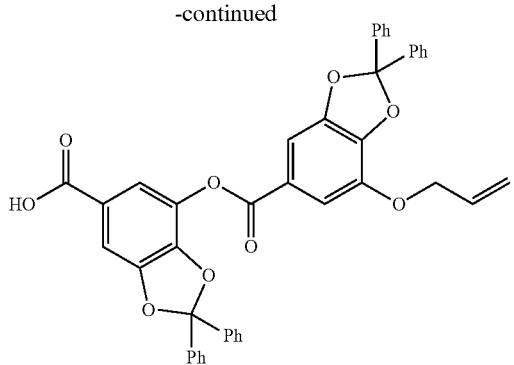

Preparation of tert-butyl 7-(allyloxy)-2,2-diphenylbenzo[d][1,3]dioxole-5-carboxylate (6)

To a solution of 7-(allyloxy)-2,2-diphenylbenzo[id][1,3]dioxole-5-carbonyl chloride (5, 30.0 g, 76.5 mmol) in tetrahydrofuran (300.0 mL) was added potassium tert-butoxide (10.3 g, 91.8 mmol) solution which in tetrahydrofuran (100 mL) under $N_2$ at 0° C. The mixture was stirred at RT for 2 h. After the reaction was complete, the residue was diluted with EtOAc, extracted with water, washed with brine, dried over anhydrous magnesium sulfate and filtered. The filtrate was stripped down in vacuo. The residue was purified by F.C. with EtOAc/hexanes (1:8) to afford the compound 6 as a white solid (32 g, 97%). $^1$H NMR (CDCl$_3$, 400 MHz) δ 7.60-7.57 (m, 4H), 7.39-7.35 (m, 6H), 7.29-7.28 (d, J=1.2 Hz, 1H), 7.22-7.21 (d, J=1.2 Hz, 1H), 6.11-6.01 (m, 1H), 5.42-5.38 (dd, J=17.2, 1.5 Hz, 1H), 5.29-5.26 (dd, J=10.5, 1.3 Hz 1H), 4.71-4.69 (d, J=5.6 Hz, 2H), 1.55 (s, 9H).

Preparation of tert-butyl 7-hydroxy-2,2-diphenylbenzo[d][1,3]dioxole-5-carboxylate (7)

To a stirred solution of tert-butyl 7-(allyloxy)-2,2-diphenylbenzo[d][1,3]dioxole-5-carboxylate (6, 32.0 g, 74.3 mmol) in anhydrous tetrahydrofuran (766.0 mL) was added aniline (5.2 mL, 37.2 mmol) and tetrakis(triphenyl phosphine)palladium (8.6 g, 7.43 mmol). The mixture was stirred at RT under $N_2$ for 16 h. The mixture was filtered through a bed of Celite and the filtrate was concentrated in vacuo. The residue was purified by F.C. with EtOAc/hexanes (1:4) to afford the compound 7 (27 g, 93%) as a white solid. $^1$H NMR (CDCl$_3$, 400 MHz) δ 7.61-7.58 (m, 4H), 7.40-7.38 (m, 7H), 7.19-7.18 (d, J=1.4 Hz, 1H), 6.14 (br, 1H), 1.58 (s, 9H).

Preparation of 6-(tert-butoxycarbonyl)-2,2-diphenylbenzo[d][1,3]dioxol-4-yl 7-(allyloxy)-2,2-diphenylbenzo[d][1,3]dioxole-5-carboxylate (8)

A mixture of the compound 7 (27 g, 69.2 mmol), 7-(allyloxy)-2,2-diphenylbenzo[d][1,3]-dioxole-5-carboxylic acid (4, 27.2 g, 72.6 mmol) and 4-dimethylaminopyridine (0.84 g, 6.9 mmol) in dichloromethane (692.0 mL) was stirred at 0° C., added 1-ethyl-3-(3-dimethyl-aminopropyl) carbodiimide (14.6 g, 76.1 mmol) and the mixture was stirred 10 mins at 0° C. then back to RT. After the reaction was complete, the mixture was extracted with water, washed with brine, dried over anhydrous magnesium sulfate and filtered. The filtrate was evaporated in vacuo. The residue was purified by F.C. with EtOAc/hexanes (1:9) to afford the compound 8 (48.2 g, 93%) as a white solid. $^1$H NMR (CDCl$_3$, 400 MHz) δ 7.64-7.61 (m, 4H), 7.59-7.56 (m, 4H), 7.54-7.53 (d, J=1.5 Hz, 1H), 7.50-7.49 (d, J=1.5 Hz, 1H), 7.47-7.45 (m, 2H), 7.43-7.38 (m, 12H), 6.16-6.06 (m, 1H), 5.48-5.43 (dd, J=17.2, 1.4 Hz, 1H), 5.34-5.31 (dd, J=10.4, 1.2 Hz, 1H), 4.78-4.76 (d, J=5.5 Hz, 2H), 1.57 (s, 9H).

Preparation of 7-((7-(allyloxy)-2,2-diphenylbenzo[d][1,3]dioxole-5-carbonyl)oxy)-2,2-diphenylbenzo[d][1,3]dioxole-5-carboxylic acid (9)

To a stirred solution of the compound 8 (28.2 g, 37.8 mmol) in anhydrous dichloromethane (377.6 mL) was added formic acid (377.6 mL) at 0° C. After 10 mins, stirred 4 h at RT. the mixture was extracted with water 3 times, washed with brine, dried over anhydrous magnesium sulfate and filtered. The filtrate was evaporated in vacuo. The residue was purified by F.C. with EtOAc/dichloromethane (3:7) to afford the compound 9 (16.0 g, 61%) as a white solid. $^1$H NMR (CDCl$_3$, 400 MHz) δ 7.61-7.58 (m, 5H), 7.56-7.53 (m, 4H), 7.51-7.49 (m, 2H), 7.46-7.45 (d, J=1.5 Hz, 1H), 7.41-7.37 (m, 12H), 6.12-6.03 (m, 1H), 5.45-5.40 (d, J=17.2, 1.5 Hz, 1H), 5.32-5.28 (d, J=10.8, 1.3 Hz, 1H), 4.75-4.73 (d, J=1.4 Hz, 5.5, 2H).

Example 3. Synthesis of 3-((3,4-dihydroxy-5-((3,4,5-trihydroxybenzoyl)oxy)benzoyl)oxy)-4,5-dihydroxybenzoic acid (14)

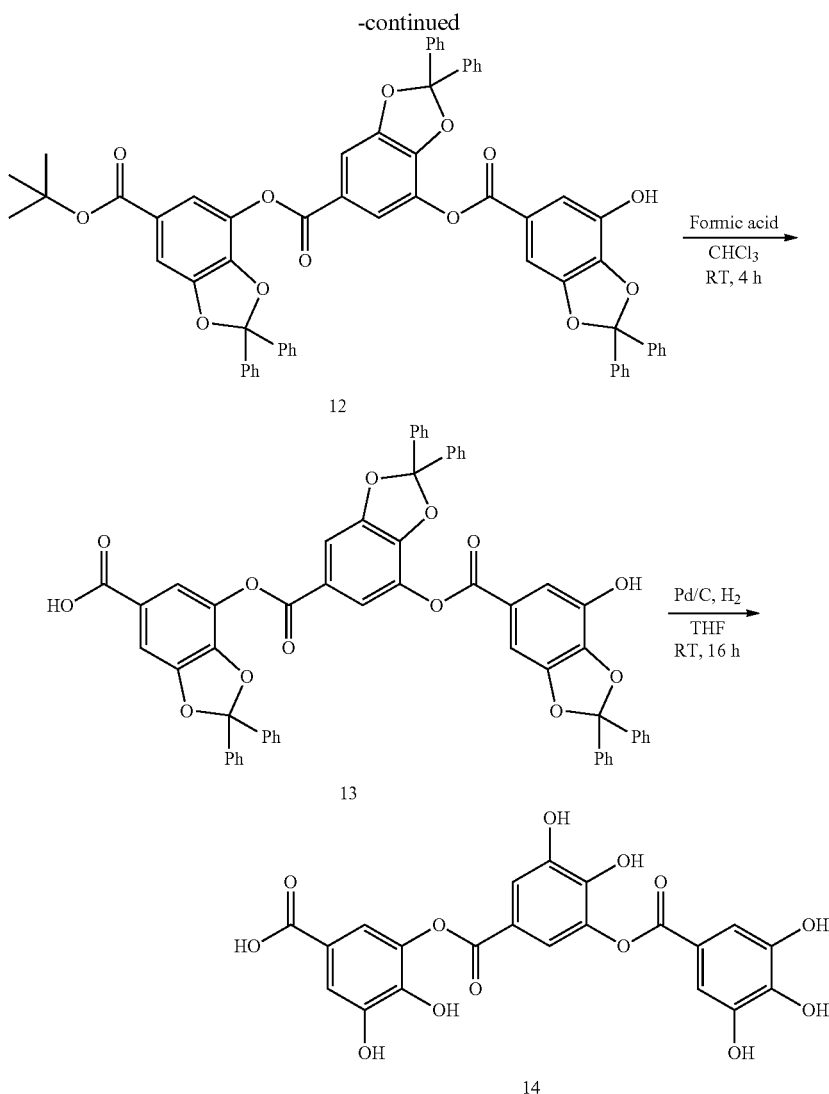

Preparation of 6-(tert-butoxycarbonyl)-2,2-diphenylbenzo[d][1,3]dioxol-4-yl 7-hydroxy-2,2-diphenylbenzo[d][1,3]dioxole-5-carboxylate (10)

To a stirred solution of 7-(allyloxy)-2,2-diphenylbenzo[d][1,3]dioxole-5-carbonyl chloride (5, 20.0 g, 26.8 mmol) in anhydrous tetrahydrofuran (267.8 mL) was added aniline (1.9 mL, 13.4 mmol) and tetrakis(triphenyl phosphine)palladium (3.1 g, 2.7 mmol). The mixture was stirred at RT under $N_2$ for 16 h. The mixture was filtered through a bed of Celite and the filtrate was concentrated in vacuo. The residue was purified by F.C. with EtOAc/hexanes (1:5) to afford the compound 10 as a white solid (17.5 g, 92%). $^1$H NMR (CDCl$_3$, 400 MHz) δ 7.62-7.58 (m, 4H), 7.58-7.54 (m, 4H), 7.52-7.51 (d, J=1.4 Hz, 1H), 7.46 (s, 1H), 7.45 (s, 1H), 7.43-7.36 (m, 13H), 5.67 (br, 1H), 1.56 (s, 9H).

Preparation of 6-(tert-butoxycarbonyl)-2,2-diphenylbenzo[d][1,3]dioxol-4-yl 7-((7-(allyloxy)-2,2-diphenylbenzo[d][1,3]dioxole-5-carbonyl)oxy)-2,2-diphenylbenzo[d][1,3]dioxole-5-carboxylate (11)

A mixture of the compound 10 (17.5 g, 24.8 mmol), 7-(allyloxy)-2,2-diphenylbenzo[d][1,3]dioxole-5-carboxylic acid (4, 9.7 g, 26.0 mmol) and 4-dimethylaminopyridine (0.3 g, 2.5 mmol) in dichloromethane (354.0 mL) was stirred at 0° C., added 1-ethyl-3-(3-dimethylaminopropyl)carbodiimide (9.7 g, 26.0 mmol) and the mixture was stirred 10 mins at 0° C. then back to RT. After the reaction was complete, the mixture was extracted with water, washed with brine, dried over anhydrous magnesium sulfate and filtered. The filtrate was evaporated in vacuo. The residue was purified by F.C. with EtOAc/hexanes (1:8) to afford the compound 11 (25.0 g, 95%) as a white solid. $^1$H NMR (CDCl$_3$, 400 MHz) δ 7.74-7.73 (d, J=1.5 Hz, 1H), 7.66-7.65 (d, J=1.5 Hz, 1H), 7.62-7.52 (m, 12H), 7.52-7.51 (d, J=1.4 Hz, 1H), 7.48-7.47 (d, J=1.4 Hz, 1H), 7.43-7.34 (m, 20H), 6.13-6.03 (m, 1H), 5.46-5.41 (dd, J=17.2, 1.4 Hz, 1H), 5.32-5.29 (dd, J=10.5, 1.1 Hz, 1H), 4.76-4.74 (d, J=5.4 Hz, 2H).

Preparation of 6-(tert-butoxycarbonyl)-2,2-diphenylbenzo[d][1,3]dioxol-4-yl 7-((7-hydroxy-2,2-diphenylbenzo[d][1,3]dioxole-5-carbonyl)oxy)-2,2-diphenylbenzo[d][1,3]dioxole-5-carboxylate (12)

To a stirred solution of the compound 11 (25.0 g, 23.5 mmol) in anhydrous tetrahydrofuran (235.2 mL) was added aniline (1.6 mL, 11.8 mmol) and tetrakis(triphenyl phosphine)palladium (2.7 g, 2.4 mmol). The mixture was stirred at RT under $N_2$ for 16 h. The mixture was filtered through a bed of Celite and the filtrate was concentrated in vacuo. The residue was purified by F.C. with EtOAc/hexanes (1:4) to afford the compound 12 as a white solid (22.2 g, 91%). $^1$H NMR (CDCl$_3$, 400 MHz) δ 7.75-7.74 (d, J=1.6 Hz, 1H), 7.67-7.66 (d, J=1.5 Hz, 1H), 7.62-7.55 (m, 12H), 7.52-7.51 (d, J=1.5 Hz, 1H), 7.45-7.37 (m, 21H), 5.50 (br, 1H), 1.56 (s, 9H).

Preparation of 7-((7-((7-hydroxy-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (13)

A solution of the compound 12 (250 mg, 0.24 mmol) in formic acid/chloroform (33 vol. %, 7.2 mL) was stirred under 60° C., 90 mins. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 13 as an off-white solid (163 mg, 69%). $^1$H NMR (CDCl$_3$, 400 MHz) δ 7.72 (d, J=1.6 Hz, 1H), 7.64 (d, J=1.6 Hz, 1H), 7.61-7.52 (m, 13H), 7.49 (dd, J=3.2, 1.5 Hz, 2H), 7.43-7.35 (m, 19H).

Preparation of 3-((3,4-dihydroxy-5-((3,4,5-trihydroxybenzoyl)oxy)benzoyl)oxy)-4,5-dihydroxybenzoic acid (14)

To a flame dried 10 wt % Pd/C solid (115 mg), anhydrous tetrahydrofuran (7.2 mL) and the compound 13 (70 mg, 0.07 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and precipitated with EtOAc/hexanes (1:25) to afford the compound 14 as an off-white solid (25 mg, 73%). $^1$H NMR (MeOD, 400 MHz) δ 7.58-7.53 (m, 1H), 7.48-7.44 (m, 1H), 7.44-7.39 (m, 1H), 7.31-7.11 (m, 3H).

Example 4. 3-((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)-4,5-dihydroxybenzoic acid (18)

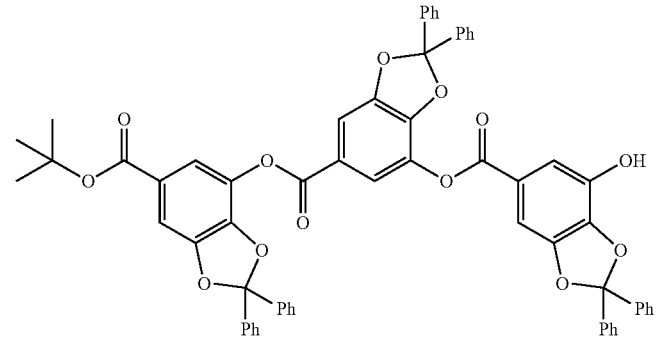

12

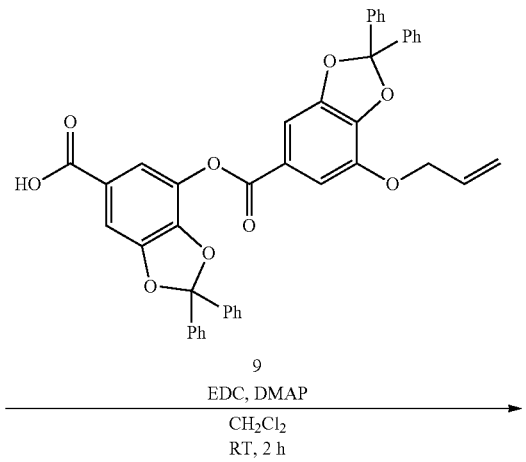

9

EDC, DMAP
CH$_2$Cl$_2$
RT, 2 h

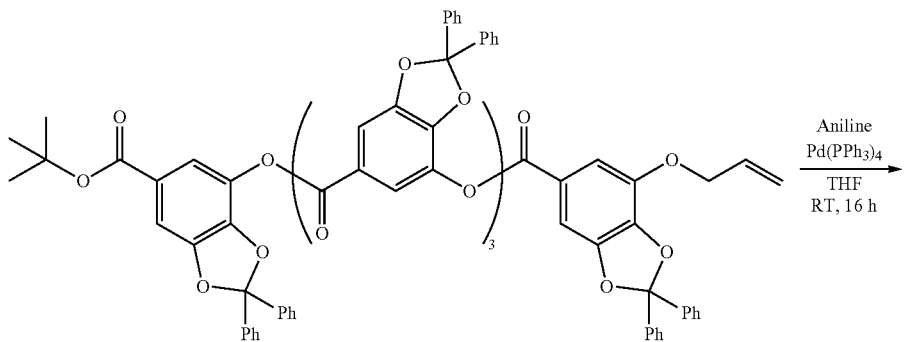

15

Aniline
Pd(PPh$_3$)$_4$
THF
RT, 16 h

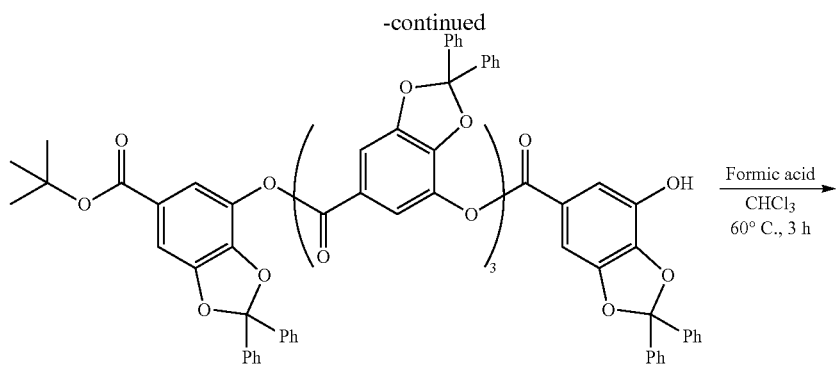

16

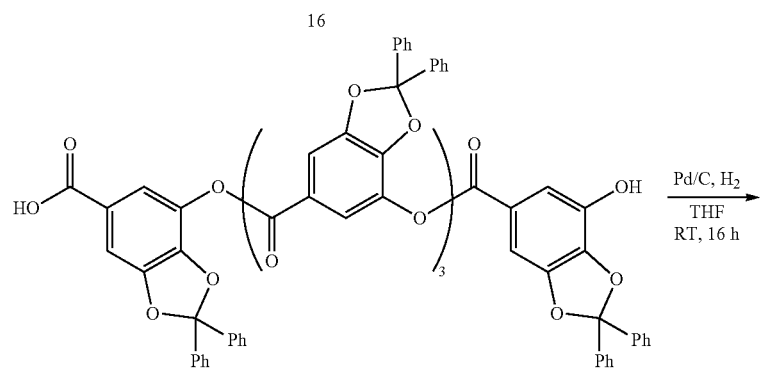

17

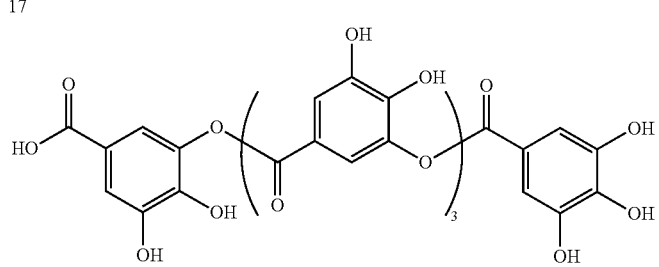

18

Preparation of 6-(tert-butoxycarbonyl)-2,2-diphenylbenzo[d][1,3]dioxol-4-yl 7-((7-((7-((7-(allyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (15)

A mixture of the compound 12 (20.0 g, 19.6 mmol), compound 9 (13.5 g, 19.6 mmol) and 4-dimethylaminopyridine (0.24 g, 2.0 mmol) in dichloromethane (325.8 mL) was stirred at 0° C., added 1-ethyl-3-(3-dimethylaminopropyl) carbodiimide (4.1 g, 21.5 mmol) and the mixture was stirred 10 mins at 0° C. then back to RT. After the reaction was complete, the mixture was extracted with water, washed with brine, dried over anhydrous magnesium sulfate and filtered. The filtrate was evaporated in vacuo. The residue was purified by F.C. with dichloromethane/hexanes (3:2) to afford the compound 15 (31.4 g, 95%) as a white solid. $^1$H NMR (CDCl$_3$, 400 MHz) δ 7.78-7.75 (m, 3H), 7.70-7.67 (m, 3H), 7.65-7.55 (m, 20H), 7.55-7.54 (d, J=1.4 Hz, 1H), 7.51-7.50 (d, J=1.4 Hz, 1H), 7.46 (s, 2H), 7.44-7.37 (m, 30H), 6.15-6.06 (m, 1H), 5.49-5.43 (dd, J=17.2, 1.4 Hz, 1H), 5.35-5.31 (dd, J=10.5, 1.2 Hz, 1H), 4.78-4.76 (d, J=5.5 Hz, 2H), 1.57 (s, 9H).

Preparation of 6-(tert-butoxycarbonyl)-2,2-diphenylbenzo[d][1,3]dioxol-4-yl 7-((7-((7-((7-hydroxy-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (16)

To a nitrogen flushed solution of the compound 15 (8.0 g, 4.72 mmol) and tetrakis(triphenyl phosphine)palladium (551 mg, 2.36 mmol) in dry tetrahydrofuran (63 mL), aniline (0.22 mL, 2.36 mmol) was added and stirred at RT for 12 h. The mixture was extracted with dichloromethane, 1 N hydrochloric acid and brine. The organic residue was dried over magnesium sulfate, evaporated, and purified by F.C. with EtOAc/dichloromethane (5/95) to afford the compound 16 as an off-white solid (7.4 g, 95%). $^1$H NMR (CD$_2$Cl$_2$, 400 MHz) δ 7.76-7.72 (m, 3H), 7.68-7.65 (m, 3H), 7.62-7.49 (m, 22H), 7.45-7.35 (m, 32H), 1.53 (s, 9H).

Preparation of 7-((7-((7-((7-(7-hydroxy-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (17)

A solution of the compound 16 (450 mg, 0.27 mmol) in formic acid/chloroform (50 vol. %, 5.4 mL) was stirred under 60° C., 2 h. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 17 as an off-white solid (252 mg, 58%). $^1$H NMR (CDCl$_3$, 400 MHz) δ 7.75-7.71 (m, 3H), 7.67-7.62 (m, 3H), 7.60-7.52 (m, 21H), 7.49 (d, J=1.5 Hz, 2H), 7.43-7.34 (m, 3H).

Preparation of 3-((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)-4,5-dihydroxybenzoic acid (18)

To a flame dried 10 wt % Pd/C solid (70 mg), anhydrous tetrahydrofuran (7.8 mL) and the compound 17 (124 mg, 0.08 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and precipitated with EtOAc/hexanes (1:25) to afford the compound 18 as an off-white solid (58 mg, 96%). $^1$H NMR (MeOD, 400 MHz) δ 7.62-7.55 (m, 2H), 7.53-7.46 (m, 2H), 7.44-7.10 (m, 6H).

Example 5. 3-((3-((3-((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (22)

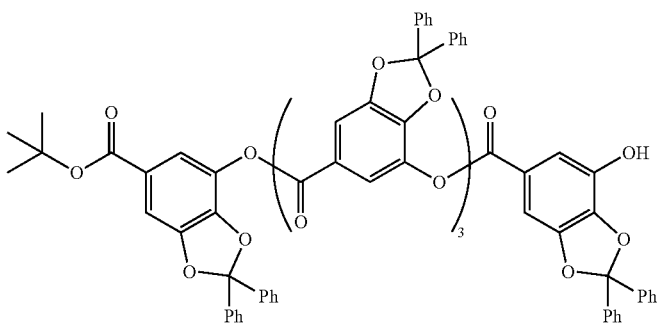

16

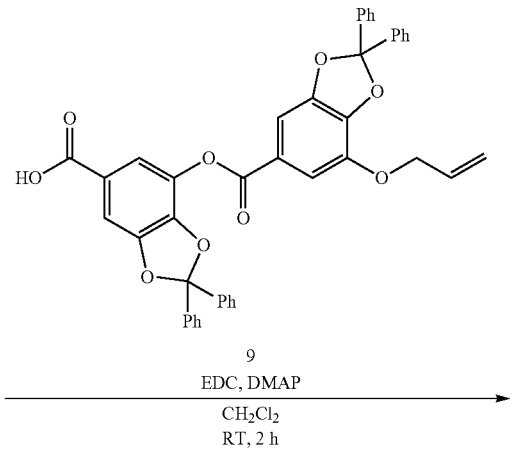

9
EDC, DMAP
CH$_2$Cl$_2$
RT, 2 h

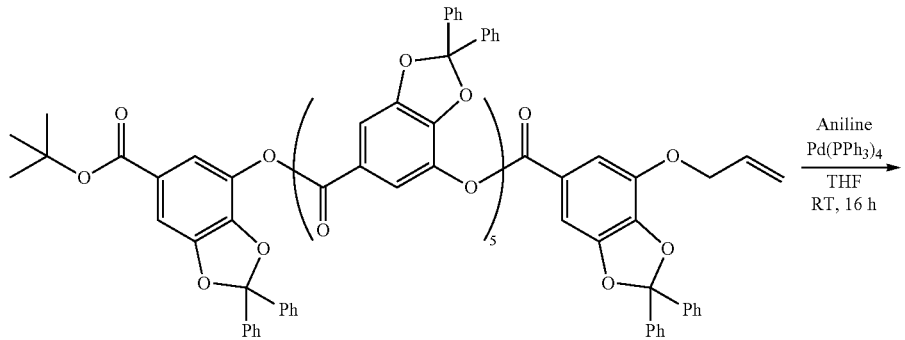

19

Aniline
Pd(PPh$_3$)$_4$
THF
RT, 16 h

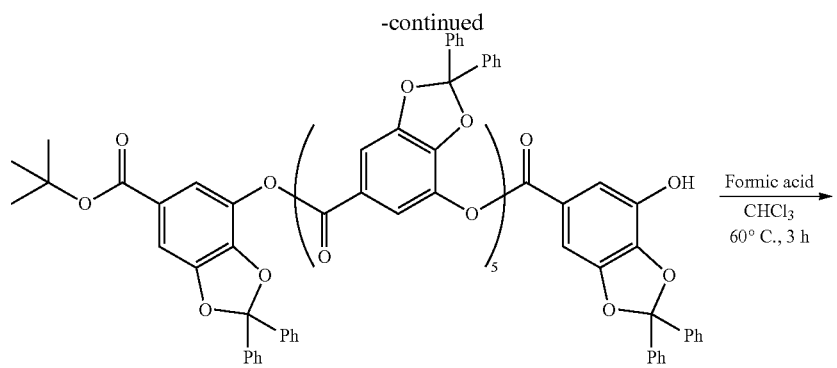

20

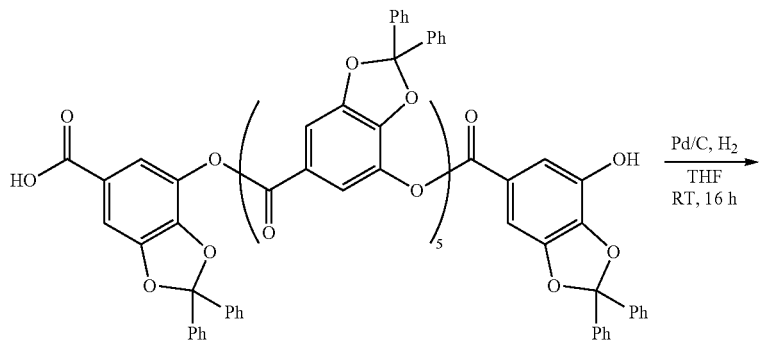

21

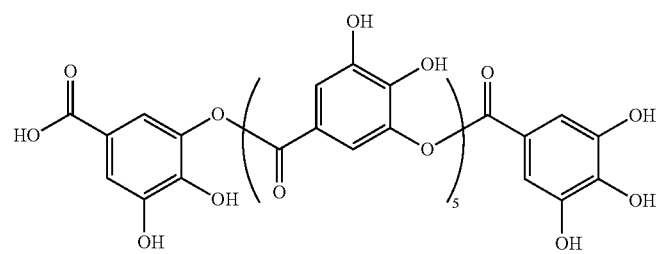

22

Preparation of 6-(tert-butoxycarbonyl)-2,2-diphenylbenzo[d][1,3]dioxol-4-yl 7-((7-((7-((7-((7-(allyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (19)

To a mixture of the compound 16 (850 mg, 0.51 mmol), compound 12 (372 mg, 0.54 mmol) and 4-dimethylaminopyridine (13 mg, 0.10 mmol) in dichloromethane (5.1 mL) at 0° C., 1-ethyl-3-(3-dimethylaminopropyl)carbodiimide hydrochloride (109 mg, 0.56 mmol) was added and stirred back to RT for 2 h. The mixture was extracted with dichloromethane, water, and brine. The organic residue was dried over anhydrous magnesium sulfate, evaporated, and purified by F.C. with hexanes/dichloromethane (30/70). The collected residue was precipitate with dichloromethane/hexanes to afford the compound 19 as an off-white solid (1033 mg, 86%). $^1$H NMR (CDCl$_3$, 400 MHz) δ 7.76-7.32 (m, 84H), 6.12-6.02 (m, 1H), 5.48-5.37 (m, 1H), 5.32-5.28 (m, 1H), 4.76-4.71 (m, 2H), 1.53 (s, 9H).

Preparation of 6-(tert-butoxycarbonyl)-2,2-diphenylbenzo[d][1,3]dioxol-4-yl 7-((7-((7-((7-((7-hydroxy-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (20)

To a nitrogen flushed solution of the compound 19 (1.0 g, 0.43 mmol) and tetrakis(triphenyl phosphine)palladium (50 mg, 0.04 mmol) in dry tetrahydrofuran (9 mL), aniline (0.03 mL, 0.26 mmol) was added and stirred at RT for 16 h. The mixture was extracted with dichloromethane, 1 N hydrochloric acid and brine. The organic residue was dried over magnesium sulfate, evaporated, and purified by F.C. with EtOAc/dichloromethane (5/95) to afford the compound 20 as an off-white solid (899 mg, 92%). $^1$H NMR (CDCl$_3$, 400 MHz) δ 7.76-7.28 (m, 84H), 1.53 (s, 9H).

Preparation of 7-((7-((7-((7-((7-((7-hydroxy-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (21)

A solution of the compound 20 (250 mg, 0.27 mmol) in formic acid/chloroform (33 vol. %, 6.5 mL) was stirred under 60° C., 2 h. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 21 as an off-white solid (142 mg, 58%). $^1$H NMR (CDCl$_3$, 400 MHz) δ 7.75-7.51 (m, 38H), 7.50-7.47 (m, 2H), 7.42-7.33 (m, 44H).

Preparation of 3-((7-((7-((7-((7-((2,2-diphenyl-7-((3,4,5-trihydroxybenzoyl)oxy)benzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-4,5-dihydroxybenzoic acid (22)

To a flame dried 10 wt % Pd/C solid (100 mg), anhydrous tetrahydrofuran (3.1 mL) and the compound 21 (70 mg, 0.03 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and precipitated with EtOAc/hexanes (1:25) to afford the compound 22 as an off-white solid (24 mg, 71%). $^1$H NMR (MeOD, 400 MHz) δ 7.64-7.54 (m, 4H), 7.53-7.46 (m, 4H), 7.44-7.09 (m, 6H).

Example 6. 3-((3-((3-((3-((3-((1H-pyrrole-2-carbonyl)oxy)-4,5-dihydroxybenzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (25)

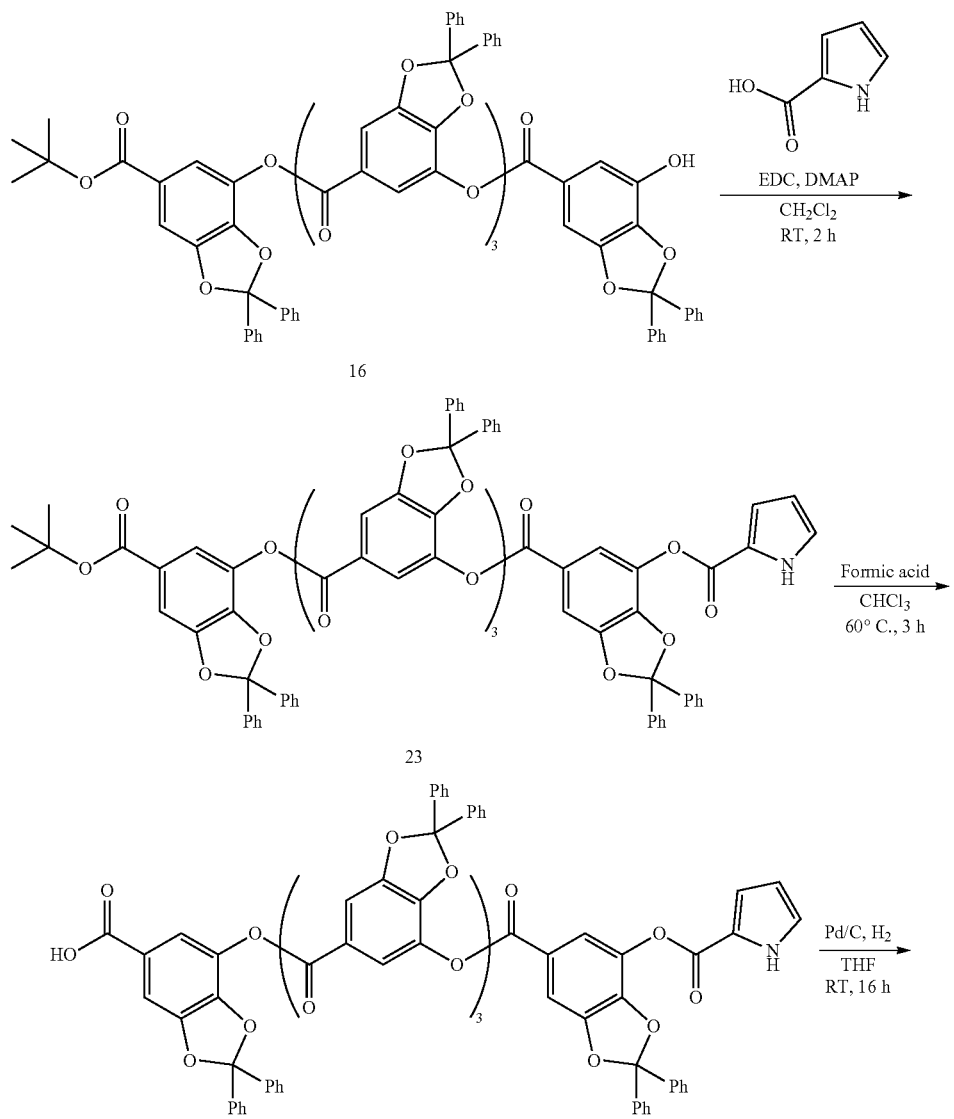

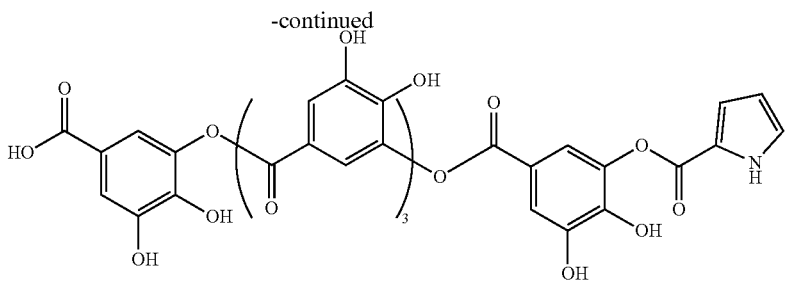

25

Preparation of 6-((((6-((((6-((((6-((((6-(tert-butoxycarbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl 1H-pyrrole-2-carboxylate (23)

To a mixture of the compound 16 (700 mg, 0.42 mmol), pyrrole-2-carboxylic acid (56 mg, 0.51 mmol) and 4-dimethylaminopyridine (145 mg, 1.18 mmol) in dichloromethane (4.2 mL) at 0° C., 1-ethyl-3-(3-dimethylaminopropyl)carbodiimide hydrochloride (98 mg, 0.51 mmol) was added and stirred back to RT for 2 h. The mixture was extracted with dichloromethane, water, and brine. The organic residue was dried over anhydrous magnesium sulfate, evaporated, and purified by F.C. with EtOAc/hexanes/dichloromethane (5/45/50). The collected residue was precipitate with dichloromethane/hexanes to afford the compound 23 as an off-white solid (600 mg, 81%). $^1$H NMR (CDCl$_3$, 400 MHz) δ 7.78-7.31 (m, 60H), 7.21-7.18 (m, 1H), 7.10-7.07 (m, 1H), 6.40-6.35 (m, 1H), 1.53 (s, 9H).

Preparation of 7-((7-((7-((7-((7-((1H-pyrrole-2-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (24)

A solution of the compound 23 (400 mg, 0.23 mmol) in formic acid/chloroform (50 vol. %, 4.6 mL) was stirred under 60° C., 2 h. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 24 as an off-white solid (200 mg, 52%). $^1$H NMR (CDCl$_3$, 400 MHz) δ 9.49 (s, 1H), 7.80-7.31 (m, 60H), 7.21-7.18 (m, 1H), 7.11-7.07 (m, 1H), 6.39-6.34 (m, 1H).

Preparation of 3-((3-((3-((3-((1H-pyrrole-2-carbonyl)oxy)-4,5-dihydroxybenzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (25)

To a flame dried 10 wt % Pd/C solid (94 mg), anhydrous tetrahydrofuran (5.9 mL) and the compound 24 (100 mg, 0.06 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and precipitated with EtOAc/hexanes (1:25) to afford the compound 25 as an off-white solid (29 mg, 57%). $^1$H NMR (MeOD, 400 MHz) δ 7.62-7.10 (m, 11H), 7.10-7.06 (m, 1H), 6.33-6.27 (m, 1H).

Example 7. 3-((3-((3-((3-((3-((1H-pyrrole-2-carbonyl)oxy)-4,5-dihydroxybenzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (28)

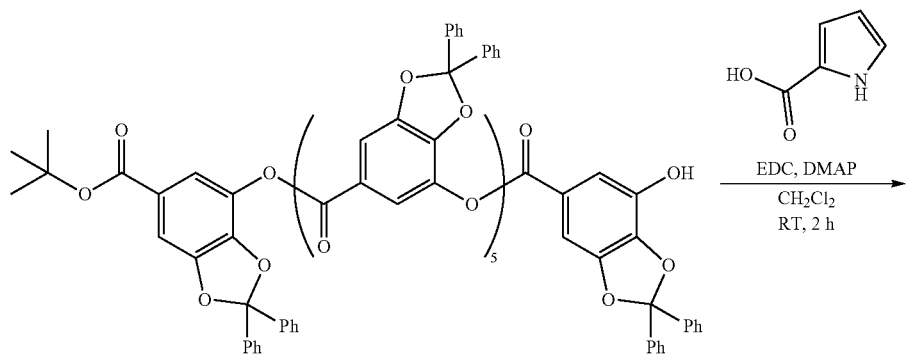

20

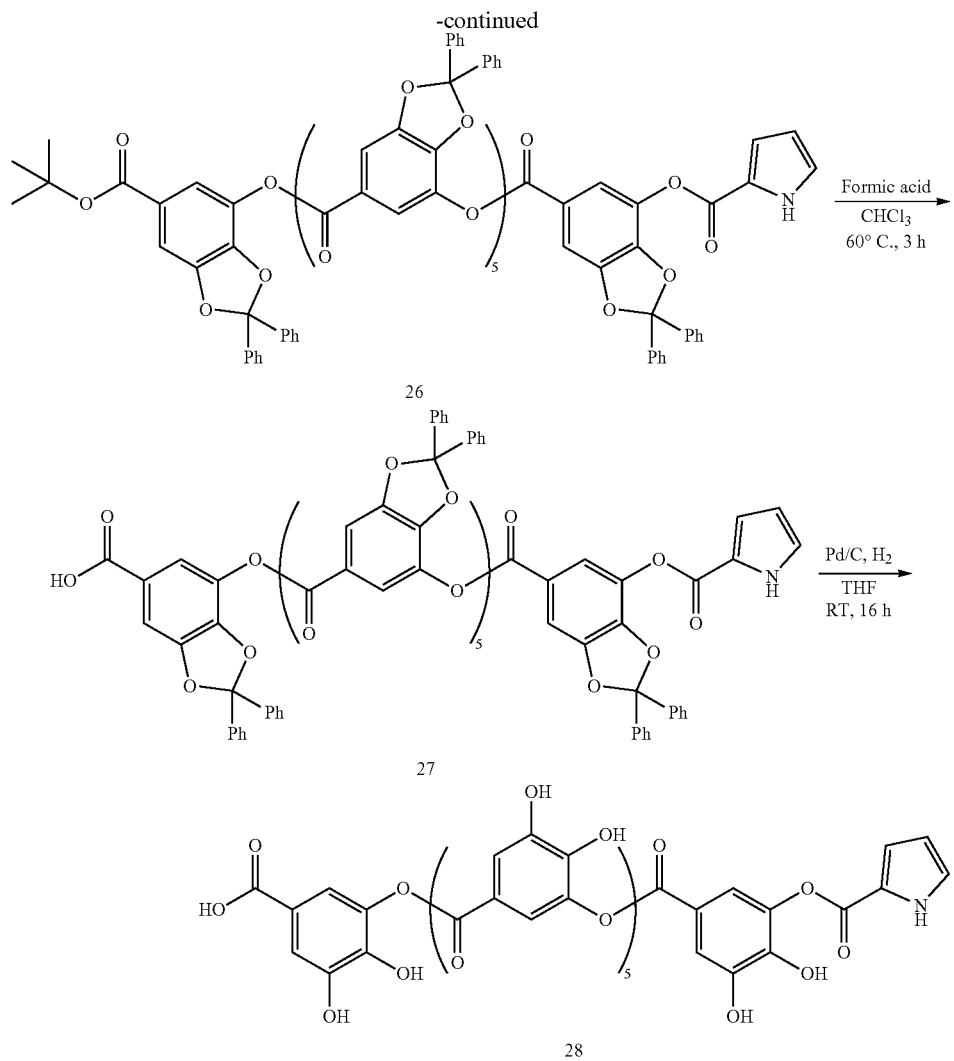

Preparation of 6-((((6-((((6-((((6-((((6-((((6-(tert-butoxycarbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl 1H-pyrrole-2-carboxylate (26)

To a mixture of the compound 20 (350 mg, 0.15 mmol), pyrrole-2-carboxylic acid (18 mg, 0.16 mmol) and 4-dimethylaminopyridine (3.7 mg, 0.03 mmol) in dichloromethane (3.1 mL) at 0° C., 1-ethyl-3-(3-dimethylaminopropyl) carbodiimide hydrochloride (33 mg, 0.17 mmol) was added and stirred back to RT for 2 h. The mixture was extracted with dichloromethane, water, and brine. The organic residue was dried over anhydrous magnesium sulfate, evaporated, and purified by F.C. with EtOAc/hexanes/dichloromethane (5/45/50). The collected residue was precipitate with dichloromethane/hexanes to afford the compound 26 as an off-white solid (250 mg, 69%). $^1$H NMR (CD$_2$Cl$_2$, 400 MHz) δ 9.37 (s, 1H), 7.78-7.32 (m, 84H), 7.20-7.16 (m, 1H), 7.12-7.10 (m, 1H), 6.44-6.33 (m, 1H), 1.52 (s, 9H).

Preparation of 7-((7-((7-((7-((7-((7-((1H-pyrrole-2-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (27)

A solution of the compound 26 (205 mg, 0.09 mmol) in formic acid/chloroform (50 vol. %, 10 mL) was stirred under 60° C., 2 h. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 27 as an off-white solid (78 mg, 39%). $^1$H NMR (CDCl$_2$, 400 MHz) δ 9.91 (s, 1H), 7.81-7.31 (m, 84H), 7.22-7.17 (m, 1H), 7.14-7.08 (m, 1H), 6.40-6.32 (m, 1H).

Preparation of 3-((3-((3-((3-((3-((3-((3-((1H-pyrrole-2-carbonyl)oxy)-4,5-dihydroxybenzoyl)oxy)-4,5-dihydroxybenzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (28)

To a flame dried 10 wt % Pd/C solid (30 mg), anhydrous tetrahydrofuran (3.4 mL) and the compound 27 (78 mg, 0.03 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and precipitated with EtOAc/hexanes (1:25) to afford the compound 28 as an off-white solid (34 mg, 85%). ¹H NMR (MeOD, 400 MHz) δ 7.63-7.05 (m, 16H), 6.32-6.28 (m, 1H).

Example 8. 3-((3-((3-((3-((3,4-dihydroxy-5-((3-phenethyl-1H-pyrazole-5-carbonyl)oxy)benzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (34)

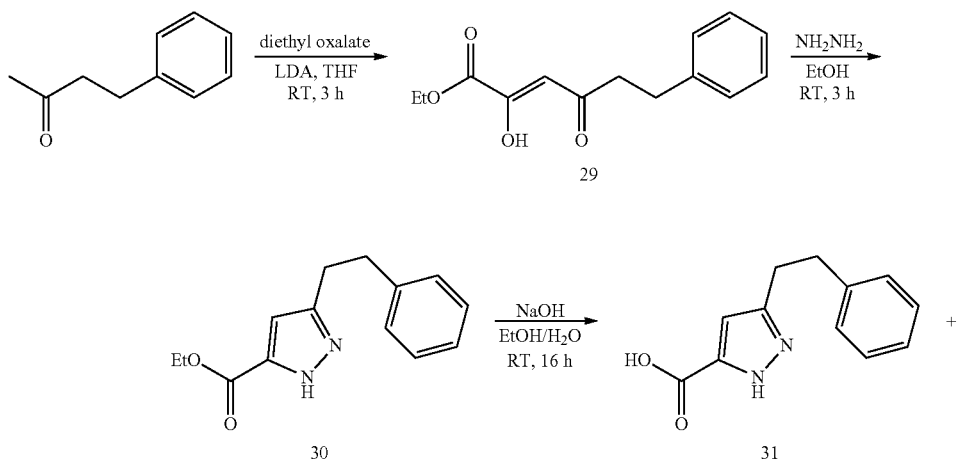

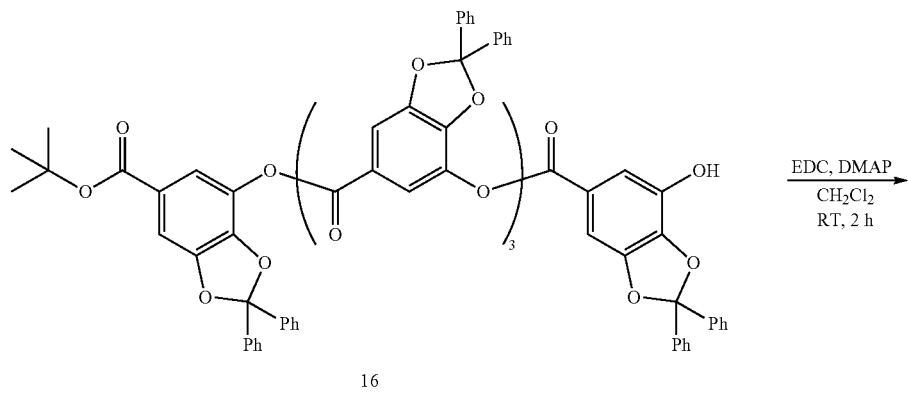

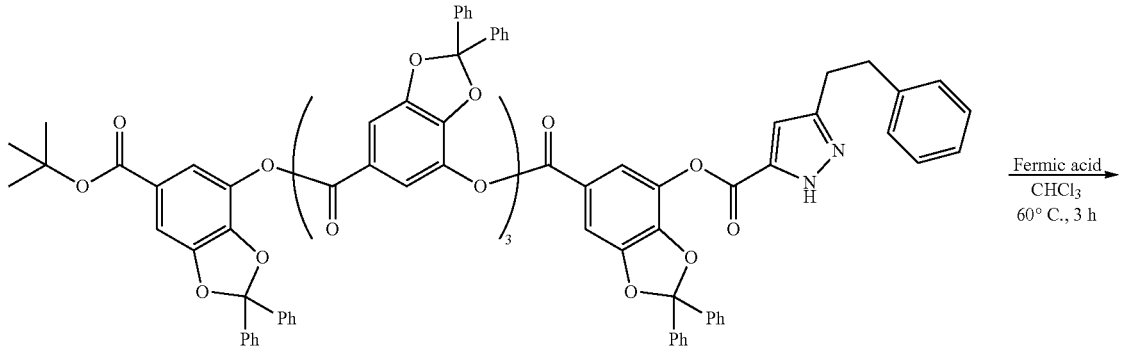

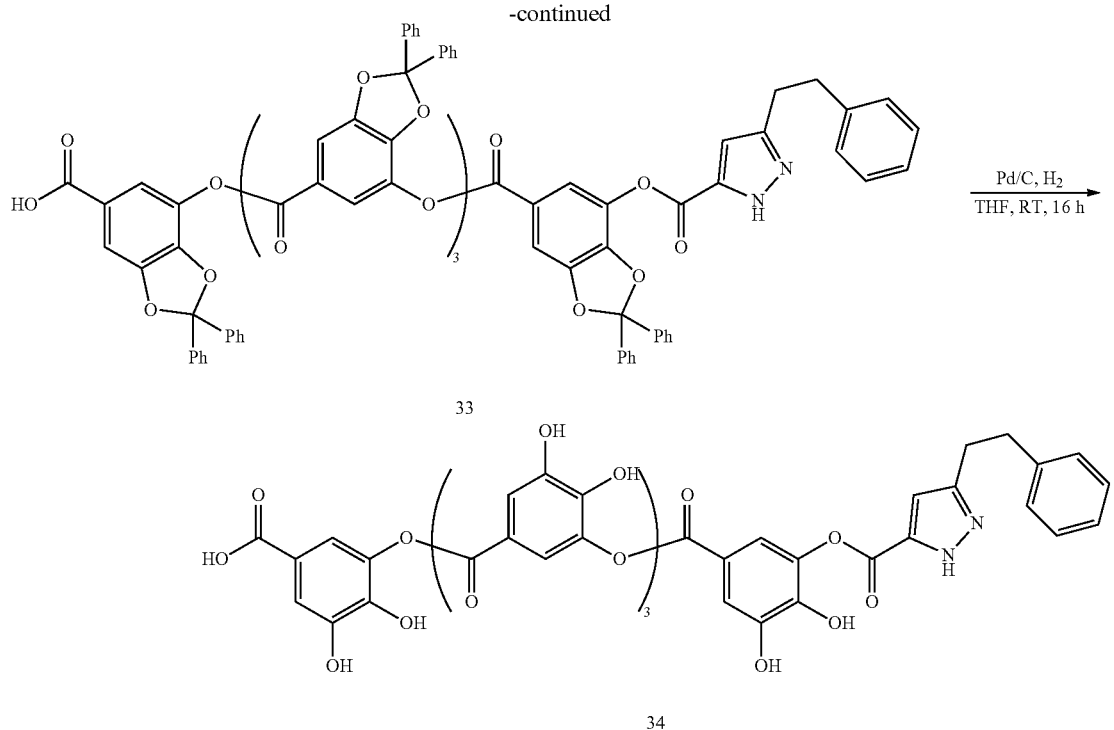

34

Preparation of ethyl (Z)-2-hydroxy-4-oxo-6-phenylhex-2-enoate (29)

To a stirring solution of benzylacetone (30.0 g, 200.0 mmol) in dry methanol (300 mL) was added dimethyl oxalate (27.0 g, 230.0 mmol) and sodium methoxide (42.0 mL, 200.0 mmol) at 0° C. The reaction was slowly warmed to RT and stirred for 16 h. The mixture was diluted with EtOAc (500 mL) and brine, dried over magnesium sulfate, filtered and evaporated. The residue was purified by F.C. with EtOAc/petroleum ether (1:3) to afford ethyl (Z)-2-hydroxy-4-oxo-6-phenylhex-2-enoate (29) as a yellow solid (13.0 g, 27%). ESI-MS, m/z=235 [M+H]⁺.

Preparation of ethyl 3-phenethyl-1H-pyrazole-5-carboxylate (30)

To a stirring solution of ethyl (Z)-2-hydroxy-4-oxo-6-phenylhex-2-enoate (29, 13.0 g, 56.0 mmol) in ethanol (56 mL) was added hydrazine (51 wt % aqueous solution) (10.0 mL, 213.9 mmol). The mixture was heated to reflux for 16 h. The reaction was concentrated in vacuo and the residue was purified by F.C. with EtOAc/petroleum (2:3) to afford ethyl 3-phenethyl-1H-pyrazole-5-carboxylate (30) as yellow oil (6.0 g, 50%). ESI-MS, m/z=231 [M+H]⁺.

Preparation of 3-phenethyl-1H-pyrazole-5-carboxylic acid (31)

To a stirring solution of ethyl 3-phenethyl-1H-pyrazole-5-carboxylate (30, 5.0 g, 20.0 mmol) in tetrahydrofuran (40 mL) was added the solution of lithium hydroxide (1.0 g, 100.0 mmol) in water (20 mL). The mixture was stirred at RT for 16 h. Most of tetrahydrofuran was evaporated in vacuo. The pH value of the mixture was adjusted to 2 with 1 N hydrochloric acid. The mixture was filtered and the solid was collected. The solid was purified by Pre-HPLC to afford 3-phenethyl-1H-pyrazole-5-carboxylic acid (31) as a white solid (83.9 mg, 2%). ¹H NMR (400 MHz, DMSO-d₆) δ 12.97 (s, 2H), 7.30-7.17 (m, 5H), 6.48 (s, 1H), 2.92 (s, 4H). ESI-MS, m/z=217 [M+H]⁺.

Preparation of 6-((((6-((((6-((((6-(tert-butoxycarbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl 3-phenethyl-1H-pyrazole-5-carboxylate (32)

To a mixture of the compound 16 (210 mg, 0.13 mmol), compound 31 (29 mg, 0.13 mmol) and 4-dimethylaminopyridine (3 mg, 0.03 mmol) in dichloromethane (2.5 mL) at 0° C., 1-ethyl-3-(3-dimethylaminopropyl)carbodiimide hydrochloride (27 mg, 0.14 mmol) was added and stirred back to RT for 2 h. The mixture was extracted with dichloromethane, water, and brine. The organic residue was dried over anhydrous magnesium sulfate, evaporated, and purified by F.C. with EtOAc/hexanes/dichloromethane (5/45/50). The collected residue was precipitate with dichloromethane/hexanes to afford the compound 32 as an off-white solid (190 mg, 81%). ¹H NMR (CD₂Cl₂, 400 MHz) δ 7.80-7.10 (m, 65H) 6.81 (s, 1H), 3.09-2.98 (m, 4H), 1.53 (s, 9H).

Preparation of 7-((7-((7-((7-((7-((3-phenethyl-1H-pyrazole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (33)

A solution of the compound 32 (182 mg, 0.10 mmol) in formic acid/chloroform (33 vol. %, 6.5 mL) was stirred under 60° C., 2 h. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 33 as an off-white solid (113 mg, 64%). ¹H NMR (CD₂Cl₂, 400 MHz) δ 7.83-7.10 (m, 65H), 6.83 (s, 1H).

Preparation of 3-((3-((3-((3-((3,4-dihydroxy-5-((3-phenethyl-1H-pyrazole-5-carbonyl)oxy)benzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (34)

To a flame dried 10 wt % Pd/C solid (32 mg), anhydrous tetrahydrofuran (3.5 mL) and the compound 33 (63 mg, 0.04 mmol) was added. The mixture was stirred at RT under H₂ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and precipitated with EtOAc/hexanes (1:25) to afford the compound 34 as an off-white solid (13 mg, 38%). ¹H NMR (MeOD, 400 MHz) δ 7.65-7.07 (m, 15H), 6.81-6.74 (m, 1H), 3.09-2.97 (m, 4H)

Example 9. 3-((3-((3-((3-((3,4-dihydroxy-5-((3-(2-(5,6,7,8-tetrahydronaphthalen-1-yl)ethyl)-1H-pyrazole-5-carbonyl)oxy)benzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (42)

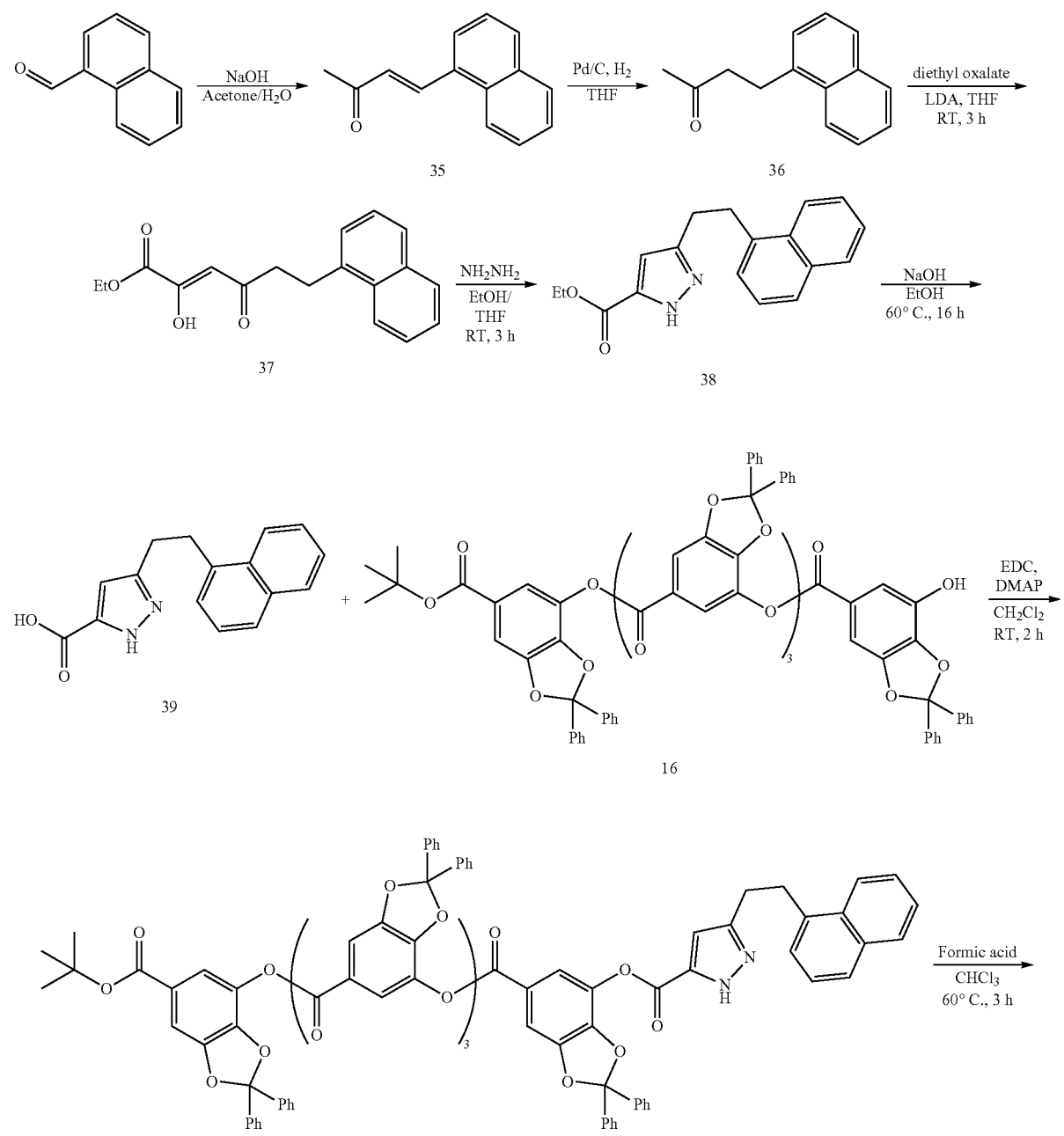

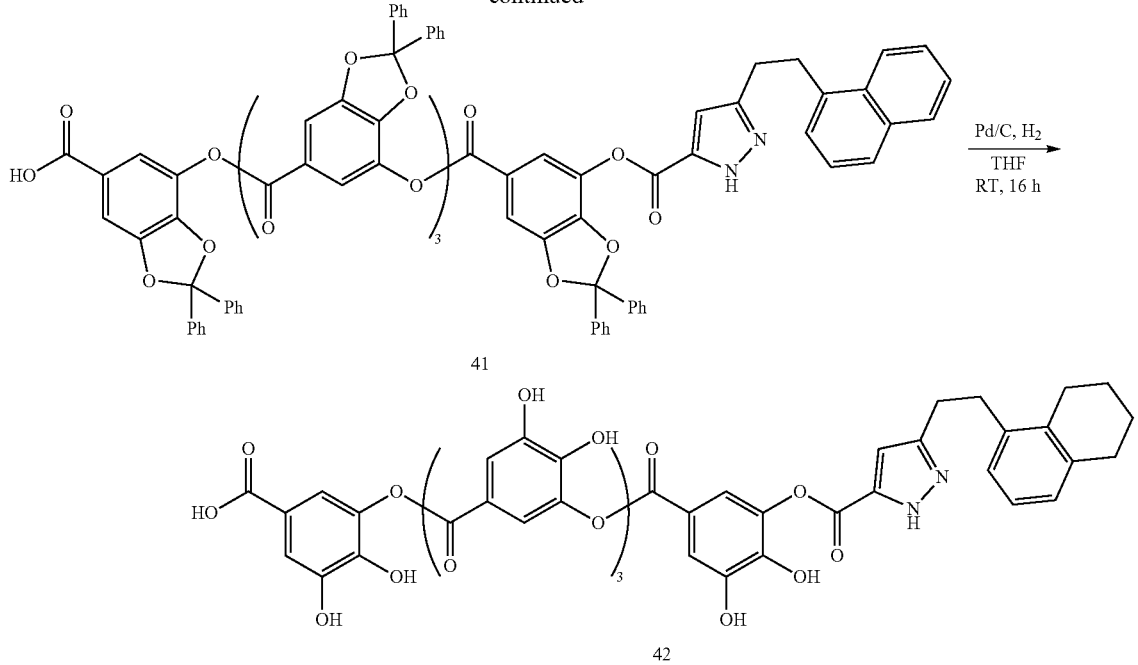

Preparation of (E)-4-(naphthalen-1-yl)but-3-en-2-one (35)

To a solution of 1-naphthaldehyde (1.0 g, 6.4 mmol) in acetone/water (1/1, 2.6 mL), sodium hydroxide aqueous solution (1 wt %, 1.6 mL) was added and stirred under 60° C. for 2 h. The crude was extracted with EtOAc and brine. The organic residue was dried over magnesium sulfate and evaporated to afford the compound 35 as a yellow oil (1.1 g, 91%) without further purification. $^1$H NMR (CDCl$_3$, 400 MHz) δ 8.38 (d, J=16.0 Hz, 1H), 8.18 (d, J=8.4 Hz, 1H), 7.90 (t, J=8.0 Hz, 2H), 7.78 (d, J=7.2 Hz, 1H), 7.63-7.45 (m, 3H), 6.82 (d, J=16.0 Hz, 1H), 2.47 (s, 3H)

Preparation of 4-(naphthalen-1-yl)butan-2-one (36)

To a flame dried 10 wt % Pd/C solid (308 mg), anhydrous tetrahydrofuran (29 mL) and the compound 35 (1137 mg, 5.79 mmol) was added. The mixture was stirred at RT under H$_2$ (1 atm) for 2 h. The mixture was then filtrated and evaporated in vacuo. The residue was extracted with EtOAc and brine. The organic residue was dried over magnesium sulfate, evaporated and purified by F.C. with EtOAc/hexanes/dichloromethane (5/90/5) to afford the compound 36 as a colorless oil (814 mg, 71%). $^1$H NMR (CDCl$_3$, 400 MHz) δ 7.99 (d, J=8.2 Hz, 1H), 7.90-7.82 (m, 1H), 7.73 (d, J=8.1 Hz, 1H), 7.57-7.45 (m, 2H), 7.44-7.30 (m, 2H), 3.37 (t, J=7.8 Hz, 2H), 2.89 (t, J=7.8 Hz, 2H), 2.16 (s, 3H).

Preparation of ethyl (Z)-2-hydroxy-6-(naphthalen-1-yl)-4-oxohex-2-enoate (37)

To a solution of the compound 36 (807 mg, 4.07 mmol) in tetrahydrofuran (27 mL) at −78° C., lithium diisopropylamide solution (2 M in tetrahydrofuran/heptane/ethylbenzene, 2.2 mL, 4.48 mmol) was added dropwise over 10 mins and stirred under −78° C. 10 mins. Diethyl oxalate (683 μL, 4.88 mmol) was added and stirred back to 0° C. for 1 h. The mixture was quenched with 1 N hydrochloric acid under 0° C. The mixture was extracted with EtOAc and brine. The organic residue was dried over magnesium sulfate, evaporated and purified by F.C. with EtOAc/hexanes/dichloromethane (10/80/10) to afford the compound 37 as a light-yellow oil (1025 mg, 84%). $^1$H NMR (CDCl$_3$, 400 MHz) δ 8.01 (d, J=8.4 Hz, 1H), 7.90-7.84 (m, 1H), 7.74 (d, J=8.1 Hz, 1H), 7.58-7.46 (m, 2H), 7.44-7.31 (m, 2H), 6.37 (s, 1H), 4.35 (q, J=7.2 Hz, 2H), 3.45 (t, J=7.8 Hz, 2H), 2.96 (t, J=7.8 Hz, 2H), 1.37 (t, J=7.2 Hz, 2H).

Preparation of ethyl 3-(2-(naphthalen-1-yl)ethyl)-1H-pyrazole-5-carboxylate (38)

To a solution of the compound 37 (1018 mg, 3.41 mmol) in tetrahydrofuran/ethanol (1/1, 11.4 mL) at 0° C., hydrazine hydrate (199 μL, 4.09 mmol) was added and stirred back to RT for 2 h. The mixture was concentrated under reduced pressure and extracted with EtOAc, 1 N hydrochloric acid, and brine. The organic residue was dried over magnesium sulfate, evaporated and purified by F.C. with methanol/dichloromethane (10/90). The collected residue was precipitate with ethanol/hexanes to afford the compound 38 as an off-white solid (658 mg, 84%). $^1$H NMR (CD$_2$Cl$_2$, 400 MHz) δ 8.09-8.00 (m, 1H), 7.91-7.84 (m, 1H), 7.74 (d, J=8.2 Hz, 1H), 7.57-7.45 (m, 2H), 7.38 (dd, J=8.1, 7.1 Hz, 1H), 7.32-7.27 (m, 1H), 6.68 (s, 1H), 4.36 (q, J=7.1 Hz, 2H), 3.49-3.37 (m, 2H), 3.22-3.07 (m, 2H), 1.37 (t, J=7.1 Hz, 2H).

Preparation of 3-(2-(naphthalen-1-yl)ethyl)-1H-pyrazole-5-carboxylic acid (39)

To a solution of the compound 38 (658 mg, 2.24 mmol) in ethanol (4.5 mL), sodium hydroxide aqueous solution (10 wt %, 4.5 mL) was added and stirred under 60° C. for 2 h. The mixture was cooled to 0° C., quenched with 1 N hydrochloric acid, and extracted with EtOAc and water. The organic residue was dried over magnesium sulfate, evaporated and precipitate with ethanol and hexanes to afford the compound 39 as an off-white solid (520 mg, 87%). $^1$H NMR (MeOD, 400 MHz) δ 8.14 (d, J=8.4 Hz, 1H), 7.96-7.88 (m, 1H), 7.77 (d, J=8.0 Hz, 2H), 7.62-7.47 (m, 2H), 7.46-7.32 (m, 2H), 6.57 (s, 1H), 3.37 (t, J=8.0 Hz, 2H), 3.01 (t, J=8.0, 2H).

Preparation of 6-(((6-(((6-(((6-(tert-butoxycarbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl 3-(2-(naphthalen-1-yl)ethyl)-1H-pyrazole-5-carboxylate (40)

To a mixture of the compound 16 (350 mg, 0.21 mmol), compound 39 (62 mg, 0.23 mmol) and 4-dimethylaminopyridine (21 mg, 0.17 mmol) in dichloromethane (4.2 mL) at 0° C., 1-ethyl-3-(3-dimethylaminopropyl)carbodiimide hydrochloride (49 mg, 0.25 mmol) was added and stirred back to RT for 2 h. The mixture was extracted with dichloromethane, water, and brine. The organic residue was dried over anhydrous magnesium sulfate, evaporated, and purified by F.C. with EtOAc/hexanes/dichloromethane (5/45/50). The collected residue was precipitate with dichloromethane/hexanes to afford the compound 40 as an off-white solid (327 mg, 81%). $^1$H NMR (CDCl$_3$, 400 MHz) δ 8.05 (d, J=8.4 Hz, 1H), 7.88 (d, J=7.7 Hz, 1H), 7.83-7.28 (m, 65H), 6.88 (s, 1H), 3.48 (t, J=7.8 Hz, 2H), 3.20 (t, J=7.8 Hz, 2H), 1.53 (s, 9H).

Preparation of 7-((7-((7-((7-((3-(2-(naphthalen-1-yl)ethyl)-1H-pyrazole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (41)

A solution of the compound 40 (327 mg, 0.10 mmol) in formic acid/chloroform (33 vol. %, 11.4 mL) was stirred under 60° C., 2 h. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 41 as an off-white solid (145 mg, 46%). $^1$H NMR (CD$_2$Cl$_2$, 400 MHz) δ 8.05 (d, J=8.3 Hz, 1H), 7.89-7.84 (m, 1H), 7.84-7.11 (m, 65H), 6.89 (s, 1H).

Preparation of 3-((3-((3-((3,4-dihydroxy-5-((3-(2-(naphthalen-1-yl)ethyl)-1H-pyrazole-5-carbonyl)oxy)benzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (42)

To a flame dried 10 wt % Pd/C solid (129 mg), anhydrous tetrahydrofuran (7.6 mL) and the compound 41 (140 mg, 0.08 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase C$_{18}$ F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/hexanes (1:25) to afford the compound 42 as an off-white solid (40 mg, 51%). $^1$H NMR (MeOD, 400 MHz) δ 7.64-6.88 (m, 13H), 6.86-6.74 (m, 1H), 3.02-2.81 (m, 4H), 2.81-2.67 (m, 4H), 2.18-1.67 (m, 4H).

Example 10. 3-((3-((3-((3-((3-(4-fluorophenethyl)-1H-pyrazole-5-carbonyl)oxy)-4,5-dihydroxybenzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (50)

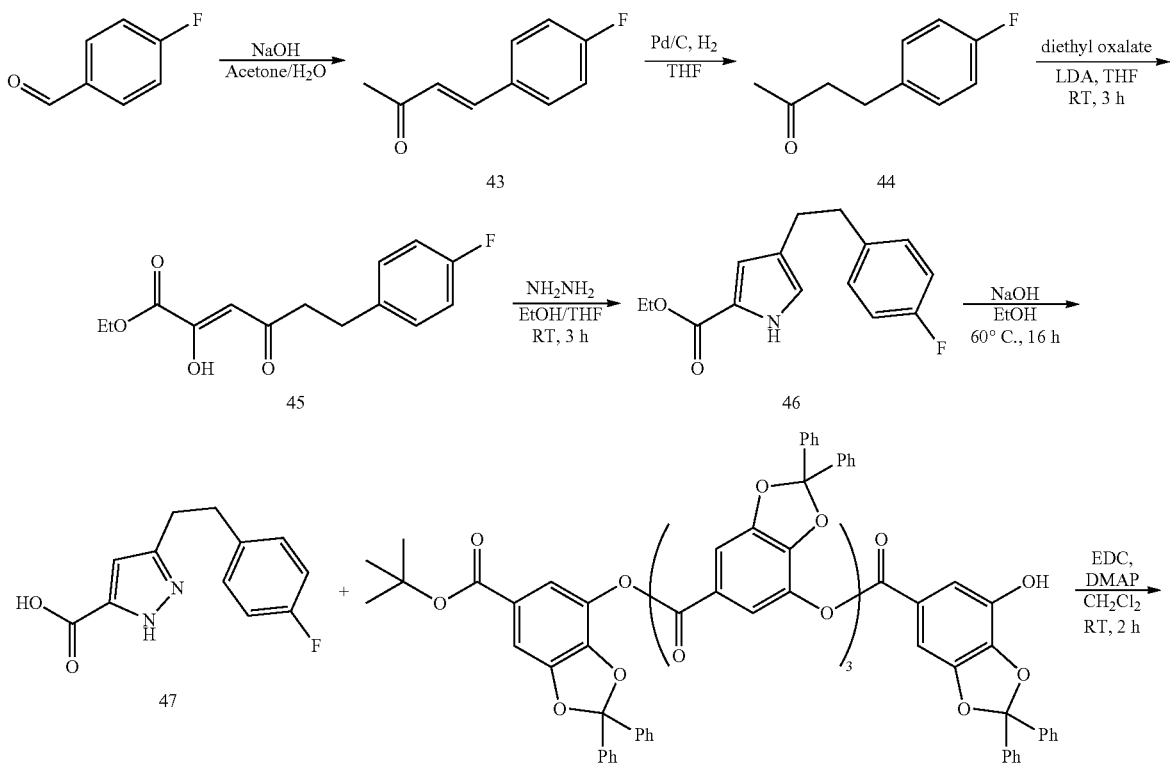

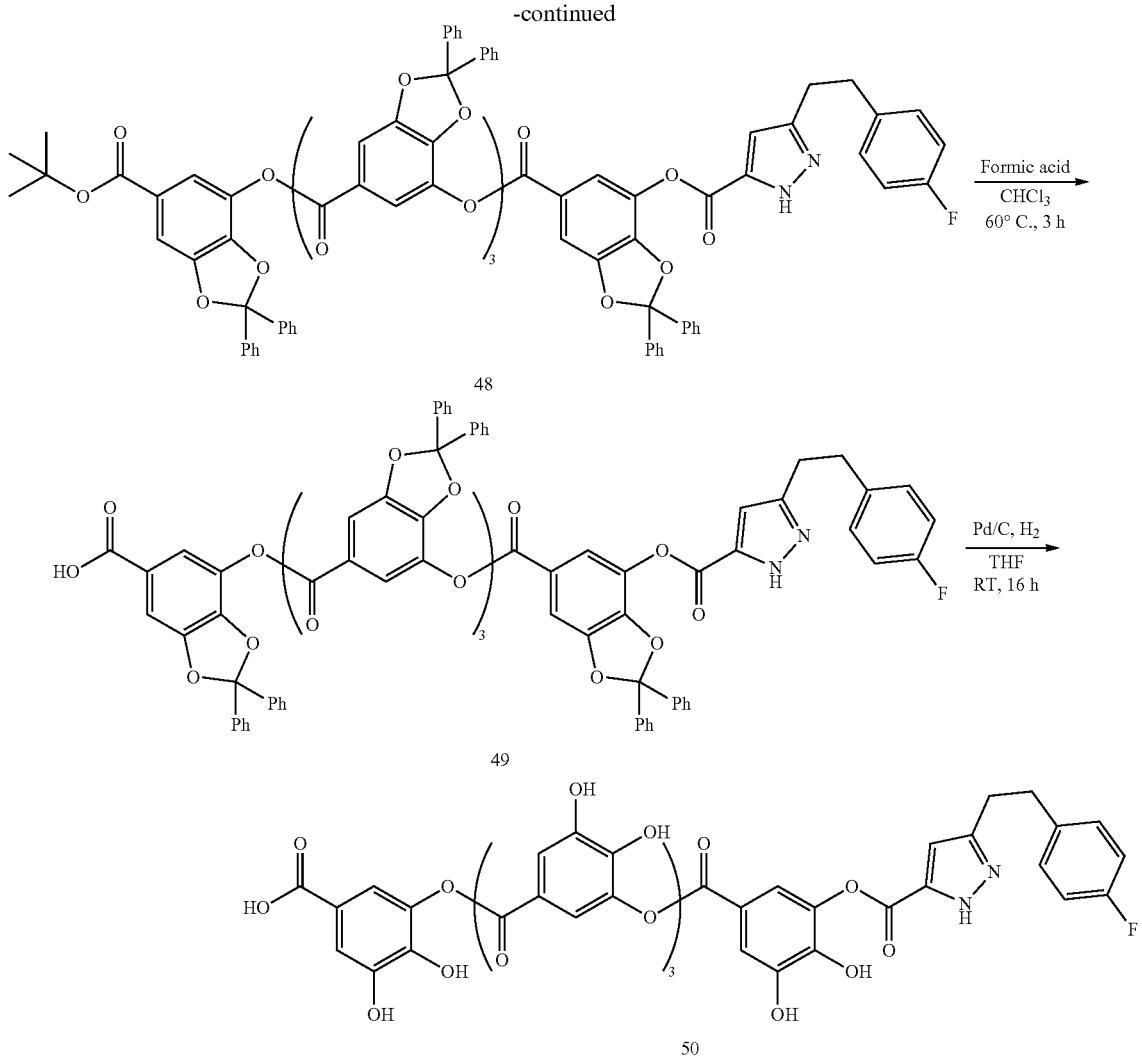

Preparation of (E)-4-(4-fluorophenyl)but-3-en-2-one (43)

To a solution of p-fluorobenzaldehyde (1.0 g, 8.06 mmol) in acetone/water (1/1, 3.2 mL), sodium hydroxide aqueous solution (1 wt %, 2.0 mL) was added and stirred under 60° C. for 2 h. The crude was extracted with EtOAc and brine. The organic residue was dried over magnesium sulfate and evaporated to afford the compound 43 as a yellow oil (1.3 g, 98%) without further purification. $^1$H NMR (CDCl$_3$, 400 MHz) δ 7.57-7.51 (m, 2H), 7.48 (d, J=16.3 Hz, 2H), 7.14-7.05 (m, 2H), 6.64 (d, J=16.2 Hz, 2H), 2.37 (s, 3H).

Preparation of 4-(4-fluorophenyl)butan-2-one (44)

To a flame dried 10 wt % Pd/C solid (399 mg), anhydrous tetrahydrofuran (38 mL) and the compound 43 (1230 mg, 7.49 mmol) was added. The mixture was stirred at RT under H$_2$ (1 atm) for 2 h. The mixture was then filtrated and evaporated in vacuo. The residue was extracted with EtOAc and brine. The organic residue was dried over magnesium sulfate, evaporated and purified by F.C. with EtOAc/hexanes/dichloromethane (5/90/5) to afford the compound 44 as a colorless oil (950 mg, 76%). $^1$H NMR (CDCl$_3$, 400 MHz) δ 7.21-7.05 (m, 2H), 7.02-6.89 (m, 2H), 2.86 (t, J=7.4 Hz, 2H), 2.73 (t, J=7.4 Hz, 2H), 2.13 (s, 3H).

Preparation of ethyl (Z)-6-(4-fluorophenyl)-2-hydroxy-4-oxohex-2-enoate (45)

To a solution of the compound 44 (750 mg, 4.51 mmol) in tetrahydrofuran (28 mL) at −78° C., lithium diisopropylamide solution (2 M in tetrahydrofuran/heptane/ethylbenzene, 2.7 mL, 5.41 mmol) was added dropwise over 10 mins and stirred under −78° C. 10 mins. Diethyl oxalate (852 μL, 6.09 mmol) was added and stirred back to 0° C. for 1 h. The mixture was quenched with 1 N hydrochloric acid under 0° C. The mixture was extracted with EtOAc and brine. The organic residue was dried over magnesium sulfate, evaporated and purified by F.C. with EtOAc/hexanes/dichloromethane (10/80/10) to afford the compound 45 as a light-yellow oil (904 mg, 75%). $^1$H NMR (CDCl$_3$, 400 MHz) δ 7.20-7.11 (m, 2H), 7.02-6.92 (m, 2H), 6.34 (s, 1H), 4.34 (q, J=7.1 Hz, 2H), 2.95 (t, J=7.6 Hz, 2H), 2.80 (t, J=7.5 Hz, 2H), 1.37 (t, J=7.2 Hz, 3H).

Preparation of ethyl 3-(4-fluorophenethyl)-1H-pyrazole-5-carboxylate (46)

To a solution of the compound 45 (26.0 g, 97.65 mmol) in ethanol (195 mL) at 0° C., hydrazine hydrate (5.2 mL, 107.41 mmol) was added and stirred back to RT for 2 h. The mixture was concentrated under reduced pressure and extracted with EtOAc, 1 N hydrochloric acid, and brine. The organic residue was dried over magnesium sulfate, evaporated and purified by F.C. with methanol/dichloromethane (10/90). The collected residue was precipitate with ethanol/hexanes to afford the compound 46 as an off-white solid (17.1 g, 67%). ¹H NMR (CDCl₃, 400 MHz) δ 7.16-7.07 (m, 2H), 7.01-6.92 (m, 2H), 6.59 (s, 1H), 4.37 (q, J=7.1 Hz, 2H), 3.04-2.89 (m, 4H), 1.38 (t, J=7.1 Hz, 3H).

Preparation of 3-(4-fluorophenethyl)-1H-pyrazole-5-carboxylic acid (47)

To a solution of the compound 46 (17.1 g, 65.35 mmol) in ethanol/tetrahydrofuran (1/1, 131 mL), sodium hydroxide aqueous solution (10 wt %, 65 mL) was added and stirred under 60° C. for 2 h. The mixture was cooled to 0° C., quenched with 1 N hydrochloric acid, and extracted with EtOAc and water. The organic residue was dried over magnesium sulfate, evaporated and precipitate with ethanol and hexanes to afford the compound 47 as an off-white solid (13.2 g, 86%). ¹H NMR (MeOD, 400 MHz) δ 7.22-7.13 (m, 2H), 7.02-6.93 (m, 2H), 6.53 (s, 1H), 3.00-2.90 (m, 4H).

Preparation of 6-(((6-(((6-(((6-(tert-butoxycarbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl 3-(4-fluorophenethyl)-1H-pyrazole-5-carboxylate (48)

To a mixture of the compound 16 (600 mg, 0.36 mmol), compound 47 (102 mg, 0.43 mmol) and 4-dimethylaminopyridine (124 mg, 1.01 mmol) in dichloromethane (3.6 mL) at 0° C., 1-ethyl-3-(3-dimethylaminopropyl)carbodiimide hydrochloride (84 mg, 0.43 mmol) was added and stirred back to RT for 2 h. The mixture was extracted with dichloromethane, water, and brine. The organic residue was dried over anhydrous magnesium sulfate, evaporated, and purified by F.C. with EtOAc/hexanes/dichloromethane (5/45/50). The collected residue was precipitate with dichloromethane/hexanes to afford the compound 48 as an off-white solid (450 mg, 66%). ¹H NMR (CDCl₃, 400 MHz) δ 7.79-7.32 (m, 60H), 7.16-7.09 (m, 2H), 7.02-6.94 (m, 2H), 6.80 (s, 1H), 3.07-2.92 (m, 4H), 1.54 (s, 9H).

Preparation of 7-((7-((7-((7-((7-((3-(4-fluorophenethyl)-1H-pyrazole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (49)

A solution of the compound 48 (404 mg, 0.22 mmol) in formic acid/chloroform (50 vol. %, 4.4 mL) was stirred under 60° C., 2 h. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 49 as an off-white solid (136 mg, 35%). ¹H NMR (CDCl₃, 400 MHz) δ 7.83-7.32 (m, 60H), 7.16-7.10 (m, 2H), 7.02-6.94 (m, 2H), 6.82 (s, 1H), 3.08-2.95 (m, 4H).

Preparation of 3-((3-((3-((3-((3-((3-(4-fluorophenethyl)-1H-pyrazole-5-carbonyl)oxy)-4,5-dihydroxybenzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (50)

To a flame dried 10 wt % Pd/C solid (60 mg), anhydrous tetrahydrofuran (6.7 mL) and the compound 49 (120 mg, 0.07 mmol) was added. The mixture was stirred at RT under H₂ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and precipitated with EtOAc/hexanes (1:25) to afford the compound 50 as an off-white solid (39 mg, 59%). ¹H NMR (MeOD, 400 MHz) δ 7.65-7.09 (m, 12H), 7.04-6.95 (m, 2H), 6.81-6.74 (m, 1H), 3.08-2.95 (m, 4H).

Example 11. 3-((3-((3-((3-((3-((3-(3,5-difluorophenethyl)-1H-pyrazole-5-carbonyl)oxy)-4,5-dihydroxybenzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (58)

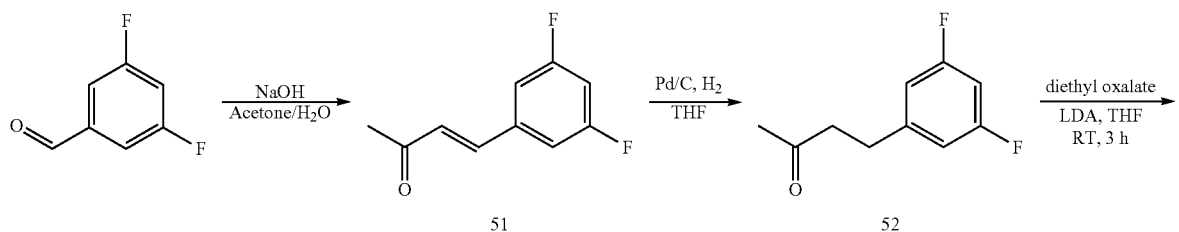

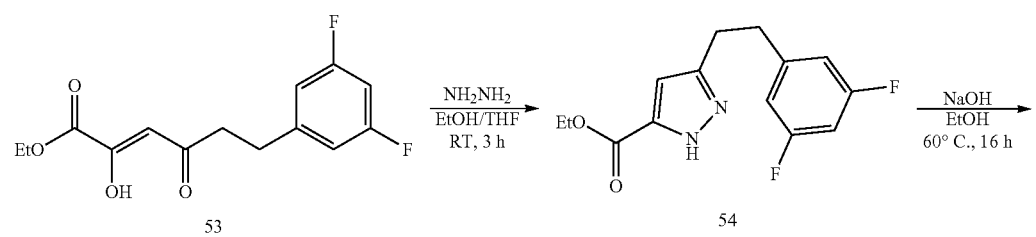

-continued
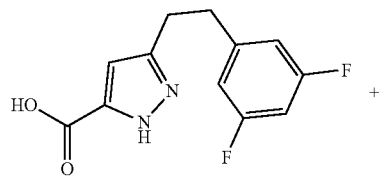
55
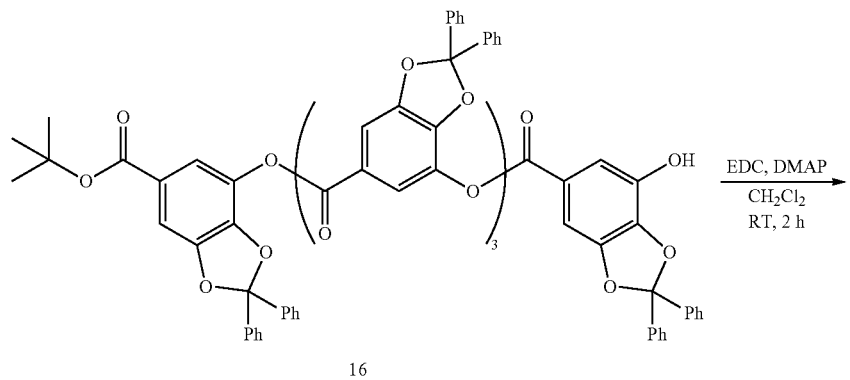
16
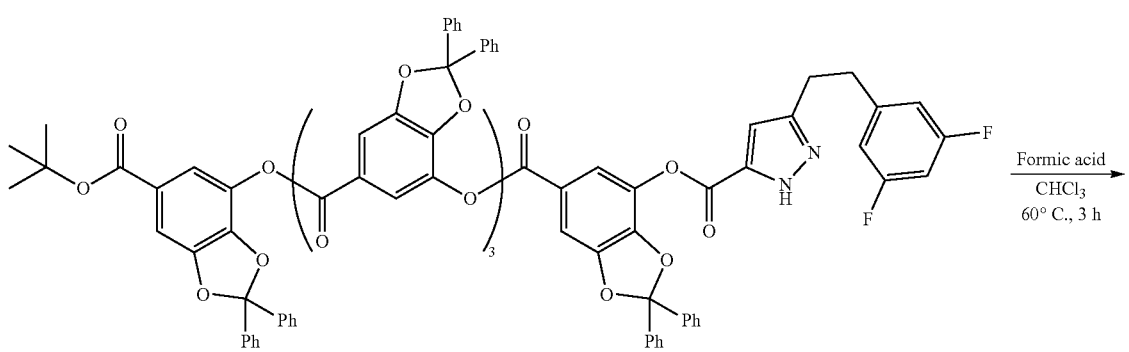
56
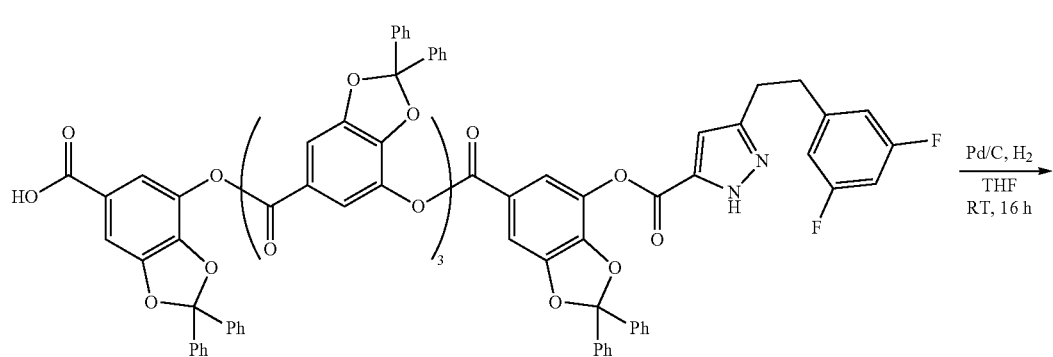
57
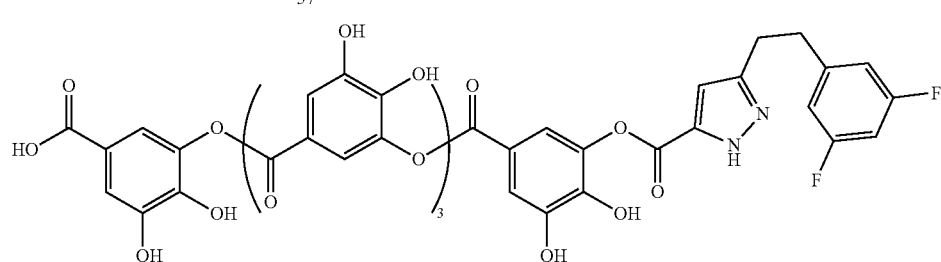
58

Preparation of (E)-4-(3,5-difluorophenyl)but-3-en-2-one (51)

To a solution of 3,5-difluorobenzaldehyde (3.0 g, 21.11 mmol) in acetone/water (1/1, 8.4 mL), sodium hydroxide aqueous solution (1 wt %, 5.3 mL) was added and stirred under 60° C. for 2 h. The crude was extracted with EtOAc and brine. The organic residue was dried over magnesium sulfate and evaporated to afford the compound 51 as a yellow oil (3.7 g, 96%) without further purification. $^1$H NMR (CDCl$_3$, 400 MHz) δ 7.39 (d, J=16.2 Hz, 2H), 7.10-7.01 (m, 2H), 6.88-6.81 (m, 1H), 6.68 (d, J=16.2 Hz, 2H), 2.38 (s, 3H).

Preparation of 4-(3,5-difluorophenyl)butan-2-one (52)

To a flame dried 10 wt % Pd/C solid (1081 mg), anhydrous tetrahydrofuran (41 mL) and the compound 51 (3700 mg, 20.31 mmol) was added. The mixture was stirred at RT under H$_2$ (1 atm) for 2 h. The mixture was then filtrated and evaporated in vacuo. The residue was extracted with EtOAc and brine. The organic residue was dried over magnesium sulfate, evaporated and purified by F.C. with EtOAc/hexanes/dichloromethane (5/90/5) to afford the compound 52 as a colorless oil (1710 mg, 46%). $^1$H NMR (CDCl$_3$, 400 MHz) δ 6.74-6.67 (m, 2H), 6.67-6.58 (m, 1H), 2.87 (t, J=7.4 Hz, 2H), 2.75 (t, J=7.2 Hz, 2H), 2.15 (s, 3H).

Preparation of ethyl (Z)-6-(3,5-difluorophenyl)-2-hydroxy-4-oxohex-2-enoate (53)

To a solution of the compound 52 (1700 mg, 9.23 mmol) in tetrahydrofuran (62 mL) at −78° C., lithium diisopropylamide solution (2 M in tetrahydrofuran/heptane/ethylbenzene, 5.1 mL, 10.15 mmol) was added dropwise over 10 mins and stirred under −78° C. 10 mins. Diethyl oxalate (1550 µL, 6.09 mmol) was added and stirred back to 0° C. for 1 h. The mixture was quenched with 1 N hydrochloric acid under 0° C. The mixture was extracted with EtOAc and brine. The organic residue was dried over magnesium sulfate, evaporated and purified by F.C. with EtOAc/hexanes/dichloromethane (10/80/10) to afford the compound 53 as a colorless oil (2161 mg, 82%). $^1$H NMR (CDCl$_3$, 400 MHz) δ 6.77-6.61 (m, 3H), 6.35 (s, 1H), 4.34 (q, J=7.1 Hz, 2H), 2.96 (t, J=7.6 Hz, 2H), 2.82 (t, J=7.4 Hz, 2H), 1.36 (t, J=7.1 Hz, 3H).

Preparation of ethyl 3-(3,5-difluorophenethyl)-1H-pyrazole-5-carboxylate (54)

To a solution of the compound 53 (2.1 g, 7.46 mmol) in ethanol/tetrahydrofuran (3/1, 20 mL) at 0° C., hydrazine hydrate (416 µL, 8.58 mmol) was added and stirred back to RT for 2 h. The mixture was concentrated under reduced pressure and extracted with EtOAc, 1 N hydrochloric acid, and brine. The organic residue was dried over magnesium sulfate, evaporated and purified by F.C. with methanol/dichloromethane (10/90). The collected residue was precipitate with ethanol/hexanes to afford the compound 54 as an off-white solid (1.5 g, 73%). $^1$H NMR (CDCl$_3$, 400 MHz) δ 6.77-6.61 (m, 3H), 6.61 (s, 1H), 4.38 (q, J=7.1 Hz, 2H), 3.08-2.94 (m, 4H), 1.38 (t, J=7.1 Hz, 3H).

Preparation of 3-(3,5-difluorophenethyl)-1H-pyrazole-5-carboxylic acid (55)

To a solution of the compound 54 (1.5 g, 5.42 mmol) in ethanol (11 mL), sodium hydroxide aqueous solution (10 wt %, 5.5 mL) was added and stirred under 60° C. for 2 h. The mixture was cooled to 0° C., quenched with 1 N hydrochloric acid, and extracted with EtOAc and water. The organic residue was dried over magnesium sulfate, evaporated and precipitate with ethanol and hexanes to afford the compound 55 as an off-white solid (1.1 g, 82%). $^1$H NMR (CDCl$_3$, 400 MHz) δ 6.58-6.78 (m, 2H), 6.78-6.70 (m, 1H), 6.57 (s, 1H), 2.99 (s, 4H).

Preparation of 6-((((6-((((6-((((6-(tert-butoxycarbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl 3-(3,5-difluorophenethyl)-1H-pyrazole-5-carboxylate (56)

To a mixture of the compound 16 (400 mg, 0.24 mmol), compound 55 (67 mg, 0.27 mmol) and 4-dimethylaminopyridine (24 mg, 0.19 mmol) in dichloromethane (4.8 mL) at 0° C., 1-ethyl-3-(3-dimethylaminopropyl)carbodiimide hydrochloride (56 mg, 0.29 mmol) was added and stirred back to RT for 2 h. The mixture was extracted with dichloromethane, water, and brine. The organic residue was dried over anhydrous magnesium sulfate, evaporated, and purified by F.C. with EtOAc/hexanes/dichloromethane (5/45/50). The collected residue was precipitate with dichloromethane/hexanes to afford the compound 56 as an off-white solid (368 mg, 81%). $^1$H NMR (CDCl$_3$, 400 MHz) δ 7.80-7.30 (m, 60H), 6.82 (s, 1H), 6.74-6.61 (m, 3H), 3.08-2.94 (m, 4H), 1.53 (s, 9H).

Preparation of 7-((7-((7-((7-((7-((3-(3,5-difluorophenethyl)-1H-pyrazole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (57)

A solution of the compound 56 (362 mg, 0.22 mmol) in formic acid/chloroform (40 vol. %, 12.8 mL) was stirred under 60° C., 2 h. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 57 as an off-white solid (239 mg, 68%). $^1$H NMR (CDCl$_3$, 400 MHz) δ 7.84-7.30 (m, 60H), 6.83 (s, 1H), 6.75-6.60 (m, 3H), 3.10-2.96 (m, 4H).

Preparation of 3-((3-((3-((3-((3-(3,5-difluorophenethyl)-1H-pyrazole-5-carbonyl)oxy)-4,5-dihydroxybenzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (58)

To a flame dried 10 wt % Pd/C solid (99 mg), anhydrous tetrahydrofuran (3.0 mL) and the compound 57 (100 mg, 0.05 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase C$_{18}$ F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/n-pentane (1:25) to afford the compound 58 as an off-white solid (32 mg, 58%). $^1$H NMR (MeOD, 400 MHz) δ 7.63-7.10 (m, 10H), 6.91-6.72 (m, 4H), 3.05 (s, 4H).

Example 12. 3-((3-((3-((3-((3,4-dihydroxy-5-((3-(4-(trifluoromethyl)phenethyl)-1H-pyrazole-5-carbonyl)oxy)benzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (66)
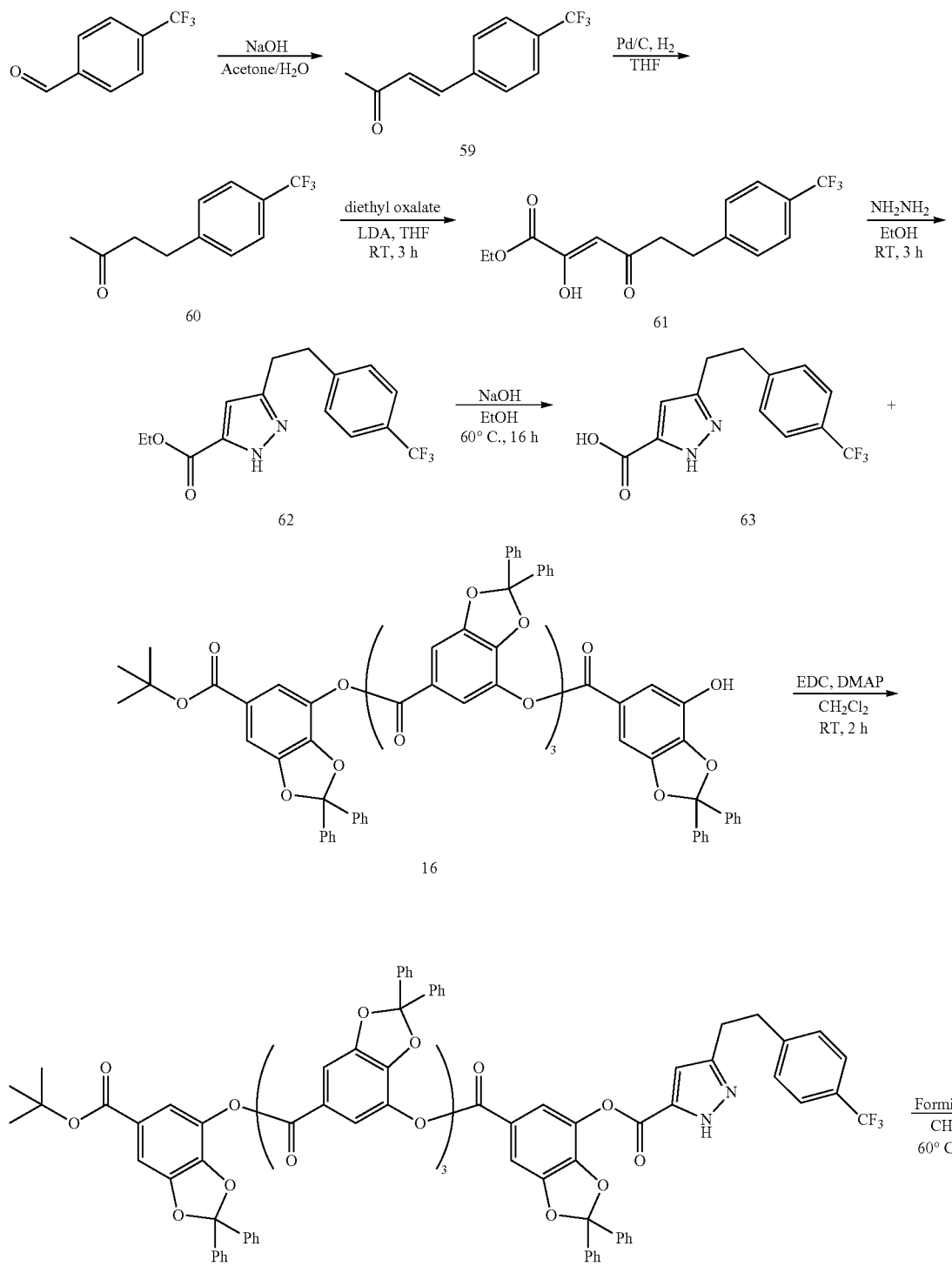

-continued

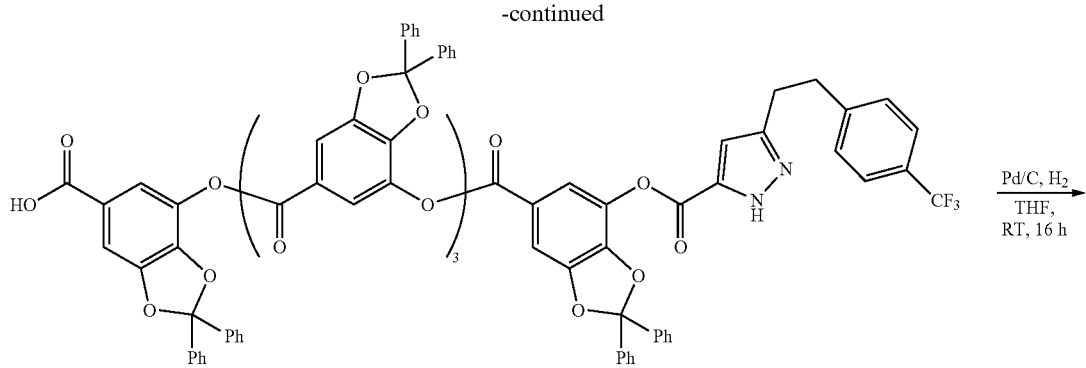

65

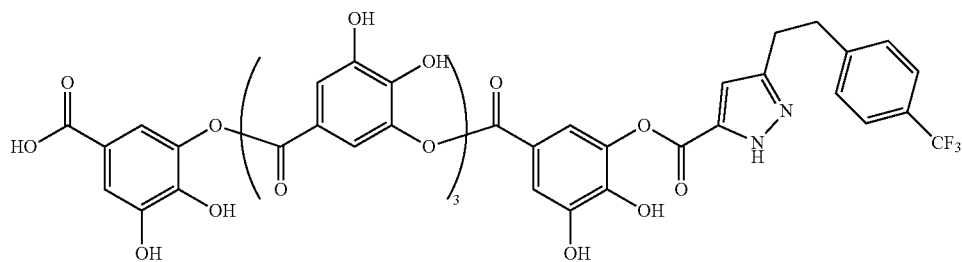

66

Preparation of (E)-4-(4-(trifluoromethyl)phenyl)but-3-en-2-one (59)

To a solution of 4-trifluoromethylbenzaldehyde (10.0 g, 57.43 mmol) in acetone/water (1/1, 23.0 mL), sodium hydroxide aqueous solution (1 wt %, 14.4 mL) was added and stirred under 60° C. for 2 h. The crude was extracted with EtOAc and brine. The organic residue was dried over magnesium sulfate and evaporated to afford the compound 59 as a yellow oil (12.0 g, 98%) without further purification. H NMR (CDCl$_3$, 400 MHz) δ7.70-7.62 (m, 4H), 7.52 (d, J=16.3 Hz, 2H), 6.77 (d, J=16.3 Hz, 2H), 2.41 (s, 3H).

Preparation of 4-(4-(trifluoromethyl)phenyl)butan-2-one (60)

To a flame dried 10 wt % Pd/C solid (2969 mg), anhydrous tetrahydrofuran (279 mL) and the compound 59 (12.0 mg, 55.79 mmol) was added. The mixture was stirred at RT under H$_2$ (1 atm) for 2 h. The mixture was then filtrated and evaporated in vacuo. The residue was extracted with EtOAc and brine. The organic residue was dried over magnesium sulfate, evaporated and purified by F.C. with EtOAc/hexanes/dichloromethane (5/90/5) to afford the compound 60 as a colorless oil (4.1 g, 34%). H NMR (CDCl$_3$, 400 MHz) δ 7.53 (d, J=8.1 Hz, 2H), 7.29 (d, J=8.1 Hz, 2H), 2.95 (t, J=7.5 Hz, 2H), 2.78 (t, J=7.5 Hz, 2H), 2.15 (s, 3H).

Preparation of ethyl (Z)-2-hydroxy-4-oxo-6-(4-(trifluoromethyl)phenyl)hex-2-enoate (61)

To a solution of the compound 60 (4140 mg, 19.15 mmol) in tetrahydrofuran (127 mL) at −78° C., lithium diisopropylamide solution (2 M in tetrahydrofuran/heptane/ethylbenzene, 10.5 mL, 21.06 mmol) was added dropwise over 10 mins and stirred under −78° C. 10 mins. Diethyl oxalate (3215 μL, 22.98 mmol) was added and stirred back to 0° C. for 1 h. The mixture was quenched with 1 N hydrochloric acid under 0° C. The mixture was extracted with EtOAc and brine. The organic residue was dried over magnesium sulfate, evaporated and purified by F.C. with EtOAc/hexanes/dichloromethane (10/80/10) to afford the compound 61 as a light-yellow oil (5500 mg, 91%). $^1$H NMR (CDCl$_3$, 400 MHz) δ 7.60-7.49 (m, 2H), 7.37-7.27 (m, 2H), 6.35 (s, 1H), 4.36 (q, J=6.7 Hz, 2H), 3.04 (t, J=7.5 Hz, 2H), 2.85 (t, J=7.5 Hz, 2H), 1.37 (t, J=7.0 Hz, 3H).

Preparation of ethyl 3-(4-(trifluoromethyl)phenethyl)-1H-pyrazole-5-carboxylate (62)

To a solution of the compound 61 (5500 mg, 17.39 mmol) in ethanol (29 mL) at 0° C., hydrazine hydrate (1012 μL, 8.58 mmol) was added and stirred back to RT for 2 h. The mixture was concentrated under reduced pressure and extracted with EtOAc, 1 N hydrochloric acid, and brine. The organic residue was dried over magnesium sulfate, evaporated and purified by F.C. with methanol/dichloromethane (10/90). The collected residue was precipitate with ethanol/hexanes to afford the compound 62 as an off-white solid (2780 mg, 51%). $^1$H NMR (CDCl$_3$, 400 MHz) δ 7.53 (d, J=8.1 Hz, 2H), 7.29 (d, J=8.1 Hz, 2H), 6.61 (s, 1H), 4.37 (q, J=7.1 Hz, 2H), 3.04 (s, 4H), 1.37 (t, J=7.1 Hz, 3H).

Preparation of 3-(4-(trifluoromethyl)phenethyl)-1H-pyrazole-5-carboxylic acid (63)

To a solution of the compound 62 (2780 mg, 8.90 mmol) in ethanol/tetrahydrofuran (1/1, 36 mL), sodium hydroxide aqueous solution (10 wt %, 18.0 mL) was added and stirred under 60° C. for 2 h. The mixture was cooled to 0° C., quenched with 1 N hydrochloric acid, and extracted with EtOAc and water. The organic residue was dried over magnesium sulfate, evaporated and precipitate with ethanol and hexanes to afford the compound 63 as an off-white solid (1895 mg, 75%). $^1$H NMR (MeOD, 400 MHz) δ 7.56 (d, J=8.0 Hz, 2H), 7.38 (d, J=8.0 Hz, 2H), 6.75 (s, 1H), 3.10-2.98 (m, 4H).

Preparation of 6-(((6-(((6-(((6-(tert-butoxycarbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl 3-(4-(trifluoromethyl)phenethyl)-1H-pyrazole-5-carboxylate (64)

To a mixture of the compound 16 (4300 mg, 2.60 mmol), compound 63 (812 mg, 2.86 mmol) and 4-dimethylaminopyridine (349 mg, 2.86 mmol) in dichloromethane (52 mL) at 0° C., 1-ethyl-3-(3-dimethylaminopropyl)carbodiimide hydrochloride (604 mg, 3.12 mmol) was added and stirred back to RT for 2 h. The mixture was extracted with dichloromethane, water, and brine. The organic residue was dried over anhydrous magnesium sulfate, evaporated, and purified by F.C. with EtOAc/hexanes/dichloromethane (5/45/50). The collected residue was precipitate with dichloromethane/hexanes to afford the compound 64 as an off-white solid (3740 mg, 75%). $^1$H NMR (CDCl$_3$, 400 MHz) δ 7.81-7.27 (m, 64H), 6.83 (s, 1H), 3.07 (s, 4H), 1.53 (s, 9H).

Preparation of 7-((7-((7-((7-((2,2-diphenyl-7-((3-(4-(trifluoromethyl)phenethyl)-1H-pyrazole-5-carbonyl)oxy)benzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (65)

A solution of the compound 64 (3740 mg, 1.95 mmol) in formic acid/dichloromethane (40 vol. %, 130 mL) was stirred under 60° C., 2 h. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 65 as an off-white solid (1300 mg, 36%). $^1$H NMR (MeOD, 400 MHz) δ 7.83-7.27 (m, 64H), 6.84 (s, 1H), 3.08 (s, 4H).

Preparation of 3-((3-((3-((3-((3,4-dihydroxy-5-((3-(4-(trifluoromethyl)phenethyl)-1H-pyrazole-5-carbonyl)oxy)benzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (66)

To a flame dried 10 wt % Pd/C solid (2920 mg), anhydrous tetrahydrofuran (38 mL) and the compound 65 (3200 mg, 1.72 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase C$_{18}$ F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/n-pentane (1:25) to afford the compound 66 as an off-white solid (1150 mg, 64%). $^1$H NMR (MeOD, 400 MHz) δ 7.64-7.09 (m, 14H), 6.82 (s, 1H), 3.09 (s, 4H).

Example 13. 3-((3-((3-((3-((3,4-dihydroxy-5-((3-(2-(trifluoromethyl)phenethyl)-1H-pyrazole-5-carbonyl)oxy)benzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (74)

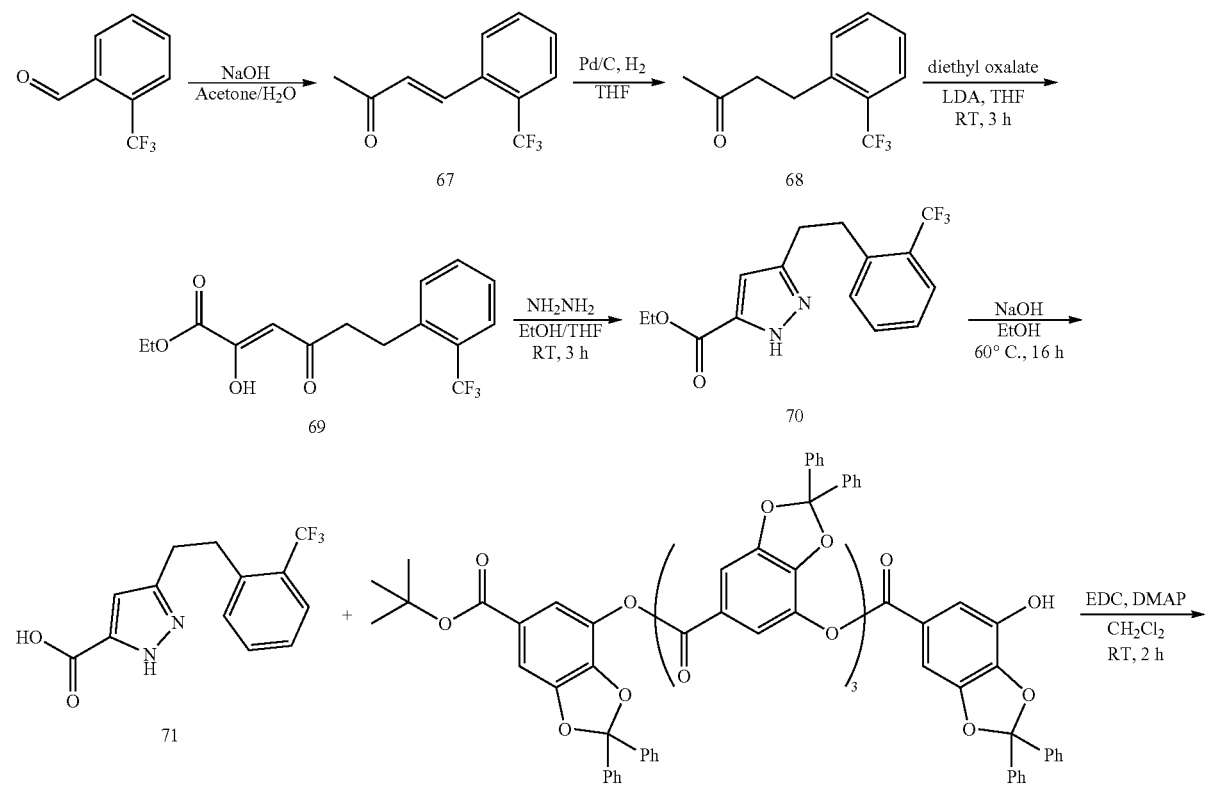

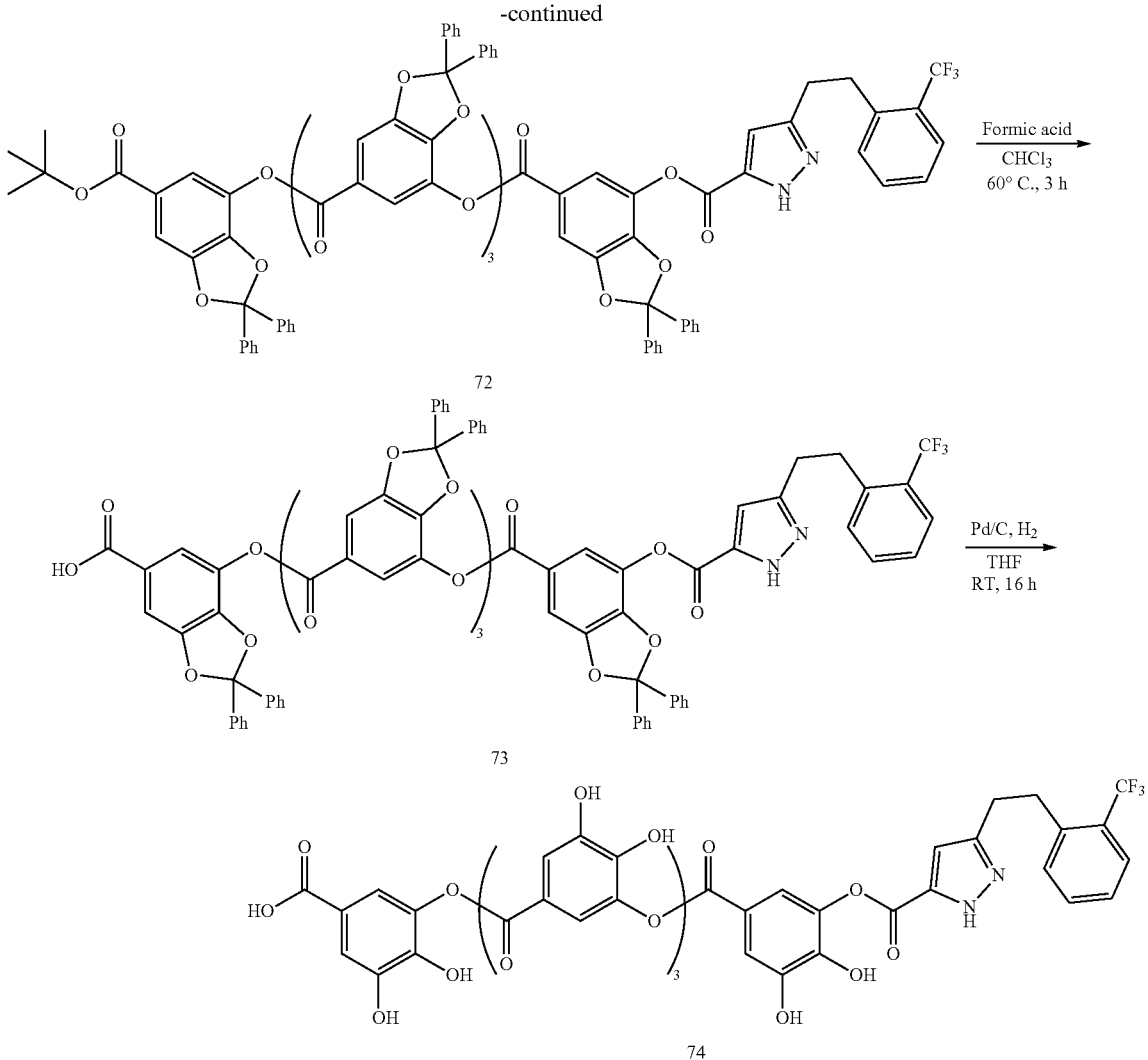

Preparation of (E)-4-(2-(trifluoromethyl)phenyl)but-3-en-2-one (67)

To a solution of 4-trifluoromethylbenzaldehyde (10.0 g, 57.43 mmol) in acetone/water (1/1, 23.0 mL), sodium hydroxide aqueous solution (1 wt %, 14.4 mL) was added and stirred under 60° C. for 2 h. The crude was extracted with EtOAc and brine. The organic residue was dried over magnesium sulfate and evaporated to afford the compound 67 as a yellow oil (8.3 g, 67%) without further purification. $^1$H NMR (CDCl$_3$, 400 MHz) δ 7.88 (dd, J=16.2, 2.0 Hz, 1H), 7.71 (d, J=8.1 Hz, 2H), 7.58 (t, J=7.6 Hz, 1H), 7.49 (t, J=7.7 Hz, 1H), 6.63 (d, J=16.2 Hz, 1H), 2.40 (s, 3H).

Preparation of 4-(2-(trifluoromethyl)phenyl)butan-2-one (68)

To a flame dried 10 wt % Pd/C solid (1992 mg), anhydrous tetrahydrofuran (41 mL) and the compound 67 (8020 mg, 37.44 mmol) was added. The mixture was stirred at RT under H$_2$ (1 atm) for 2 h. The mixture was then filtrated and evaporated in vacuo. The residue was extracted with EtOAc and brine. The organic residue was dried over magnesium sulfate, evaporated and purified by F.C. with EtOAc/hexanes/dichloromethane (5/90/5) to afford the compound 68 as a light-yellow oil (4380 mg, 54%). $^1$H NMR (CDCl$_3$, 400 MHz) δ 7.62 (d, J=7.8 Hz, 1H), 7.46 (t, J=7.5 Hz, 1H), 7.35-7.27 (m, 2H), 3.07 (t, J=7.8 Hz, 2H), 2.75 (t, J=7.8 Hz, 2H), 2.16 (s, 3H).

Preparation of ethyl (Z)-2-hydroxy-4-oxo-6-(2-(trifluoromethyl)phenyl)hex-2-enoate (69)

To a solution of the compound 68 (4380 mg, 20.26 mmol) in tetrahydrofuran (135 mL) at −78° C., lithium diisopropylamide solution (2 M in tetrahydrofuran/heptane/ethylbenzene, 11.1 mL, 22.28 mmol) was added dropwise over 10 mins and stirred under −78° C. 10 mins. Diethyl oxalate (3401 μL, 24.31 mmol) was added and stirred back to 0° C. for 1 h. The mixture was quenched with 1 N hydrochloric acid under 0° C. The mixture was extracted with EtOAc and brine. The organic residue was dried over magnesium sulfate, evaporated and purified by F.C. with EtOAc/hexanes/dichloromethane (10/80/10) to afford the compound 69 as a light-yellow oil (5560 mg, 87%). $^1$H NMR (CDCl$_3$, 400 MHz) δ 7.67-7.59 (m, 1H), 7.51-7.42 (m, 1H), 7.36-7.27 (m, 2H), 6.35 (s, 1H), 4.35 (q, J=7.1 Hz, 2H), 3.15 (t, J=7.8 Hz, 2H), 2.82 (t, J=7.8 Hz, 2H), 1.37 (t, J=7.1 Hz, 3H).

Preparation of ethyl 3-(2-(trifluoromethyl)phenethyl)-1H-pyrazole-5-carboxylate (70)

To a solution of 69 (5560 mg, 17.58 mmol) in ethanol (29 mL) at 0° C., hydrazine hydrate (1023 μL, 21.1 mmol) was added and stirred back to RT for 2 h. The mixture was concentrated under reduced pressure and extracted with EtOAc, 1 N hydrochloric acid, and brine. The organic residue was dried over magnesium sulfate, evaporated and purified by F.C. with methanol/dichloromethane (10/90). The collected residue was precipitate with ethanol/hexanes to afford the compound 70 as an off-white solid (3790 mg, 69%). $^1$H NMR (MeOD, 400 MHz) δ 7.66 (d, J=7.7 Hz, 1H), 7.53 (t, J=7.5 Hz, 1H), 7.43-7.32 (m, 2H), 6.56 (s, 1H), 4.34 (q, J=7.1 Hz, 2H), 3.20-3.10 (m, 2H), 3.05-2.91 (m, 2H), 1.37 (t, J=7.1 Hz, 3H).

Preparation of 3-(2-(trifluoromethyl)phenethyl)-1H-pyrazole-5-carboxylic acid (71)

To a solution of the compound 70 (3788 mg, 12.13 mmol) in ethanol/tetrahydrofuran (1/1, 49 mL), sodium hydroxide aqueous solution (10 wt %, 49 mL) was added and stirred under 60° C. for 2 h. The mixture was cooled to 0° C., quenched with 1 N hydrochloric acid, and extracted with EtOAc and water. The organic residue was dried over magnesium sulfate, evaporated and precipitate with ethanol and hexanes to afford the compound 71 as an off-white solid (3138 mg, 91%). $^1$H NMR (MeOD, 400 MHz) δ 7.66 (d, J=7.8 Hz, 1H), 7.53 (t, J=7.5 Hz, 1H), 7.43-7.32 (m, 2H), 6.57 (s, 1H), 3.20-3.09 (m, 2H), 3.04-2.93 (m, 2H).

Preparation of 6-(((6-(((6-(((6-(((6-(tert-butoxycarbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl)oxy)carbonyl)-2,2-diphenylbenzo[d][1,3]dioxol-4-yl 3-(2-(trifluoromethyl)phenethyl)-1H-pyrazole-5-carboxylate (72)

To a mixture of the compound 16 (4600 mg, 2.78 mmol), compound 71 (869 mg, 3.06 mmol) and 4-dimethylaminopyridine (373 mg, 3.06 mmol) in dichloromethane (56 mL) at 0° C., 1-ethyl-3-(3-dimethylaminopropyl)carbodiimide hydrochloride (646 mg, 3.33 mmol) was added and stirred back to RT for 2 h. The mixture was extracted with dichloromethane, water, and brine. The organic residue was dried over anhydrous magnesium sulfate, evaporated, and purified by F.C. with EtOAc/hexanes/dichloromethane (5/45/50). The collected residue was precipitate with dichloromethane/hexanes to afford the compound 72 as an off-white solid (4443 mg, 83%). $^1$H NMR (CDCl$_3$, 400 MHz) δ 7.79-7.27 (m, 64H), 6.87 (s, 1H), 3.21-3.11 (m, 2H), 3.08-2.99 (m, 2H), 1.53 (s, 9H).

Preparation of 7-((7-((7-((7-((2,2-diphenyl-7-((3-(2-(trifluoromethyl)phenethyl)-1H-pyrazole-5-carbonyl)oxy)benzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (73)

A solution of the compound 72 (4443 mg, 2.31 mmol) in formic acid/dichloromethane (40 vol. %, 154 mL) was stirred under 60° C., 2 h. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 73 as an off-white solid (1300 mg, 36%). $^1$H NMR (CDCl$_3$, 400 MHz) δ 7.84-7.27 (m, 64H), 6.89 (s, 1H), 3.25-3.13 (m, 2H), 3.11-3.02 (m, 2H).

Preparation of 3-((3-((3-((3-((3,4-dihydroxy-5-((3-(2-(trifluoromethyl)phenethyl)-1H-pyrazole-5-carbonyl)oxy)benzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (74)

To a flame dried 10 wt % Pd/C solid (2829 mg), anhydrous tetrahydrofuran (37 mL) and the compound 73 (3100 mg, 1.66 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase C$_{18}$ F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/n-pentane (1:25) to afford the compound 74 as an off-white solid (1170 mg, 67%). $^1$H NMR (MeOD, 400 MHz) δ 7.73-7.04 (m, 14H), 6.89-6.73 (m, 1H), 3.26-3.14 (m, 2H), 3.11-3.00 (m, 2H).

Example 14. 3-((3-((3-((3-((3-(benzoyloxy)-4,5-dihydroxybenzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (77)

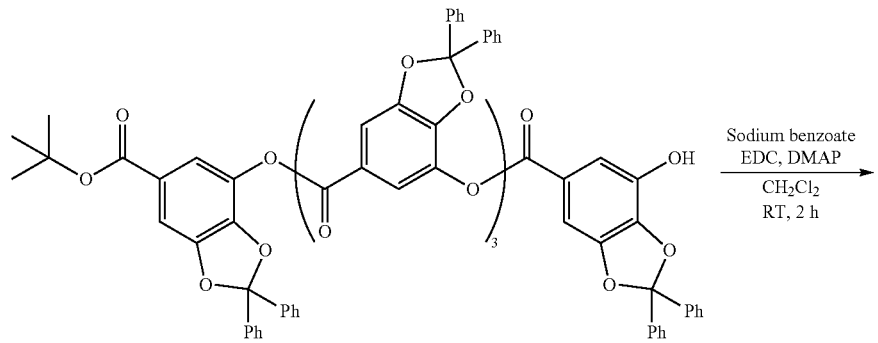

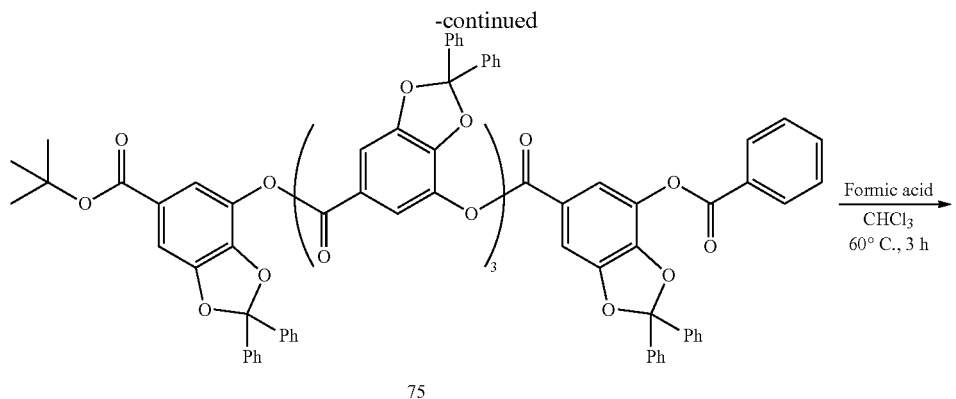

75

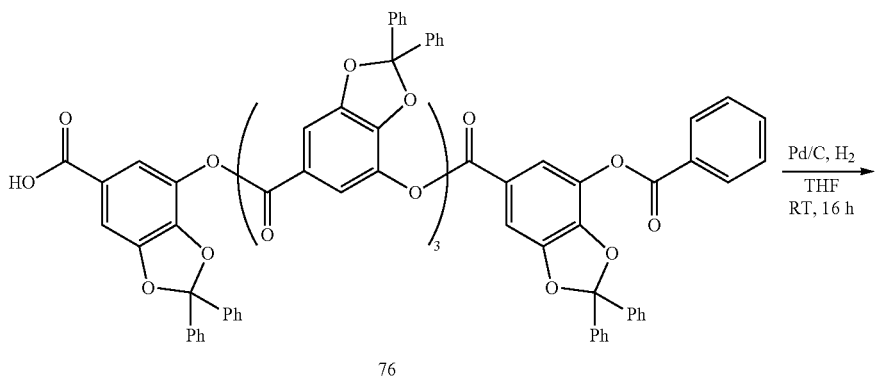

76

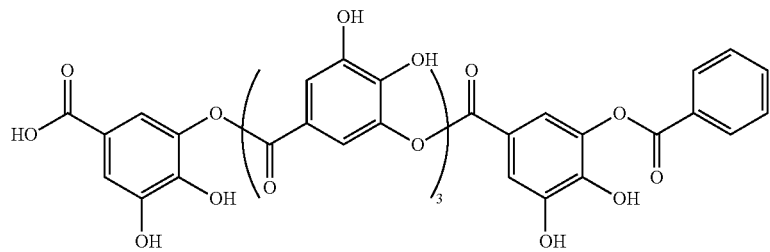

77

Preparation of 6-(tert-butoxycarbonyl)-2,2-diphenylbenzo[d][1,3]dioxol-4-yl 7-((7-((7-((7-(benzoyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (75)

To a mixture of the compound 16 (400 mg, 0.24 mmol), sodium benzoate (37 mg, 0.25 mmol) and 4-dimethylaminopyridine (6 mg, 0.05 mmol) in dichloromethane (5 mL) at 0° C., 1-ethyl-3-(3-dimethylaminopropyl)carbodiimide hydrochloride (52 mg, 0.27 mmol) was added and stirred back to RT for 2 h. The mixture was extracted with dichloromethane, water, and brine. The organic residue was dried over anhydrous magnesium sulfate, evaporated, and purified by F.C. with EtOAc/hexanes/dichloromethane (5/45/50). The collected residue was precipitate with dichloromethane/hexanes to afford the compound 75 as an off-white solid (367 mg, 86%). $^1$H NMR (CDCl$_3$, 400 MHz) δ 8.30-8.21 (m, 2H), 7.82-7.30 (m, 63H), 1.53 (s, 9H).

Preparation of 7-((7-((7-((7-(benzoyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (76)

A solution of the compound 75 (350 mg, 0.20 mmol) in formic acid/chloroform (33 vol. %, 13 mL) was stirred under 60° C., 2 h. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 76 as an off-white solid (212 mg, 63%). $^1$H NMR (CDCl$_3$, 400 MHz) δ 8.28-8.21 (m, 2H), 7.81-7.30 (m, 63H).

Preparation of 3-((3-((3-((3-(benzoyloxy)-4,5-dihydroxybenzoyl)oxy)-4,5-dihydroxybenzoyl)oxy)-4,5-dihydroxybenzoyl)oxy)-4,5-dihydroxybenzoic acid (77)

To a flame dried 10 wt % Pd/C solid (80 mg), anhydrous tetrahydrofuran (5 mL) and the compound 76 (80 mg, 0.05 mmol) was added. The mixture was stirred at RT under H₂ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase C₁₈ F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/n-pentane (1:25) to afford the compound 77 as an off-white solid (40 mg, 97%). ¹H NMR (MeOD, 400 MHz) δ 8.26-8.18 (m, 2H), 7.75-7.06 (m, 13H).

Example 15. 3-((3-((3-((3-(2-cyclohexylacetoxy)-4,5-dihydroxybenzoyl)oxy)-4,5-dihydroxybenzoyl)oxy)-4,5-dihydroxybenzoyl)oxy)-4,5-dihydroxybenzoic acid (80)

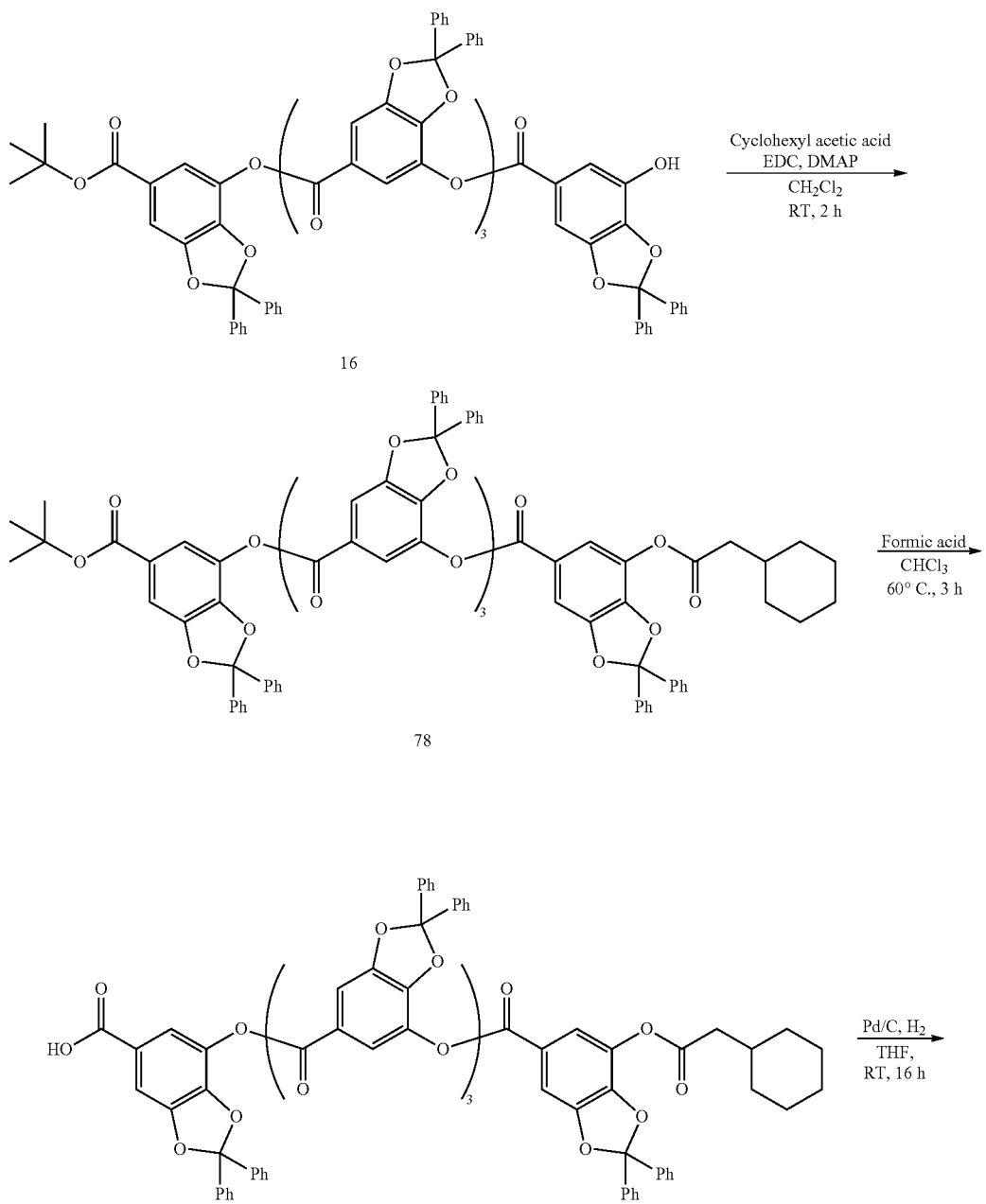

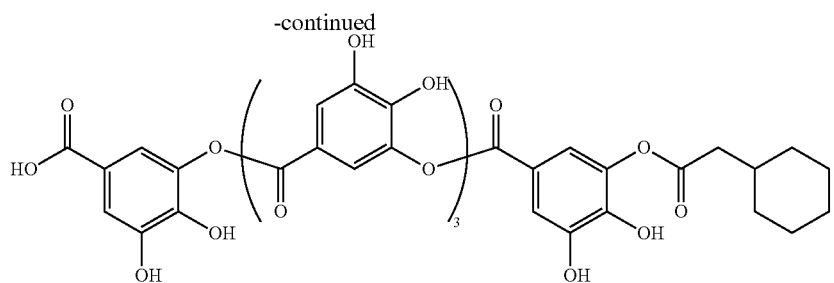

80

Preparation of 6-(tert-butoxycarbonyl)-2,2-diphenylbenzo[d][1,3]dioxol-4-yl 7-((7-((7-((7-(2-cyclohexylacetoxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (78)

To a mixture of the compound 16 (500 mg, 0.30 mmol), cyclohexyl acetic acid (47 mg, 0.33 mmol) and 4-dimethylaminopyridine (18 mg, 0.15 mmol) in dichloromethane (6 mL) at 0° C., 1-ethyl-3-(3-dimethylaminopropyl)carbodiimide hydrochloride (70 mg, 0.36 mmol) was added and stirred back to RT for 2 h. The mixture was extracted with dichloromethane, water, and brine. The organic residue was dried over anhydrous magnesium sulfate, evaporated, and purified by F.C. with EtOAc/hexanes/dichloromethane (5/45/50). The collected residue was precipitate with dichloromethane/hexanes to afford the compound 78 as an off-white solid (387 mg, 72%). $^1$H NMR (CDCl$_3$, 400 MHz) δ 7.75-7.31 (m, 60H), 2.50 (d, J=7.0 Hz, 2H), 2.03-1.84 (m, 3H), 1.82-1.64 (m, 3H), 1.53 (s, 9H), 1.42-1.02 (m, 5H).

Preparation of 7-((7-((7-((7-(2-cyclohexylacetoxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (79)

A solution of the compound 78 (387 mg, 0.22 mmol) in formic acid/chloroform (40 vol. %, 15 mL) was stirred under 60° C., 2 h. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 79 as an off-white solid (214 mg, 57%). $^1$H NMR (CDCl$_3$, 400 MHz) δ 7.76-7.32 (m, 60H), 2.50 (d, J=7.0 Hz, 2H), 2.04-1.86 (m, 3H), 1.82-1.64 (m, 3H), 1.41-1.04 (m, 5H).

Preparation of 3-((3-((3-((3-(2-cyclohexylacetoxy)-4,5-dihydroxybenzoyl)oxy)-4,5-dihydroxybenzoyl)oxy)-4,5-dihydroxybenzoyl)oxy)-4,5-dihydroxybenzoyl)oxy)-4,5-dihydroxybenzoic acid (80)

To a flame dried 10 wt % Pd/C solid (148 mg), anhydrous tetrahydrofuran (5 mL) and the compound 79 (150 mg, 0.09 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase C$_{18}$ F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/n-pentane (1:25) to afford the compound 80 as an off-white solid (53 mg, 68%). $^1$H NMR (MeOD, 400 MHz) δ 7.65-7.09 (m, 10H), 2.56-2.46 (m, 2H), 2.00-1.84 (m, 3H), 1.82-1.64 (m, 3H), 1.44-1.04 (m, 5H).

Example 16. 5-((5-((5-((2,3-dihydroxy-5-(phenoxycarbonyl)phenoxy)carbonyl)-2,3-dihydroxyphenoxy)carbonyl)-2,3-dihydroxyphenoxy)carbonyl)-2,3-dihydroxyphenyl 3-(benzoyloxy)-4,5-dihydroxybenzoate (85)

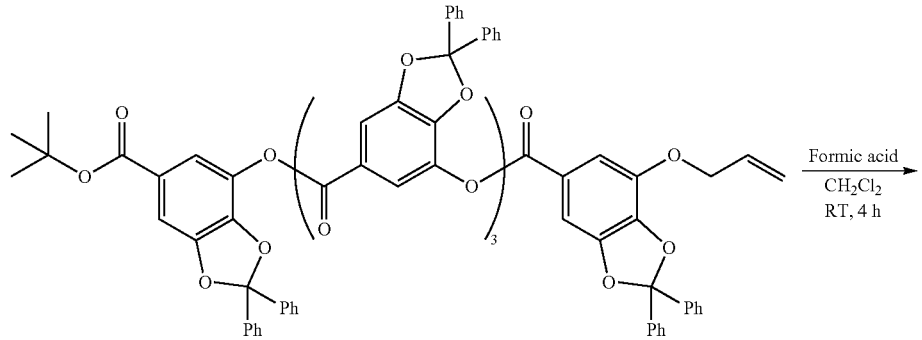

15

-continued
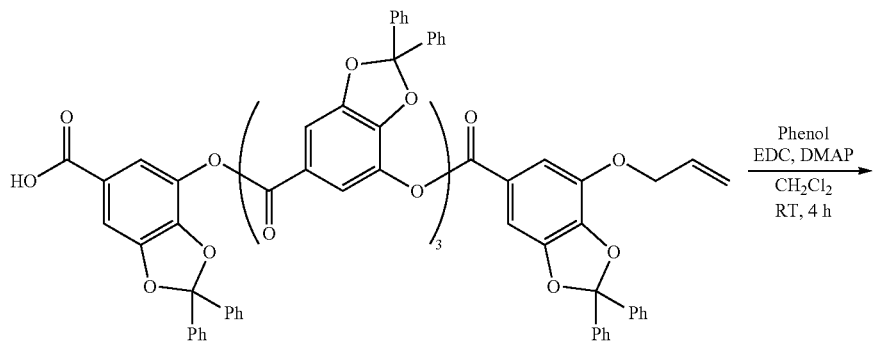
81
Phenol
EDC, DMAP
CH₂Cl₂
RT, 4 h
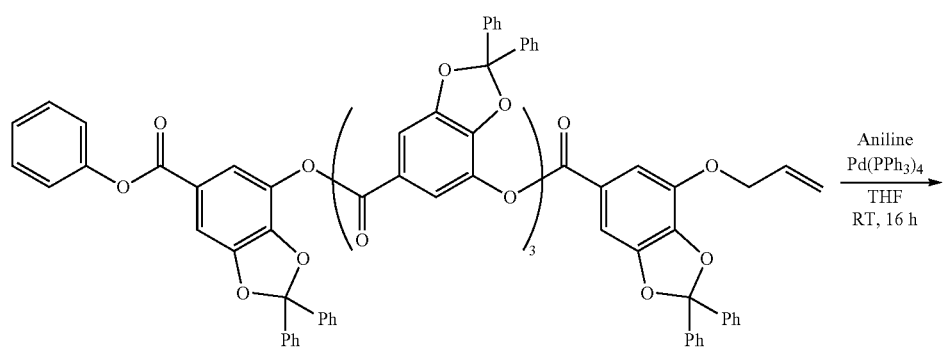
82
Aniline
Pd(PPh₃)₄
THF
RT, 16 h
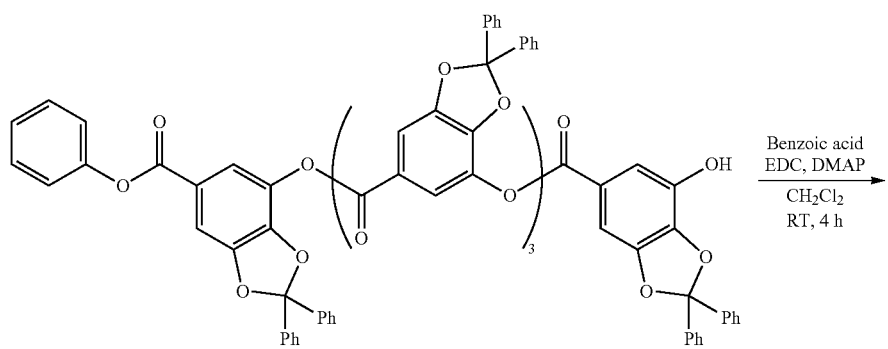
83
Benzoic acid
EDC, DMAP
CH₂Cl₂
RT, 4 h
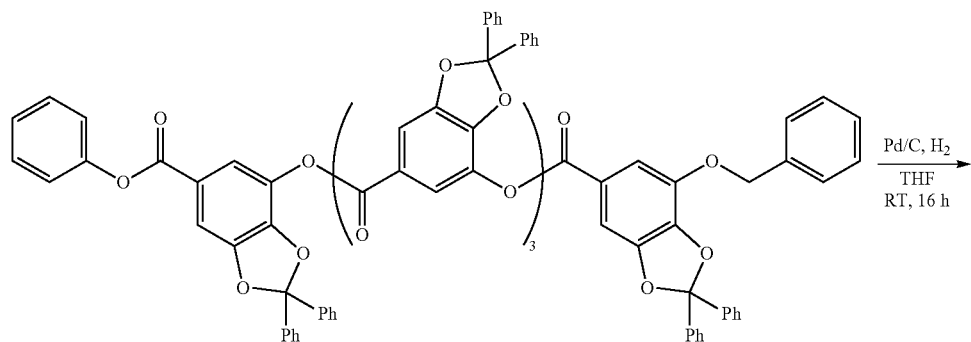
84
Pd/C, H₂
THF
RT, 16 h -continued

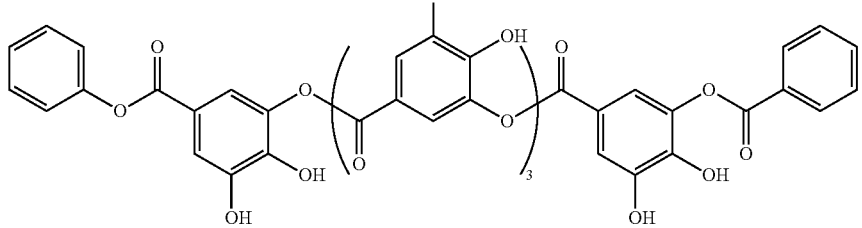

85

Preparation of 7-((7-((7-((7-((7-(allyloxy)-2,2-diphenyl-benzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (81)

To a stirred solution of the compound 15 (30.0 g, 17.7 mmol) in anhydrous dichloromethane (176.9 mL) was added formic acid (88.5 mL) at 0° C. After 10 mins, stirred 4 h at RT. the mixture was extracted with water 3 times, washed with brine, dried over anhydrous magnesium sulfate and filtered. The filtrate was evaporated in vacuo. The residue was purified by F.C. with EtOAc/dichloromethane (1:8) to afford the compound 81 (22.5 g, 78%) as a white solid. $^1$H NMR (CDCl$_3$, 400 MHz) δ 7.74-7.71 (m, 3H), 7.66-7.63 (m, 3H), 7.61-7.53 (m, 21H), 7.51-7.50 (d, J=1.5 Hz, 1H), 7.50-7.49 (d, J=1.5 Hz, 1H), 7.47-7.46 (d, J=1.5 Hz, 1H), 7.41-7.35 (m, 30H), 6.12-6.02 (m, 1H), 5.45-5.39 (dd, J=17.2, 1.5 Hz, 1H), 5.31-5.28 (dd, J=10.5, 1.3 Hz, 1H), 4.75-4.73 (d, J=5.5 Hz, 2H).

Preparation of 6-(phenoxycarbonyl)-2,2-diphenylbenzo[d][1,3]dioxol-4-yl 7-((7-((7-((7-(allyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (82)

To a mixture of the compound 81 (6200 mg, 3.78 mmol), phenol (391 mg, 4.16 mmol) and 4-dimethylaminopyridine (370 mg, 3.03 mmol) in dichloromethane (76 mL) at 0° C., 1-ethyl-3-(3-dimethylaminopropyl)carbodiimide hydrochloride (879 mg, 4.54 mmol) was added and stirred back to RT for 2 h. The mixture was extracted with dichloromethane, water, and brine. The organic residue was dried over anhydrous magnesium sulfate, evaporated, and purified by F.C. with hexanes/dichloromethane (30/70). The collected residue was precipitate with dichloromethane/hexanes to afford the compound 82 as an off-white solid (5648 mg, 87%). $^1$H NMR (CD$_2$Cl$_2$, 400 MHz) δ 7.78-7.34 (m, 62H), 7.31-7.21 (m, 1H), 7.21-7.14 (m, 2H), 6.17-6.03 (m, 1H), 5.49-5.39 (m, 1H), 5.32-5.27 (m, 1H), 4.78-4.71 (m, 2H).

Preparation of 6-(phenoxycarbonyl)-2,2-diphenylbenzo[d][1,3]dioxol-4-yl 7-((7-((7-((7-hydroxy-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (83)

To a nitrogen flushed solution of the compound 82 (6100 mg, 3.56 mmol) and tetrakis(triphenyl phosphine)palladium (415 mg, 0.36 mmol) in dry tetrahydrofuran (71 mL), aniline (0.20 mL, 2.13 mmol) was added and stirred at RT for 16 h. The mixture was extracted with dichloromethane, 1 N hydrochloric acid and brine. The organic residue was dried over magnesium sulfate, evaporated, and purified by F.C. with EtOAc/dichloromethane (5/95) to afford the compound 83 as an off-white solid (5270 mg, 89%). $^1$H NMR (CDCl$_3$, 400 MHz) δ 7.76-7.31 (m, 62H), 7.25-7.13 (m, 3H).

Preparation of 6-(phenoxycarbonyl)-2,2-diphenylbenzo[d][1,3]dioxol-4-yl 7-((7-((7-((7-(benzoyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (84)

To a mixture of the compound 83 (135 mg, 0.08 mmol), benzoic acid (11 mg, 0.09 mmol) and 4-dimethylaminopyridine (4 mg, 0.03 mmol) in dichloromethane (2 mL) at 0° C., 1-ethyl-3-(3-dimethylaminopropyl)carbodiimide hydrochloride (20 mg, 0.10 mmol) was added and stirred back to RT for 2 h. The mixture was extracted with dichloromethane, water, and brine. The organic residue was dried over anhydrous magnesium sulfate, evaporated, and purified by F.C. with hexanes/dichloromethane (30/70). The collected residue was precipitate with dichloromethane/hexanes to afford the compound 84 as an off-white solid (122 mg, 85%). $^1$H NMR (CD$_2$Cl$_2$, 400 MHz) δ 8.28-8.21 (m, 2H), 7.82-7.35 (m, 65H), 7.32-7.21 (m, 1H), 7.20-7.15 (m, 2H).

Preparation of 5-((5-((5-((2,3-dihydroxy-5-(phenoxycarbonyl)phenoxy)carbonyl)-2,3-dihydroxyphenoxy)carbonyl)-2,3-dihydroxyphenoxy)carbonyl)-2,3-dihydroxyphenyl 3-(benzoyloxy)-4,5-dihydroxybenzoate (85)

To a flame dried 10 wt % Pd/C solid (118 mg), anhydrous tetrahydrofuran (4 mL) and the compound 84 (118 mg, 0.07 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase C$_{18}$ F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/n-pentane (1:25) to afford the compound 85 as an off-white solid (36 mg, 57%). $^1$H NMR (MeOD, 400 MHz) δ 8.29-8.17 (m, 2H), 7.74-7.66 (m, 1H), 7.64-7.23 (m, 15H), 7.23-7.16 (m, 2H).

Example 17. 6-(tert-butoxycarbonyl)-2,2-diphenyl-benzo[d][1,3]dioxol-4-yl 7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (89)
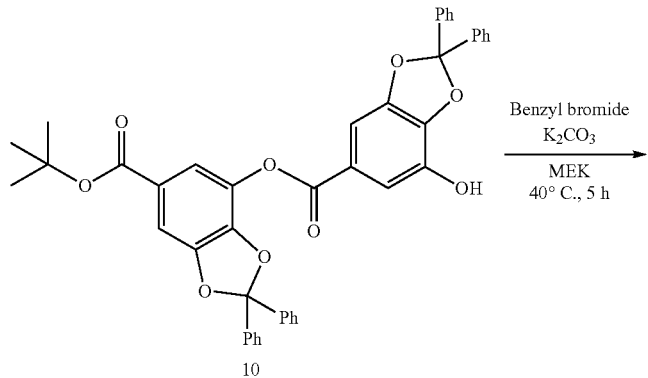
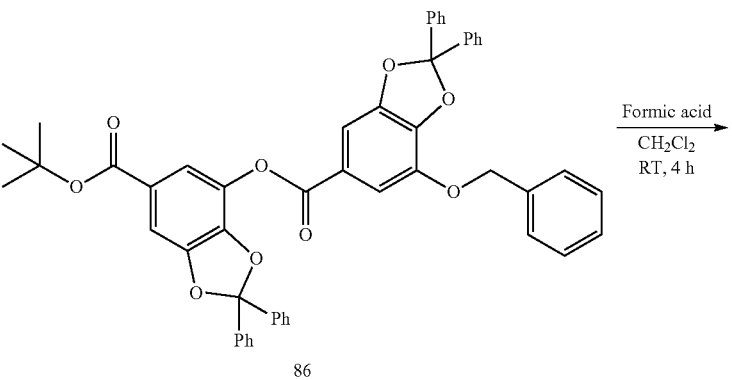
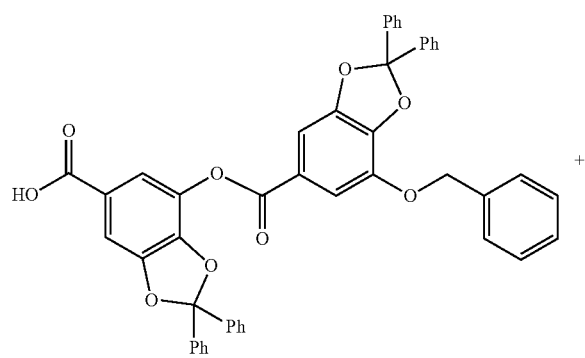

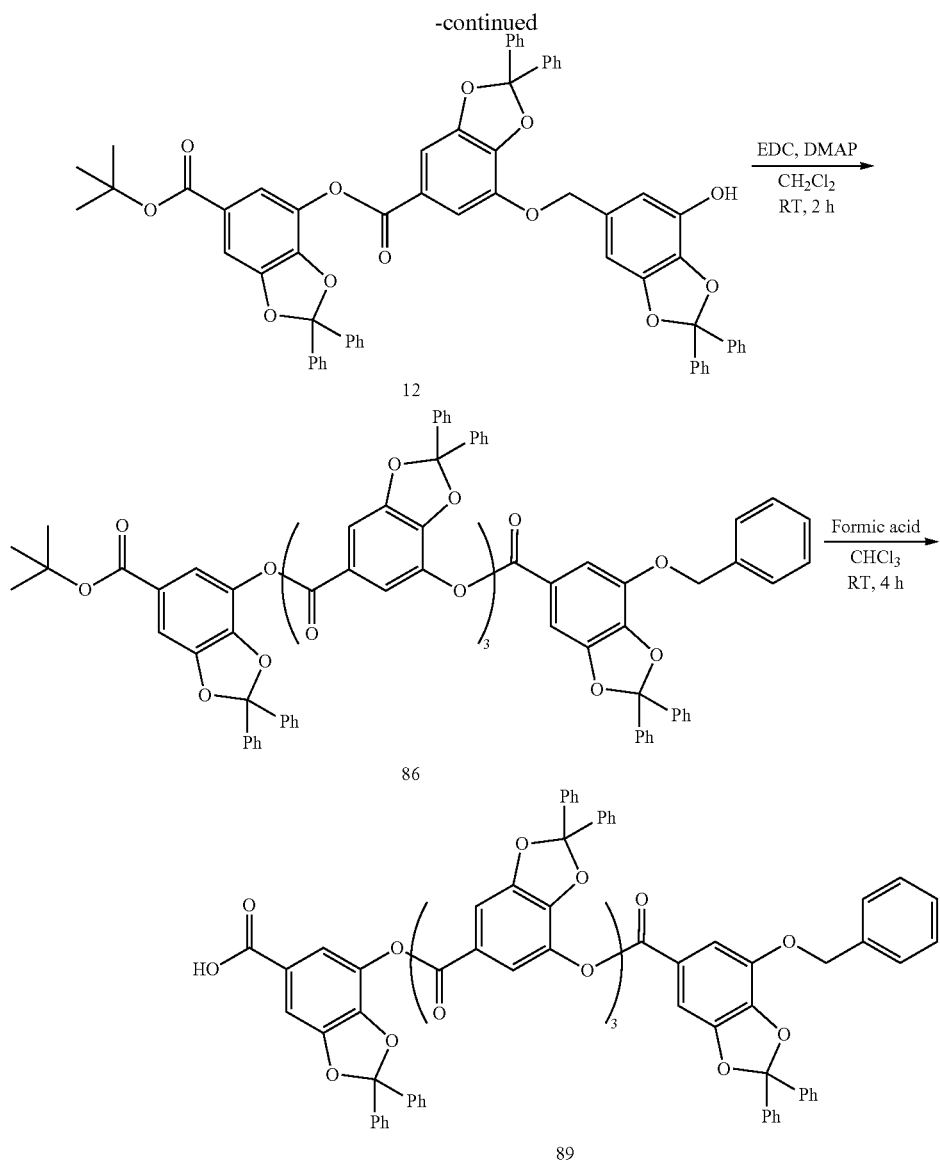

Preparation of 6-(tert-butoxycarbonyl)-2,2-diphenylbenzo[d][1,3]dioxol-4-yl 7-(benzyloxy)-2,2-diphenylbenzo[d][1,3]dioxole-5-carboxylate (86)

To a solution of compound 10 (2.5 g, 3.5 mmol) in methyl ethyl ketone (35.4 mL) was added potassium carbonate (1.5 g, 10.6 mmol) and benzyl bromide (1.3 mL, 10.6 mmol). The mixture was stirred at 40° C. for 6 h. After the reaction was complete, the mixture was concentrated in vacuo. The residue was diluted with dichloromethane, extracted with water, washed with brine, dried over anhydrous magnesium sulfate and filtered. The filtrate was stripped down in vacuo. The residue was purified by F.C. with EtOAc/hexanes (1:8) to afford the compound 86 as a white solid (2.6 g, 92%). $^1$H NMR (CDCl$_3$, 400 MHz) δ 7.61-7.55 (m, 9H), 7.48-7.33 (m, 20H), 5.29 (s, 2H), 1.56 (s, 9H).

Preparation of 7-((7-(benzyloxy)-2,2-diphenylbenzo[d][1,3]dioxole-5-carbonyl)oxy)-2,2-diphenylbenzo[d][1,3]dioxole-5-carboxylic acid (87)

To a stirred solution of the compound 86 (2.5 g, 3.1 mmol) in anhydrous dichloromethane (31.4 mL) was added formic acid (31.4 mL) at 0° C. After 10 mins, stirred 4 h at RT. the mixture was extracted with water 3 times, washed with brine, dried over anhydrous magnesium sulfate and filtered. The filtrate was evaporated in vacuo. The residue was purified by F.C. with EtOAc/dichloromethane (10%) to afford the compound 87 (1.3 g, 60%) as a white solid. $^1$H NMR (CDCl$_3$, 400 MHz) δ 7.60-7.53 (m, 10H), 7.52-7.51 (d, J=1.5 Hz, 1H), 7.47-7.45 (m, 3H), 7.41-7.32 (m, 15H), 5.28 (s, 2H).

Preparation of 6-(tert-butoxycarbonyl)-2,2-diphenylbenzo[d][1,3]dioxol-4-yl 7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (88)

To a mixture of the compound 12 (2800 mg, 2.74 mmol), compound 87 (2129 mg, 2.87 mmol) and 4-dimethylaminopyridine (33 mg, 0.27 mmol) in dichloromethane (27 mL) at 0° C., 1-ethyl-3-(3-dimethylaminopropyl)carbodiimide hydrochloride (583 mg, 3.01 mmol) was added and stirred back to RT for 2 h. The mixture was extracted with dichloromethane, water, and brine. The organic residue was dried over anhydrous magnesium sulfate, evaporated, and purified by F.C. with hexanes/dichloromethane (30/70). The collected residue was precipitate with dichloromethane/hexanes to afford the compound 88 as an off-white solid (4471 mg, 94%). $^1$H NMR (CDCl$_3$, 400 MHz) δ 7.76-7.29 (m, 65H), 5.28 (s, 2H), 1.54 (s, 9H).

Preparation of 7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (89)

A solution of the compound 88 (4470 mg, 2.56 mmol) in formic acid/chloroform (40 vol. %, 171 mL) was stirred under 60° C., 2 h. The mixture was cooled to RT and extracted with dichloromethane, water and brine. The organic residue was dried over magnesium sulfate, evaporated, and purified by F.C. with EtOAc/dichloromethane=10% and additional 0.5% formic acid. The collected residue was precipitate with dichloromethane/hexanes to afford the compound 89 as an off-white solid (2679 mg, 62%). $^1$H NMR (CDCl$_3$, 400 MHz) δ 7.76-7.29 (m, 65H), 5.27 (s, 2H).

Example 18. 5-((5-((5-((5-(((3-(4-fluorophenethyl)-1H-pyrazol-5-yl)methoxy)carbonyl)-2,3-dihydroxyphenoxy)carbonyl)-2,3-dihydroxyphenoxy)carbonyl)-2,3-dihydroxyphenoxy)carbonyl)-2,3-dihydroxyphenyl 3,4,5-trihydroxybenzoate (92)

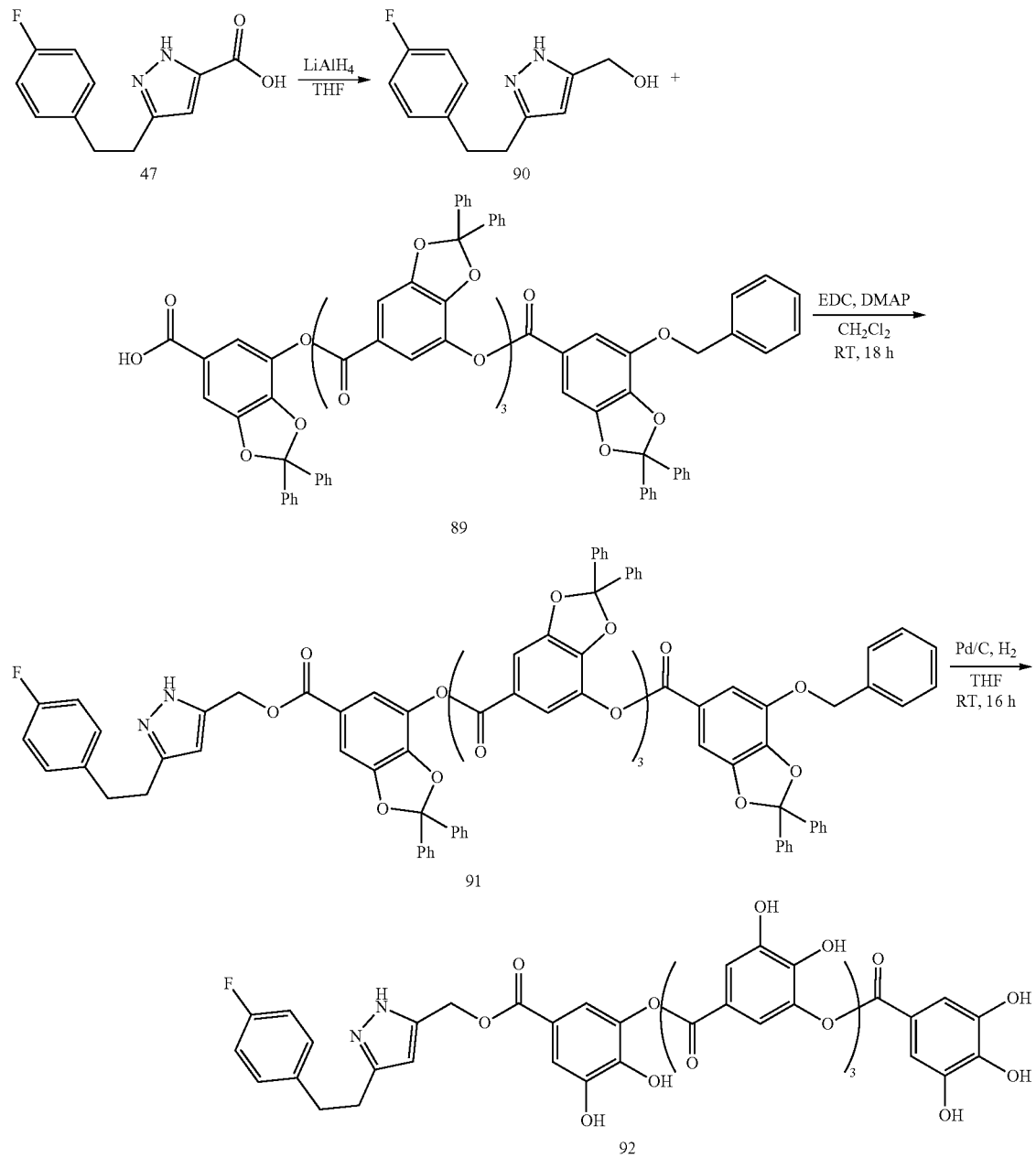

Preparation of (3-(4-fluorophenethyl)-1H-pyrazol-5-yl)methanol (90)

To a solution of the compound 47 (500 mg, 2.13 mmol) in anhydrous tetrahydrofuran (21 mL) at −78° C., lithium aluminum hydride (2.4 M in tetrahydrofuran, 3.6 mL, 8.54 mmol) was added dropwise over 5 mins and stirred back to RT for 2 days. The mixture was cooled to 0° C. and quenched with 1 N hydrochloric acid to pH 1. Solid anhydrous magnesium sulfate was added till saturated and extracted with n-butanol. The organic residue was dried over magnesium sulfate, evaporated, and purified by F.C. with methanol/dichloromethane=10%. The collected residue was precipitate with ethanol/hexanes to afford the compound 90 as a pale-yellow solid (380 mg, 81%). $^1$H NMR (MeOD, 400 MHz) δ 7.24-7.16 (m, 2H), 7.05-6.96 (m, 2H), 6.43 (s, 1H), 4.72 (s, 2H), 3.11-2.97 (m, 4H).

Preparation of 6-(((34-fluorophenethyl)-1H-pyrazol-5-yl)methoxy)carbonyl)-2,2-diphenylbenzo[d][1,3]dioxol-4-yl 7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (91)

To a mixture of the compound 90 (389 mg, 0.23 mmol), compound 90 (61 mg, 0.28 mmol) and 4-dimethylaminopyridine (23 mg, 0.18 mmol) in dichloromethane (5 mL) at 0° C., 1-ethyl-3-(3-dimethylaminopropyl)carbodiimide hydrochloride (58 mg, 0.30 mmol) was added and stirred back to RT for 2 h. The mixture was extracted with dichloromethane, water, and brine. The organic residue was dried over anhydrous magnesium sulfate, evaporated, and purified by F.C. with EtOAc/hexanes/dichloromethane (5/45/50). The collected residue was precipitate with dichloromethane/hexanes to afford the compound 91 as an off-white solid (145 mg, 33%). $^1$H NMR (CDCl$_3$, 400 MHz) δ 7.77-7.28 (m, 65H), 7.17-7.08 (m, 2H), 6.99-6.87 (m, 2H), 6.36-6.17 (m, 1H), 5.56-5.29 (m, 2H), 5.29-5.24 (m, 2H), 3.24-2.79 (m, 4H).

Preparation of 5-((5-((5-(((3-(4-fluorophenethyl)-1H-pyrazol-5-yl)methoxy)carbonyl)-2,3-dihydroxyphenoxy)carbonyl)-2,3-dihydroxyphenoxy)carbonyl)-2,3-dihydroxyphenoxy)carbonyl)-2,3-dihydroxyphenyl 3-(benzyloxy)-4,5-dihydroxybenzoate (92)

To a flame dried 10 wt % Pd/C solid (50 mg), anhydrous tetrahydrofuran (4 mL) and the compound 91 (80 mg, 0.04 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase C$_{18}$ F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/n-pentane (1:25) to afford the compound 92 as an off-white solid (40 mg, 97%). $^1$H NMR (MeOD, 400 MHz) δ 7.64-6.85 (m, 14H), 6.19-6.09 (m, 1H), 5.29-5.20 (m, 2H), 2.99-2.84 (m, 4H).

Example 19. 5-((5-((5-((2,3-dihydroxy-5-((pyridin-3-yloxy)carbonyl)phenoxy)carbonyl)-2,3-dihydroxyphenoxy)carbonyl)-2,3-dihydroxyphenoxy)carbonyl)-2,3-dihydroxyphenyl 3,4,5-trihydroxybenzoate hydrochloride salt (94)

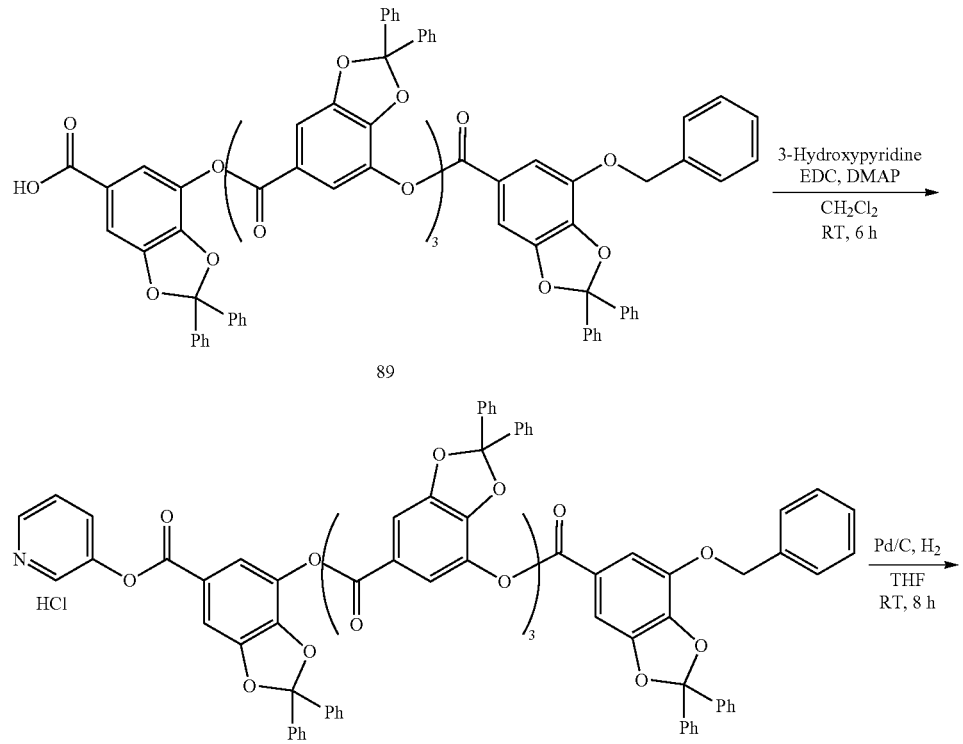

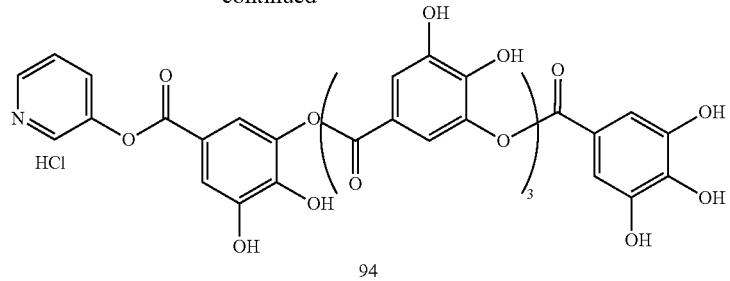

94

Preparation of 2,2-diphenyl-6-((pyridin-3-yloxy)carbonyl)benzo[d][1,3]dioxol-4-yl 7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (93)

To a mixture of the compound 89 (400 mg, 0.24 mmol), 3-hydroxypyridine (25 mg, 0.26 mmol) and 4-dimethylaminopyridine (15 mg, 0.12 mmol) in dichloromethane (5 mL) at 0° C., 1-ethyl-3-(3-dimethylaminopropyl)carbodiimide hydrochloride (55 mg, 0.28 mmol) was added and stirred back to RT for 2 h. The mixture was extracted with dichloromethane, water, and brine. The organic residue was dried over anhydrous magnesium sulfate, evaporated, and purified by F.C. with EtOAc/hexanes/dichloromethane (5/45/50). The collected residue was precipitate with dichloromethane/hexanes to afford the compound 93 as an off-white solid (286 mg, 68%). $^1$H NMR (CDCl$_3$, 400 MHz) δ 8.57-8.46 (m, 2H), 7.77-7.28 (m, 67H), 5.28 (s, 2H).

Preparation of 5-((5-((5-((2,3-dihydroxy-5-((pyridin-3-yloxy)carbonyl)phenoxy)carbonyl)-2,3-dihydroxyphenoxy)carbonyl)-2,3-dihydroxyphenoxy)carbonyl)-2,3-dihydroxyphenyl 3,4,5-trihydroxybenzoate (94)

To a flame dried 10 wt % Pd/C solid (154 mg), anhydrous tetrahydrofuran (4 mL) and the compound 93 (160 mg, 0.14 mmol) was added. The mixture was stirred at RT under H$_2$ (8 atm) for 8 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase C$_{18}$ F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/n-pentane (1:25) to afford the compound 94 as an off-white solid (37 mg, 46%). $^1$H NMR (MeOD, 400 MHz) δ 8.58-8.38 (m, 2H), 7.85-7.71 (m, 1H), 7.65-7.19 (m, 11H).

Example 20. Cyclohexyl 3-((3-((3-((3,4-dihydroxy-5-((3,4,5-trihydroxybenzoyl)oxy) benzoyl)oxy)-4,5-dihydroxybenzoyl)oxy)-4,5-dihydroxybenzoyl)oxy)-4,5-dihydroxybenzoate (96)

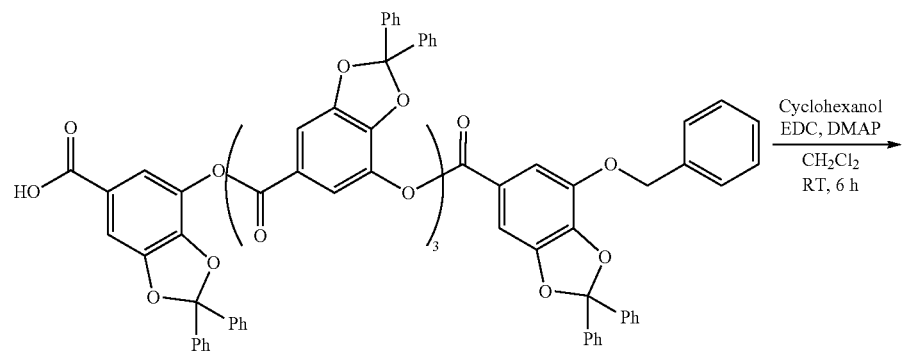

89

-continued

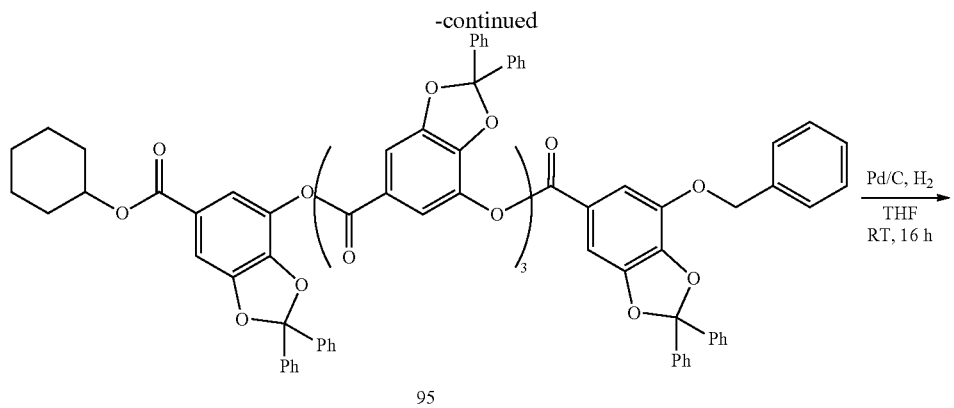

95

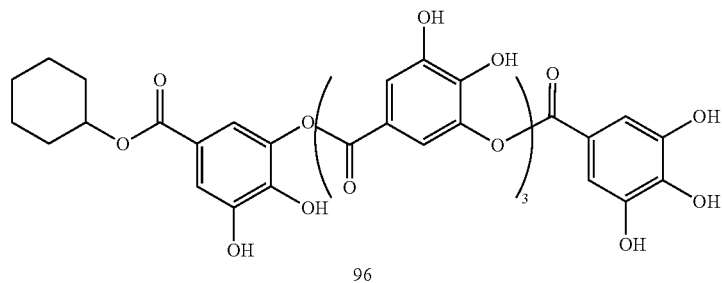

96

Preparation of cyclohexyl 7-((7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (95)

To a mixture of the compound 89 (4000 mg, 2.37 mmol), cyclohexanol (1186 mg, 11.84 mmol) and 4-dimethylaminopyridine (347 mg, 2.84 mmol) in dichloromethane (30 mL) at 0° C., 1-ethyl-3-(3-dimethylaminopropyl)carbodiimide hydrochloride (1146 mg, 5.92 mmol) was added and stirred back to RT for 2 h. The mixture was extracted with dichloromethane, water, and brine. The organic residue was dried over anhydrous magnesium sulfate, evaporated, and purified by F.C. with hexanes/dichloromethane (30/70). The collected residue was precipitate with dichloromethane/hexanes to afford the compound 95 as an off-white solid (3787 mg, 90%). $^1$H NMR (CDCl$_3$, 400 MHz) δ 7.75-7.29 (m, 65H), 5.28 (s, 2H), 5.02-4.91 (m, 1H), 1.96-1.81 (m, 2H), 1.81-1.66 (m, 2H), 1.55-1.22 (m, 6H).

Preparation of cyclohexyl 3-((3-((3-((3-((3-(benzyloxy)-4,5-dihydroxybenzoyl)oxy)-4,5-dihydroxybenzoyl)oxy)-4-hydroxybenzoyl)oxy)-4,5-dihydroxybenzoyl)oxy)-4,5-dihydroxybenzoate (96)

To a flame dried 10 wt % Pd/C solid (3075 mg), anhydrous tetrahydrofuran (38 mL) and the compound 95 (3200 mg, 1.81 mmol) was added. The mixture was stirred at RT under H$_2$ (8 atm) for 8 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase C$_{18}$ F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/n-pentane (1:25) to afford the compound 96 as an off-white solid (1030 mg, 66%). $^1$H NMR (MeOD, 400 MHz) δ 7.62-7.10 (m, 10H), 4.99-4.89 (m, 1H), 1.99-1.34 (m, 10H).

Example 21. 5-((5-((5-((5-(cyclopropoxycarbonyl)-2,3-dihydroxyphenoxy)carbonyl)-2,3-dihydroxyphenoxy)carbonyl)-2,3-dihydroxyphenoxy)carbonyl)-2,3-dihydroxyphenyl 3,4,5-trihydroxybenzoate (98)

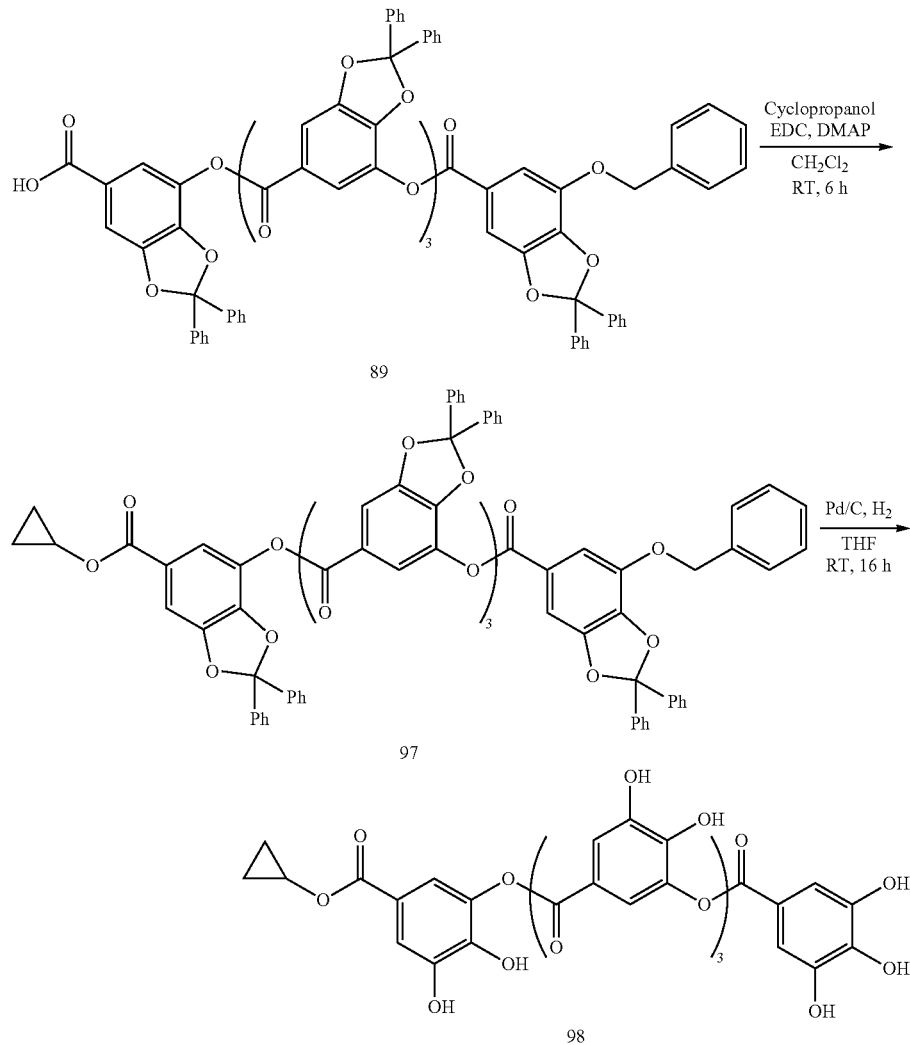

Preparation of 6-(cyclopropoxycarbonyl)-2,2-diphenylbenzo[d][1,3]dioxol-4-yl 7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (97)

To a mixture of the compound 89 (450 mg, 0.27 mmol), cyclopropanol (77 mg, 1.33 mmol) and 4-dimethylaminopyridine (38 mg, 0.32 mmol) in dichloromethane (3 mL) at 0° C., 1-ethyl-3-(3-dimethylaminopropyl)carbodiimide hydrochloride (129 mg, 0.67 mmol) was added and stirred back to RT for 2 h. The mixture was extracted with dichloromethane, water, and brine. The organic residue was dried over anhydrous magnesium sulfate, evaporated, and purified by F.C. with hexanes/dichloromethane (30/70). The collected residue was precipitate with dichloromethane/hexanes to afford the compound 97 as an off-white solid (343 mg, 75%). $^1$H NMR (CDCl$_3$, 400 MHz) δ 7.78-7.29 (m, 65H), 5.28 (s, 2H), 0.83-0.67 (m, 4H).

Preparation of 5-((5-((5-((5-(cyclopropoxycarbonyl)-2,3-dihydroxyphenoxy)carbonyl)-2,3-dihydroxyphenoxy)carbonyl)-2,3-dihydroxyphenoxy)carbonyl)-2,3-dihydroxyphenyl 3-(benzyloxy)-4,5-dihydroxybenzoate (98)

To a flame dried 10 wt % Pd/C solid (167 mg), anhydrous tetrahydrofuran (4 mL) and the compound 97 (170 mg, 0.10 mmol) was added. The mixture was stirred at RT under H$_2$ (8 atm) for 8 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase C18 F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/n-pentane (1:25) to afford the compound 98 as an off-white solid (23 mg, 29%). 1H NMR (MeOD, 400 MHz) δ 7.62-7.03 (m, 10H), 4.37-4.20 (m, 1H), 0.85-0.70 (m, 4H).

Example 22. cycloheptyl 3-((3-((3-((3,4-dihydroxy-5-((3,4,5-trihydroxybenzoyl)oxy) benzoyl)oxy)-4,5-dihydroxybenzoyl)oxy)-4,5-dihydroxybenzoyl)oxy)-4,5-dihydroxybenzoate (100)

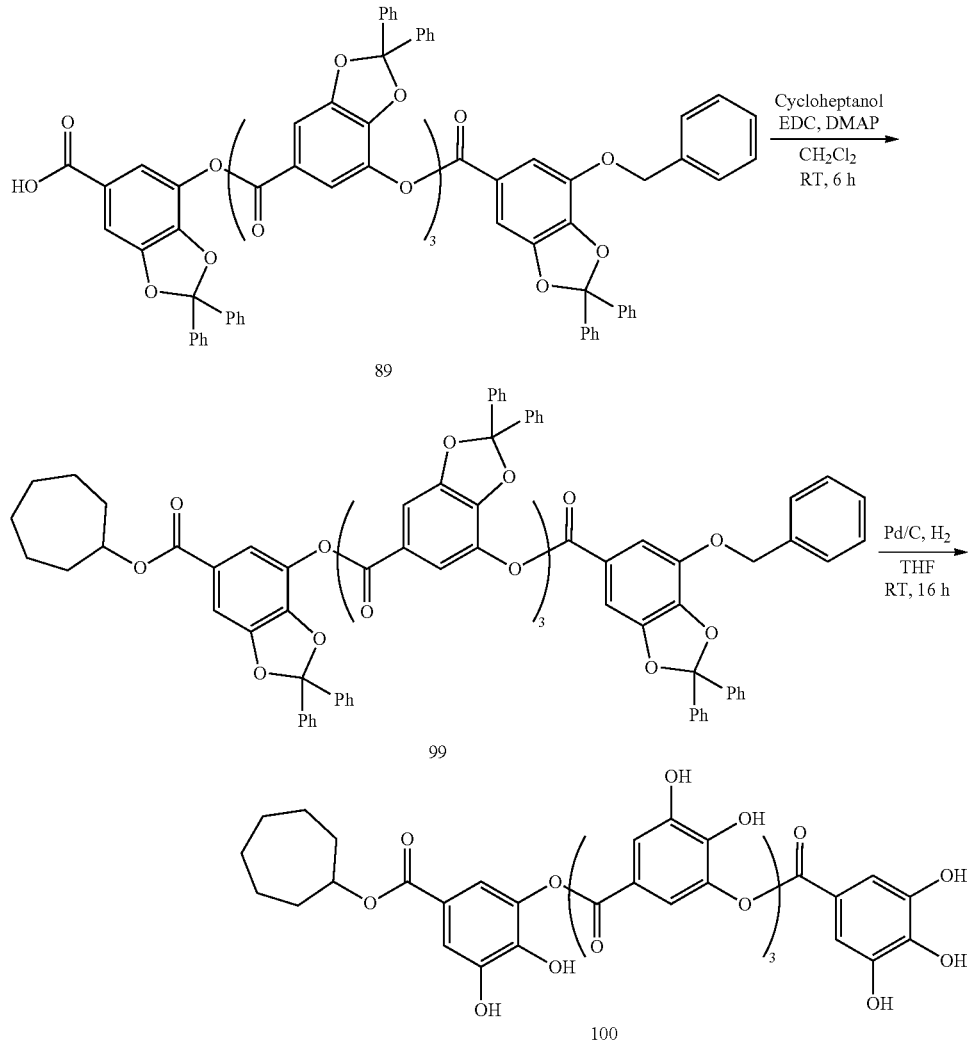

Preparation of cycloheptyl 7-((7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (99)

To a mixture of the compound 89 (450 mg, 0.27 mmol), cyclopropanol (77 mg, 1.33 mmol) and 4-dimethylaminopyridine (38 mg, 0.32 mmol) in dichloromethane (3 mL) at 0° C., 1-ethyl-3-(3-dimethylaminopropyl)carbodiimide hydrochloride (129 mg, 0.67 mmol) was added and stirred back to RT for 2 h. The mixture was extracted with dichloromethane, water, and brine. The organic residue was dried over anhydrous magnesium sulfate, evaporated, and purified by F.C. with hexanes/dichloromethane (30/70). The collected residue was precipitate with dichloromethane/hexanes to afford the compound 99 as an off-white solid (377 mg, 79%). $^1$H NMR (CDCl$_3$, 400 MHz) δ 7.76-7.29 (m, 65H), 5.28 (s, 2H), 5.19-5.08 (m, 1H), 2.00-1.90 (m, 2H), 1.83-1.64 (m, 4H), 1.62-1.56 (m, 4H), 1.54-1.41 (m, 2H).

Preparation of cycloheptyl 3-((3-((3-((3-((3-(benzyloxy)-4,5-dihydroxybenzoyl)oxy)-4,5-dihydroxybenzoyl)oxy)-4,5-dihydroxybenzoyl)oxy)-4,5-dihydroxybenzoyl)oxy)-4,5-dihydroxybenzoate (100)

To a flame dried 10 wt % Pd/C solid (162 mg), anhydrous tetrahydrofuran (4 mL) and the compound 99 (170 mg, 0.10 mmol) was added. The mixture was stirred at RT under H$_2$ (8 atm) for 8 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase C$_{18}$ F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/n-pentane (1:25) to afford the compound 100 as an off-white solid (60 mg, 72%). $^1$H NMR (MeOD, 400 MHz) δ 7.67-7.04 (m, 10H), 5.17-5.07 (m, 1H), 2.08-1.93 (m, 2H), 1.91-1.70 (m, 4H), 1.70-1.45 (m, 6H).

Example 23. 5-(benzoyloxy)-1,3-phenylene bis(3-((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)-4,5-dihydroxybenzoate) (103)
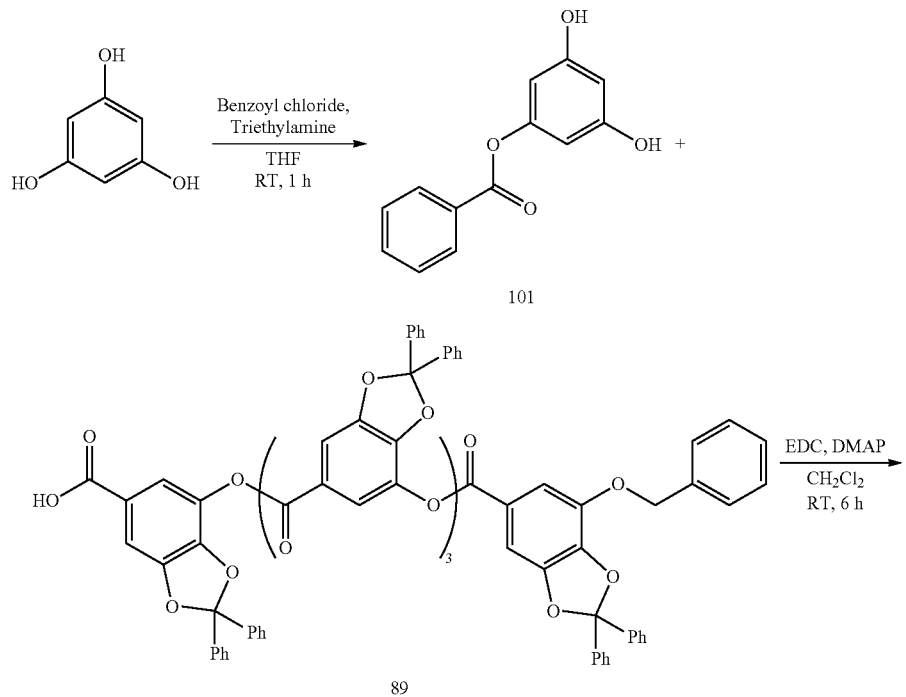
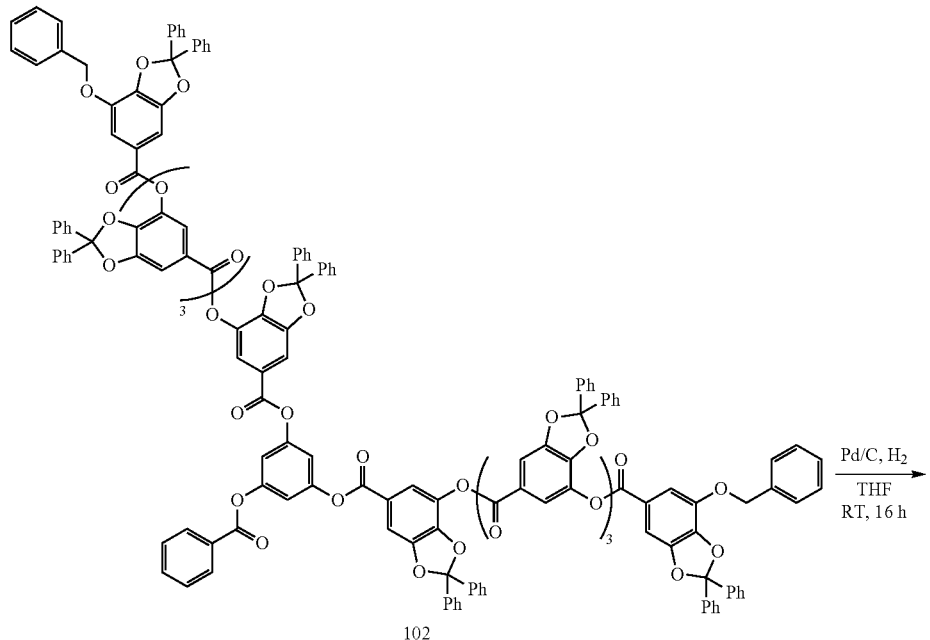

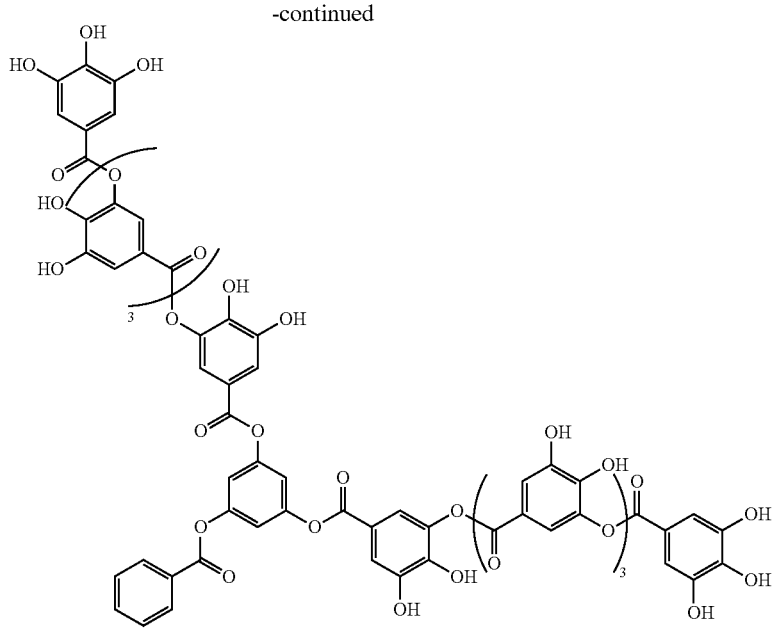

103

Preparation of 3,5-dihydroxyphenyl benzoate (101)

To a mixture of the phloroglucinol (500 mg, 3.97 mmol) in tetrahydrofuran (150 mL) at 0° C., benzoyl chloride (557 mg, 3.97 mmol) and triethylamine (2.0 g, 19.82 mmol) was added and stirred back to RT for 1 h. The mixture was extracted with ethylacetate, water, and brine. The organic residue was dried over anhydrous magnesium sulfate, evaporated, and purified by F.C. with ethylacetate/hexanes (20/80). The collected residue was precipitate with ethylacetate/hexanes to afford the compound 101 as an off-white solid (150 mg, 16%). $^1$H NMR (Acetone-$d_6$, 400 MHz) δ 8.58 (s, 2H), 8.15-8.12 (m, 2H), 7.70-7.65 (m, 1H), 7.57-7.53 (m, 2H), 6.36-6.32 (m, 3H).

Preparation of 5-(benzoyloxy)-1,3-phenylene bis(7-((7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (102)

To a mixture of the compound 89 (734 mg, 0.43 mmol), compound 101 (50 mg, 0.22 mmol) and 4-dimethylaminopyridine (53 mg, 0.43 mmol) in dichloromethane (7 mL) at 0° C., 1-ethyl-3-(3-dimethylaminopropyl)carbodiimide hydrochloride (83 mg, 0.43 mmol) was added and stirred back to RT for 6 h. The mixture was extracted with dichloromethane, water, and brine. The organic residue was dried over anhydrous magnesium sulfate, evaporated, and purified by F.C. with dichloromethane. The collected residue was precipitate with dichloromethane/hexanes to afford the compound 102 as an off-white solid (450 mg, 58%). $^1$H NMR (CDCl$_3$, 400 MHz) δ 8.18-8.16 (d, 2H), 7.73-7.28 (m, 135H), 7.09-7.05 (m, 3H).

Preparation of 5-(benzoyloxy)-1,3-phenylene bis(3-((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)-4,5-dihydroxybenzoate) (103)

To a flame dried 10 wt % Pd/C solid (240 mg), anhydrous tetrahydrofuran (7 mL) and the compound 102 (240 mg, 0.07 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase Cis F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/n-pentane (1:25) to afford the compound 103 as an off-white solid (60 mg, 51%). $^1$H NMR (MeOD, 400 MHz) δ 8.20-8.18 (d, 2H), 7.69-7.67 (d, 1H), 7.58-7.57 (m, 8H), 7.50-7.46 (m, 6H), 7.31-7.23 (m, 8H), 7.17-7.15 (m, 3H).

Example 24. 5-((3-(4-(trifluoromethyl)phenethyl)-1H-pyrazole-5-carbonyl)oxy)-1,3-phenylene bis(3-((3-((3,4-dihydroxy-5-((3,4,5-trihydroxybenzoyl)oxy)benzoyl)oxy)-4,5-dihydroxybenzoyl)oxy)-4,5-dihydroxybenzoate) (107)
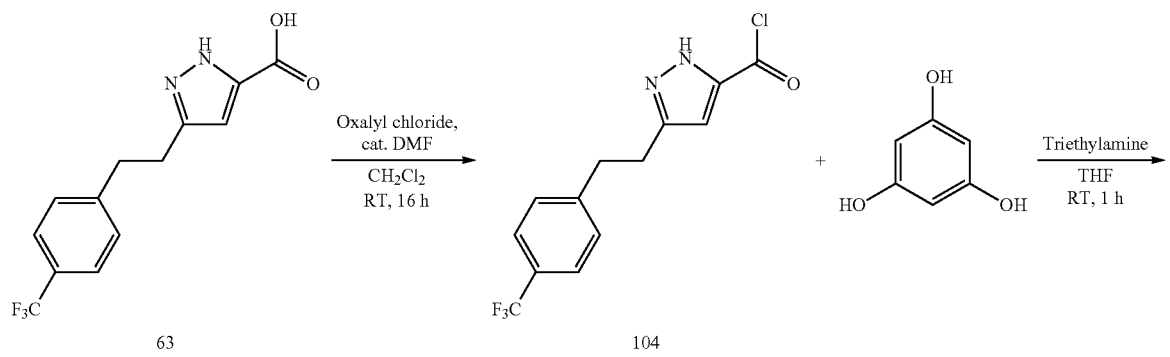
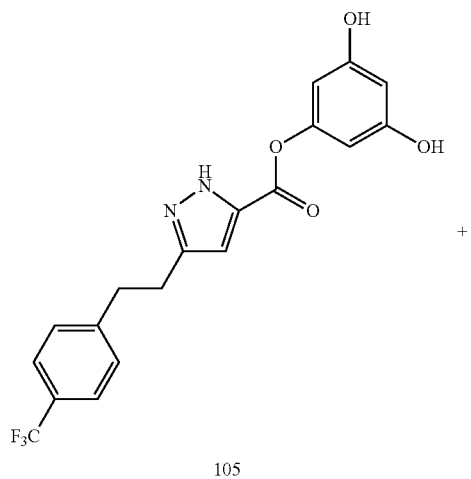
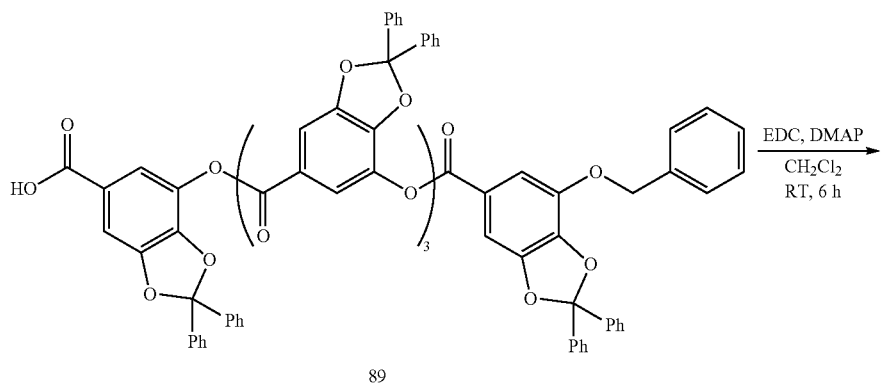

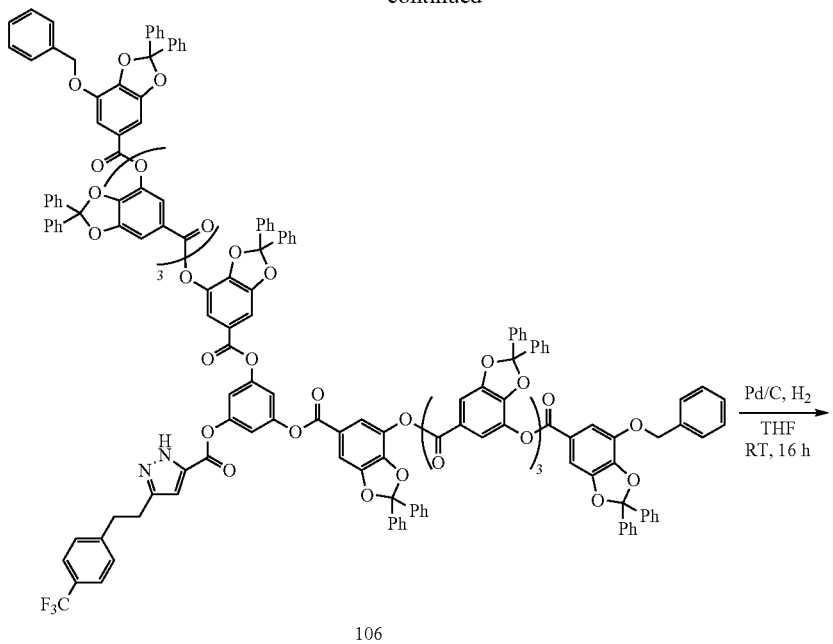

106

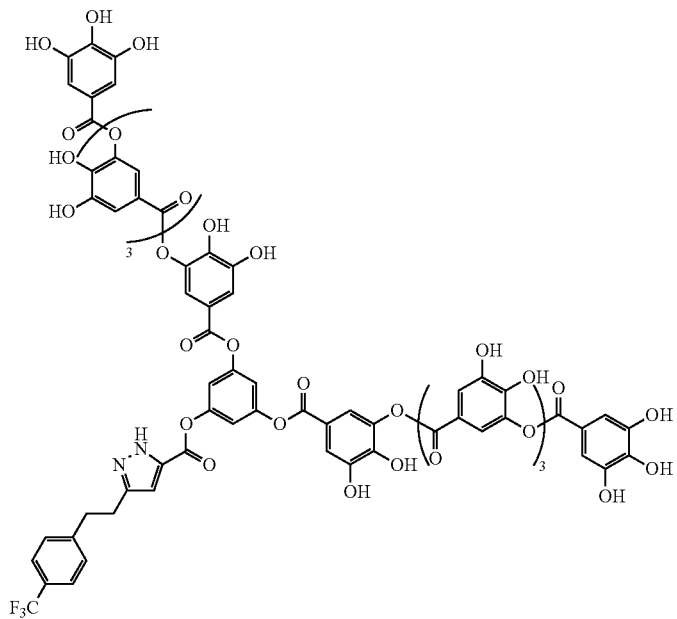

107

Preparation of 3-(4-(trifluoromethyl)phenethyl)-1H-pyrazole-5-carbonyl chloride (104)

To a stirring solution of the compound 63 (820 mg, 2.88 mmol) in dichloromethane (15.00 mL) was added oxalyl chloride (0.74 mL, 8.65 mmol) and DMF (0.05 mL) at 0° C. The mixture was stirred at RT for 16 h. The mixture was concentrated under vacuum to afford 3-(4-(trifluoromethyl) phenethyl)-1H-pyrazole-5-carbonyl chloride (104, 864 mg, crude) as a yellow solid.

Preparation of 3,5-dihydroxyphenyl 3-(4-(trifluoromethyl) phenethyl)-1H-pyrazole-5-carboxylate (105)

To a mixture of the phloroglucinol (300 mg, 2.38 mmol) in tetrahydrofuran (120 mL), and the compound 104 (720 mg, 2.38 mmol) at 0° C., triethylamine (1.2 g, 11.89 mmol) was added and stirred back to RT for 1 h. The mixture was extracted with ethylacetate, water, and brine. The organic residue was dried over anhydrous magnesium sulfate, evaporated, and purified by reverse phase $C_{18}$ F.C. with acetonitrile/water (40%~50%). The collected residue was extracted with EtOAc, 1 N hydrochloric acid, and brine. The organic residue was dried over magnesium sulfate, evaporated to afford the compound 105 as an off-white solid (83 mg, 9%). $^1$H NMR (Acetone-$d_6$, 400 MHz) δ 8.57 (br, 1H), 7.64-7.62 (m, 2H), 7.51-7.47 (m, 2H), 6.79 (s, 1H), 6.29-6.24 (m, 3H), 3.14-3.06 (m, 4H).

Preparation of 5-((3-(4-(trifluoromethyl)phenethyl)-1H-pyrazole-5-carbonyl)oxy)-1,3-phenylene bis(7-((7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (106)

To a mixture of the compound 89 (689 mg, 0.41 mmol), compound 105 (80 mg, 0.2 mmol) and 4-dimethylaminopyridine (49 mg, 0.41 mmol) in dichloromethane (6 mL) at 0° C., 1-ethyl-3-(3-dimethylaminopropyl)carbodiimide hydrochloride (78 mg, 0.41 mmol) was added and stirred back to RT for 6 h. The mixture was extracted with dichloromethane, water, and brine. The organic residue was dried over anhydrous magnesium sulfate, evaporated, and purified by F.C. with ethylacetate/dichloromethane (0%~5%). The collected residue was precipitate with dichloromethane/hexanes to afford the compound 106 as an off-white solid (300 mg, 40%). $^1$H NMR (CDCl$_3$, 400 MHz) δ 7.66-7.25 (m, 136H), 7.06-7.09 (m, 3H), 6.77 (s, 1H), 5.26 (s, 4H), 3.04 (s, 4H).

Preparation of 5-((3-(4-(trifluoromethyl)phenethyl)-1H-pyrazole-5-carbonyl)oxy)-1,3-phenylene bis(3-((3-((3,4-dihydroxy-5-((3,4,5-trihydroxybenzoyl)oxy)benzoyl)oxy)-4,5-dihydroxybenzoyl)oxy)-4,5-dihydroxybenzoate) (107)

To a flame dried 10 wt % Pd/C solid (200 mg), anhydrous tetrahydrofuran (5 mL) and the compound 106 (200 mg, 0.05 mmol) was added. The mixture was stirred at RT under H$_2$ (8 atm) for 16 h. The mixture was then filtered through Celite, washed with tetrahydrofuran and the combined filtrates were evaporated in vacuo. The residue was extracted with EtOAc, 1 N hydrochloric acid, and brine. The organic residue was dried over magnesium sulfate, evaporated, and purified by reverse phase C$_{18}$ F.C. with acetonitrile/water (30%~40%) with additional 1% formic acid. The collected residue was extracted with EtOAc, 1 N hydrochloric acid, and brine. The organic residue was dried over magnesium sulfate, evaporated, and precipitated with EtOAc/n-pentane (1:25) to afford the compound 107 as an off-white solid (28 mg, 27%). $^1$H NMR (MeOD, 400 MHz) δ 7.57 (m, 8H), 7.50-7.47 (m, 7H), 7.41-7.38 (m, 2H), 7.30-7.23 (m, 8H), 7.18-7.12 (m, 3H), 6.80 (s, 1H), 3.08 (s, 4H).

Example 25. Synthesis of 7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (111)

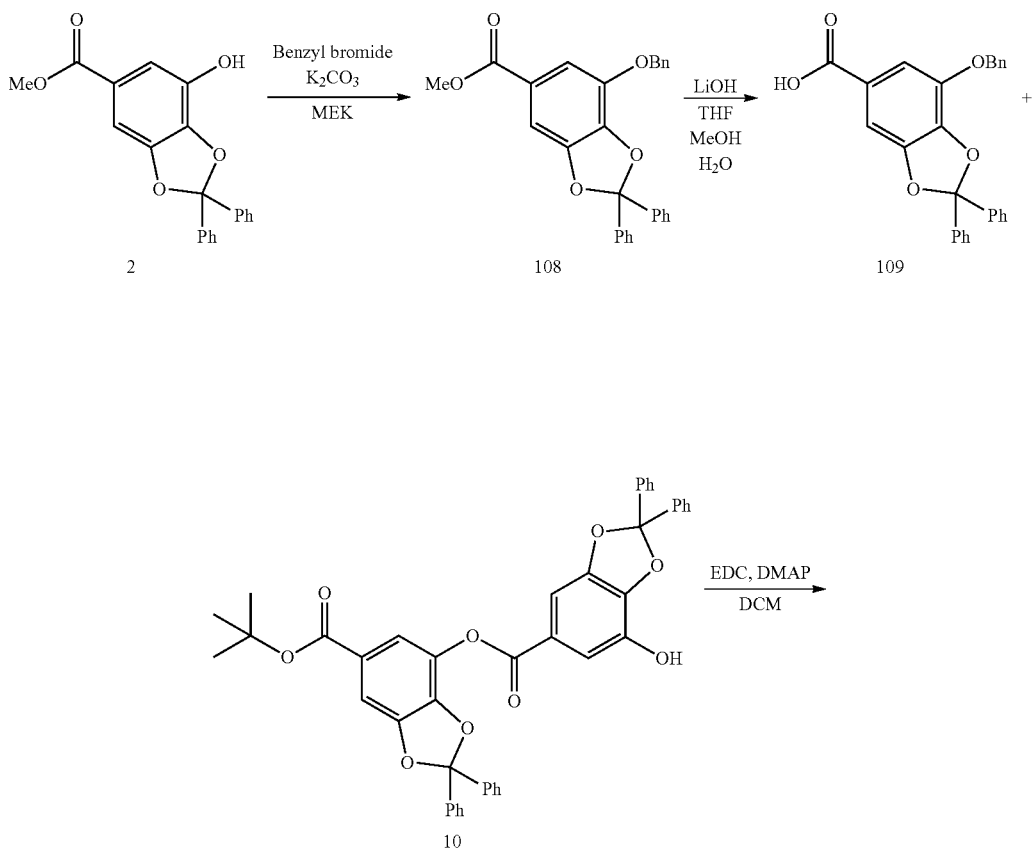

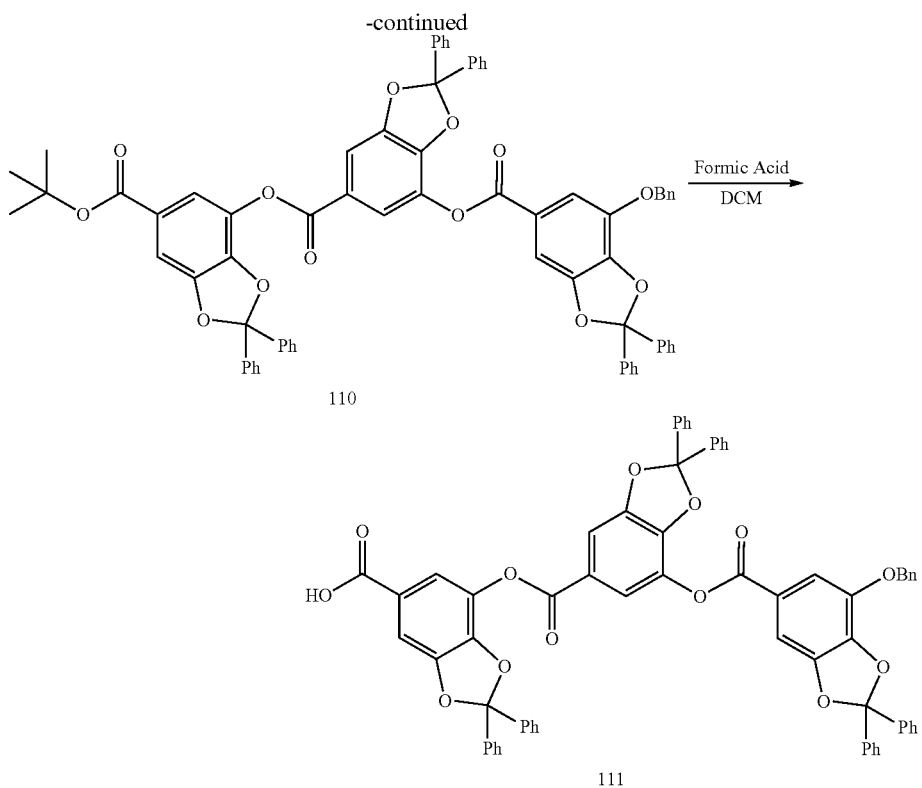

Preparation of methyl 7-(benzyloxy)-2,2-diphenylbenzo[d][1,3]dioxole-5-carboxylate (108)

To a solution of compound 2 (40.0 g, 115 mmol) in methyl ethyl ketone (450 mL) was added potassium carbonate (29.4 g, 212 mmol) and benzyl bromide (25.2 mL, 212 mmol). The mixture was stirred at 55° C. for 3 h. After the reaction was complete, the mixture was concentrated in vacuo. The residue was diluted with DCM, extracted with water, washed with brine, dried over anhydrous magnesium sulfate and filtered. The filtrate was concentrated in vacuo and precipitated with EtOAc and hexanes to afford the compound 108 as a white solid (47.3 g, 97%). $^1$H NMR (CDCl$_3$, 500 MHz) δ 7.61-7.54 (m, 4H), 7.46-7.42 (m, 2H), 7.41-7.30 (n, 10H), 7.29-7.27 (pseudo d, J=1.5 Hz, 1H), 5.24 (s, 2H), 3.86 (s, 3H).

Preparation of 7-(benzyloxy)-2,2-diphenylbenzo[d][1,3]dioxole-5-carboxylic acid (109)

To a stirred solution of the compound 108 (47.3 g, 111 mmol) in TH/MeOH (1/1, 260 mL) was added LiOH$_{(aq)}$ (3 M, 75 mL) and stirred under 50° C. 4 h. The mixture cooled to RT, diluted with EtOAc and quenched with 1 N hydrochloric acid to pH=2. The mixture was extracted with EtOAc/water, washed with brine, dried over anhydrous magnesium sulfate and filtered. The filtrate was evaporated in vacuo and precipitated with EtOAc/hexanes to afford the compound 109 (38.7 g, 85%) as a white solid. $^1$H NMR (CDCl$_3$, 500 MHz) δ 7.62-7.56 (m, 4H), 7.48-7.43 (m, 3H), 7.43-7.31 (m, 10H), 5.26 (s, 2H).

Preparation of 6-(tert-butoxycarbonyl)-2,2-diphenylbenzo[d][1,3]dioxol-4-yl 7-((7-(benzyloxy)-2,2-diphenylbenzo[d][1,3]dioxole-5-carbonyl)oxy)-2,2-diphenylbenzo[d][1,3]dioxole-5-carboxylate (110)

To a mixture of the compound 109 (5.0 g, 12.2 mmol), compound 10 (8.5 g, 12.2 mmol) and 4-dimethylaminopyridine (150 mg, 1.2 mmol) in DCM (125 mL) at 0° C., 1-ethyl-3-(3-dimethylaminopropyl)carbodiimide hydrochloride (2.5 g, 13.4 mmol) was added and stirred back to RT for 3 h. The mixture was extracted with DCM, water, and brine. The organic residue was dried over anhydrous magnesium sulfate, evaporated, and purified by F.C. with DCM/hexanes=60%~75%. The collected residue was precipitate with DCM/hexanes to afford the compound 110 as an off-white solid (6.8 g, 50%). $^1$H NMR (CDCl$_3$, 400 MHz) δ 7.72 (pseudo d, J=1.4 Hz, 1H), 7.65 (pseudo d, J=1.6 Hz, 1H), 7.62-7.50 (m, 13H), 7.50-7.28 (m, 26H), 5.28 (s, 2H), 1.54 (s, 9H).

Preparation of 7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (111)

To a stirred solution of the compound 110 (28 g, 25 mmol) in anhydrous DCM (127 mL) was added formic acid (127 mL) at 0° C. and stirred under 50° C. 4 h. The mixture was extracted with water 3 times, washed with brine, dried over anhydrous magnesium sulfate and filtered. The filtrate was evaporated in vacuo. The residue was purified by F.C. with EtOAc/DCM (10%) to afford the compound 111 (19.4 g, 73%) as a white solid. $^1$H NMR (CDCl$_3$, 400 MHz) δ 7.74 (pseudo d, J=1.5 Hz, 1H), 7.66 (pseudo d, J=1.4 Hz, 1H), 7.63-7.29 (m, 39H), 5.29 (s, 2H).

Example 26. Synthesis of 7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (113)

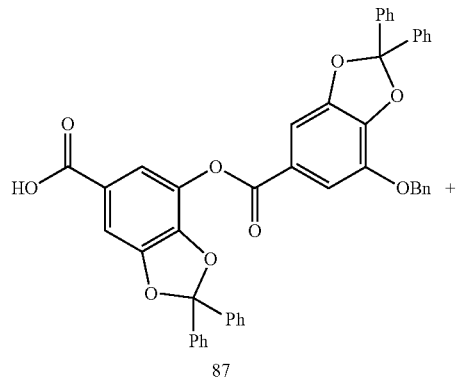

87

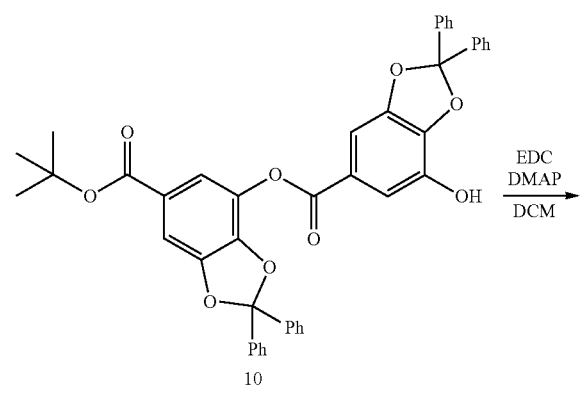

10

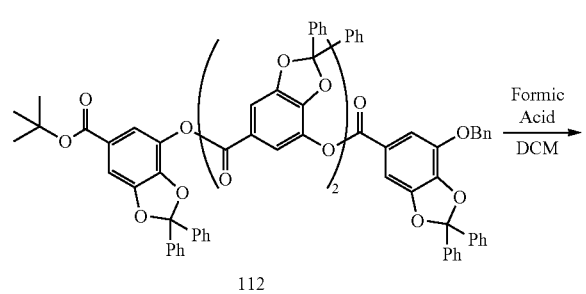

112

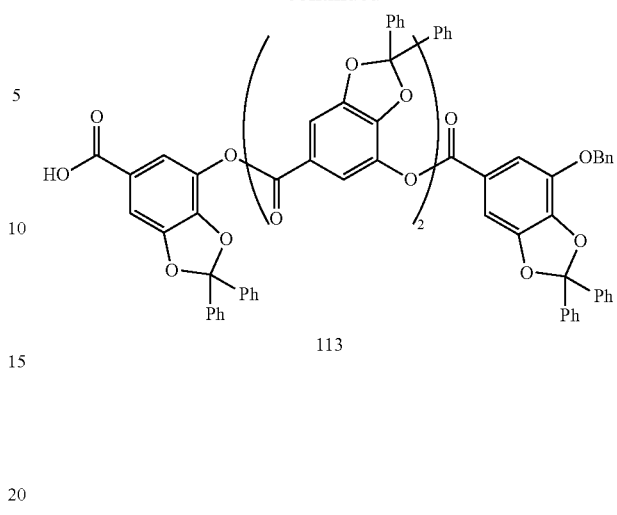

113

Preparation of 6-(tert-butoxycarbonyl)-2,2-diphenylbenzo[d][1,3]dioxol-4-yl 7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate (112)

To a mixture of the compound 87 (2201 mg, 2.97 mmol), compound 10 (2000 mg, 2.83 mmol) and 4-dimethylaminopyridine (69 mg, 0.57 mmol) in DCM (28 mL) at 0° C., 1-ethyl-3-(3-dimethylaminopropyl)carbodiimide hydrochloride (658 mg, 3.40 mmol) was added and stirred back to RT for 2 h. The mixture was extracted with DCM, water, and brine. The organic residue was dried over anhydrous magnesium sulfate, evaporated, and purified by F.C. with DCM/hexanes (70/30). The collected residue was precipitate with DCM/hexanes to afford the compound 112 as an off-white solid (3951 mg, 98%). $^1$H NMR (CDCl$_3$, 400 MHz) δ 7.73 (pseudo dd, J=5.6, 1.5 Hz, 2H), 7.65 (pseudo dd, J=4.7, 1.5 Hz, 2H), 7.63-7.50 (m, 17H), 7.50-7.29 (m, 32H), 5.28 (s, 2H), 1.54 (s, 9H).

Preparation of 7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylic acid (113)

To a stirred solution of the compound 112 (4.0 g, 2.8 mmol) in anhydrous DCM (138 mL) was added formic acid (138 mL) at 0° C. and stirred under 50° C. 4 h. The mixture was extracted with water 3 times, washed with brine, dried over anhydrous magnesium sulfate and filtered. The filtrate was evaporated in vacuo. The residue was purified by F.C. with EtOAc/DCM (10%) to afford the compound 113 (2.0 g, 53%) as a white solid. $^1$H NMR (CDCl$_3$, 400 MHz) δ 7.73 (pseudo dd, J=5.6, 1.5 Hz, 2H), 7.65 (pseudo dd, J=4.7, 1.5 Hz, 2H), 7.63-7.50 (m, 17H), 7.50-7.29 (m, 32H), 5.28 (s, 2H).

Example 27. Synthesis of (2R,3R,4S,5R)-tetrahydro-2H-pyran-2,3,4,5-tetrayl tetrakis(3,4-dihydroxy-5-((3,4,5-trihydroxybenzoyl)oxy)benzoate) (117)
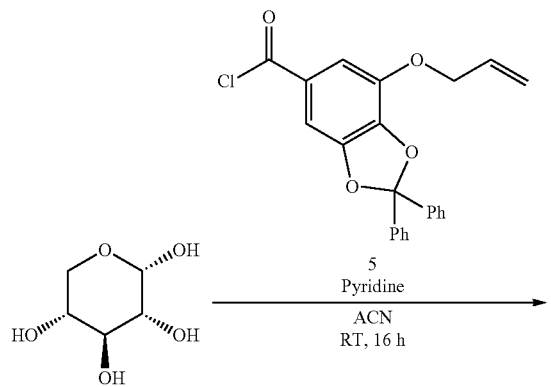
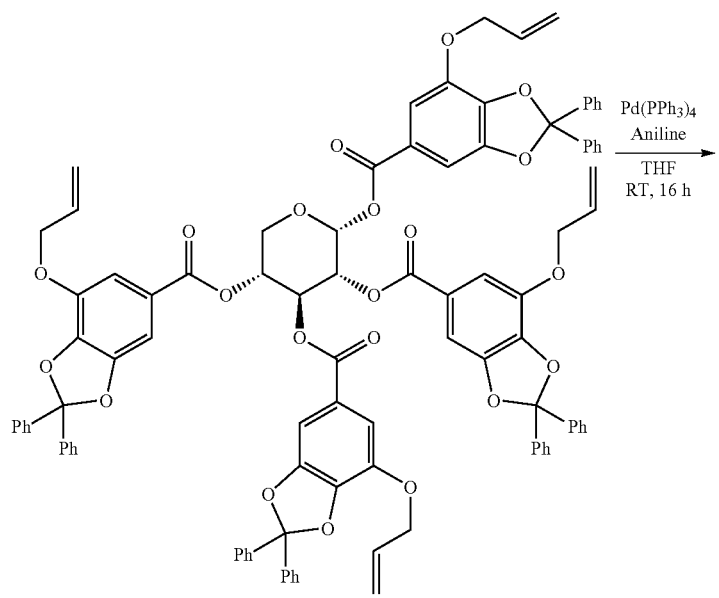
114

-continued
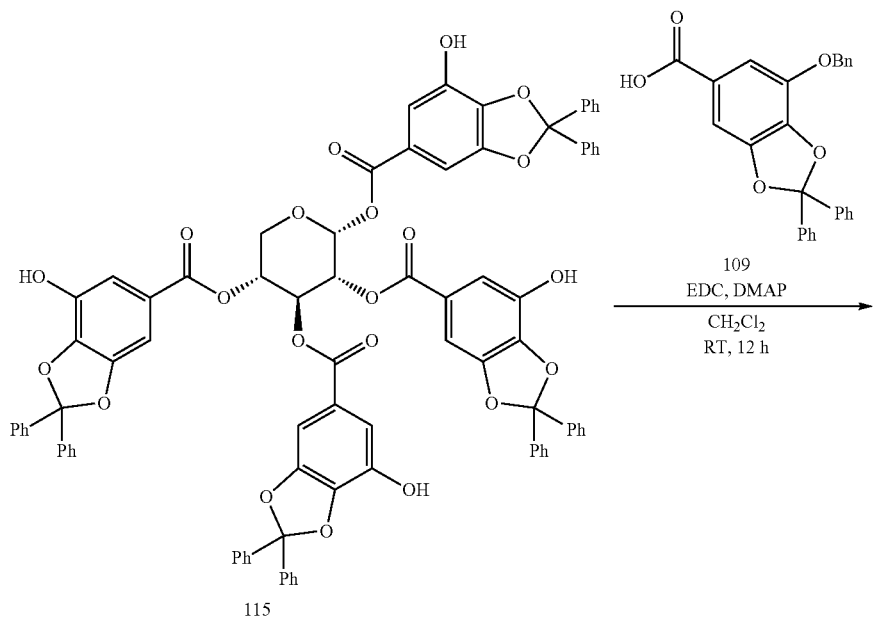
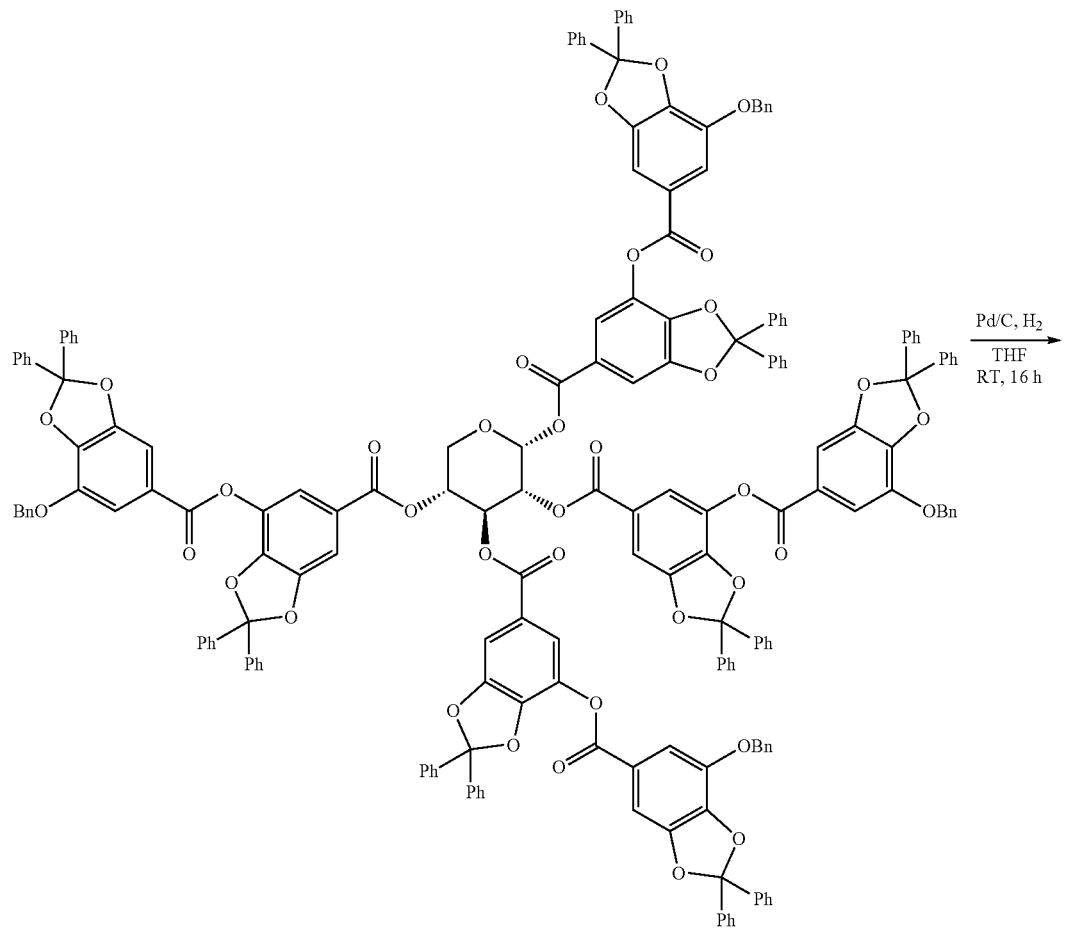

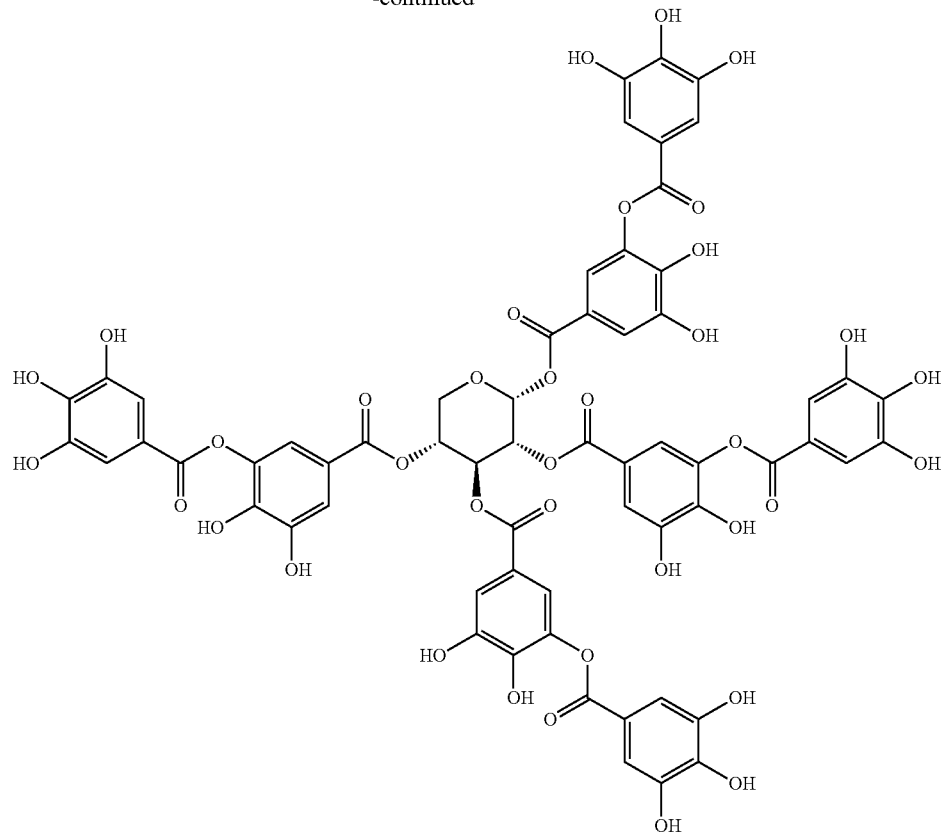

117

Preparation of (2R,3R,4S,5R)-tetrahydro-2H-pyran-2,3,4,5-tetrayl tetrakis(7-(allyloxy)-2,2-diphenylbenzo[d][1,3]dioxole-5-carboxylate) (114)

To a slurry solution of the α-D-(+)-xylose (1.0 g, 6.7 mmol), compound 5 (11.8 g, 30.0 mmol) in anhydrous acetonirile (33.0 mL) was added anhydrous pyridine (4.7 mL, 60.0 mmol) at 0° C. and stirred under RT 16 h. The crude mixture was cooled to 0° C., quenched with 1N hydrochloric acid, and extracted with EtOAc and brine. The slurry organic layer was filtrated, dried over anhydrous magnesium sulfate and filtered again. The organic solution was evaporated in vacuo, purified by normal phase F.C. with DCM/hexanes (50%~70%) to afford the compound 114 (8.9 g, 85%) as a white bubble form solid. $^1$H NMR (CDCl$_3$, 500 MHz) δ 7.65-7.58 (m, 4H), 7.58-7.46 (m, 12H), 7.41-7.28 (m, 27H), 7.23-7.20 (m, 2H), 7.18-7.13 (m, 2H), 7.11 (pseudo d, J=1.4 Hz, 1H), 6.63 (d, J=3.7 Hz, 1H), 6.12-5.92 (m, 4H), 5.90-5.78 (m, 1H), 5.47-5.17 (m, 9H), 5.13-5.07 (m, 1H), 4.76-4.70 (m, 2H), 4.69-4.57 (m, 4H), 4.48-4.42 (m, 2H), 4.21 (dd, J=11.2, 5.8 Hz, 1H), 3.90 (t, J=11.0 Hz, 1H).

Preparation of (2R,3R,4S,5R)-tetrahydro-2H-pyran-2,3,4,5-tetrayl tetrakis(7-hydroxy-2,2-diphenylbenzo[d][1,3]dioxole-5-carboxylate) (115)

To a argon flushed solution of the compound 114 (8.9 g, 5.65 mmol) and tetrakis(triphenyl phosphine)palladium (659 mg, 0.56 mmol) in dry tetrahydrofuran (113 mL), aniline (1.56 mL, 16.95 mmol) was added and stirred under RT 16 h. The mixture was extracted with DCM, 1 N hydrochloric acid and brine. The organic residue was dried over magnesium sulfate, evaporated, purified by F.C. with EtOAc/DCM=0%~10%, and precipitated with DCM/hexanes ~10% to afford the compound 115 as an off-white solid (7.4 g, 92%). $^1$H NMR (CDCl$_3$, 400 MHz) δ 7.61-7.41 (m, 17H), 7.40-7.26 (m, 23H), 7.25-7.03 (m, 8H), 6.54 (d, J=3.5 Hz, 1H), 6.05 (t, J=9.9 Hz, 1H), 5.42 (dd, J=10.2, 3.5 Hz, 1H), 5.39-5.32 (m, 1H), 4.19-4.07 (m, 1H), 3.85 (t, J=11.0 Hz, 1H).

Preparation of (2R,3R,4S,5R)-tetrahydro-2H-pyran-2,3,4,5-tetrayl tetrakis(7-((7-(benzyloxy)-2,2-diphenylbenzo[d][1,3]dioxole-5-carbonyl)oxy)-2,2-diphenylbenzo[d][1,3]dioxole-5-carboxylate) (116)

To a slurry solution of the compound 115 (300 mg, 0.21 mmol), compound 109 (378 mg, 0.89 mmol) and 4-dimethylaminopyridine (16 mg, 0.13 mmol) in DCM (6.8 mL) at 0° C., 1-ethyl-3-(3-dimethylaminopropyl)carbodiimide (189 mg, 0.98 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 116 (505 mg, 78%) as a white solid. $^1$H NMR (CDCl$_3$, 400 MHz) δ 7.60-7.21 (m, 116H), 6.66 (d, J=3.7 Hz, 1H), 6.07 (t, J=9.9 Hz, 1H), 5.44 (dd, J=10.1, 4.0 Hz, 1H), 5.41-5.33 (m, 1H), 5.20 (s, 4H), 5.17 (s, 2H), 5.14 (s, 2H), 4.15 (dd, J=11.0, 5.6 Hz, 1H), 3.90 (t, J=11.0 Hz, 1H).

Preparation of (2R,3R,4S,5R)-tetrahydro-2H-pyran-2,3,4,5-tetrayl tetrakis(3,4-dihydroxy-5-((3,4,5-trihydroxybenzoyl)oxy)benzoate) (117)

To a solution of the compound 116 (505 mg, 0.17 mmol) in anhydrous tetrahydrofuran (10.0 mL), the dried 10 wt % Pd/C solid (513 mg) was added. The mixture was stirred at RT under $H_2$ (8 atm) for 16 h. The crude mixture was filtered, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase $C_{18}$ F.C. with ACN/$H_2O$=25%~40% with 1% formic acid as additive.

The collected residue was extracted with EtOAc/brine. The organic layer was dried over magnesium sulfate, evaporated, and precipitated with EtOAc/n-pentane (~10%) to afford the compound 117 as an off-white solid (150 mg, 66%). $^1$H NMR (MeOD, 400 MHz) δ 7.62-7.31 (m, 3H), 7.31-7.13 (m, 11H), 7.12-6.95 (m, 2H), 6.75-6.62 (m, 1H), 6.11 (td, J=9.9, 3.8 Hz, 1H), 5.65-5.44 (m, 2H), 4.33-4.17 (m, 1H), 4.14-3.99 (m, 1H).

Example 28. Synthesis of (2R,3R,4S,5R)-tetrahydro-2H-pyran-2,3,4,5-tetrayl tetrakis(3-((3,4-dihydroxy-5-((3,4,5-trihydroxybenzoyl)oxy)benzoyl)oxy)-4,5-dihydroxybenzoate) (119)

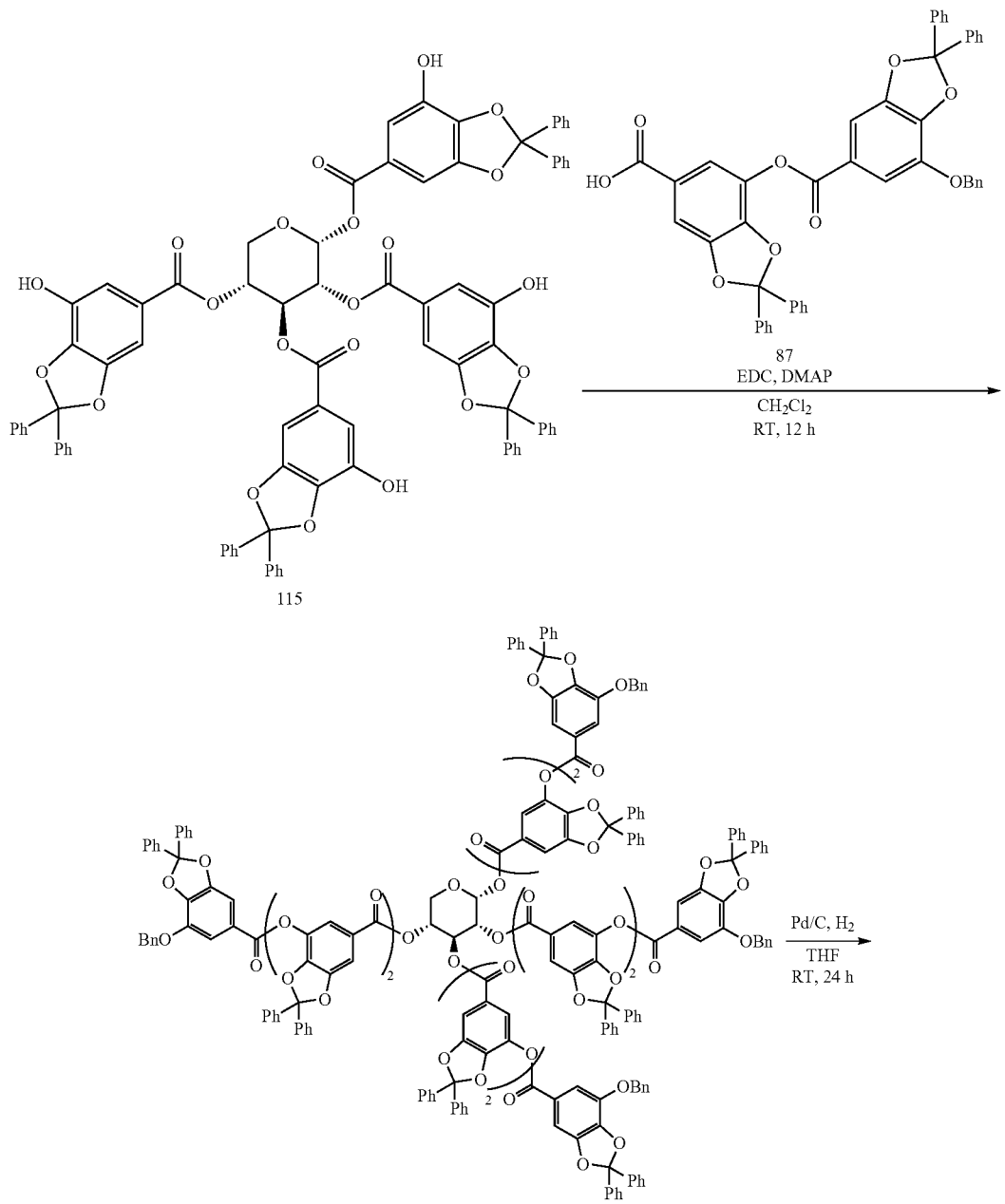

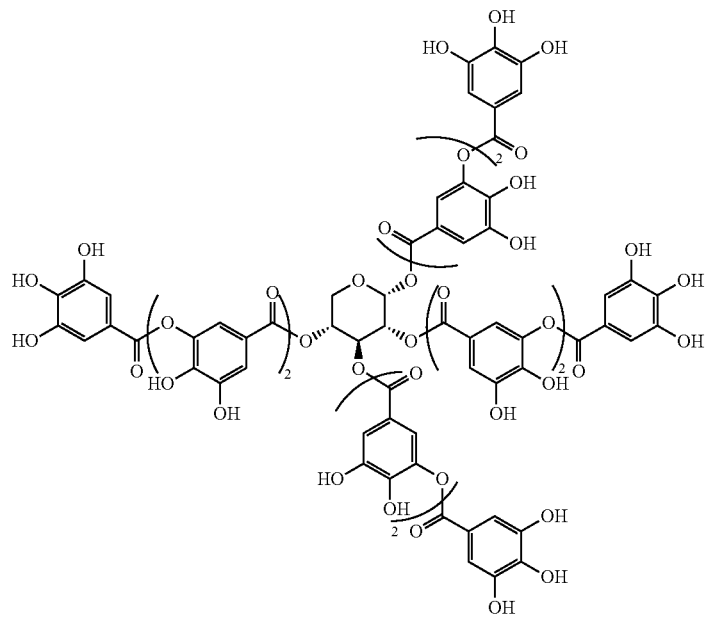

119

Preparation of (2R,3R,4S,5R)-tetrahydro-2H-pyran-2,3,4,5-tetrayl tetrakis(7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (118)

To a slurry solution of the compound 115 (200 mg, 0.14 mmol), compound 87 (440 mg, 0.59 mmol) and 4-dimethylaminopyridine (10 mg, 0.08 mmol) in DCM (6.4 mL) at 0° C., 1-ethyl-3-(3-dimethylaminopropyl)carbodiimide (126 mg, 0.65 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 118 (500 mg, 82%) as a white solid. $^1$H NMR (CDCl$_3$, 400 MHz) δ 7.71-7.12 (m, 164H), 6.65 (d, J=3.7 Hz, 1H), 6.07 (t, J=9.9 Hz, 1H), 5.44 (dd, J=10.3, 4.0 Hz, 1H), 5.42-5.33 (m, 1H), 5.24-5.12 (m, 6H), 5.06 (s, 2H), 4.15 (dd, J=11.0, 5.3 Hz, 1H), 3.90 (t, J=11.0 Hz, 1H).

Preparation of (2R,3R,4S,5R)-tetrahydro-2H-pyran-2,3,4,5-tetrayl tetrakis(3-((3,4-dihydroxy-5-((3,4,5-trihydroxybenzoyl)oxy)benzoyl)oxy)-4,5-dihydroxybenzoate) (119)

To a solution of the compound 118 (505 mg, 0.12 mmol) in anhydrous tetrahydrofuran (10.0 mL), the dried 10 wt % Pd/C solid (100 mg) was added. The mixture was stirred at RT under H$_2$ (8 atm) for 24 h. The crude mixture was filtrated, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase C$_{18}$ F.C. with ACN/H$_2$O=25%~40% with 1% formic acid as additive. The collected residue was extracted with EtOAc/brine. The organic layer was dried over magnesium sulfate, evaporated, and precipitated with EtOAc/n-pentane (~10%) to afford the compound 119 as an off-white solid (145 mg, 63%). $^1$H NMR (MeOD, 400 MHz) δ 7.65-7.15 (m, 22H), 7.15-6.94 (m, 2H), 6.76-6.62 (m, 1H), 6.19-6.07 (m, 1H), 5.65-5.45 (m, 2H), 4.33-4.17 (m, 1H), 4.17-3.97 (m, 1H).

Example 29. Synthesis of (2R,3R,4S,5R)-tetrahydro-2H-pyran-2,3,4,5-tetrayl tetrakis(3-((3-((3,4-dihydroxy-5-((3,4,5-trihydroxybenzoyl)oxy)benzoyl)oxy)-4,5-dihydroxybenzoyl)oxy)-4,5-dihydroxybenzoate) (121)
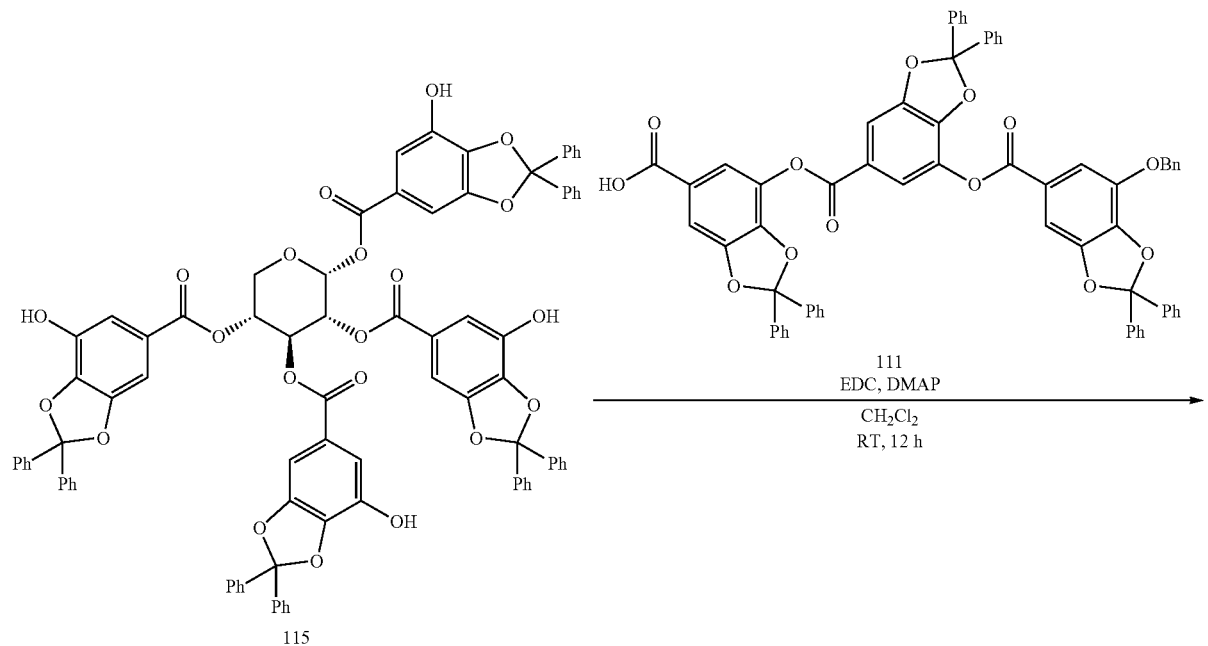
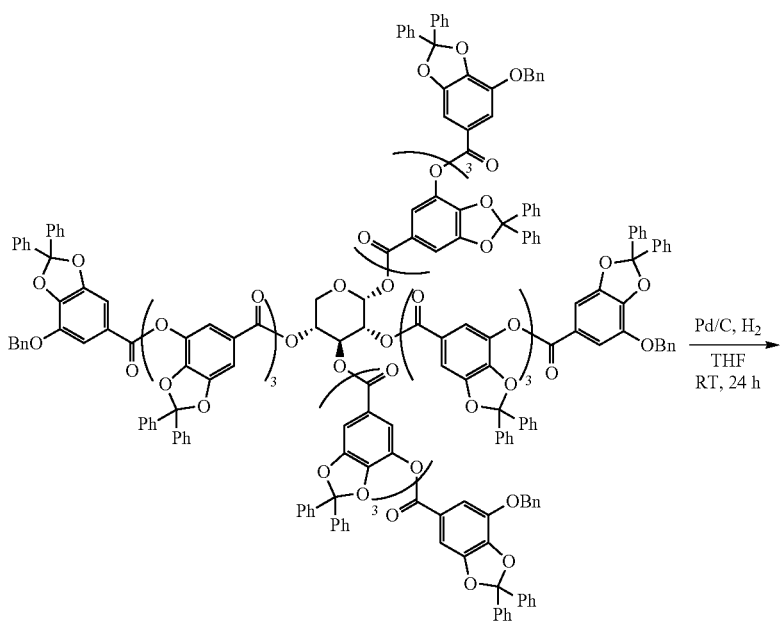

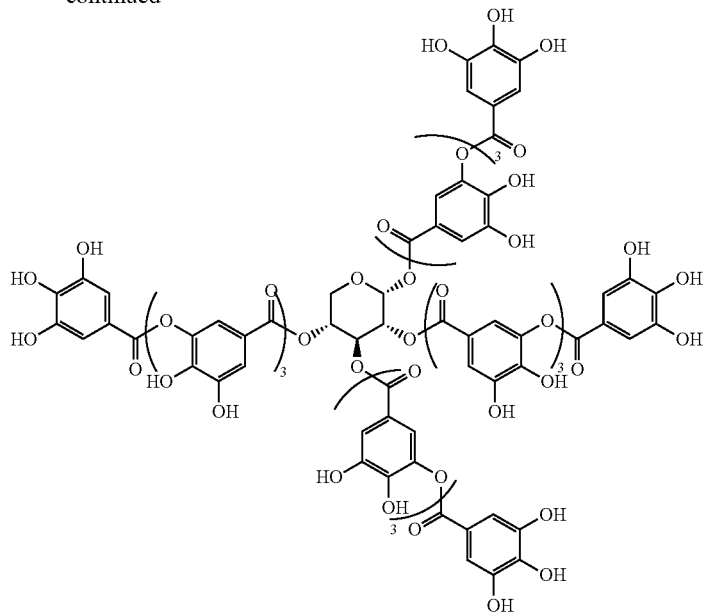

121

Preparation of (2R,3R,4S,5R)-tetrahydro-2H-pyran-2,3,4,5-tetrayl tetrakis(7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (120)

To a slurry solution of the compound 115 (170 mg, 0.12 mmol), compound 111 (533 mg, 0.50 mmol) and 4-dimethylaminopyridine (9 mg, 0.07 mmol) in DCM (7 mL) at 0° C., 1-ethyl-3-(3-dimethylaminopropyl)carbodiimide (107 mg, 0.55 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 120 (530 mg, 79%) as a white solid. $^1$H NMR (CDCl$_3$, 400 MHz) δ 7.75-7.11 (m, 212H), 6.65 (d, J=3.5 Hz, 1H), 6.07 (t, J=9.8 Hz, 1H), 5.43 (dd, J=10.3, 3.8 Hz, 1H), 5.41-5.33 (m, 1H), 5.26-5.18 (m, 6H), 5.15 (s, 2H), 4.21-4.10 (m, 1H), 3.89 (t, J=10.6 Hz, 1H).

Preparation of (2R,3R,4S,5R)-tetrahydro-2H-pyran-2,3,4,5-tetrayl tetrakis(3-((3-((3,4-dihydroxy-5-((3,4,5-trihydroxybenzoyl)oxy)benzoyl)oxy)-4,5-dihydroxybenzoyl)oxy)-4,5-dihydroxybenzoate) (121)

To a solution of the compound 120 (505 mg, 0.03 mmol) in anhydrous tetrahydrofuran (10.0 mL), the dried 10 wt % Pd/C solid (511 mg) was added. The mixture was stirred at RT under H$_2$ (8 atm) for 24 h. The crude mixture was filtrated, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase C$_{18}$ F.C. with ACN/H$_2$O=25%~40% with 1% formic acid as additive. The collected residue was extracted with EtOAc/brine. The organic layer was dried over magnesium sulfate, evaporated, and precipitated with EtOAc/n-pentane (~10%) to afford the compound 121 as an off-white solid (140 mg, 60%). $^1$H NMR (MeOD, 400 MHz) δ 7.64-7.18 (m, 30H), 7.14-6.96 (m, 2H), 6.77-6.62 (m, 1H), 6.20-6.05 (m, 1H), 5.67-5.45 (m, 2H), 4.33-4.16 (m, 1H), 4.16-3.99 (m, 1H).

Example 30. Synthesis of (2R,3R,4S,5R)-tetrahydro-2H-pyran-2,3,4,5-tetrayl tetrakis(3-((3-((3,4-dihydroxy-5-((3,4,5-trihydroxybenzoyl)oxy)benzoyl)oxy)-4,5-dihydroxybenzoyl)oxy)-4,5-dihydroxybenzoate) (123)
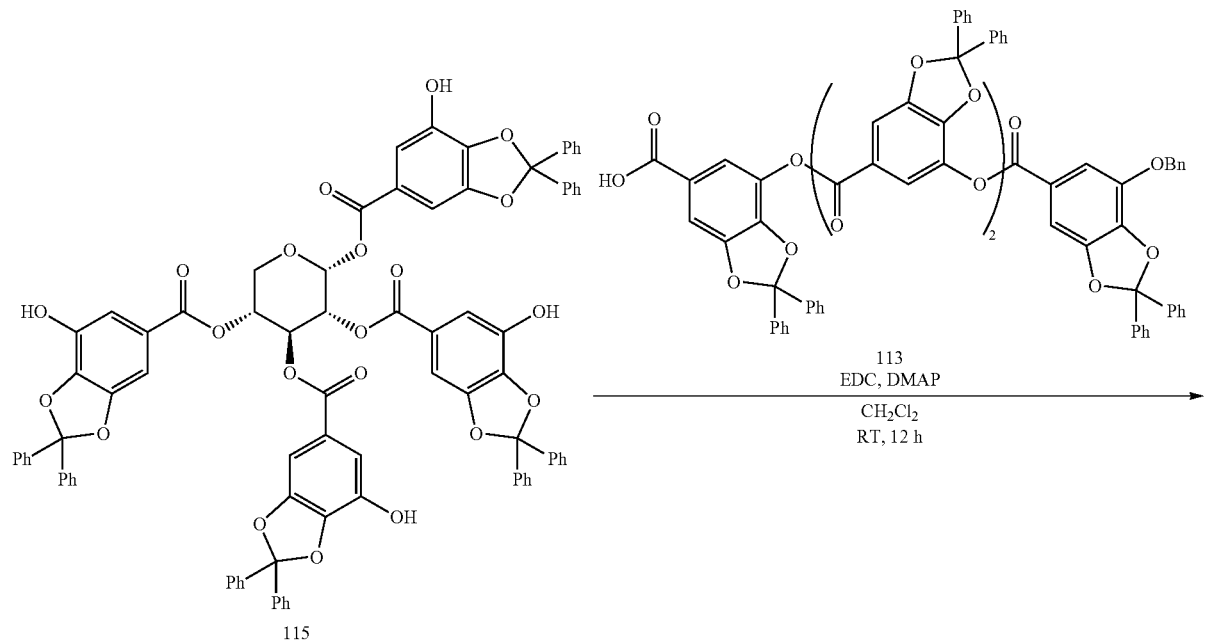
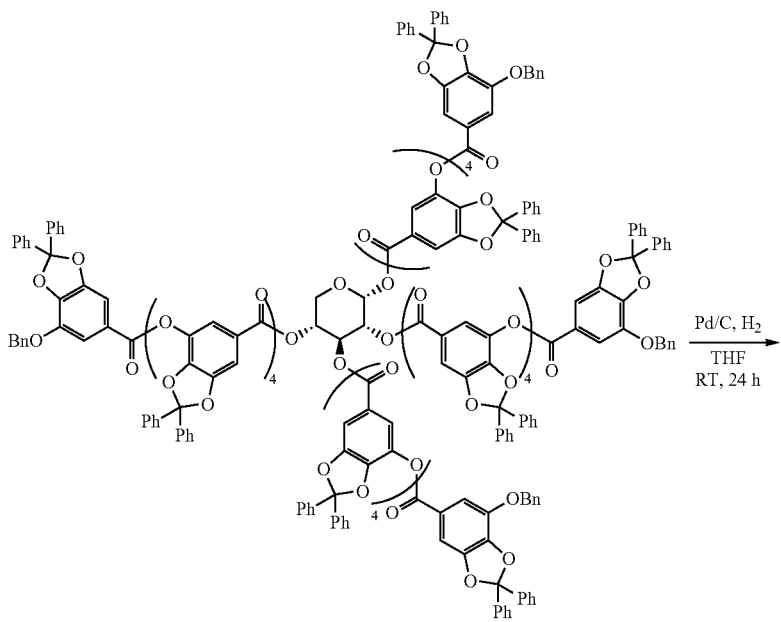

-continued

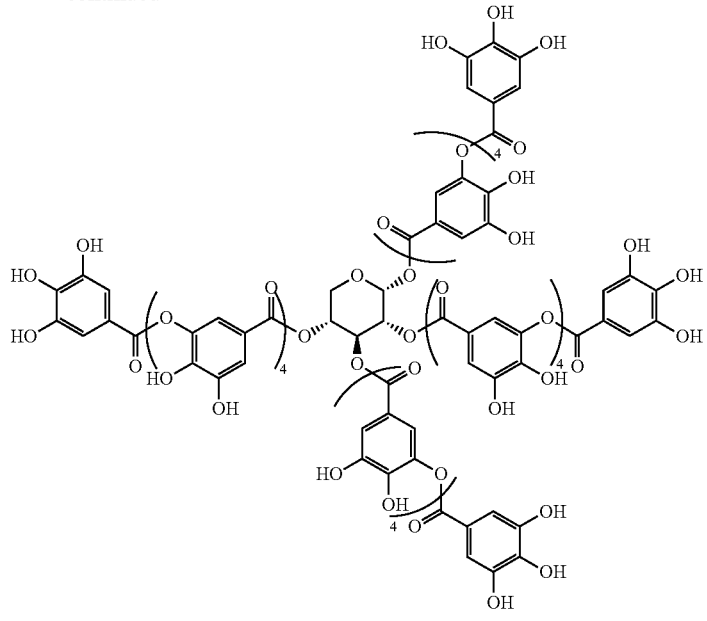

123

Preparation of (2R,3R,4S,5R)-tetrahydro-2H-pyran-2,3,4,5-tetrayl tetrakis(7-((7-((7-((7-((7-(benzyloxy)-2,2-diphenyl-benzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (122)

To a slurry solution of the compound 115 (140 mg, 0.10 mmol), compound 113 (571 mg, 0.42 mmol) and 4-dimethylaminopyridine (7 mg, 0.06 mmol) in DCM (7.1 mL) at 0° C., 1-ethyl-3-(3-dimethylaminopropyl)carbodiimide (88 mg, 0.46 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 122 (560 mg, 83%) as a white solid. $^1$H NMR (CDCl$_3$, 500 MHz) δ 7.77-7.11 (m, 260H), 6.65 (d, J=3.5 Hz, 1H), 6.07 (t, J=9.8 Hz, 1H), 5.43 (dd, J=10.2, 3.7 Hz, 1H), 5.41-5.32 (m, 1H), 5.28-5.18 (m, 8H), 4.21-4.10 (m, 1H), 3.89 (t, J=10.5 Hz, 1H).

Preparation of (2R,3R,4S,5R)-tetrahydro-2H-pyran-2,3,4,5-tetrayl tetrakis(3-((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)-4,5-dihydroxybenzoate) (123)

To a solution of the compound 122 (505 mg, 0.07 mmol) in anhydrous tetrahydrofuran (10.0 mL), the dried 10 wt % Pd/C solid (511 mg) was added. The mixture was stirred at RT under H$_2$ (8 atm) for 24 h. The crude mixture was filtrated, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase C$_{18}$ F.C. with ACN/H$_2$O=25%~40% with 1% formic acid as additive. The collected residue was extracted with EtOAc/brine. The organic layer was dried over magnesium sulfate, evaporated, and precipitated with EtOAc/n-pentane (~10%) to afford the compound 123 as an off-white solid (150 mg, 64%). $^1$H NMR (MeOD, 400 MHz) δ 7.71-7.17 (m, 38H), 7.15-6.95 (m, 2H), 6.77-6.64 (m, 1H), 6.21-6.07 (m, 1H), 5.64-5.45 (m, 2H), 4.33-4.16 (m, 1H), 4.16-4.01 (m, 1H).

Example 31. Synthesis of (2S,3R,4S,5R)-tetrahydro-2H-pyran-2,3,4,5-tetrayl tetrakis(3-((3,4-dihydroxy-5-((3,4,5-trihydroxybenzoyl)oxy)benzoyl)oxy)-4,5-dihydroxybenzoate) (126)

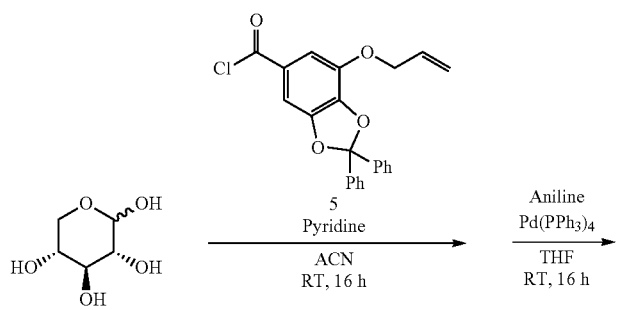

-continued
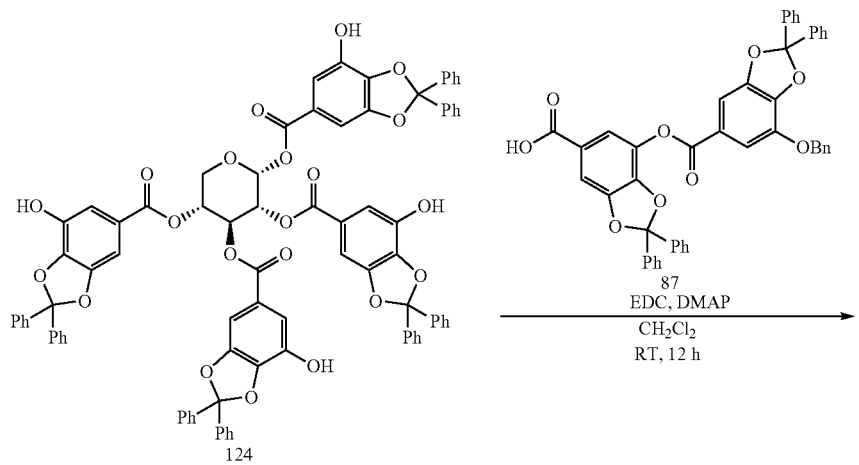
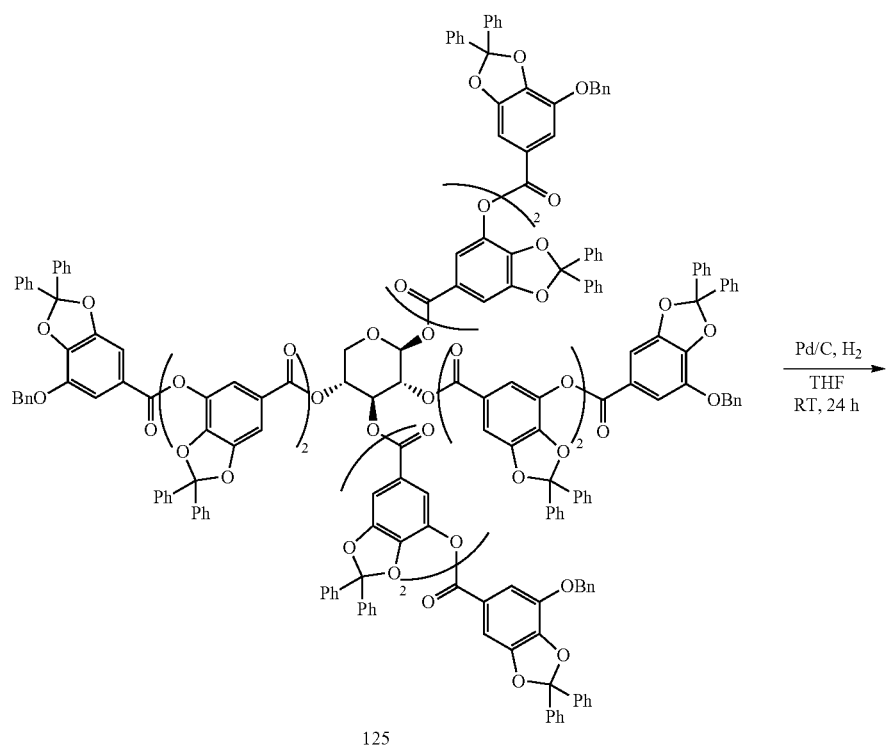

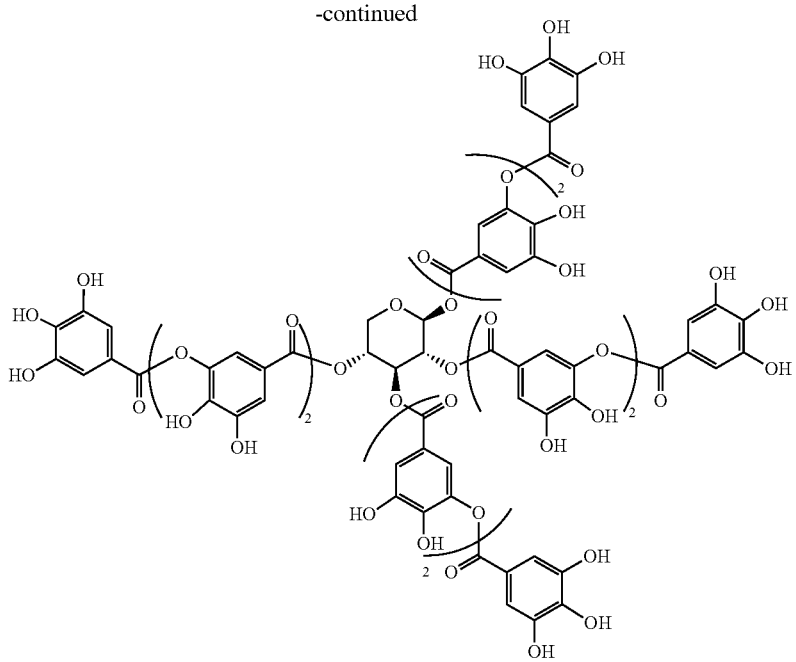

126

Preparation of (2S,3R,4S,5R)-tetrahydro-2H-pyran-2,3,4,5-tetrayl tetrakis(7-hydroxy-2,2-diphenylbenzo[d][1,3]dioxole-5-carboxylate) (124)

To a slurry solution of the D-(+)-xylose (890 mg, 5.93 mmol), compound 5 (10.0 g, 25.49 mmol) in anhydrous acetonirile (29.6 mL) was added anhydrous pyridine (6.8 mL, 82.99 mmol) at 0° C. and stirred under RT 16 h. The crude mixture was cooled to 0° C., quenched with 1N hydrochloric acid, and extracted with EtOAc and brine. The slurry organic layer was filtrated, dried over anhydrous magnesium sulfate and filtered again. The organic solution was evaporated in vacuo, purified by normal phase F.C. with DCM/hexanes (50%~70%) to afford the crude intermediate (1100 mg). To the Ar(g) flushed intermediate solution in THF (19.1 mL) tetrakis(triphenyl phosphine)palladium (111 mg, 0.10 mmol) and aniline (0.22 mL, 2.36 mmol) was added and stirred under RT 16 h. The mixture was extracted with DCM, 1 N hydrochloric acid and brine. The organic residue was dried over magnesium sulfate, evaporated, and purified by F.C. with EtOAc/DCM=5%~12% and precipitated with DCM/hexanes ~10% to afford the compound 124 as an off-white solid (210 mg, 3%). $^1$H NMR (CDCl$_3$, 400 MHz) δ 7.55-7.44 (m, 16H), 7.38-7.26 (m, 25H), 7.25-7.08 (m, 7H), 6.07 (d, J=6.0 Hz, 1H), 5.71 (t, J=7.4 Hz, 1H), 5.51 (t, J=13.5 Hz, 1H), 5.27-5.15 (m, 1H), 4.28-4.18 (m, 1H), 3.65 (dd, J=11.7, 7.6 Hz, 1H).

Preparation of (2S,3R,4S,5R)-tetrahydro-2H-pyran-2,3,4,5-tetrayl tetrakis(7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (125)

To a slurry solution of the compound 124 (100 mg, 0.07 mmol), compound 87 (230 mg, 0.31 mmol) and 4-dimethylaminopyridine (5 mg, 0.04 mmol) in DCM (3.3 mL) at 0° C., 1-ethyl-3-(3-dimethylaminopropyl)carbodiimide (66 mg, 0.31 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 125 (243 mg, 80%) as a white solid. $^1$H NMR (CDCl$_3$, 400 MHz) δ 7.70-7.16 (m, 164H), 6.02 (d, J=6.8 Hz, 1H), 5.78 (t, J=8.6 Hz, 1H), 5.59 (t, J=8.2 Hz, 1H), 5.25-5.11 (m, 8H), 4.42-4.32 (m, 1H), 3.75-3.63 (m, 1H).

Preparation of (2S,3R,4S,5R)-tetrahydro-2H-pyran-2,3,4,5-tetrayl tetrakis(3-((3,4-dihydroxy-5-((3,4,5-trihydroxybenzoyl)oxy)benzoyl)oxy)-4,5-dihydroxybenzoate) (126)

To a solution of the compound 125 (220 mg, 0.05 mmol) in anhydrous tetrahydrofuran (4.4 mL), the dried 10 wt % Pd/C solid (228 mg) was added. The mixture was stirred at RT under H$_2$ (8 atm) for 24 h. The crude mixture was filtrated, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase C$_{18}$ F.C. with ACN/H$_2$O=25%~40% with 1% formic acid as additive. The collected residue was extracted with EtOAc/brine. The organic layer was dried over magnesium sulfate, evaporated, and precipitated with EtOAc/n-pentane (~10%) to afford the compound 126 as an off-white solid (64 mg, 63%). $^1$H NMR (MeOD, 400 MHz) δ 7.66-7.15 (m, 22H), 7.15-6.95 (m, 2H), 6.27-6.13 (m, 1H), 6.04-5.84 (m, 1H), 5.73-5.55 (m, 1H), 5.52-5.34 (m, 1H), 4.46-4.30 (m, 1H), 3.97-3.83 (m, 1H).

Example 32. Synthesis of (2S,3R,4S,5R)-tetrahydro-2H-pyran-2,3,4,5-tetrayl tetrakis(3-((3-((3,4-dihydroxy-5-((3,4,5-trihydroxybenzoyl)oxy)benzoyl)oxy)-4,5-dihydroxybenzoyl)oxy)-4,5-dihydroxybenzoate) (128)
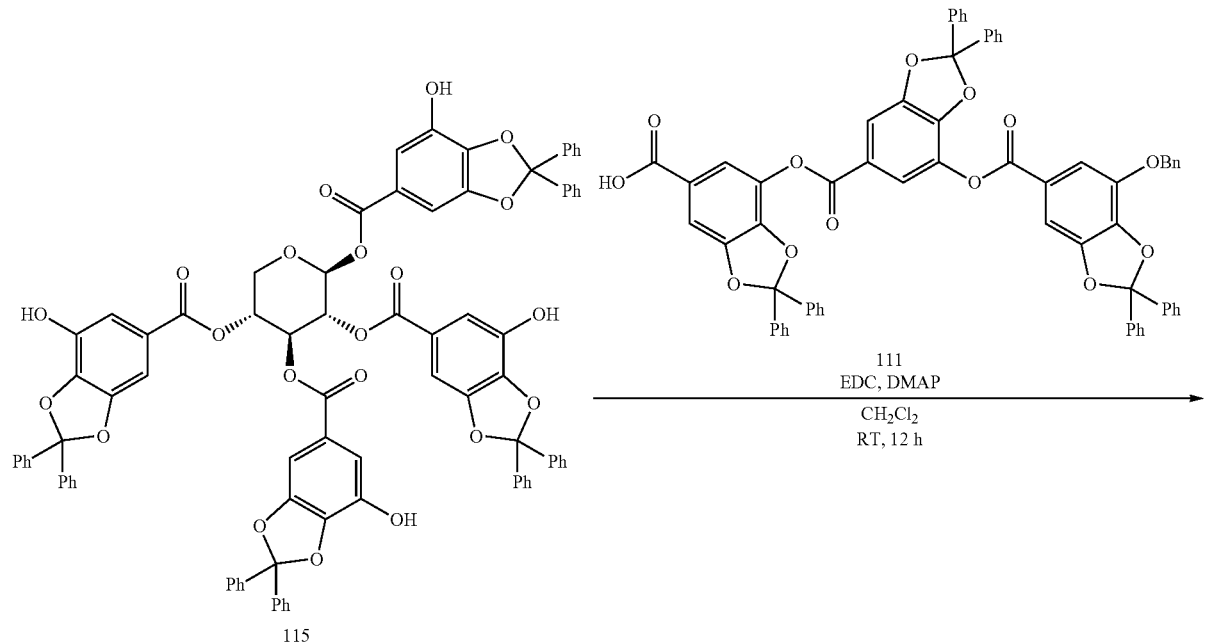
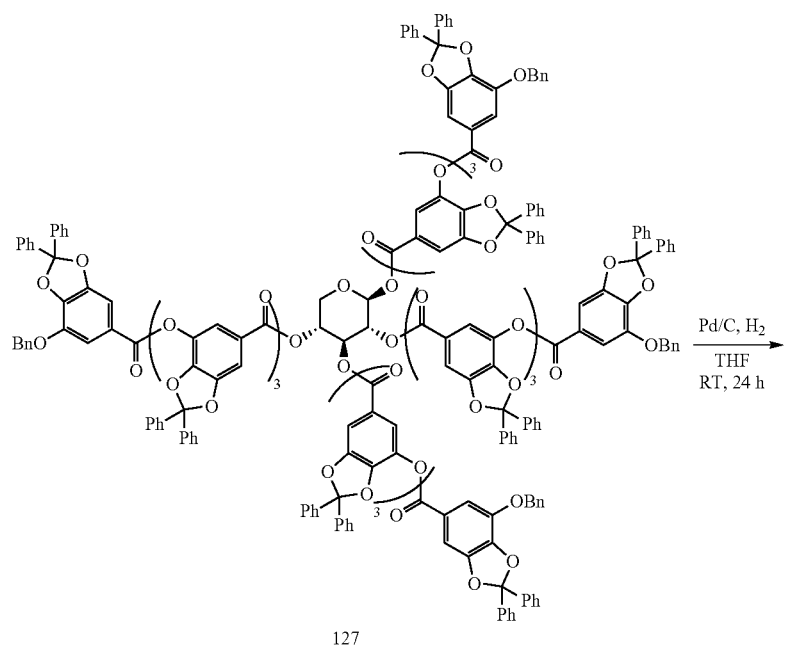

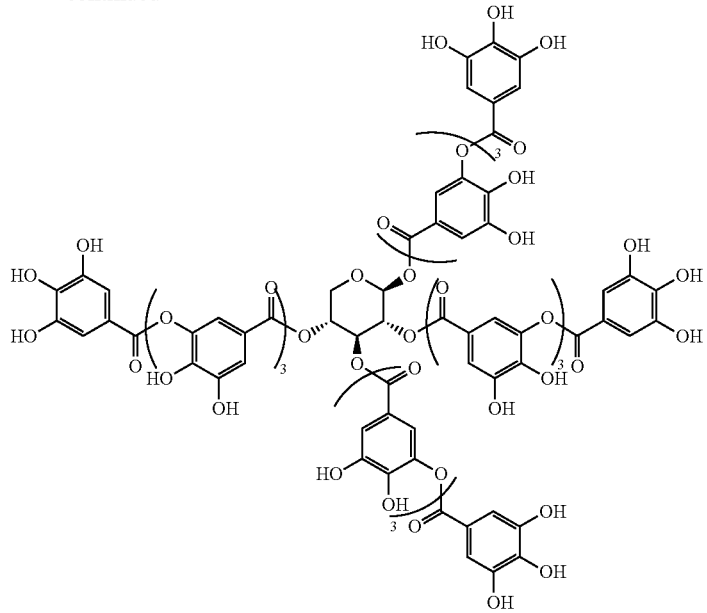

128

Preparation of (2S,3R,4S,5R)-tetrahydro-2H-pyran-2,3,4,5-tetrayl tetrakis(7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (127)

To a slurry solution of the compound 124 (80 mg, 0.06 mmol), compound 111 (263 mg, 4.4 mmol) and 4-dimethylaminopyridine (4 mg, 0.03 mmol) in DCM (3.4 mL) at 0° C., 1-ethyl-3-(3-dimethylaminopropyl)carbodiimide (53 mg, 4.8 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 127 (226 mg, 72%) as a white solid. $^1$H NMR (CDCl$_3$, 400 MHz) δ 7.69-7.18 (m, 212H), 6.02 (d, J=7.1 Hz, 1H), 5.78 (t, J=8.8 Hz, 1H), 5.59 (t, J=8.1 Hz, 1H), 5.26-5.13 (m, 8H), 4.43-4.30 (m, 1H), 3.73-3.63 (m, 1H).

Preparation of (2S,3R,4S,5R)-tetrahydro-2H-pyran-2,3,4,5-tetrayl tetrakis(3-((3-((3,4-dihydroxy-5-((3,4,5-trihydroxybenzoyl)oxy)benzoyl)oxy)-4,5-dihydroxybenzoyl)oxy)-4,5-dihydroxybenzoate) (128)

To a solution of the compound 127 (210 mg, 0.04 mmol) in anhydrous tetrahydrofuran (4.2 mL), the dried 10 wt %

Pd/C solid (233 mg) was added. The mixture was stirred at RT under H$_2$ (8 atm) for 24 h. The crude mixture was filtrated, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase C$_{18}$ F.C. with ACN/H$_2$O=25%~40% with 1% formic acid as additive. The collected residue was extracted with EtOAc/brine. The organic layer was dried over magnesium sulfate, evaporated, and precipitated with EtOAc/n-pentane (~10%) to afford the compound 128 as an off-white solid (57 mg, 59%). $^1$H NMR (MeOD, 400 MHz) δ 7.65-7.16 (m, 30H), 7.16-6.97 (m, 2H), 6.25-6.11 (m, 1H), 6.03-5.85 (m, 1H), 5.72-5.56 (m, 1H), 5.51-5.34 (m, 1H), 4.46-4.28 (m, 1H), 3.99-3.81 (m, 1H).

Example 33. Synthesis of (2S,3R,4R,5R)-5-(((7-hydroxy-2,2-diphenylbenzo[d][1,3]dioxole-5-carbonyl)oxy)methyl)tetrahydrofuran-2,3,4-triyl tris(7-hydroxy-2,2-diphenylbenzo[d][1,3]dioxole-5-carboxylate) (132)
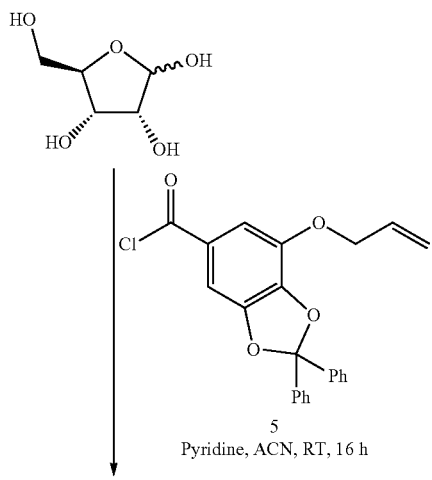
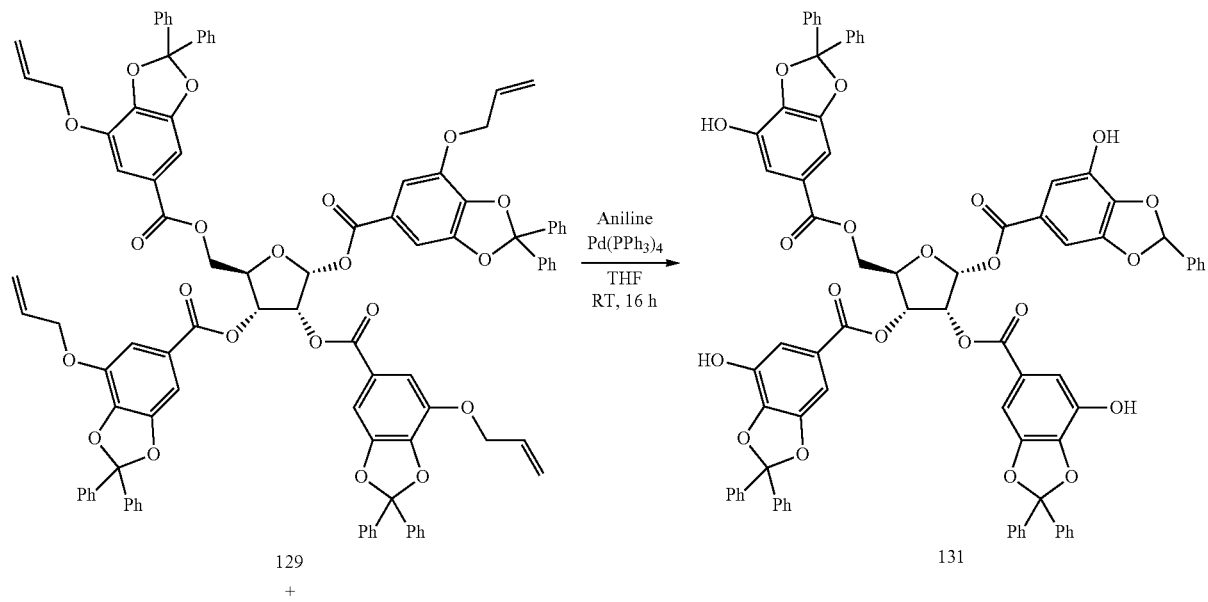

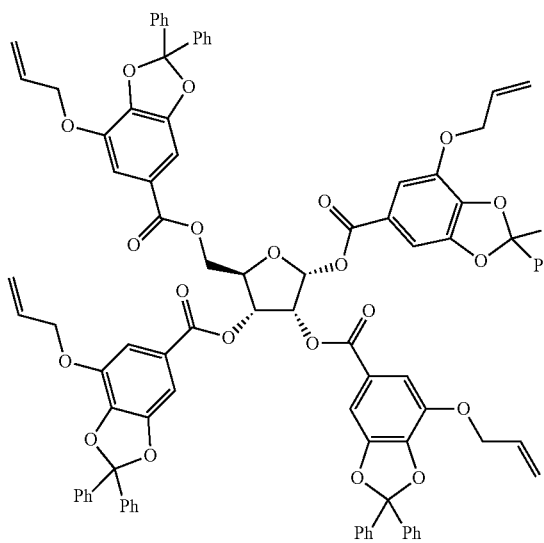

130

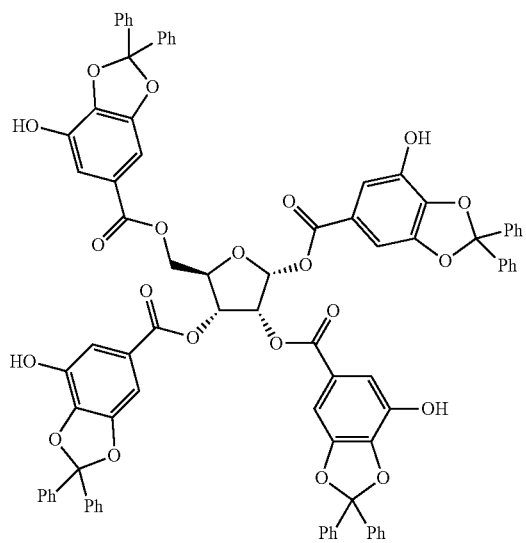

132

Preparation of (2R,3R,4R,5R)-5-(((7-(allyloxy)-2,2-diphenylbenzo[d][1,3]dioxole-5-carbonyl)oxy)methyl)tetrahydrofuran-2,3,4-triyl tris(7-(allyloxy)-2,2-diphenylbenzo[d][1,3]dioxole-5-carboxylate) (129) and (2S,3R,4R,5R)-5-(((7-(allyloxy)-2,2-diphenylbenzo[d][1,3]dioxole-5-carbonyl)oxy)methyl)tetrahydrofuran-2,3,4-triyl tris(7-(allyloxy)-2,2-diphenylbenzo[d][1,3]dioxole-5-carboxylate) (130)

To a slurry solution of the α-D-(−)-ribose (230 mg, 1.5 mmol), compound 5 (3.0 g, 7.7 mmol) in anhydrous acetonirile (7.7 mL) was added anhydrous pyridine (1.8 mL, 21.5 mmol) at 0° C. and stirred under RT 16 h. The cured mixture was cooled to 0° C., quenched with 1N hydrochloric acid, and extracted with EtOAc and brine. The slurry organic layer was filtrated, dried over anhydrous magnesium sulfate and filtered again. The organic solution was evaporated in vacuo, purified by normal phase F.C. with DCM/hexanes=55%~80% and EtOAc/DCM=1%~5% to afford the compound 129 (1.1 g, 44%) as a bubble form white solid. $^1$H NMR (CDCl$_3$, 400 MHz) δ 7.62-7.54 (m, 8H), 7.54-7.44 (m, 8H), 7.43-7.27 (m, 28H), 7.19 (pseudo d, J=8.8 Hz, 4H), 6.37 (d, J=6.0 Hz, 1H), 6.11-5.97 (m, 2H), 5.95-5.68 (m, 3H), 5.54 (dd, J=6.1, 3.4 Hz, 1H), 5.50-5.45 (m, 1H), 5.41 (dd, J=17.2, 1.4 Hz, 1H), 5.29-4.98 (m, 7H), 4.69 (pseudo d, J=5.2 Hz, 2H), 4.53 (pseudo d, J=5.4 Hz, 2H), 4.42-4.36 (m, 2H), 4.34 (pseudo d, J=5.5 Hz, 2H), 4.25 (dd, J=11.9, 4.1 Hz, 1H), 4.15 (dd, J=12.0, 7.5 Hz, 1H). And the compound 130 (600 mg, 25%) as a bubble form white solid. $^1$H NMR (CDCl$_3$, 400 MHz) δ 7.54-7.43 (m, 16H), 7.37-7.22 (m, 28H), 7.22-7.04 (m, 4H), 6.45 (pseudo s, 1H), 6.05 (pseudo s, 1H), 5.79-5.60 (m, 4H), 5.53 (pseudo s, 1H), 5.47-5.34 (m, 1H), 5.21-4.91 (m, 8H), 4.40-4.16 (m, 9H), 4.02 (dd, J=11.2, 4.7 Hz, 1H).

Preparation of (2R,3R,4R,5R)-5-(((7-hydroxy-2,2-diphenylbenzo[d][1,3]dioxole-5-carbonyl)oxy)methyl)tetrahydrofuran-2,3,4-triyl tris(7-hydroxy-2,2-diphenylbenzo[d][1,3]dioxole-5-carboxylate) (131)

To a argon flushed solution of the compound 129 (1.1 g, 0.67 mmol) and tetrakis(triphenyl phosphine)palladium (77 mg, 0.07 mmol) in dry tetrahydrofuran (6.7 mL), aniline (0.13 mL, 1.40 mmol) was added and stirred under RT 16 h. The mixture was extracted with DCM, 1 N hydrochloric acid and brine. The organic residue was dried over magnesium sulfate, evaporated, purified by F.C. with EtOAc/DCM (5/95), and precipitated with DCM/hexanes ~10% to afford the compound 131 as an off-white solid (855 mg, 91%). $^1$H NMR (CDCl$_3$, 400 MHz) δ 7.59-7.46 (m, 16H), 7.39-7.27 (m, 27H), 7.23-7.10 (m, 5H), 6.40 (d, J=3.7 Hz, 1H), 5.85 (t, J=3.4 Hz, 1H), 5.53 (t, J=3.5 Hz, 1H), 5.49-5.41 (m, 1H), 4.23-4.16 (m, 1H), 4.11-4.04 (m, 1H).

Preparation of (2S,3R,4R,5R)-5-(((7-hydroxy-2,2-diphenylbenzo[d][1,3]dioxole-5-carbonyl)oxy)methyl)tetrahydrofuran-2,3,4-triyl tris(7-hydroxy-2,2-diphenylbenzo[d][1,3]dioxole-5-carboxylate) (132)

To a argon flushed solution of the compound 130 (600 mg, 0.38 mmol) and tetrakis(triphenyl phosphine)palladium (44 mg, 0.04 mmol) in dry tetrahydrofuran (1.9 mL), aniline (0.08 mL, 0.80 mmol) was added and stirred under RT 16 h. The mixture was extracted with DCM, 1 N hydrochloric acid and brine. The organic residue was dried over magnesium sulfate, evaporated, purified by F.C. with EtOAc/DCM (5/95), and precipitated with DCM/hexanes ~10% to afford the compound 132 as an off-white solid (427 mg, 79%). $^1$H NMR (CDCl$_3$, 400 MHz) δ 7.56-7.46 (m, 16H), 7.40-7.27 (m, 27H), 7.25-7.04 (m, 5H), 6.43 (pseudo s, 1H), 6.01 (pseudo s, 1H), 5.51 (pseudo s, 1H), 5.42-5.33 (m, 1H), 4.26 (t, J=10.2 Hz, 1H), 3.99-3.87 (m, 1H).

Example 34. Synthesis of (2R,3R,4R,5R)-5-(((3,4-dihydroxy-5-(((3,4,5-trihydroxybenzoyl)oxy)benzoyl)oxy)methyl)tetrahydrofuran-2,3,4-triyl tris(3,4-dihydroxy-5-(((3,4,5-trihydroxybenzoyl)oxy)benzoate) (134)
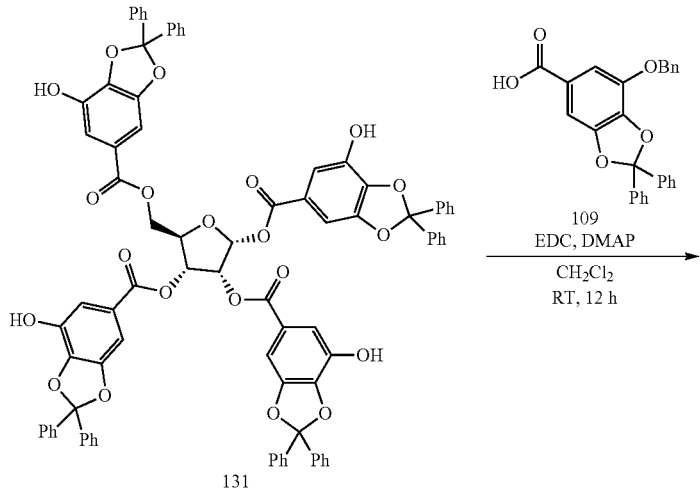
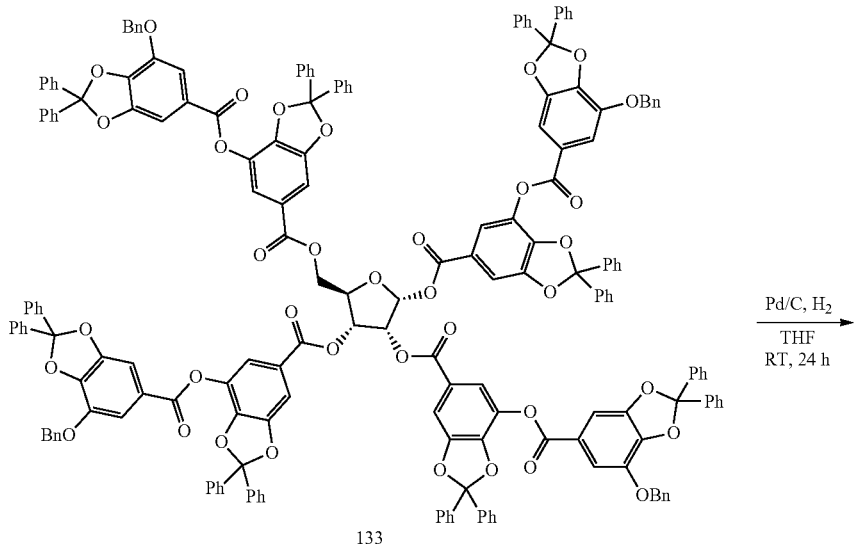

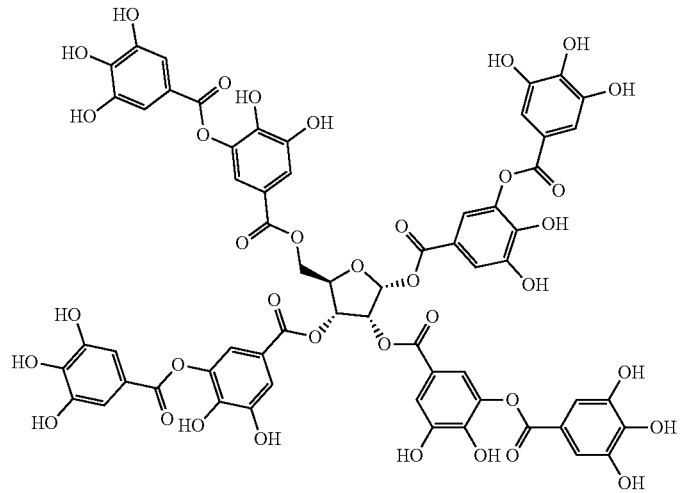

134

Preparation of (2R,3R,4R,5R)-5-(((7-((7-(benzyloxy)-2,2-diphenylbenzo[d][1,3]dioxole-5-carbonyl)oxy)-2,2-diphenylbenzo[d][1,3]dioxole-5-carbonyl)oxy)methyl)tetrahydrofuran-2,3,4-triyl tris(7-((7-(benzyloxy)-2,2-diphenylbenzo[d][1,3]dioxole-5-carbonyl)oxy)-2,2-diphenylbenzo[d][1,3]dioxole-5-carboxylate) (133)

To a slurry solution of the compound 131 (200 mg, 0.14 mmol), compound 109 (246 mg, 0.58 mmol) and 4-dimethylaminopyridine (10.4 mg, 0.08 mmol) in DCM (4.5 mL) at 0° C., 1-ethyl-3-(3-dimethylaminopropyl)carbodiimide (123 mg, 0.64 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 133 (318 mg, 74%) as a white solid. $^1$H NMR (CDCl$_3$, 400 MHz) δ 7.62-7.17 (m, 116H), 6.39 (d, J=6.0 Hz, 1H), 6.04 (pseudo s, 1H), 5.51 (dd, J=5.9, 3.4 Hz, 1H), 5.50-5.41 (m, 1H), 5.25 (s, 2H), 5.11 (s, 4H), 5.08 (s, 2H), 4.26-4.08 (m, 2H).

Preparation of (2R,3R,4R,5R)-5-(((3,4-dihydroxy-5-((3,4,5-trihydroxybenzoyl)oxy)benzoyl)oxy)methyl)tetrahydrofuran-2,3,4-triyl tris(3,4-dihydroxy-5-((3,4,5-trihydroxybenzoyl)oxy)benzoate) (134)

To a solution of the compound 133 (300 mg, 0.10 mmol) in anhydrous tetrahydrofuran (6.0 mL), the dried 10 wt % Pd/C solid (304 mg) was added. The mixture was stirred at RT under H$_2$ (8 atm) for 24 h. The crude mixture was filtered, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase C$_{18}$ F.C. with ACN/H$_2$O=25%~40% with 1% formic acid as additive. The collected residue was extracted with EtOAc/brine. The organic layer was dried over magnesium sulfate, evaporated, and precipitated with EtOAc/n-pentane (~10%) to afford the compound 134 as an off-white solid (77 mg, 57%). $^1$H NMR (MeOD, 500 MHz) δ 7.50-7.12 (m, 15H), 7.08-6.96 (m, 1H), 6.49-6.37 (m, 1H), 6.24-6.05 (m, 1H), 5.61-5.44 (m, 2H), 4.39-4.18 (m, 2H).

Example 35. Synthesis of (2R,3R,4R,5R)-5-(((3-((3,4-dihydroxy-5-((3,4,5-trihydroxybenzoyl)oxy)benzoyl)oxy)-4,5-dihydroxybenzoyl)oxy)methyl)tetrahydrofuran-2,3,4-triyl tris(3-((3,4-dihydroxy-5-((3,4,5-trihydroxybenzoyl)oxy)benzoyl)oxy)-4,5-dihydroxybenzoate) (136)
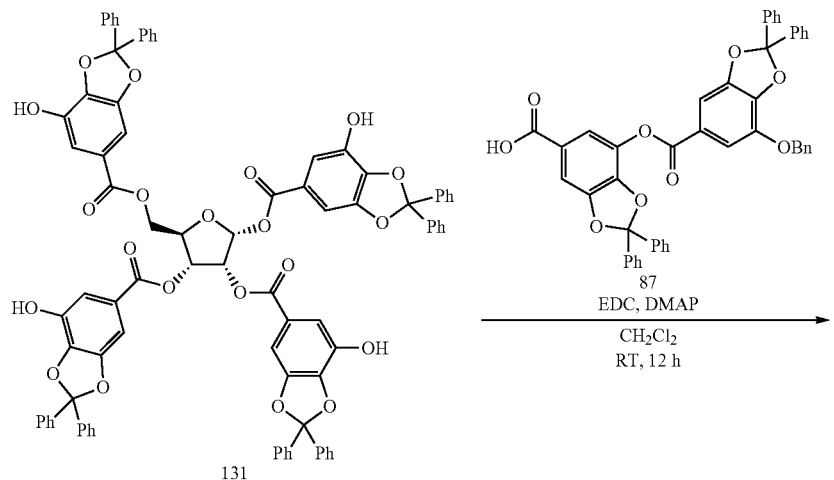
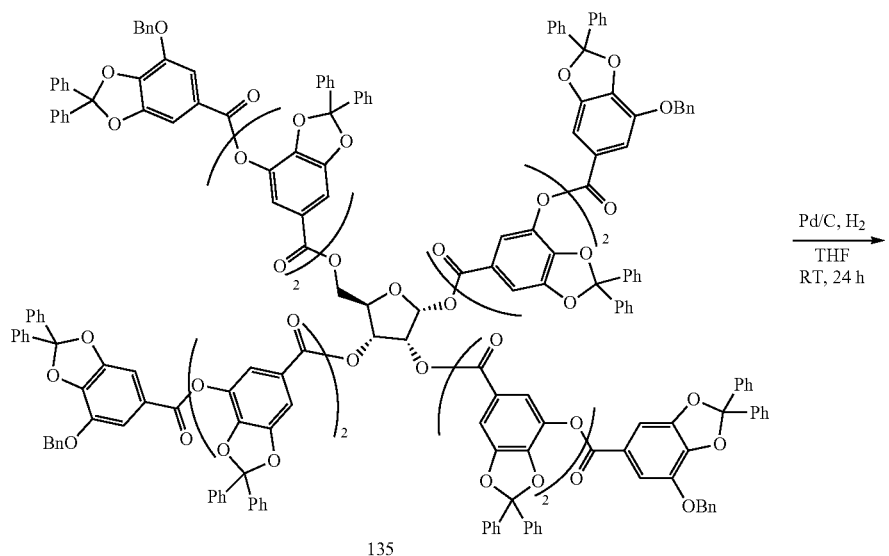

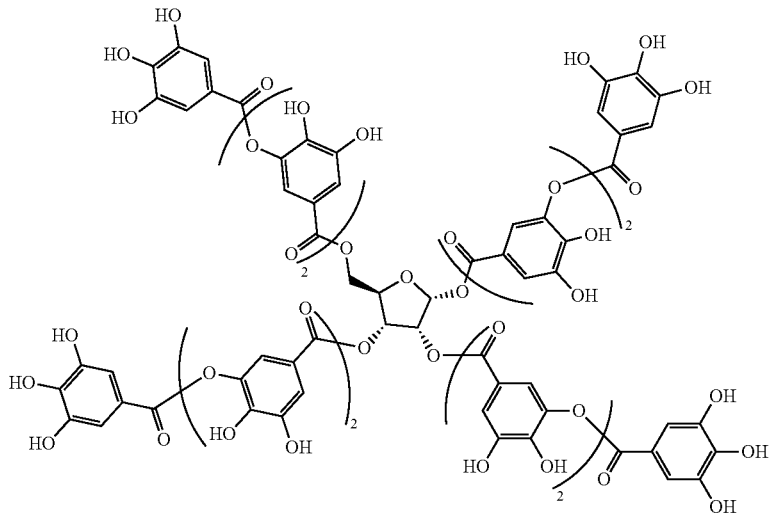

136

Preparation of (2R,3R,4R,5R)-5-(((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)methyl)tetrahydrofuran-2,3,4-triyl tris(7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (135)

To a slurry solution of the compound 131 (140 mg, 0.10 mmol), compound 87 (300 mg, 0.41 mmol) and 4-dimethylaminopyridine (7 mg, 0.06 mmol) in DCM (4.4 mL) at 0° C., 1-ethyl-3-(3-dimethylaminopropyl)carbodiimide (86 mg, 0.45 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 135 (295 mg, 69%) as a white solid. $^1$H NMR (CDCl$_3$, 400 MHz) δ 7.74-7.04 (m, 164H), 6.39 (d, J=4.1 Hz, 1H), 6.00 (pseudo s, 1H), 5.57-5.43 (m, 2H), 5.25 (s, 2H), 5.10 (s, 2H), 5.03-4.81 (m, 4H), 4.25-4.07 (m, 2H).

Preparation of (2R,3R,4R,5R)-5-(((3-((3,4-dihydroxy-5-((3,4,5-trihydroxybenzoyl)oxy)benzoyl)oxy)-4,5-dihydroxybenzoyl)oxy)methyl)tetrahydrofuran-2,3,4-triyl tris(3-((3,4-dihydroxy-5-((3,4,5-trihydroxybenzoyl)oxy)benzoyl)oxy)-4,5-dihydroxybenzoate) (136)

To a solution of the compound 135 (280 mg, 0.07 mmol) in anhydrous tetrahydrofuran (5.6 mL), the dried 10 wt % Pd/C solid (291 mg) was added. The mixture was stirred at RT under H$_2$ (8 atm) for 24 h. The crude mixture was filtrated, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase C$_{18}$ F.C. with ACN/H$_2$O=25%~40% with 1% formic acid as additive. The collected residue was extracted with EtOAc/brine. The organic layer was dried over magnesium sulfate, evaporated, and precipitated with EtOAc/n-pentane (~10%) to afford the compound 136 as an off-white solid (77 mg, 60%). $^1$H NMR (MeOD, 500 MHz) δ 7.64-7.13 (m, 23H), 7.10-7.00 (m, 1H), 6.51-6.37 (m, 1H), 6.24-6.00 (m, 1H), 5.63-5.44 (m, 2H), 4.41-4.16 (m, 2H).

Example 36. Synthesis of (2R,3R,4R,5R)-5-(((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)methyl)tetrahydrofuran-2,3,4-triyl tris(3-((3-((3,4-dihydroxy-5-((3,4,5-trihydroxybenzoyl)oxy)benzoyl)oxy)-4,5-dihydroxybenzoyl)oxy)-4,5-dihydroxybenzoate) (138)
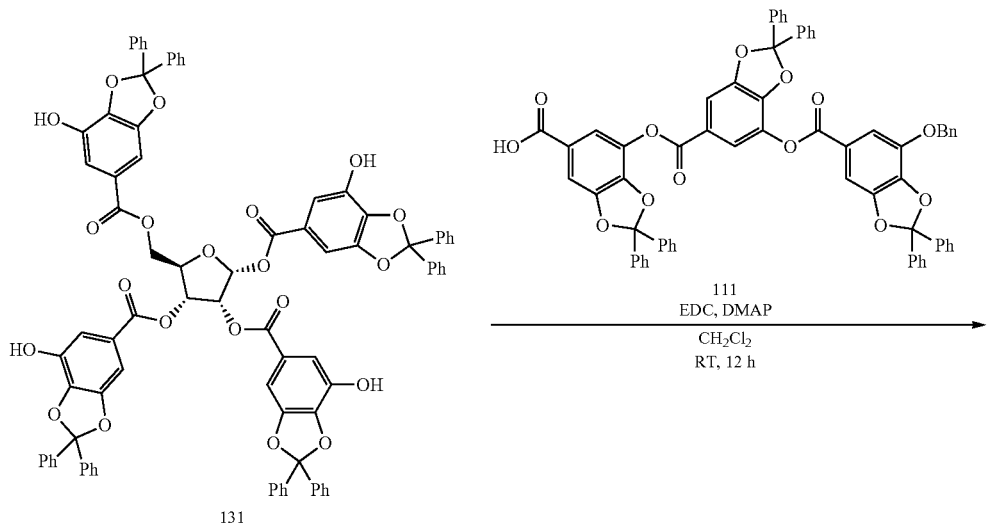
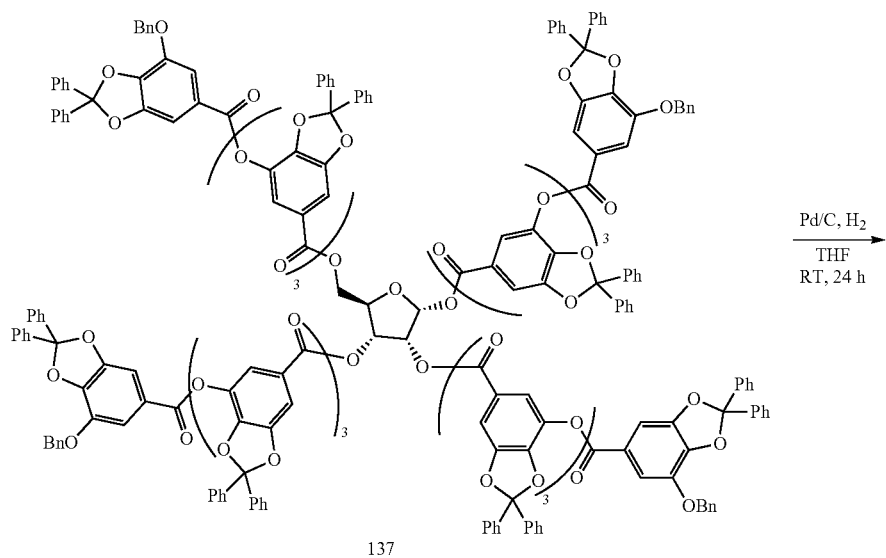

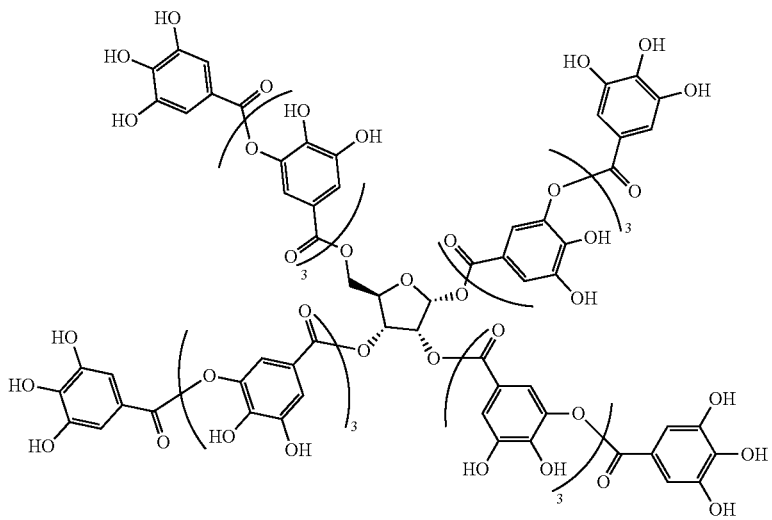

138

Preparation of (2R,3R,4R,5R)-5-(((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)methyl)tetrahydrofuran-2,3,4-triyl tris(7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (137)

To a slurry solution of the compound 131 (90 mg, 0.06 mmol), compound 111 (289 mg, 0.27 mmol) and 4-dimethylaminopyridine (6 mg, 0.08 mmol) in DCM (3.8 mL) at 0° C., 1-ethyl-3-(3-dimethylaminopropyl)carbodiimide (62 mg, 0.32 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 137 (250 mg, 71%) as a white solid. $^1$H NMR (CDCl$_3$, 500 MHz) δ 7.77-7.03 (m, 212H), 6.39 (pseudo s, 1H), 6.00 (pseudo s, 1H), 5.57-5.40 (m, 2H), 5.25 (s, 2H), 5.17 (s, 2H), 5.14-5.03 (m, 4H), 4.27-4.07 (m, 2H).

Preparation of (2R,3R,4R,5R)-5-(((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)methyl)tetrahydrofuran-2,3,4-triyl tris(3-((3-((3,4-dihydroxy-5-((3,4,5-trihydroxybenzoyl)oxy)benzoyl)oxy)-4,5-dihydroxybenzoyl)oxy)-4,5-dihydroxybenzoate) (138)

To a solution of the compound 137 (225 mg, 0.04 mmol) in anhydrous tetrahydrofuran (4.5 mL), the dried 10 wt % Pd/C solid (236 mg) was added. The mixture was stirred at RT under H$_2$ (8 atm) for 24 h. The crude mixture was filtrated, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase C$_{18}$ F.C. with ACN/H$_2$O=25%~40% with 1% formic acid as additive. The collected residue was extracted with EtOAc/brine. The organic layer was dried over magnesium sulfate, evaporated, and precipitated with EtOAc/n-pentane (~10%) to afford the compound 138 as an off-white solid (77 mg, 74%). $^1$H NMR (MeOD, 400 MHz) δ 7.66-7.13 (m, 31H), 7.11-7.01 (m, 1H), 6.52-6.36 (m, 1H), 6.26-6.02 (m, 1H), 5.66-5.44 (m, 2H), 4.44-4.16 (m, 2H).

Example 37. Synthesis of (2R,3R,4R,5R)-5-(((3-((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)methyl)tetrahydrofuran-2,3,4-triyl tris(3-((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)-4,5-dihydroxybenzoate) (140)
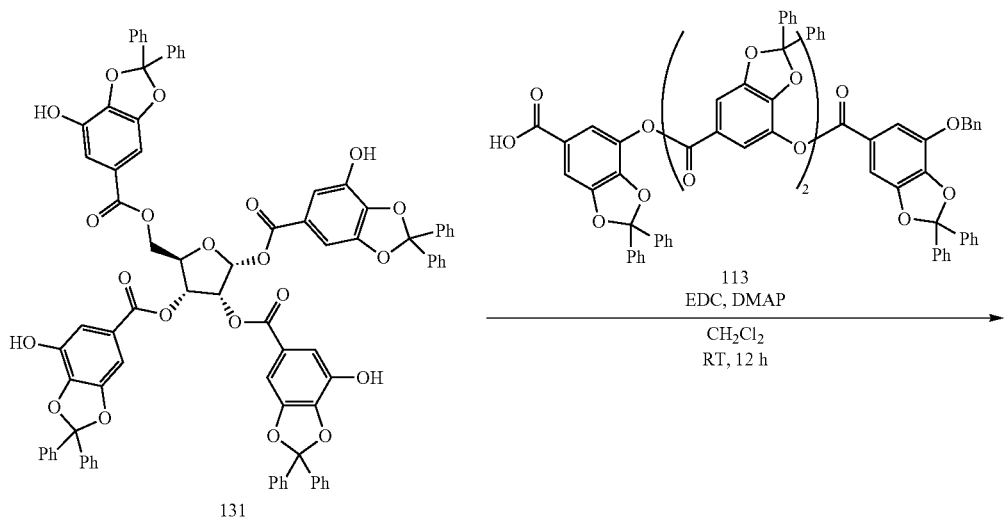
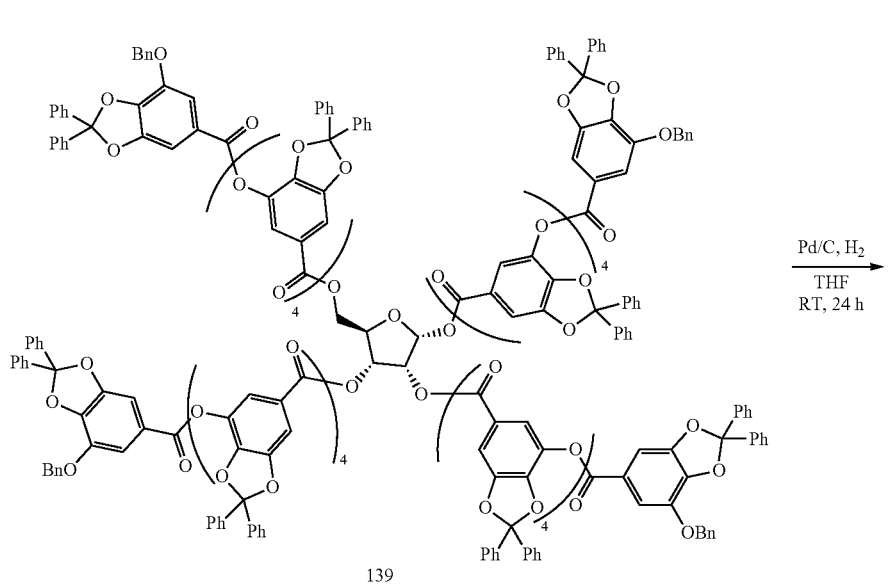

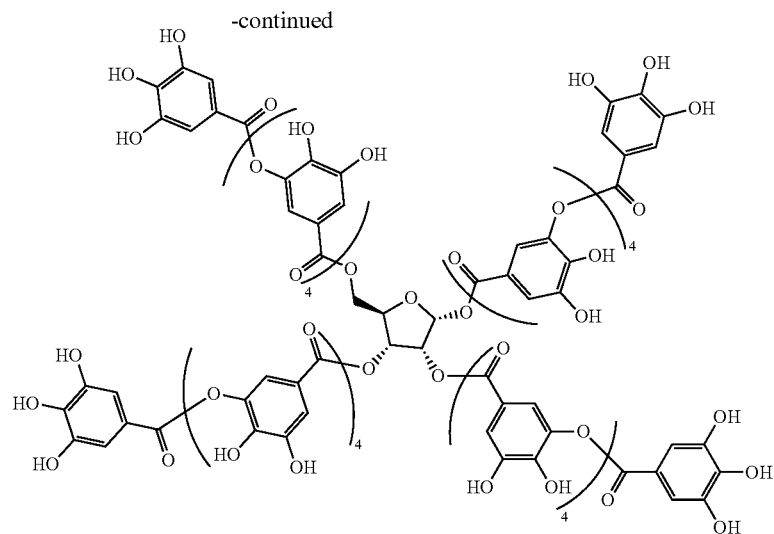

140

Preparation of (2R,3R,4R,5R)-5-(((7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)methyl)tetrahydrofuran-2,3,4-triyl tris(7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (139)

To a slurry solution of the compound 131 (70 mg, 0.05 mmol), compound 113 (292 mg, 0.21 mmol) and 4-dimethylaminopyridine (4.8 mg, 0.04 mmol) in DCM (3.6 mL) at 0° C., 1-ethyl-3-(3-dimethylaminopropyl)carbodiimide (48 mg, 0.25 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 139 (240 mg, 71%) as a white solid. $^1$H NMR (CDCl$_3$, 500 MHz) δ 7.78-7.01 (m, 260H), 6.40 (pseudo s, 1H), 6.00 (pseudo s, 1H), 5.59-5.40 (m, 2H), 5.26 (s, 2H), 5.21 (s, 2H), 5.19-5.03 (m, 4H), 4.31-4.03 (m, 2H).

Preparation of (2R,3R,4R,5R)-5-(((3-((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)-4,5-dihydroxybenzoyl)oxy)methyl)tetrahydrofuran-2,3,4-triyl tris(3-((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)-4,5-dihydroxybenzoate) (140)

To a solution of the compound 139 (235 mg, 0.03 mmol) in anhydrous tetrahydrofuran (4.7 mL), the dried 10 wt % Pd/C solid (238 mg) was added. The mixture was stirred at RT under H$_2$ (8 atm) for 24 h. The crude mixture was filtrated, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase C$_{18}$ F.C. with ACN/H$_2$O=25%~40% with 1% formic acid as additive. The collected residue was extracted with EtOAc/brine. The organic layer was dried over magnesium sulfate, evaporated, and precipitated with EtOAc/n-pentane (~10%) to afford the compound 140 as an off-white solid (65 mg, 59%). $^1$H NMR (MeOD, 400 MHz) δ 7.68-7.13 (m, 39H), 7.10-6.99 (m, 1H), 6.50-6.37 (m, 1H), 6.27-6.03 (m, 1H), 5.64-5.47 (m, 2H), 4.39-4.19 (m, 2H).

Example 38. Synthesis of (2S,3R,4R,5R)-5-(((3,4-dihydroxy-5-((3,4,5-trihydroxybenzoyl)oxy)benzoyl)oxy)methyl)tetrahydrofuran-2,3,4-triyl tris(3,4-dihydroxy-5-((3,4,5-trihydroxybenzoyl)oxy)benzoate) (142)
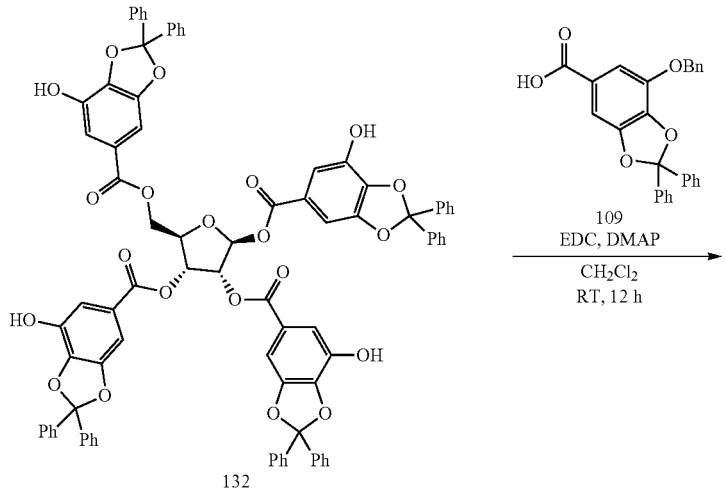
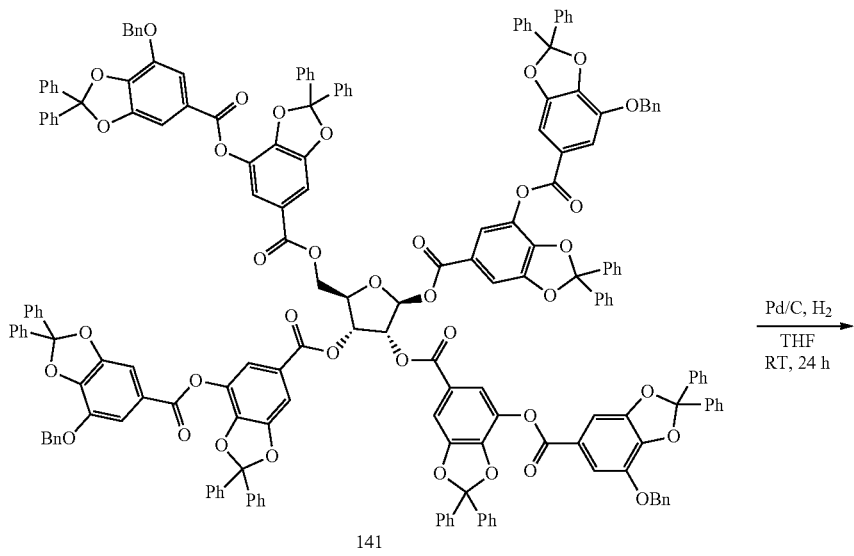

-continued

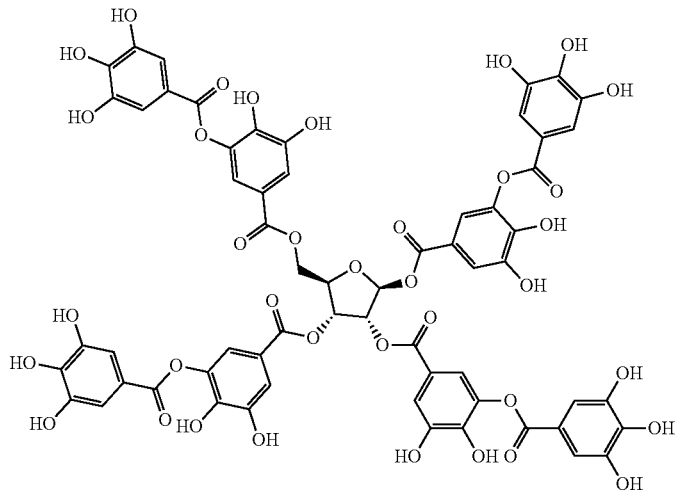

142

Preparation of (2S,3R,4R,5R)-5-(((7-((7-(benzyloxy)-2,2-diphenylbenzo[d][1,3]dioxole-5-carbonyl)oxy)-2,2-diphenylbenzo[d][1,3]dioxole-5-carbonyl)oxy)methyl)tetrahydrofuran-2,3,4-triyl tris(7-((7-(benzyloxy)-2,2-diphenylbenzo[d][1,3]dioxole-5-carbonyl)oxy)-2,2-diphenylbenzo[d][1,3]dioxole-5-carboxylate) (141)

To a slurry solution of the compound 132 (150 mg, 0.11 mmol), compound 109 (184 mg, 0.43 mmol) and 4-dimethylaminopyridine (8 mg, 0.06 mmol) in DCM (3.3 mL) at 0° C., 1-ethyl-3-(3-dimethylaminopropyl)carbodiimide (92 mg, 0.48 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 141 (254 mg, 79%) as a white solid. $^1$H NMR (CDCl$_3$, 400 MHz) δ 7.97-7.03 (m, 116H), 6.54 (pseudo s, 1H), 6.08 (pseudo s, 1H), 5.67-5.50 (m, 1H), 5.50-5.37 (m, 1H), 5.18 (s, 2H), 5.07 (s, 2H), 4.97 (s, 2H), 4.85 (s, 2H), 4.34 (t, J=10.8 Hz, 1H), 3.95 (dd, J=10.9, 5.0 Hz, 1H).

Preparation of (2S,3R,4R,5R)-5-(((3,4-dihydroxy-5-((3,4,5-trihydroxybenzoyl)oxy)benzoyl)oxy)methyl)tetrahydrofuran-2,3,4-triyl tris(3,4-dihydroxy-5-((3,4,5-trihydroxybenzoyl)oxy)benzoate) (142)

To a solution of the compound 141 (245 mg, 0.08 mmol) in anhydrous tetrahydrofuran (4.9 mL), the dried 10 wt % Pd/C solid (249 mg) was added. The mixture was stirred at RT under H$_2$ (8 atm) for 24 h. The crude mixture was filtrated, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase C$_{18}$ F.C. with ACN/H$_2$O=25%~40% with 1% formic acid as additive. The collected residue was extracted with EtOAc/brine. The organic layer was dried over magnesium sulfate, evaporated, and precipitated with EtOAc/n-pentane (~10%) to afford the compound 142 as an off-white solid (67 mg, 61%). $^1$H NMR (MeOD, 500 MHz) δ 7.66-7.11 (m, 15H), 7.11-6.91 (m, 1H), 6.65-6.42 (m, 1H), 6.26-6.02 (m, 1H), 5.77-5.62 (m, 1H), 5.57-5.43 (m, 1H), 4.51-4.38 (m, 1H), 4.16-4.00 (m, 1H).

Example 39. Synthesis of (2S,3R,4R,5R)-5-(((3,4-dihydroxy-5-((3,4,5-trihydroxybenzoyl)oxy)benzoyl)oxy)-4,5-dihydroxybenzoyl)oxy)methyl)tetrahydrofuran-2,3,4-triyl tris(3-((3,4-dihydroxy-5-((3,4,5-trihydroxybenzoyl)oxy)benzoyl)oxy)-4,5-dihydroxybenzoate) (144)
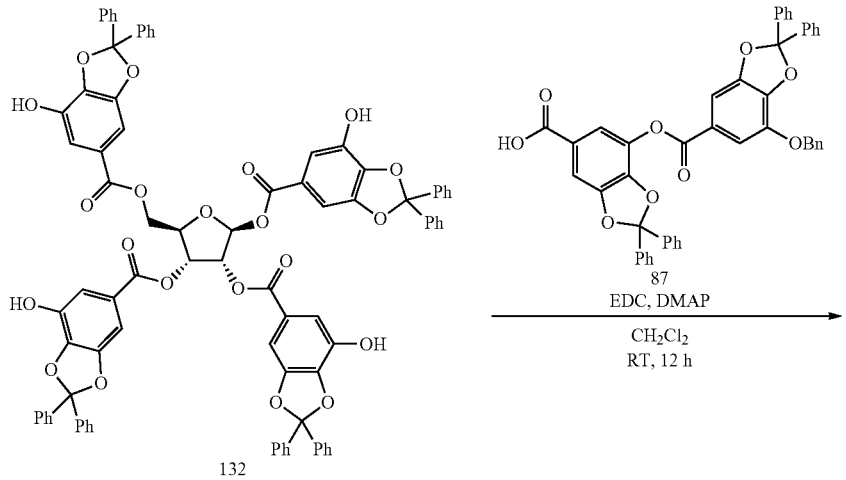
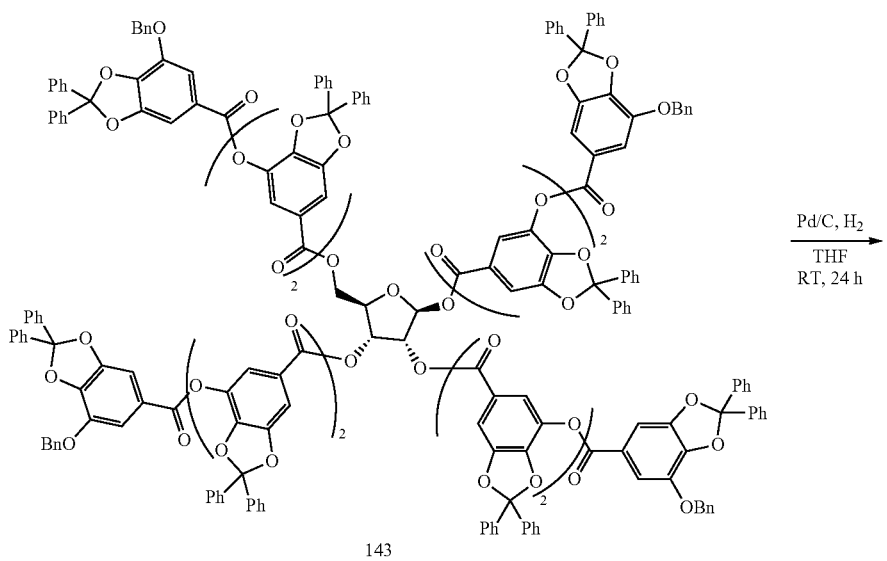

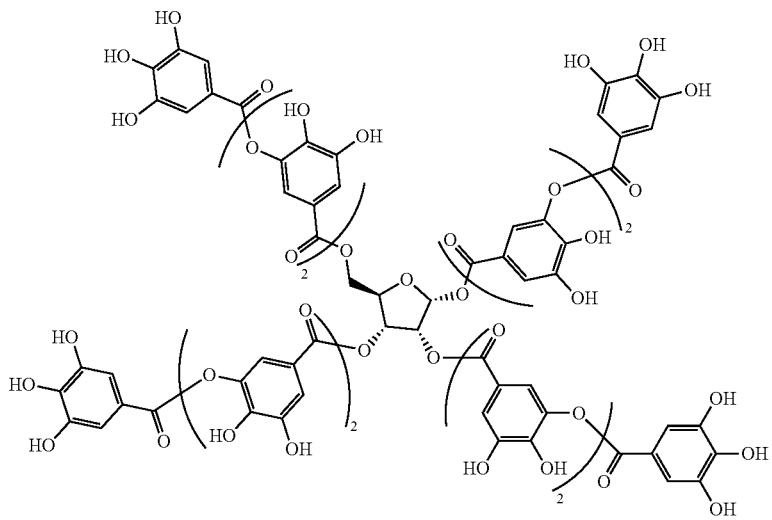

144

Preparation of (2S,3R,4R,5R)-5-(((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)methyl)tetrahydrofuran-2,3,4-triyl tris(7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (143)

To a slurry solution of the compound 132 (100 mg, 0.07 mmol), compound 87 (215 mg, 19.6 mmol) and 4-dimethylaminopyridine (5 mg, 0.04 mmol) in DCM (3.2 mL) at 0° C., 1-ethyl-3-(3-dimethylaminopropyl)carbodiimide (62 mg, 0.32 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 143 (240 mg, 79%) as a white solid. $^1$H NMR (CDCl$_3$, 400 MHz) δ 7.92-6.81 (m, 164H), 6.54 (pseudo s, 1H), 6.09 (pseudo s, 1H), 5.66-5.49 (m, 1H), 5.49-5.37 (m, 1H), 5.28-5.03 (m, 4H), 4.92-4.61 (m, 4H), 4.35 (t, J=10.9 Hz, 1H), 4.02-3.89 (m, 1H).

Preparation of (2S,3R,4R,5R)-5-(((3-((3,4-dihydroxy-5-((3,4,5-trihydroxybenzoyl)oxy)benzoyl)oxy)-4,5-dihydroxybenzoyl)oxy)methyl)tetrahydrofuran-2,3,4-triyl tris(3-((3,4-dihydroxy-5-((3,4,5-trihydroxybenzoyl)oxy)benzoyl)oxy)-4,5-dihydroxybenzoate) (144)

To a solution of the compound 143 (223 mg, 0.05 mmol) in anhydrous tetrahydrofuran (4.5 mL), the dried 10 wt % Pd/C solid (237 mg) was added. The mixture was stirred at RT under H$_2$ (8 atm) for 24 h. The crude mixture was filtrated, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase C$_{18}$ F.C. with ACN/H$_2$O=25%~40% with 1% formic acid as additive. The collected residue was extracted with EtOAc/brine. The organic layer was dried over magnesium sulfate, evaporated, and precipitated with EtOAc/n-pentane (~10%) to afford the compound 144 as an off-white solid (62 mg, 61%). $^1$H NMR (MeOD, 500 MHz) δ 7.68-7.12 (m, 23H), 7.12-6.95 (m, 1H), 6.65-6.38 (m, 1H), 6.27-6.00 (m, 1H), 5.82-5.58 (m, 1H), 5.58-5.43 (m, 1H), 4.53-4.37 (m, 1H), 4.17-3.95 (m, 1H).

Example 40. Synthesis of (2S,3R,4R,5R)-5-(((3-((3-(3,4-dihydroxy-5-((3,4,5-trihydroxybenzoyl)oxy)benzoyl)oxy)-4,5-dihydroxybenzoyl)oxy)-4,5-dihydroxybenzoyl)oxy)methyl)tetrahydrofuran-2,3,4-triyl tris(3-((3-((3,4-dihydroxy-5-((3,4,5-trihydroxybenzoyl)oxy)benzoyl)oxy)-4,5-dihydroxybenzoyl)oxy)-4,5-dihydroxybenzoate) (146)
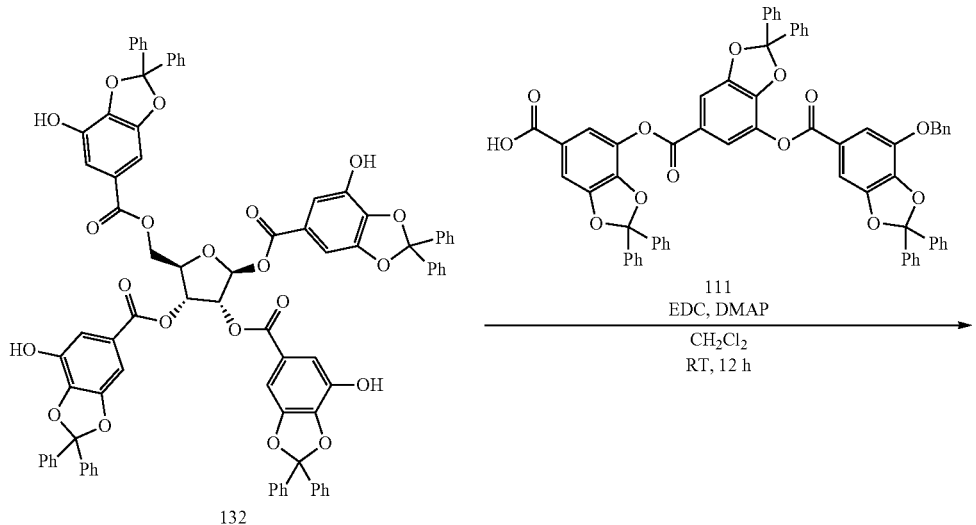
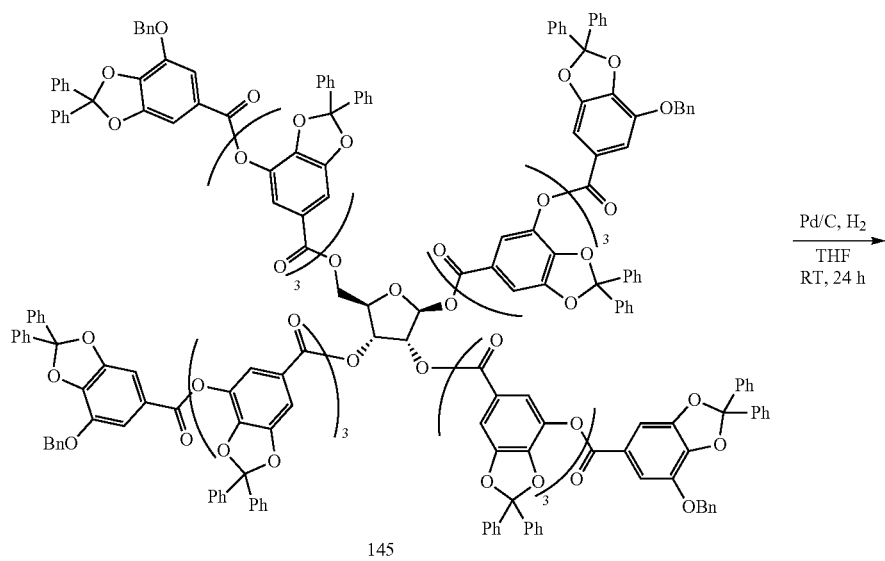

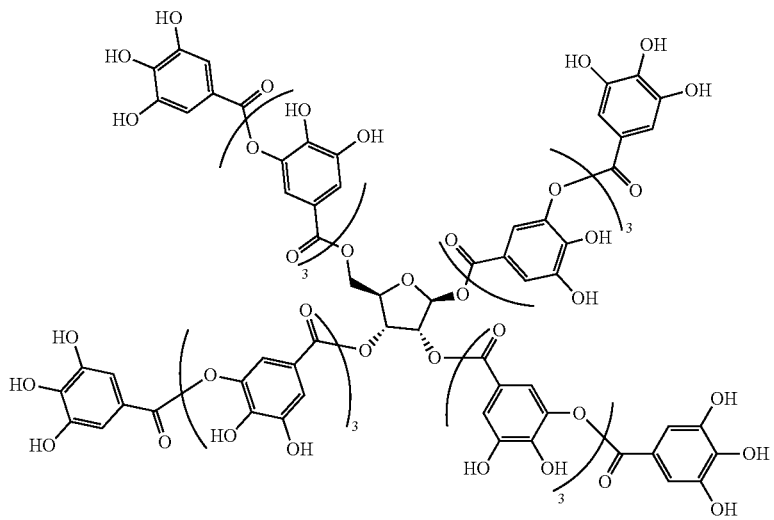

146

Preparation of (2S,3R,4R,5R)-5-(((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)methyl)tetrahydrofuran-2,3,4-triyl tris(7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (145)

To a slurry solution of the compound 132 (90 mg, 0.06 mmol), compound 111 (289 mg, 0.27 mmol) and 4-dimethylaminopyridine (6 mg, 0.05 mmol) in DCM (3.8 mL) at 0° C., 1-ethyl-3-(3-dimethylaminopropyl)carbodiimide (62 mg, 0.32 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 145 (235 mg, 66%) as a white solid. $^1$H NMR (CDCl$_3$, 400 MHz) δ 8.03-6.82 (m, 212H), 6.52 (pseudo s, 1H), 6.09 (pseudo s, 1H), 5.61-5.51 (m, 1H), 5.49-5.40 (m, 1H), 5.27-5.12 (m, 4H), 5.07-4.92 (m, 4H), 4.38 (t, J=10.9 Hz, 1H), 4.02-3.89 (m, 1H).

Preparation of (2S,3R,4R,5R)-5-(((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)methyl)tetrahydrofuran-2,3,4-triyl tris(3-((3-((3,4-dihydroxy-5-((3,4,5-trihydroxybenzoyl)oxy)benzoyl)oxy)-4,5-dihydroxybenzoyl)oxy)-4,5-dihydroxybenzoate) (146)

To a solution of the compound 145 (225 mg, 0.04 mmol) in anhydrous tetrahydrofuran (4.5 mL), the dried 10 wt % Pd/C solid (232 mg) was added. The mixture was stirred at RT under H$_2$ (8 atm) for 24 h. The crude mixture was filtered, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase C$_{18}$ F.C. with ACN/H$_2$O=25%~40% with 1% formic acid as additive. The collected residue was extracted with EtOAc/brine. The organic layer was dried over magnesium sulfate, evaporated, and precipitated with EtOAc/n-pentane (~10%) to afford the compound 146 as an off-white solid (55 mg, 53%). $^1$H NMR (MeOD, 400 MHz) δ 7.68-7.13 (m, 31H), 7.12-6.91 (m, 1H), 6.66-6.39 (m, 1H), 6.31-5.97 (m, 1H), 5.78-5.59 (m, 1H), 5.58-5.43 (m, 1H), 4.54-4.38 (m, 1H), 4.21-3.95 (m, 1H).

Example 41. Synthesis of (2S,3R,4R,5R)-5-(((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)methyl)tetrahydrofuran-2,3,4-triyl tris(3-((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)-4,5-dihydroxybenzoate) (148)

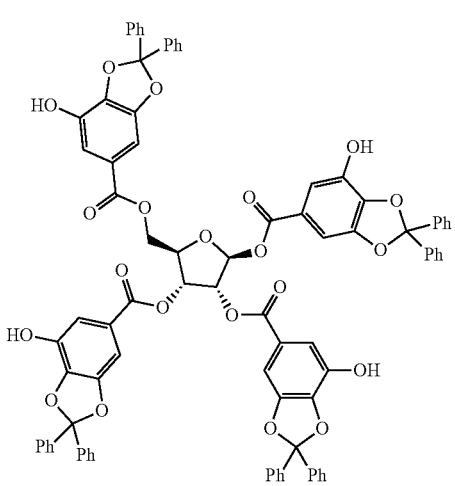

132

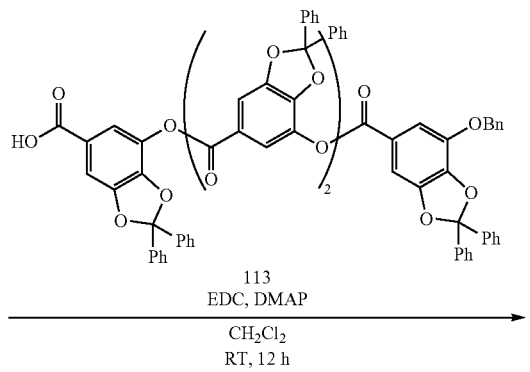

113

$$\xrightarrow[\text{CH}_2\text{Cl}_2 \\ \text{RT, 12 h}]{\text{EDC, DMAP}}$$

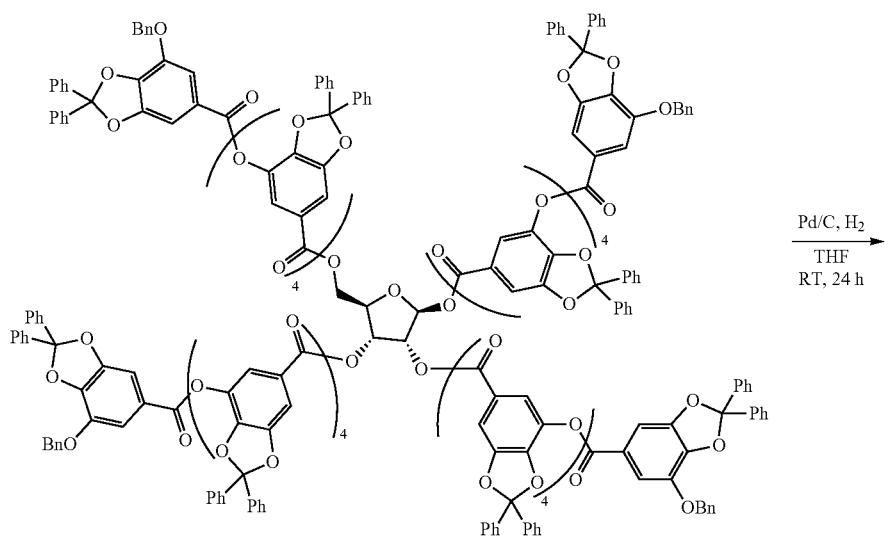

147

$$\xrightarrow[\text{THF} \\ \text{RT, 24 h}]{\text{Pd/C, H}_2}$$

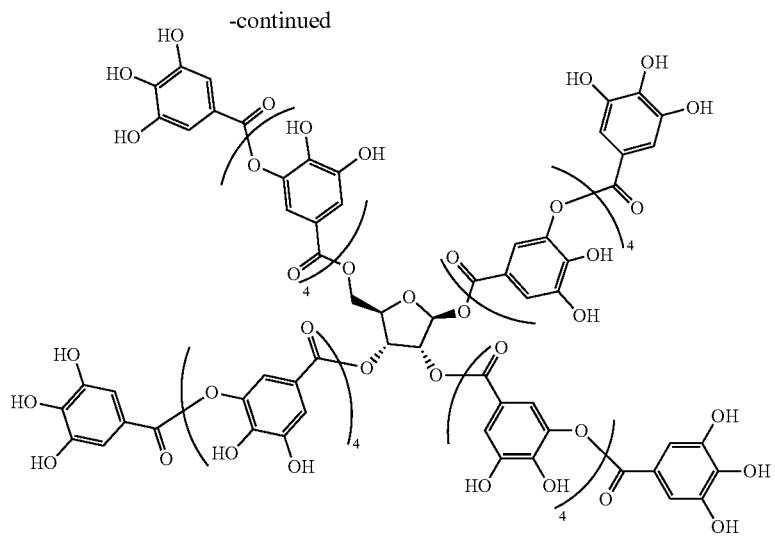

148

Preparation of (2S,3R,4R,5R)-5-(((7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)methyl) tetrahydrofuran-2,3,4-triyl tris(7-((7-((7-((7-(benzyloxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carbonyl)oxy)-2,2-diphenylbenzo[d][1,3]dioxole-5-carboxylate) (147)

To a slurry solution of the compound 132 (56 mg, 0.04 mmol), compound 113 (234 mg, 0.17 mmol) and 4-dimethylaminopyridine (4 mg, 0.03 mmol) in DCM (2.9 mL) at 0° C., 1-ethyl-3-(3-dimethylaminopropyl)carbodiimide (38 mg, 0.02 mmol) was added and stirred back to RT 12 h. The crude mixture was extracted with DCM/water and washed with brine. The organic layer was dried over anhydrous magnesium sulfate filtered and evaporated in vacuo. The residue was purified by F.C. with DCM/hexanes=60%~80% and precipitate with DCM/hexanes ~10% to afford off-white solid compound 147 (206 mg, 76%) as a white solid. $^1$H NMR (CDCl$_3$, 400 MHz) δ 7.98-6.87 (m, 260H), 6.52 (pseudo s, 1H), 6.10 (pseudo s, 1H), 5.61-5.50 (m, 1H), 5.48-5.40 (m, 1H), 5.27-5.16 (m, 4H), 5.09-4.96 (m, 4H), 4.38 (t, J=10.2 Hz, 1H), 4.02-3.89 (m, 1H).

Preparation of (2S,3R,4R,5R)-5-(((3-((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)-4,5-dihydroxybenzoyl)oxy)methyl)tetrahydrofuran-2,3,4-triyl tris (3-((3-((3-((3,4-dihydroxy-5-((3,4,5-trihydroxybenzoyl)oxy)benzoyl)oxy)-4,5-dihydroxybenzoyl)oxy)-4,5-dihydroxybenzoyl)oxy)-4,5-dihydroxybenzoate) (148)

To a solution of the compound 147 (191 mg, 0.03 mmol) in anhydrous tetrahydrofuran (3.8 mL), the dried 10 wt % Pd/C solid (208 mg) was added. The mixture was stirred at RT under H$_2$ (8 atm) for 24 h. The crude mixture was filtrated, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase C$_{18}$ F.C. with ACN/H$_2$O=25%~40% with 1% formic acid as additive. The collected residue was extracted with EtOAc/brine. The organic layer was dried over magnesium sulfate, evaporated, and precipitated with EtOAc/n-pentane (~10%) to afford the compound 148 as an off-white solid (45 mg, 50%). $^1$H NMR (MeOD, 400 MHz) δ 7.66-7.12 (m, 39H), 7.12-6.94 (m, 1H), 6.66-6.38 (m, 1H), 6.28-5.97 (m, 1H), 5.80-5.59 (m, 1H), 5.59-5.43 (m, 1H), 4.52-4.39 (m, 1H), 4.15-3.97 (m, 1H).

Example 42. Synthesis of 3-((3-((3,4-dihydroxy-5-((3,4,5-trihydroxybenzoyl)oxy)benzoyl)oxy)-4,5-dihydroxybenzoyl)oxy)-4,5-dihydroxybenzoic acid (149)

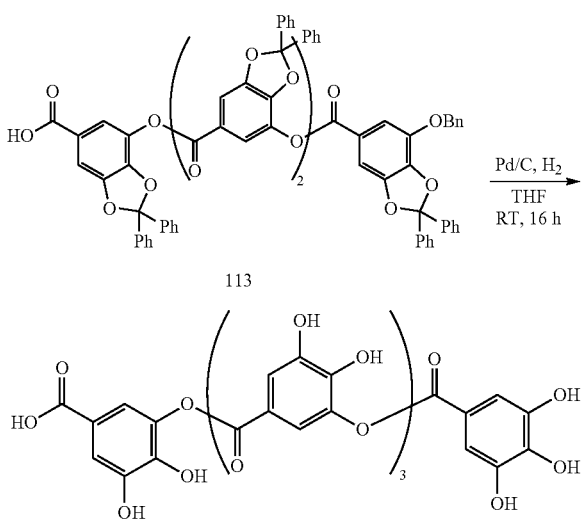

Preparation of 3-((3-((3,4-dihydroxy-5-((3,4,5-trihydroxybenzoyl)oxy)benzoyl)oxy)-4,5-dihydroxybenzoyl)oxy)-4,5-dihydroxybenzoic acid (149)

To a solution of the compound 113 (500 mg, 0.36 mmol) in anhydrous tetrahydrofuran (5.0 mL), the dried 10 wt % Pd/C solid (500 mg) was added. The mixture was stirred at RT under $H_2$ (8 atm) for 24 h. The crude mixture was filtrated, washed with tetrahydrofuran and EtOAc, the combined filtrates were evaporated in vacuo. The residue was extracted with EtOAc, 1 N hydrochloric acid, and brine. The organic residue was dried over magnesium sulfate, evaporated, and precipitated with EtOAc/hexanes (10%). The solid crude was further purified by reverse phase $C_{18}$ F.C. with $ACN/H_2O$=25%~40% with 1% formic acid as additive. The collected residue was extracted with EtOAc/brine. The organic layer was dried over magnesium sulfate, evaporated, and precipitated with EtOAc/n-pentane (~10%) to afford the compound 148 as an off-white solid (65 mg, 29%). $^1$H NMR (MeOD, 400 MHz) δ 7.61-7.39 (m, 4H), 7.33-7.09 (m, 4H).

Example 43. In Vitro Measurements of Human D-Amino Acid Oxidase (hDAAO) Activity The hDAAO inhibitory activities were measured by using D-Serine as a substrate to produce $H_2O_2$. The produced $H_2O_2$ would be oxidized by peroxidase, and the produced free radicals would further react with Amplex Red reagent to emit fluorescence. The intensity of fluorescence at 590 nm would be measured to represent the activity of hDAAO. All compounds were dissolved in DMSO. Each compound was diluted with DMSO in 3-fold serial dilution to create a dose response curve. Each sample was added in triplicate, 1 L/well, into 96-well black plates. Positive control wells were added with 1 μL of DMSO. Then 49 μL of assay buffer (100 mM Tris-HCl, pH 8.5) containing 1.2 ng/mL hDAAO, 900 nM FAD, 0.2 units/mL HRP, and 100 μM Amplex Red was added to each well of the plate using a multichannel pipette. Next, 50 μL of 100 mM D-Serine in assay buffer was added. The reaction plates were then incubated in the dark at room temperature. The fluorescence readout was detected at 0 and 20 mins by Molecular Device Gemini EM fluorescence reader using the following settings: excitation filter 530 nm, and emission filter 590 nm. The percentage of inhibition values for each well was calculated with the following equation:

The percentage of inhibition=(fluorescence sample, 20 min−fluorescence sample, 0 min)/(fluorescence DMSO, 20 min−fluorescence DMSO, 0 min)×100%

The nonlinear curve fitting model in GraphPad Prism was used to calculate $IC_{50}$ value for each compound. The results are shown in Table 2.

All the compounds in Table 2 show superior inhibitory activities of hDAAO and the $IC_{50}$ ranges from 2.4 to 299.0 nM. Moreover, the compound 123 shows the highest potency of DAAO inhibition, 2.4 nM.

TABLE 2

The $IC_{50}$ values of exemplary compounds of Formula (I)

| Compound number | $IC_{50}$ (nM) |
|---|---|
| 14 | 299.0 |
| 18 | 121.0 |
| 22 | 63.0 |
| 25 | 89.0 |
| 28 | 82.0 |
| 34 | 68.0 |
| 42 | 31.0 |
| 50 | 38.0 |
| 58 | 33.0 |
| 66 | 25.0 |
| 74 | 31.0 |
| 77 | 72.0 |
| 80 | 58.0 |
| 85 | 31.0 |
| 92 | 23.0 |
| 94 | 42.0 |
| 96 | 26.0 |
| 98 | 33.0 |
| 100 | 19.0 |
| 103 | 7.0 |
| 107 | 7.0 |
| 117 | 9.0 |
| 119 | 5.0 |
| 121 | 2.5 |
| 123 | 2.4 |
| 126 | 3.6 |
| 128 | 3.3 |
| 134 | 8.0 |
| 136 | 6.0 |
| 138 | 4.0 |
| 140 | 3.0 |
| 142 | 19.0 |
| 144 | 8.0 |
| 146 | 4.0 |
| 148 | 4.0 |
| 149 | 48.0 |

Example 44. Therapeutic Effects of Compound 66

The Effects of Compound 66 on MK-801 Treated Mice

C57BL/6J male mice were group housed (3-5 mice per cage) with food and water available ad libitum in polysulfone ventilated cages (Alternative Design, AR, USA) in the animal room of SyneuRx. The colony was maintained on a 12/12-h light/dark cycle at the temperature of 22±2° C. and all behavioral studies were performed during the dark cycle. All animals used in this study were adult mice (at least 2.5 months of age). All animal procedures were performed according to the protocols approved by Institutional Animal Care and Use Committee (IACUC).

The mice were randomly assigned into five groups for open field test, Group 1: vehicle control, Group 2: MK-801, Group 3: Compound 66 at 10 mg/kg+MK-801, Group 4: Compound 66 at 30 mg/kg+MK-801, Group 5: Compound 66 at 100 mg/kg+MK-801. Mice at Group 2-5 received an acute administration of MK-801 (Sigma-Aldrich USA), a NMDA receptor antagonist, dissolved in normal saline, at 0.2 mg/kg for open field. For pre-pulse inhibition (PPI) test, animal was randomly assigned for four groups, Group 1: vehicle control, Group 2: MK-801, Group 3: Compound 66 at 3 mg/kg+MK-801, Group 4: Compound 66 at 10 mg/kg. Group 2-4 was received 0.3 mg/kg, MK-801. MK-801 was administrated by i.p. injection 20 minutes prior to open field and PPI tests. Test article, compound 66 (dissolved in $ddH_2O$ with 65% PEG400 and 10% DMSO), was orally treated 20 minutes prior to the MK-801 administration.

The open field task is a common measurement of novelty induced exploratory behavior and general activity in both mice and rats. The objective of this experiment was to evaluate the efficacy of compound 66 on attenuating the MK-801 induced hyper-locomotion. In this study, the mice were placed in a Plexiglas cage (37.5 cm×21.5 cm×18 cm) under 50-65 lux light intensity. Their spontaneous locomotor activities were measured for 60 minutes using the Photo-beam Activity System (PAS)-open field (San Diego Instruments, San Diego, CA, USA). The total number of photo beam breaks of each mouse was measured as an index of locomotion activity.

Pre-pulse inhibition, using SR-LAB startle apparatus (San Diego Instruments, San Diego, CA, USA), was used to determine the efficacy of compound 66 on attenuating the MK-801 induced deficit of sensorimotor gating function in mice. Under 65 dB background noise, each session was composed of a 5-minute accumulation period followed by 64 trials in four blocks. The pulse alone (PA) trial was a 40 ms, 120 dB white noise burst. In the prepulse (pp)+pulse trials, a 20 ms white noise prepulse stimuli of 71 dB (pp6), 75 dB (pp10), and 83 dB (pp18) were presented 100 ms before a 40 ms 120 dB pulse. The non-stimulus (NS) trials presented the background noise only. The initial and the last blocks were composed of six PA trials, respectively. Two middle blocks consisted of PA, pp+pulse, and NS trials. These trials were presented pseudo-randomly and separated by intertribal intervals of 15 seconds on average (varying between 10 to 20 s). The percentage of prepulse inhibition was evaluated by the following formula: % PPI=100×[(PA score)−(pp-P score)]/(PA score), where the PA score was the average of the PA value in the middle blocks.

FIG. 1 shows the effect of compound 66 on locomotion in MK-801 treated mice. Compared to the vehicle control group, MK-801 treated group exhibits hyper-locomotion in open field task. In comparison to MK-801 group, compound 66, significantly reduced MK-801 induced hyper-locomotion in all three tested doses (10 mg/kg, 30 mg/kg, and 100 mg/kg) in dose-dependent manner. Moreover, high dose (100 mg/kg) relieves, 67% of MK801-induced hyperactivity on Schizophrenia model.

Figure 2:
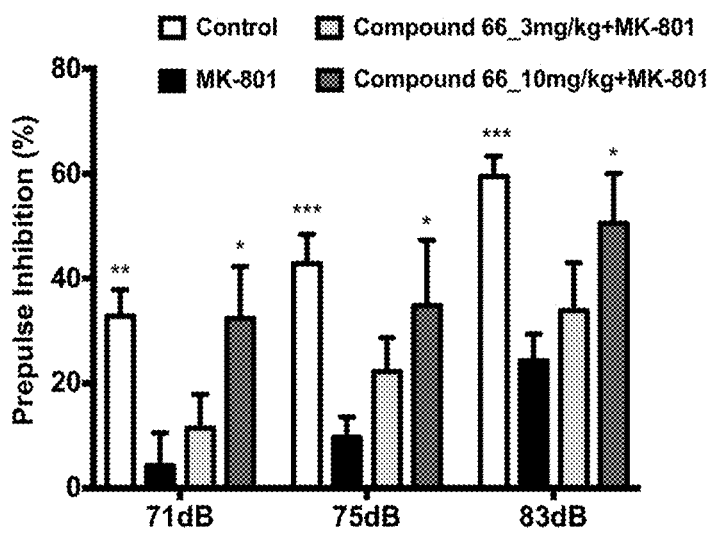
FIG. 2 is a diagram showing the effects of compound 66 on pre-pulse inhibition in MK-801 treated mice.

FIG. 2 shows the effects of compound 66 on pre-pulse inhibition in MK-801 treated mice. Compared to the vehicle control group, the MK-801 group displayed pre-pulse inhibition deficits in all pre-pulse intensity. In 75 dB and 83 dB pre-pulse inhibition, compound 66 showed marginal improvement at 3 mg/kg and displayed significantly higher percentage of pre-pulse inhibition at 10 mg/kg. At 71 dB pre-pulse intensities, compound 66, 10 mg/kg, relieve PPI deficit to basal level, which shows similar PPI performance as vehicle control group. Overall, compound 66 shows superior therapeutic effects in alleviating hyperactivity disorder and PPI deficit of NMDA-hypofunction model.

Example 45: Therapeutic Effects of Compound 74

The Effects of Compound 74 on MK-801 Treated Mice

C57BL/6J male mice were group housed (3-5 mice per cage) with food and water available ad libitum in polysulfone ventilated cages (Alternative Design, AR, USA) in the animal room of SyneuRx. The colony was maintained on a 12/12-h light/dark cycle at the temperature of 22±2° C. and all behavioral studies were performed during the dark cycle. All animals used in this study were adult mice (at least 2.5 months of age). All animal procedures were performed according to the protocols approved by Institutional Animal Care and Use Committee (IACUC).

The mice were randomly assigned into five groups for open field test, Group 1: vehicle control, Group 2: MK-801, Group 3: Compound 74 at 10 mg/kg+MK-801, Group 4: Compound 74 at 30 mg/kg+MK-801, Group 5: Compound 74 at 100 mg/kg+MK-801. Mice at Group 2-5 received an acute administration of MK-801 (Sigma-Aldrich USA), a NMDA receptor antagonist, dissolved in normal saline, at 0.2 mg/kg for open field test. For pre-pulse inhibition (PPI) test, animal was randomly assigned for four groups, Group 1: vehicle control, Group 2: MK-801, Group 3: Compound 74 at 3 mg/kg+MK-801, Group 4: Compound 74 at 10 mg/kg. Group 2-4 was received 0.3 mg/kg, MK-801. MK-801 was administrated by i.p. injection 20 minutes prior to open field and PPI tests. Test article, compound 74 (dissolved in ddH$_2$O with 65% PEG400 and 10% DMSO), was orally treated 20 minutes prior to the MK-801 administration.

All mice were tested with open field and pre-pulse inhibition tasks. The open field and pre-pulse inhibition tasks were used to evaluate the efficacy of the compound 74 on attenuating the MK-801 induced hyper-locomotion and deficit of sensorimotor gating function in mice, respectively. The apparatus and recording method of open field and pre-pulse inhibition task were as described above in Example 45.

Figure 3:
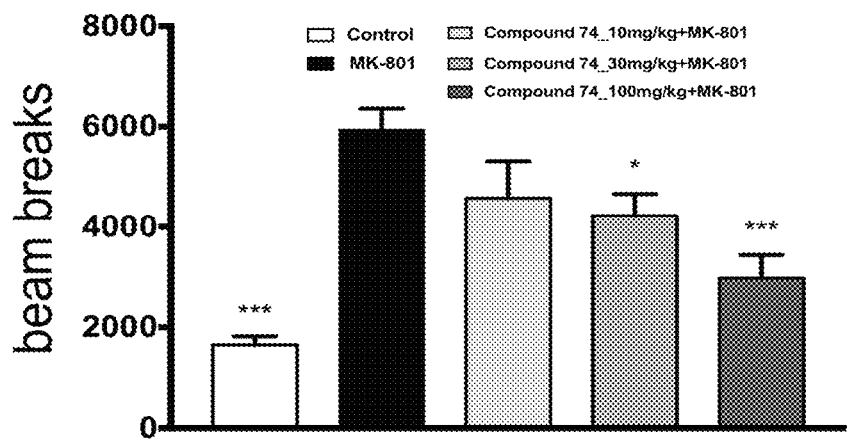
FIG. 3 is a diagram showing the effect of compound 74 on locomotion in MK-801 treated mice.

FIG. 3 shows the effect of compound 74 on locomotion in MK-801 treated mice. Compared to the vehicle control group, MK-801 treated group displayed hyper-locomotion in open field task. In comparison to MK-801 group, low dose (10 mg/kg) of compound 74 displayed marginally lower locomotion activity, while middle (30 mg/kg) and high dose (100 mg/kg) of compound 74 significantly reduced MK-801 induced hyper-locomotion, which relieves 69% of MK801-induced hyperactivity.

Figure 4:
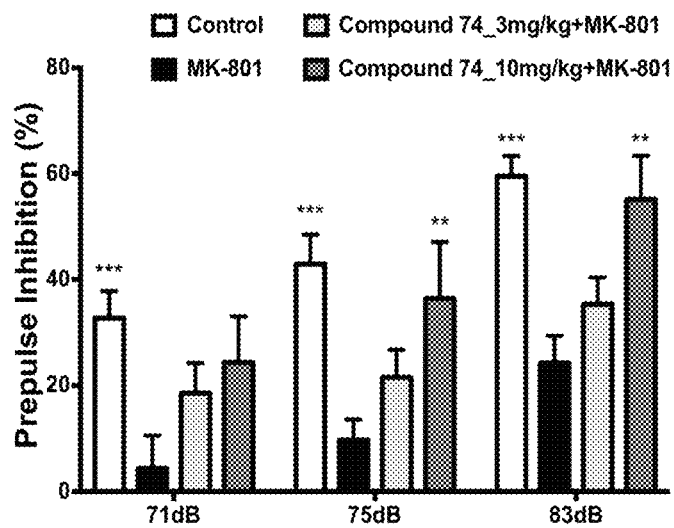
FIG. 4 is a diagram showing the effects of compound 74 on pre-pulse inhibition in MK-801 treated mice.

FIG. 4 shows the effects of compound 74 on PPI in MK-801 treated mice. Compared to the vehicle control group, the MK-801 group displayed PPI deficits in all pre-pulse intensity. In 75 and 83 dB conditions, compound 74 at 10 mg/kg dose alleviates MK-801 induced PPI deficits and displayed significantly improved PPI, compared with MK-801 group. To sum up, compound 74 displays superior antipsychotic effect in two tested behavioral tests, open field and PPI, on NMDA hypofunction model.

Example 46: Therapeutic Effects of Compound 121

The Effects of Compound 121 on MK-801 Treated Mice

C57BL/6J male mice were group housed (3-5 mice per cage) with food and water available ad libitum in polysulfone ventilated cages (Alternative Design, AR, USA) in the animal room of SyneuRx. The colony was maintained on a 12/12-h light/dark cycle at the temperature of 22±2° C. and all behavioral studies were performed during the dark cycle. All animals used in this study were adult mice (at least 2.5 months of age). All animal procedures were performed according to the protocols approved by Institutional Animal Care and Use Committee (IACUC).

The mice were randomly assigned into five groups for open field test, Group 1: vehicle control, Group 2: MK-801, Group 3: Compound 121 at 3 mg/kg+MK-801, Group 4: Compound 121 at 10 mg/kg+MK-801, Group 5: Compound 121 at 30 mg/kg+MK-801. Mice at Group 2-5 received an acute administration of MK-801 (Sigma-Aldrich USA), a NMDA receptor antagonist, dissolved in normal saline, at 0.2 mg/kg for open field test. For pre-pulse inhibition (PPI) test, animal was randomly assigned for four groups, Group 1: vehicle control, Group 2: MK-801, Group 3: Compound 121 at 3 mg/kg+MK-801, Group 4: Compound 121 at 10 mg/kg, Group 5: Compound 121 at 30 mg/kg+MK-801. Group 2-5 was received 0.3 mg/kg, MK-801. MK-801 was administrated by i.p. injection 20 minutes prior to open field and PPI tests. Test article, compound 121 (dissolved in ddH$_2$O with 65% PEG400 and 10% DMSO), was orally treated 20 minutes prior to the MK-801 administration.

The open field task is a common measurement of novelty induced exploratory behavior and general activity in both mice and rats. The objective of this experiment was to evaluate the efficacy of compound 121 on attenuating the MK-801 induced hyper-locomotion. In this study, the mice were placed in a Plexiglas cage (37.5 cm×21.5 cm×18 cm) under 50-65 lux light intensity. Their spontaneous locomotor activities were measured for 60 minutes using the Photo-beam Activity System (PAS)-open field (San Diego Instruments, San Diego, CA, USA). The total number of photo beam breaks of each mouse was measured as an index of locomotion activity.

Pre-pulse inhibition, using SR-LAB startle apparatus (San Diego Instruments, San Diego, CA, USA), was used to determine the efficacy of compound 121 on attenuating the MK-801 induced deficit of sensorimotor gating function in mice. Under 65 dB background noise, each session was composed of a 5-minute accumulation period followed by 64 trials in four blocks. The pulse alone (PA) trial was a 40 ms, 120 dB white noise burst. In the prepulse (pp)+pulse trials, a 20 ms white noise prepulse stimuli of 71 dB (pp6), 75 dB (pp10), and 83 dB (pp18) were presented 100 ms before a 40 ms 120 dB pulse. The non-stimulus (NS) trials presented the background noise only. The initial and the last blocks were composed of six PA trials, respectively. Two middle blocks consisted of PA, pp+pulse, and NS trials. These trials were presented pseudo-randomly and separated by intertribal intervals of 15 seconds on average (varying between 10 to 20 s). The percentage of prepulse inhibition was evaluated by the following formula: % PPI=100×[(PA score)−(pp-P score)]/(PA score), where the PA score was the average of the PA value in the middle blocks.

Figure 5:
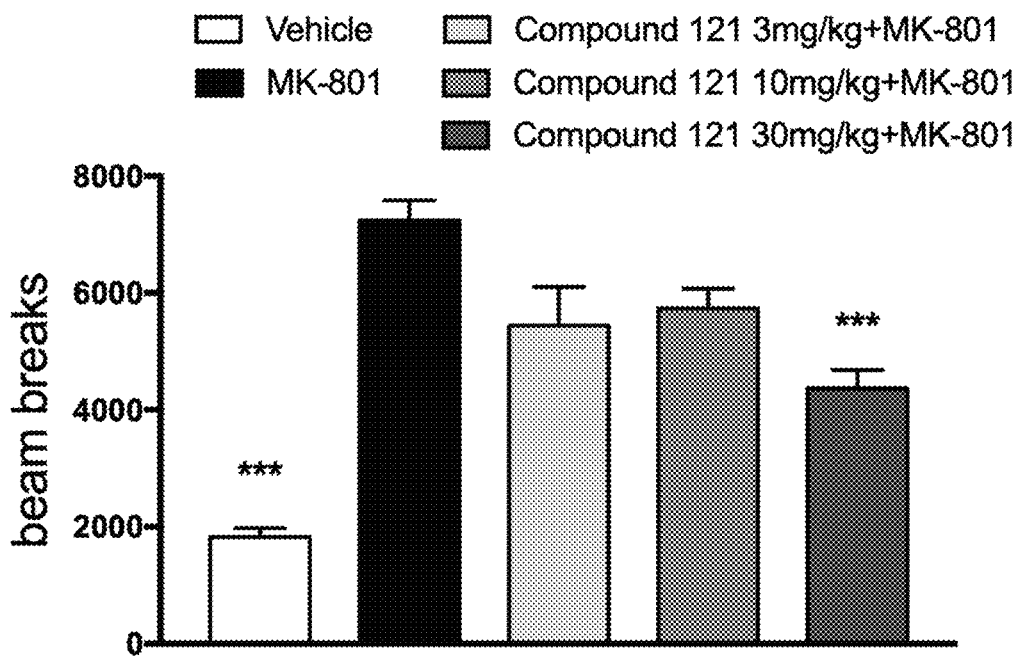
FIG. 5 is a diagram showing the effect of compound 121 on locomotion in MK-801 treated mice.

FIG. 5 shows the effect of compound 121 on locomotion in MK-801 treated mice. Compared to the vehicle control group, MK-801 treated group displayed hyper-locomotion in open field task. In comparison to MK-801 group, low dose (3 mg/kg) and middle dose (10 mg/kg) of compound 121 displayed marginally lower locomotion activity, while high dose (30 mg/kg) of compound 121 significantly reduced MK-801 induced hyper-locomotion, which relieves 48% of MK801-induced hyperactivity.

Figure 6:
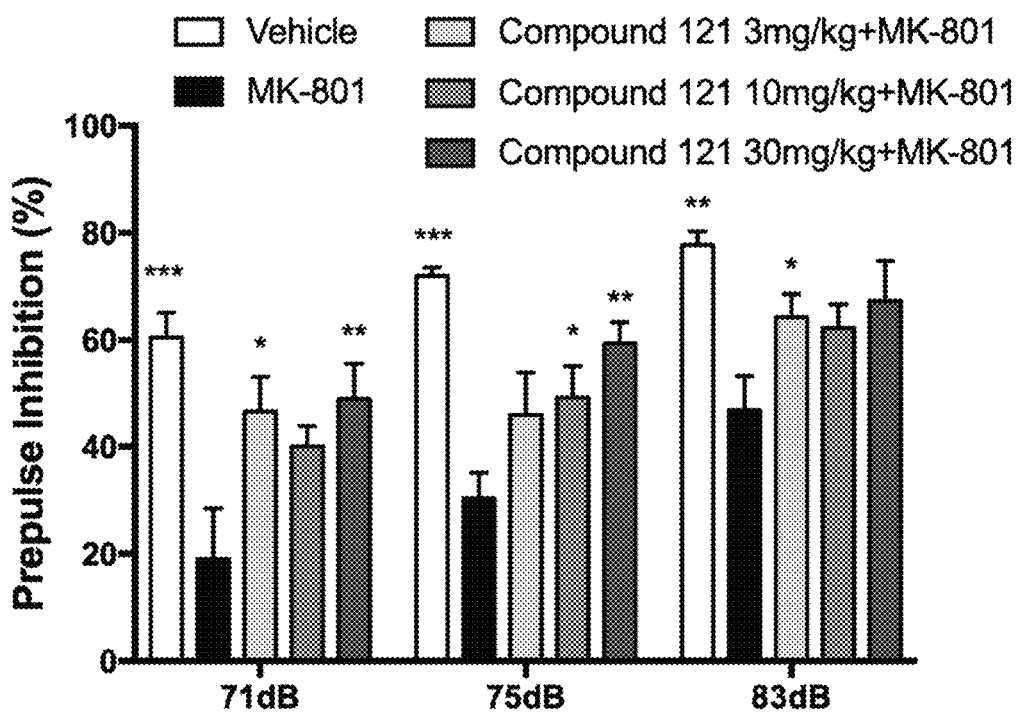
FIG. 6 is a diagram showing the effects of compound 121 on pre-pulse inhibition in MK-801 treated mice.

FIG. 6 shows the effects of compound 121 on PPI in MK-801 treated mice. Compared to the vehicle control group, the MK-801 group displayed PPI deficits in all pre-pulse intensity. In 75 and 83 dB conditions, compound 121 consistently shows higher potency in all tested dose (3, 10 and 30 mg/kg) of PPI test, compared with MK-801 group. To sum up, compound 121 displays superior antipsychotic effect in two tested behavioral tests, open field and PPI, on NMDA hypofunction model.

Example 47. Therapeutic Effects of Compound 138

The Effects of Compound 138 on MK-801 Treated Mice

C57BL/6J male mice were group housed (3-5 mice per cage) with food and water available ad libitum in polysulfide ventilated cages (Alternative Design, AR, USA) in the animal room of SyneuRx. The colony was maintained on a 12/12-h light/dark cycle at the temperature of 22±2° C. and all behavioral studies were performed during the dark cycle. All animals used in this study were adult mice (at least 2.5 months of age). All animal procedures were performed according to the protocols approved by Institutional Animal Care and Use Committee (IACUC).

The mice were randomly assigned into five groups for open field test, Group 1: vehicle control, Group 2: MK-801, Group 3: Compound 138 at 3 mg/kg+MK-801, Group 4: Compound 138 at 10 mg/kg+MK-801, Group 5: Compound 138 at 30 mg/kg+MK-801. Mice at Group 2-5 received an acute administration of MK-801 (Sigma-Aldrich USA), a NMDA receptor antagonist, dissolved in normal saline, at 0.2 mg/kg for open field. For pre-pulse inhibition (PPI) test, animal was randomly assigned for four groups, Group 1: vehicle control, Group 2: MK-801, Group 3: Compound 138 at 3 mg/kg+MK-801, Group 4: Compound 138 at 10 mg/kg, Group 5: Compound 138 at 30 mg/kg+MK-801. Group 2-5 was received 0.3 mg/kg, MK-801. MK-801 was administrated by i.p. injection 20 minutes prior to open field and PPI tests. Test article, compound 138 (dissolved in ddH$_2$O with 65% PEG400 and 10% DMSO), was orally treated 20 minutes prior to the MK-801 administration.

All mice were tested with open field and pre-pulse inhibition tasks. The open field and pre-pulse inhibition tasks were used to evaluate the efficacy of the compound 138 on attenuating the MK-801 induced hyper-locomotion and deficit of sensorimotor gating function in mice, respectively. The apparatus and recording method of open field and pre-pulse inhibition task were as described above in Example 47.

Figure 7:
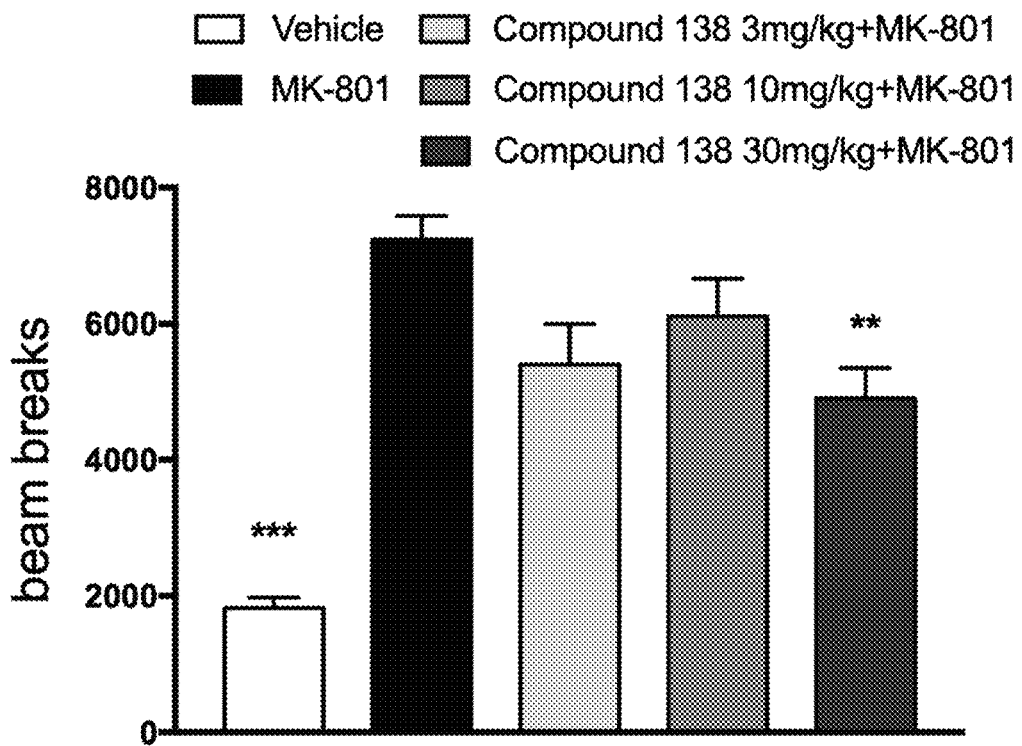
FIG. 7 is a diagram showing the effect of compound 138 on locomotion in MK-801 treated mice.

FIG. 7 shows the effect of compound 138 on locomotion in MK-801 treated mice. Compared to the vehicle control group, MK-801 treated group exhibits hyper-locomotion in open field task. In comparison to MK-801 group, compound 138, significantly reduced MK-801 induced hyper-locomotion in all three tested doses (3 mg/kg, 10 mg/kg, and 30 mg/kg) in dose-dependent manner. Moreover, high dose (30 mg/kg) relieves, 43% of MK801-induced hyperactivity on Schizophrenia model.

Figure 8:
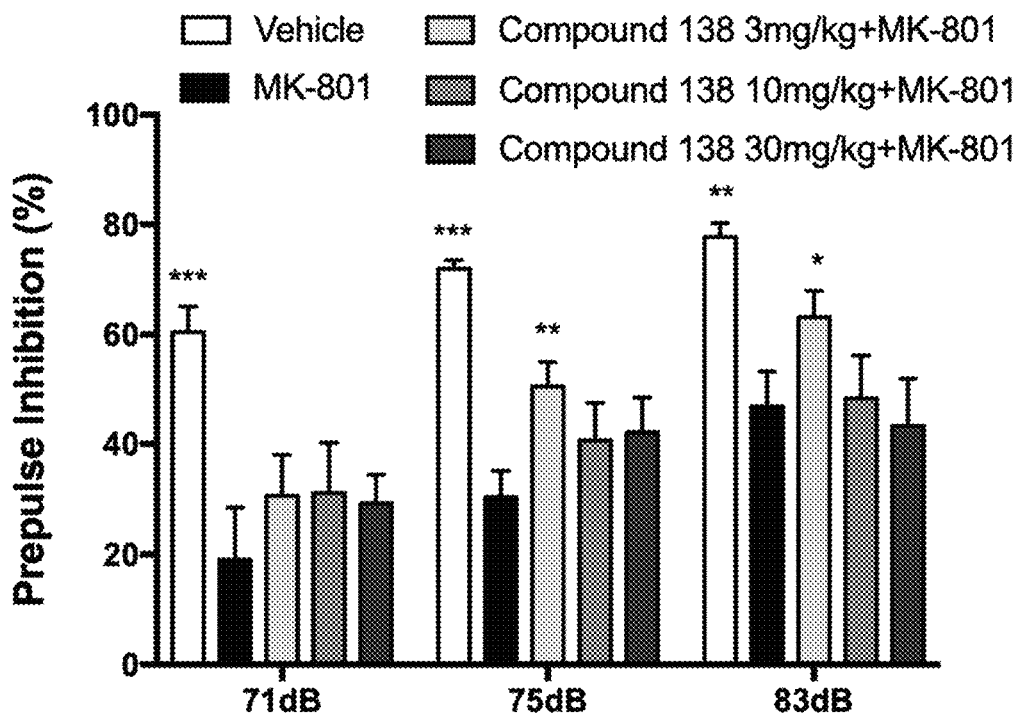
FIG. 8 is a diagram showing the effects of compound 138 on pre-pulse inhibition in MK-801 treated mice.

FIG. 8 shows the effects of compound 138 on pre-pulse inhibition in MK-801 treated mice. Compared to the vehicle control group, the MK-801 group displayed pre-pulse inhibition deficits in all pre-pulse intensity. In 75 dB and 83 dB pre-pulse inhibition, compound 138, 3 mg/kg, relieve PPI deficit.

Overall, compound 138 shows superior therapeutic effects in alleviating hyperactivity disorder and PPI deficit of NMDA-hypofunction model.

Example 48 Inhibition of 3CL Protease (3CLPro) of SARS-CoV-2 by Test Compounds

To study the inhibitory activities against SARS-CoV-2 3CLPro of test compounds, an assay was determined in vitro by measuring the enhanced fluorescence due to cleavage of the fluorogenic substrate (Dabcyl-KTSAVLQSGFRKME-Edans). For analyzing the inhibition potential, various compounds were dissolved in 1, 8 or 40% dimethyl sulfoxide (DMSO) aqueous solution as the compound stocks. Different concentration of each stocks (5 μl) was pre-incubated with 45 μl reaction mixture (50 nM SARS-CoV-2 viral 3CL protease in 20 mM Bis-Tris, pH 7.4) at 37° C. for 30 minutes. Afterwards, 50 μl of the fluorogenic peptide substrate (6 μM) was added into the mixture and gently mixed to get the final DMSO concentration 0.05, 0.40 or 2.00% solution. The difference of fluorescence intensity resulting from the reaction was measured at 485 nm with excitation at 360 nm using a fluorescence plate reader at 37° C. for 4 min. The protease activity was presented as fluorescence intensity and calculated by the following equation:

Inhibition (%)=1−[(fluorescence$_{sample,\ 4\ min}$−fluorescence$_{sample,\ 0\ min}$)/(fluorescence$_{ddH2O,\ 4\ min}$−fluorescence$_{ddH2O,\ 0\ min}$)]×100%.

The 50% inhibition concentration (IC$_{50}$) of the test compounds against SARS-CoV-2 3CLPro was shown in Table 3. Among these samples, the compound 119 displayed half maximal inhibition (IC$_{50}$) at the lowest concentration (1.039 μg/mL). In addition, compound 123 and compound 138 showed good inhibitory activities against SARS-CoV-2 3CLPro. The IC$_{50}$ of these samples was below 1.5 μg/mL. In sum, all test compounds had inhibition against proteolytic activity of SARS-CoV-2 3CLPro.

TABLE 3

Inhibitory Activities of Exemplary Formula (I) Compounds Against 2019-nCoV 3CLPro

| Compound Number | IC$_{50}$ (μM) | IC$_{50}$ (μg/mL) | Final DMSO concentration (%) |
|---|---|---|---|
| 14 | >15.625 | >7.411 | 2 |
| 18 | 5.497 | 4.280 | 0.4 |
| 58 | 10.410 | 10.532 | 2 |
| 66 | >15.625 | >16.309 | 2 |
| 74 | >31.250 | >32.618 | 2 |
| 77 | 4.329 | 3.821 | 0.4 |
| 80 | >62.500 | >56.420 | 2 |
| 85 | 2.369 | 2.271 | 2 |
| 92 | 2.418 | 2.372 | 2 |
| 96 | >15.625 | >13.448 | 2 |
| 98 | >15.625 | >12.791 | 2 |
| 100 | >15.625 | >13.667 | 2 |
| 103 | 1.925 | 3.371 | 0.4 |
| 117 | 1.238 | 1.692 | 0.05 |
| 119 | 0.526 | 1.039 | 0.05 |
| 121 | 0.585 | 1.510 | 0.4 |
| 123 | 0.380 | 1.212 | 0.4 |
| 126 | 0.706 | 1.395 | 0.4 |
| 128 | 0.604 | 1.560 | 0.4 |
| 134 | 1.016 | 1.389 | 0.4 |

TABLE 3-continued

Inhibitory Activities of Exemplary Formula (I) Compounds Against 2019-nCoV 3CLPro

| Compound Number | IC$_{50}$ (μM) | IC$_{50}$ (μg/mL) | Final DMSO concentration (%) |
|---|---|---|---|
| 136 | 0.841 | 1.661 | 0.05 |
| 138 | 0.552 | 1.425 | 0.4 |
| 140 | 0.658 | 2.100 | 0.4 |
| 142 | 1.699 | 2.322 | 0.4 |
| 144 | 0.870 | 1.718 | 0.4 |
| 146 | 1.528 | 3.948 | 0.4 |
| 148 | 0.724 | 2.310 | 0.4 |
| 149 | 4.659 | 2.919 | 0.4 |
| The Enriched tannic acid (SNB01) | 0.924 | 1.571 | 0.05 |
| The Enriched tannic acid (SNB01) | 0.976 | 1.660 | 0.40 |
| The Enriched tannic acid (SNB01) | 2.811 | 4.782 | 2.00 |

What is claimed is:

1. A compound of Formula (III), or a pharmaceutically acceptable salt thereof:
   wherein the compound is of Formula (III)

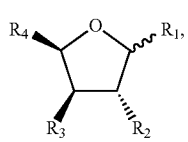

in which R$_4$ is of the formula

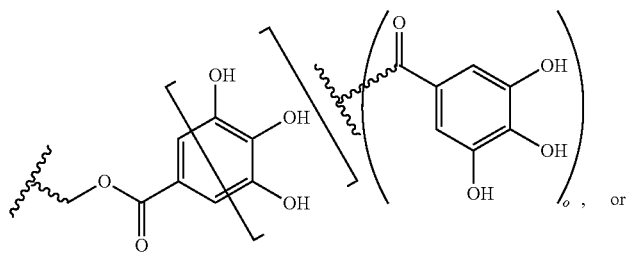

, or

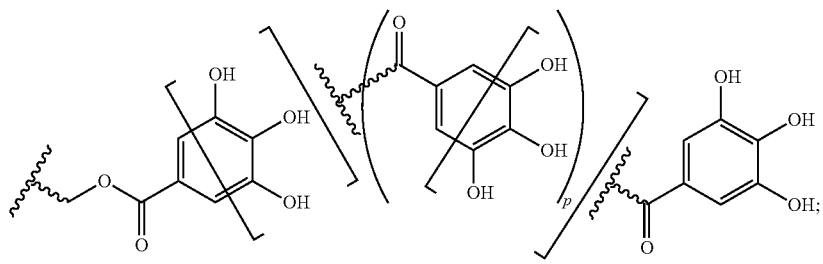

and each of $R_1$, $R_2$, and $R_3$, independently, is selected from the group consisting of:

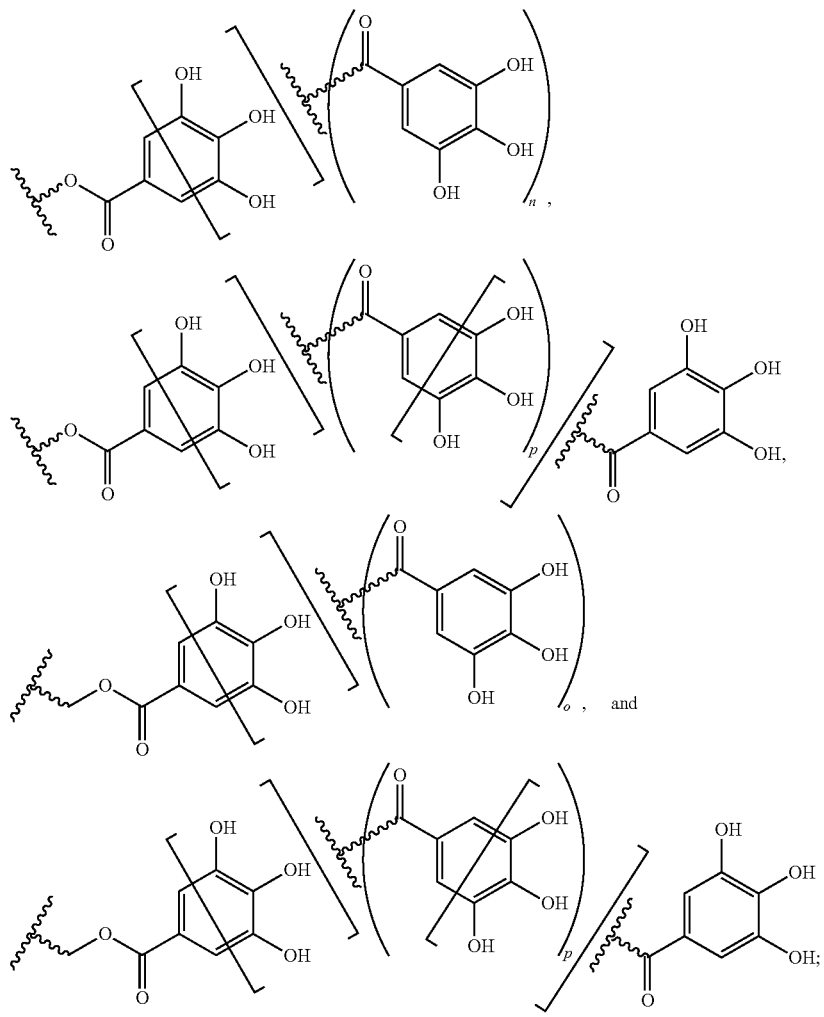

each of n and o being, independently, 0 or 1; and each of m and p being, independently, 1, 2, 3, 4, or 5.

2. The compound of claim 1, wherein each of $R_1$, $R_2$, $R_3$, and $R_4$, is, independently, unsubstituted or substituted with 1, 2, 3, 4, or 5 substituents selected from the group consisting of $C_{1-3}$ alkyl, halogen, —$CF_3$, —CN, —$NO_2$, —SH, —OH, —S($C_{1-3}$ alkyl), —$NH_2$, NH($C_{1-3}$ alkyl), N($C_{1-3}$ alkyl)$_2$, and —O($C_{1-3}$ alkyl).

3. The compound of claim 1, wherein the compound is of Formula (III) and wherein $R_4$ is selected from the group consisting of

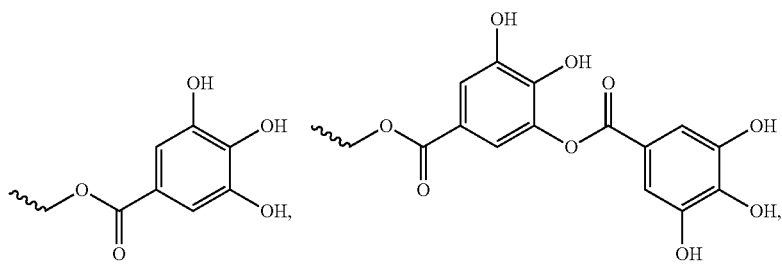

-continued
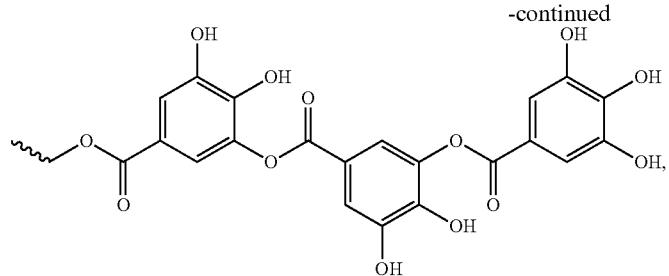
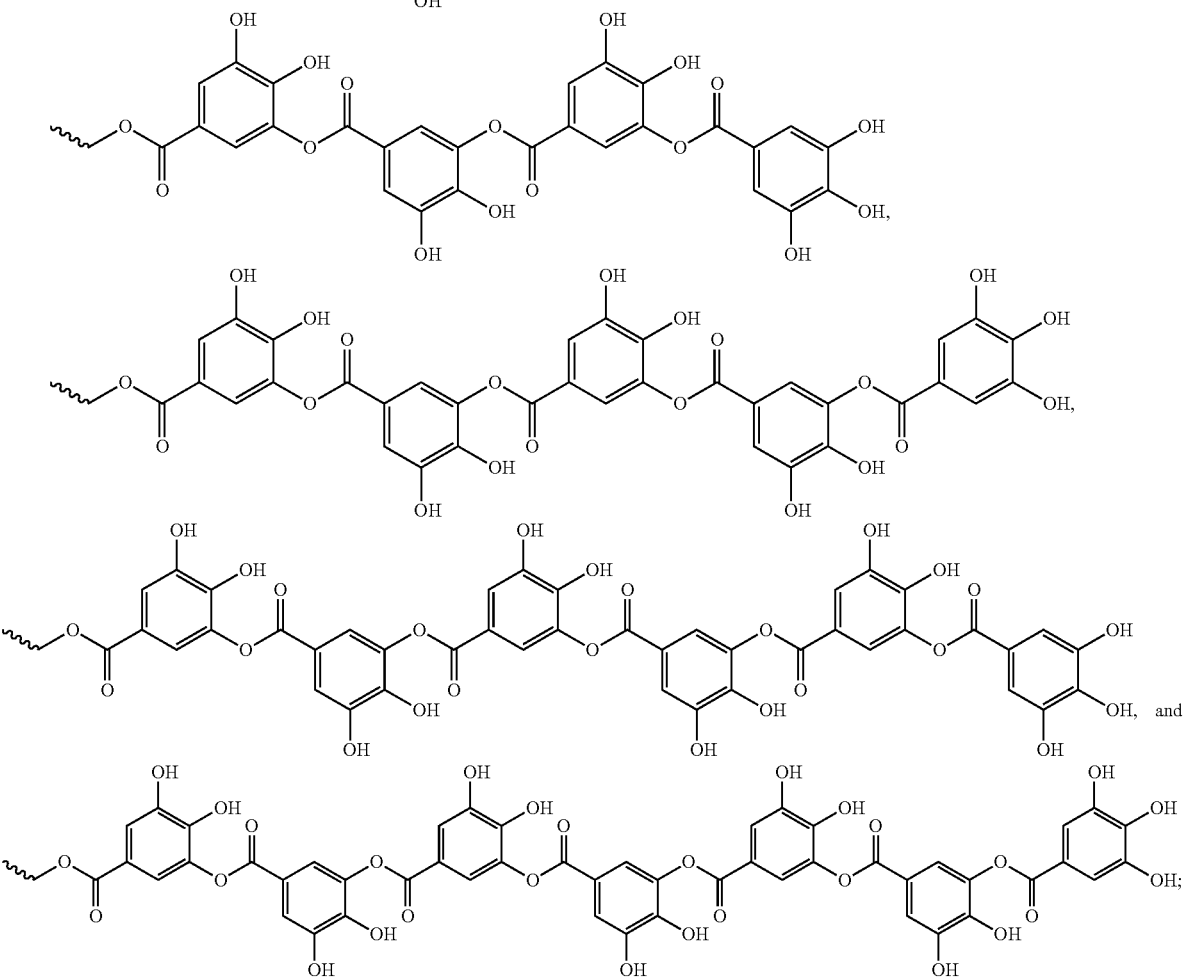
and
wherein each of $R_1$, $R_2$, and $R_3$, independently, is selected from the group consisting of
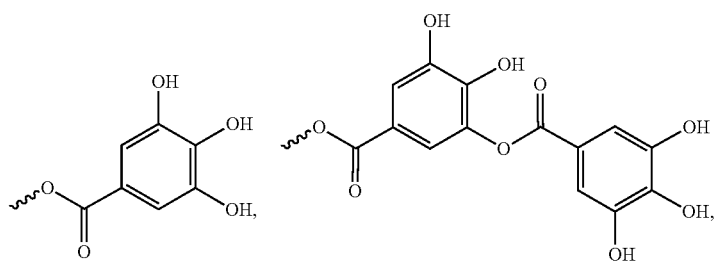

-continued

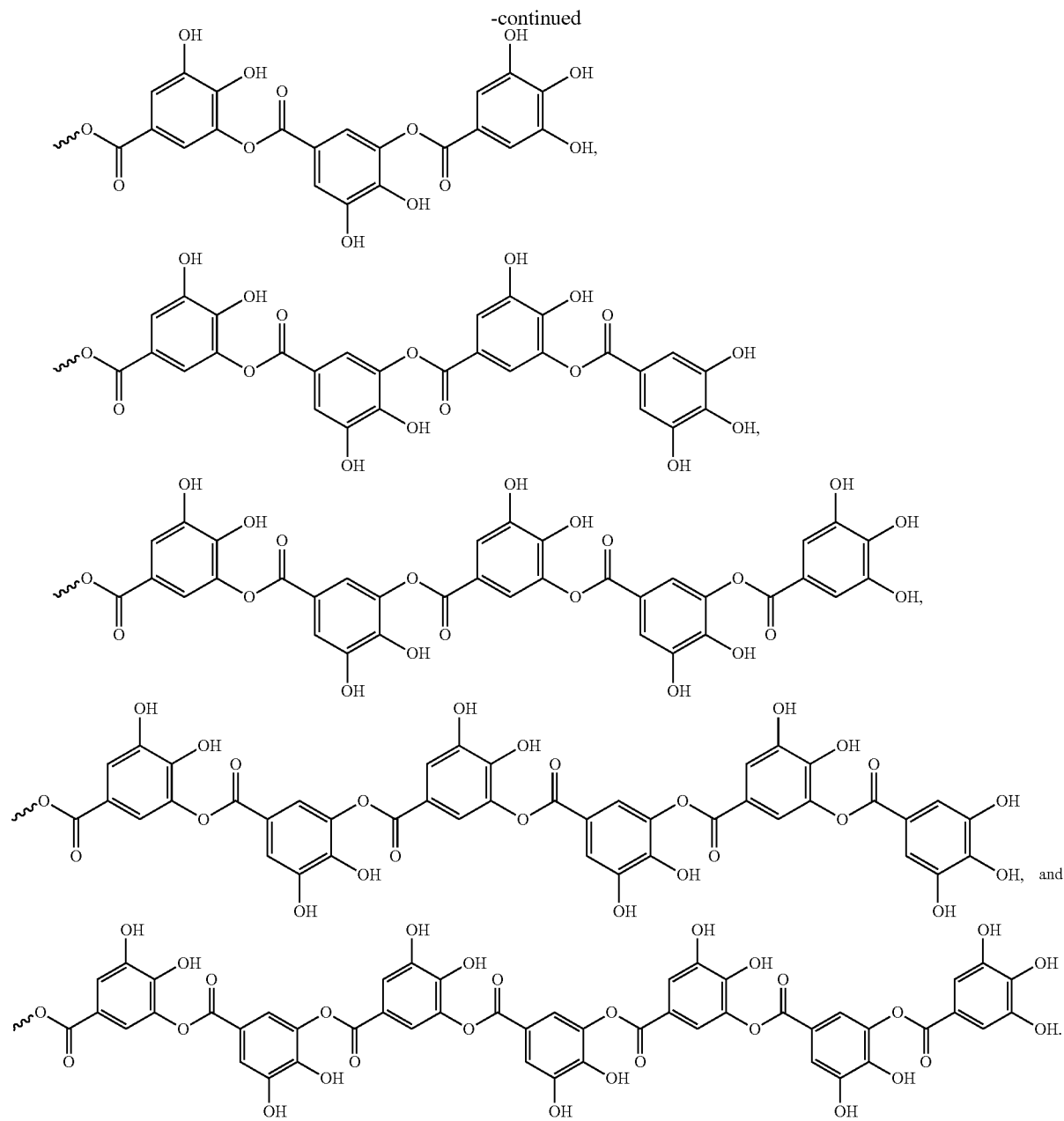

4. The compound of claim 3, wherein the compound of Formula (III) is α-Rib-8G, α-Rib-12G, α-Rib-16G, α-Rib-20G, α-Rib-24G, β-Rib-8G, β-Rib-12G, β-Rib-16G, β-Rib-20G, or β-Rib-24G.

5. A composition, comprising one or more compounds of claim 1 and a carrier.

6. The composition of claim 5, wherein the composition is a nutraceutical composition, a health food, or a medical food.

7. A method of inhibiting D-amino acid oxidase (DAAO) in a subject, comprising administering to a subject in need thereof an effective amount of the composition of claim 5.

8. The method of claim 7, wherein the subject is a human having, suspected of having, or at risk for a central nervous system (CNS) disorder or a metabolic disorder.

9. The method of claim 8, wherein the CNS disorder is selected from the group consisting of schizophrenia, psychotic disorders, Alzheimer's disease, frontotemporal dementia, vascular dementia, dementia with Lewy bodies, senile dementia, mild cognitive impairment, benign forgetfulness, closed head injury, autistic spectrum disorder, Asperger's disorder, fragile X syndrome, attention deficit hyperactivity disorders, attention deficit disorder, obsessive compulsive disorder, tic disorders, childhood learning disorders, premenstrual syndrome, depression, major depressive disorder, anhedonia, suicidal ideation and/or behaviors, bipolar disorder, anxiety disorders, panic disorder, post-traumatic stress disorder, chronic mild and unpredictable stress, eating disorders, addiction disorders, personality disorders, Parkinson's disorder, Huntington's disorder, multiple sclerosis, amyotrophic lateral sclerosis, ataxia, Friedreich's ataxia, Tourette's syndrome, nocturnal enuresis, non-epileptic seizures, blepharospasm, Duchenne muscular dystrophy, and stroke.

10. The method of claim 8, wherein the metabolic disorder is selected from the group consisting of obesity, hyperlipidemia, hypercholesterolemia, hyperglycemia, hyperinsulinemia, insulin resistance, and diabetes.

11. The method of claim 9, wherein the human subject is further treated by one or more additional pharmaceutical agents for treating and/or reducing the risk for a CNS disorder.

12. The method of claim 8, wherein the composition is administered to the subject by oral administration, by injection, by topical administration, or by inhalation.

13. The method of claim 8, wherein the composition is placed in a medical device selected from the group consisting of an inhaler, a nebulizer, a nasal spray, and a vaporization aerosol device for administration to the subject.

14. The method of claim 8, wherein the subject is administered the composition continuously or at a frequency of every five minutes to one time every three months.

\* \* \* \* \*

UNITED STATES PATENT AND TRADEMARK OFFICE
CERTIFICATE OF CORRECTION

PATENT NO. : 11,793,823 B2  
APPLICATION NO. : 17/699784  
DATED : October 24, 2023  
INVENTOR(S) : Guochuan Emil Tsai et al.

Page 1 of 1

It is certified that error appears in the above-identified patent and that said Letters Patent is hereby corrected as shown below:

In the Claims

In Column 246, Claim 1, Lines 29-35, replace:

"  (III) "

With:

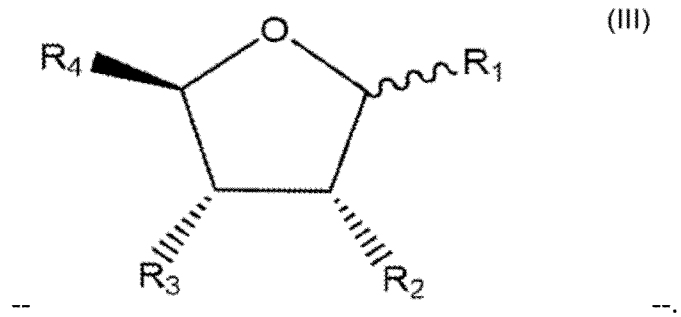 (III)

--                                                                  --.

Signed and Sealed this  
Seventeenth Day of September, 2024

Katherine Kelly Vidal  
*Director of the United States Patent and Trademark Office*